US010184151B2

(12) United States Patent
Weiner et al.

(10) Patent No.: US 10,184,151 B2
(45) Date of Patent: Jan. 22, 2019

(54) MICRORNAS IN NEURODEGENERATIVE DISORDERS

(71) Applicants: The Brigham and Women's Hospital, Inc., Boston, MA (US); The General Hospital Corporation, Boston, MA (US)

(72) Inventors: Howard Weiner, Brookline, MA (US); Oleg Butovsky, Boston, MA (US); Merit Cudkowicz, Newton, MA (US); James Berry, Belmont, MA (US)

(73) Assignees: The Brigham and Women's Hospital, Inc., Boston, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 14/350,977

(22) PCT Filed: Oct. 11, 2012

(86) PCT No.: PCT/US2012/059671
§ 371 (c)(1),
(2) Date: Apr. 10, 2014

(87) PCT Pub. No.: WO2013/055865
PCT Pub. Date: Apr. 18, 2013

(65) Prior Publication Data
US 2014/0235697 A1 Aug. 21, 2014

Related U.S. Application Data

(60) Provisional application No. 61/601,205, filed on Feb. 21, 2012, provisional application No. 61/545,968, filed on Oct. 11, 2011.

(51) Int. Cl.
*C12N 15/11* (2006.01)
*C12Q 1/6883* (2018.01)
*C12N 15/113* (2010.01)

(52) U.S. Cl.
CPC .......... *C12Q 1/6883* (2013.01); *C12N 15/113* (2013.01); *C12N 2310/113* (2013.01); *C12N 2310/3231* (2013.01); *C12Q 2600/158* (2013.01); *C12Q 2600/178* (2013.01)

(58) Field of Classification Search
CPC ................ C12N 15/111; C12N 15/113; C12N 2310/141
See application file for complete search history.

(56) References Cited

U.S. PATENT DOCUMENTS

| 2009/0143326 | A1 | 6/2009 | Obad et al. | |
|---|---|---|---|---|
| 2010/0111952 | A1* | 5/2010 | Beckman | C07K 14/70578 424/134.1 |
| 2010/0286234 | A1* | 11/2010 | Elmen et al. | 514/44 A |
| 2010/0286385 | A1 | 11/2010 | Tuschl et al. | |
| 2011/0142789 | A1 | 6/2011 | Gitler et al. | |
| 2012/0064122 | A1* | 3/2012 | Baltimore | A61K 31/7088 424/278.1 |

FOREIGN PATENT DOCUMENTS

| JP | A-2005-511061 | 4/2005 | |
|---|---|---|---|
| JP | A-2009-532044 | 9/2009 | |
| WO | WO 1999/21542 | 5/1999 | |
| WO | WO 1999/29731 | 6/1999 | |
| WO | WO 2000/74718 | 12/2000 | |
| WO | 2003/048773 | 12/2003 | |
| WO | WO 2003/048773 | 12/2003 | |
| WO | WO 2004/046160 | 6/2004 | |
| WO | WO 2005/013901 | 2/2005 | |
| WO | WO 2005/061710 | 7/2005 | |
| WO | WO 2006/069584 | 7/2006 | |
| WO | WO 2007/112753 | 11/2007 | |
| WO | 2008/153692 | 12/2008 | |
| WO | 2009/029690 | 5/2009 | |
| WO | 2009/117418 | 9/2009 | |
| WO | WO 2011/048125 | 4/2011 | |
| WO | 2013/134403 | 9/2013 | |
| WO | WO 2013/133403 A1 * | 9/2013 | ........... C12N 15/113 |
| WO | WO 2016/196978 | 12/2016 | |

OTHER PUBLICATIONS

Koval et al., Method for widespread microRNA-155 inhibition prolongs survival in ALS-model mice, 2013, Human Molecular Genetics, vol. 22, pp. 4127-4135.*
Sun et al., MicroRNA-124 protects neurons against apoptosis in cerebral ischemic stroke, 2013, CNS Neuroscience & Therapeutics, vol. 19, pp. 813-819.*
Krützfeldt et al., Silencing of microRNAs in vivo with 'antagomirs', 2005, Nature, vol. 438, pp. 685-689.*
Pagani et al., Calcium signaling pathways mediating synaptic potentiation triggered by amyotrophic lateral sclerosis IgG in motor nerve terminals, 2006, The Journal of Neuroscience, vol. 26, pp. 2661-2672.*
Smith et al., Immunosuppression and anti-inflammatory agents in ALS, 2000, Amyotrophic Lateral Sclerosis and Other Motor Neuron Disorders, vol. 1, pp. 33-43.*
Krützfeldt et al., Specificity, duplex degradation and subcellular localization of antagomirs, 2007, Nucleic Acids Research, vol. 35, pp. 2885-2892.*
Davis et al., Improved targeting of miRNA with antisense oligonucleotides, 2006, Nucleic Acids Research, vol. 34, pp. 2294-2304.*
Shefner et al., A clinical trial of creatine in ALS, 2004, Neurology, vol. 63, pp. 1656-1661.*

(Continued)

*Primary Examiner* — Dana H Shin
(74) *Attorney, Agent, or Firm* — Fish & Richardson P.C.

(57) ABSTRACT

Provided herein are methods of treating a neurodegenerative disorder such as Amyotrophic Lateral Sclerosis (ALS) or Multiple Sclerosis (MS) that include administering to a subject at least one inhibitory nucleic acid that decreases the level or activity of microRNA hsa-miR-155.

11 Claims, 63 Drawing Sheets
Specification includes a Sequence Listing.

(56) References Cited

OTHER PUBLICATIONS

Michael Benatar, Lost in translation: Treatment trials in the SOD1 mouse and in human ALS, 2007, Neurobiology of Disease, vol. 26, pp. 1-13.*
Chen et al., microRNAs in cardiovascular development, 2012, Journal of Molecular and Cellular Cardiology, vol. 52, pp. 949-957.*
Susanna Obad, et al., "Silencing of microRNA families by seed-targeting tiny LNAs", Nature Genetics, Apr. 2011, vol. 43, No. 4, pp. 371-378.
Elijah W. Stommel et al., "Efficacy of thalidomide for the treatment of amyotrophic lateral sclerosis: A phase II open label clinical trial," Amyotrophic Lateral Sclerosis, 2009, 21 pgs.
International Search Report and Written Opinion dated Jan. 31, 2013 in international application No. PCT/US 2012/059671, 11 pgs.
Alexianu et al., "Immune reactivity in a mouse model of familial ALS correlates with disease progression," Neurology, 57:1282-1289 (2001).
Banerjee et al., "Adaptive immune neuroprotection in G93A-SOD1 amyotrophic lateral sclerosis mice," PLoS ONE, 3:e2740 (2008).
Beers et al., "CD4+ T cells support glial neuroprotection, slow disease progression, and modify glial morphology in an animal model of inherited ALS," Proc. Natl. Acad. Sci. USA, 105:15558-15563 (2008).
Beers et al., "Wild-type microglia extend survival in PU.1 knockout mice with familial amyotrophic lateral sclerosis," Proc. Natl. Acad. Sci., USA, 103:16021-16026 (2006).
Butovsky et al., "IN9-2 RNA Metabolism in Neurodegeneration Identification of a Unique MiRNA Signature in CD14+/CD16- Blood-Monocytes in ALS Subjects Identical to that Observed in SOD Mice," Neurology, (Apr. 2012) Retrieved from the Internet: URL:http://www.neurology.org/cgi/content/meeting_abstract/78/1_MeetingAbstracts/IN9-2.002?sid=808357b9-1304-4f1c-8ae0-79472alf51fd [retrieved on Jan. 27, 2015].
Butovsky et al., "Modulating inflammatory monocytes with a unique microRNA gene signature ameliorates murine ALS," Journal of Clinical Investigation, 122(9):3063-3087 (Aug. 2012).
Butovsky et al., "Targeting miR-155 restores abnormal microglia and attenuates disease in SOD1 mice," Annals of Neurology, 77(1):75-99 (Jan. 2015).
Cardona et al., "Isolation of murine microglial cells for RNA analysis or flow cytometry," Nat. Protoc., 1:1947-1951 (2006).
Chiu et al., "Activation of innate and humoral immunity in the peripheral nervous system of ALS transgenic mice," Proc. Natl. Acad. Sci. USA, 106:20960-20965 (2009).
Chiu et al., "T lymphocytes potentiate endogenous neuroprotective inflammation in a mouse model of ALS," Proc. Natl. Acad. Sci. USA, 105:17913-17918 (2008).
Examination Report issued in NZ623459 dated Feb. 12, 2015 (2 pages).
Getts et al., "Ly6c+ "inflammatory monocytes" are microglial precursors recruited in a pathogenic manner in West Nile virus encephalitis," J. Exp. Med., 205:2319-2337 (2008).
Hall et al., "Relationship of microglial and astrocytic activation to disease onset and progression in a transgenic model of familial ALS," Glia, 23:249-256 (1998).
Henkel et al., "Presence of dendritic cells, MCP-1, and activated microglia/macrophages in amyotrophic lateral sclerosis spinal cord tissue," Ann. Neurol., 55:221-235 (2004).
Hirata et al., "Sp1 is an essential transcription factor for LPS-induced tissue factor expression in THP-1 monocytic cells, and nobiletin represses the expression through inhibition of NF-kappaB, AP-1, and Sp1 activation," Biochemical pharmacology, 75:1504-14 (2008).
International Preliminary Report on Patentability in International Application No. PCT/US2012/059671, dated Apr. 15, 2014, 7 pages.

Junn et al., "MicroRNAs in neurodegenerative diseases and their therapeutic potential," Pharmacology and Therapeutics, 133(2):142-150 (Oct. 2011).
Kim et al., "The Nod2 sensor promotes intestinal pathogen eradication via the chemokine CCL2-dependent recruitment of inflammatory monocytes," Immunity, 34:769-780 (2011).
King et al., "Circulating Ly-6C+ myeloid precursors migrate to the CNS and play a pathogenic role during autoimmune demyelinating disease," Blood, 113:3190-3197 (2009).
Koval et al., "Method for widespread microRNA-155 inhibition prolongs survival in ALS-model mice," Human Molecular Genetics, 22(20):4127-4135 (Jun. 2013).
Lu et al., "Foxp3-dependent microRNA155 confers competitive fitness to regulatory T cells by targeting SOCS1 protein," Immunity, 30:80-91v (2009).
McGeer and McGeer., "Inflammatory processes in amyotrophic lateral sclerosis," Muscle Nerve, 26:459-470 (2002).
Meissner et al., "Mutant superoxide dismutase 1-induced IL-1beta accelerates ALS pathogenesis," Proc. Natl. Acad. Sci. USA, 107:13046-13050 (2010).
Moore et al., "miR-155 as a multiple sclerosis-relevant regulator of myeloid cell polarization," Ann Neurol, 74:709-20 (2013).
Murugaiyan et al., "Silencing microRNA-155 ameliorates experimental autoimmune encephalomyelitis," J. Immunol., 187:2213-2221 (2011).
Obad et al., "Silencing of microRNA families by seed-targeting tiny LNAs," Nat Genet. 43(4):371-378 (2011).
O'Connell et al., "MicroRNA-155 is induced during the macrophage inflammatory response," Proc Natl Acad Sci U S A 104: 1604-9 (2007).
O'Connell et al., "MicroRNA-155 promotes autoimmune inflammation by enhancing inflammatory T cell development," Immunity, 33:607-19 (2010).
Park et al., "Signaling pathways and genes that inhibit pathogen-induced macrophage apoptosis—CREB and NF-kappaB as key regulators," Immunity, 23: 319-29 (2005).
Patrick et al., "Stress-dependent cardiac remodeling occurs in the absence of microRNA-21 in mice," J Clin Invest, 120(11):3912-3916 (2010).
Supplementary European Search Report issued in EP12839637 dated Jan. 29, 2015 (9 pages).
Williams et al., "MicroRNA-206 Delays ALS Progression and Promotes Regeneration of Neuromuscular Synapses in Mice," Science, 326(5959):1549-1554 (Dec. 2009).
Worm et al., "Silencing of microRNA-155 in mice during acute inflammatory response leads to derepression of c/ebp Beta and down-regulation of G-CSF," Nucleic Acids Res., 37:5784-5792 (2009).
Anneser er al., "Immunosuppressant FK506 does not exert beneficial effects in symptomatic G93A superoxide dismutase-1 transgenic mice," Neuroreport. Aug. 28, 2001;12(12):2663-5.
Bartfeld et al., "Immunoregulatory and activated T cells in amyotrophic lateral sclerosis patients," J Neuroimmunol. Aug. 1985;9(3-4):131-7 (Abstract only).
Brown et al., "Failure of Immunosuppression With a Ten- to 14-Day Course of High-Dose Intravenous Cyclophosphamide to Alter the Progression of Amyotrophic Lateral Sclerosis" Arch. Neurol. 43:383-384 (1986).
Chinese Office Action in corresponding Chinese Application No. 201280061082, dated Sep. 28, 2015, 8 pages.
Drachman et al., "Trial of immunosuppression in amyotrophic lateral sclerosis using total lymphoid irradiation," Ann Neurol. Feb. 1994;35(2):142-50 (abstract only).
Dutta and Ahmad, "The efficacy and safety of tacrolimus in rheumatoid arthritis," Ther. Adv. Mosculoskel. Dis., 2011, 3(6):283-291.
European Office Action in corresponding European Application No. 12839637, dated Oct. 15, 2015, 3 pages.
Moreno-Otero et al., "Autoimmune hepatitis after long-term methotrexate therapy for rheumatoid arthritis," Curr. Drug Saf., Jul. 2011, 6(3):197-200.
Pagani et al., "Autoimmunity in Amyotrophic Lateral Sclerosis: Past and Present," Neurol Res Int. 2011:497080 (2011).

(56) References Cited

OTHER PUBLICATIONS

Stankiewicz et al., "Role of Immunosuppressive Therapy for the Treatment of Multiple Sclerosis," Neurotherapeutics, 2013, 10:77-88.
Troost et al., "Immunohistochemical characterization of the inflammatory infiltrate in amyotrophic lateral sclerosis," Neuropathol. Appl. Neurobiol., Oct. 1990, 16:401-410.
Weiner, "Immunosuppressive treatment in multiple sclerosis," J. Neurol. Sci., Aug. 2004, 223:1-11 (abstract only).
Obad et al., "Silencing of microRNA families by seed-targeting tiny LNAs," Nat Genet. Mar. 20, 2011;43(4):371-8.
Garchow et al., "Silencing of microRNA-21 in vivo ameliorates autoimmune splenomegaly in lupus mice," EMBO Mol Med 3, 605-615 (2011).
Patrick et al., "Stress-dependent cardiac remodeling occurs in the absence of microRNA-21 in mice" J Clin Invest. 120(11):3912-3916.
Hullinger et al., "Inhibition of miR-15 protects against cardiac ischemic injury," Circ Res. 110(1): 71-81 (2012).
Stenvang et al., "Inhibition of microRNA function by antimiR oligonucleotides," Silence 3:1 (2012).
Lujambio and Lowe, "The microcosmos of cancer" Nature 482:347-355 (2012).
Appel et al., "A double-blind study of the effectiveness of cyclosporine in amyotrophic lateral sclerosis," Archives of Neurology, 1988, 45(4): 381-386.
Beers et al., "Endogenous regulatory T lymphocytes ameliorate amyotrophic lateral sclerosis in mice and correlate with disease progression in patients with amyotrophic lateral sclerosis," Brain, 2011, 134:1293-1314.
Beghi et al., "A randomized controlled trial of recombinant interferon beta-la in ALS," American Academy of Neurology, Jan. 25, 2000, 54(2):469-474.
Bosco, "Wild-type and mutant SOD1 share an aberrant conformation and a common pathogenic pathway in ALS," Nature Neuroscience, Nov. 2010, 13(11): 1396-1403.
Brown et al., "Failure of Immunosuppression With a Ten- to 14-Day Course of High-Dose Intravenous Cyclophosphamide to Alter the Progression of Amyotrophic Lateral Sclerosis," Arch Neurol, 1986, 43(4): 383-384.
Choi, "Glutamate Neurotoxicity and Diseases of the Nervous System," Neuron, Oct. 1988, 1(8): 623-634.
Coumans and Terstappen, "Detection and Characterization of Circulating Tumor Cells by the CellSearch Approach," Methods Mol Biol, 2015, 1347: 263-78.
Cudkowicz et al., "Trial of Celecoxib in Amyotrophic Lateral Sclerosis," Ann Neurol, 2006, 60:22-31.
Dalakas et al., "Effect of High-Dose Intravenous Immunoglobulin on Amyotrophic Lateral Sclerosis and Multifocal Motor Neuropathy," Sep. 1994, 51(9): 861-864.
Dejaco et al., "Imbalance of regulatory T cells in human autoimmune diseases," Immunology, Mar. 2006, 117(3): 289-300.
Dziadzio et al., Is TNFα really a good therapeutic target in motoneuronal degeneration? A case of amyotrophic lateral sclerosis in a patient with RA receiving infliximab, Rheumatology, 2006, 45(11): 1445-1446.
Gordon et al., "Efficacy of minocycline in patients with amyotrophic lateral sclerosis: a phase III randomised trial," Dec. 2007, 6(12): 1045-1053.
Henkel et al., "Regulatory T-lymphocytes mediate amyotrophic lateral sclerosis progression and survival," EMBO Mol Med, Jan. 2013, 5(1): 64-79.
Kohlhaas et al., Cutting Edge: The Foxp3 Target miR-155 Contributes to the Development of Regulatory T Cells, The Journal of Immunology, Mar. 1, 2009, 182(5): 2578-2582.
Meininger et al., "Glatiramer acetate has no impact on disease progression in ALS at 40 mg/day: A double- blind, randomized, multicentre, placebo-controlled trial," Amyotrophic Lateral Sclerosis, 2009, 10(5-6): 378-383.

Meucci et al., "Intravenous immunoglobulin therapy in amyotrophic lateral sclerosis," J Neurol, Feb. 1996, 243: 117-120.
Plaitakis and Caroscio, "Abnormal Glutamate Metabolism in Amyotrophic Lateral Sclerosis," Ann. Neurology, 1987, 22:575-579.
Rilutek (riluzole) Tablets Description, Sanofi-Aventis U.S. LLC, revised Nov. 2012, 3 pages.
Rotunno et al., "An emerging role for misfolded wild-type SOD1 in sporadic ALS pathogenesis," Cell Neurosci., 2013, 7: 253.
Silani et al., "Plasma Exchange Ineffective in Amyotrophic Lateral Sclerosis," Arch Neurol, Aug. 1980, 37(8): 511-513.
Tan et al., "Immunosuppressive Treatment of Motor Neuron Syndromes," Arch Neurol, Feb. 1994, 51(2): 194-200.
Werdelin et al., "Immunosuppressive treatment of patients with amyotrophic lateral sclerosis," Acta Neurologica Scandinavica, Aug. 1990, 82(2): 132-134.
Yates D., "Motor neuron disease: Misfolded wild-type SOD1 may link sporadic and familial ALS," Nature Reviews Neurology, 2010, 6:645.
Appel et al., "The Microglial-Motoneuron dialogue in ALS," Acta Myologica 2011;1:4-8.
Brennecke et al., "Principles of microRNA-target recognition," PLOS Biology, Mar. 2005, 3(3):e85.
Brites and Vaz, "Microglia centered pathogenesis in ALS: insights in cell interconnectivity," Front Cell Neurosci. 2014; 8:117.
Chinese Office Action in Chinese Application No. 201280061082, dated Aug. 16, 2016, 5 pages (English translation).
Corcia et al., "Molecular Imaging of Microglial Activation in Amyotrophic Lateral Sclerosis," PLoS One. 2012; 7(12): e52941.
Henkel et al., "Microglia in ALS: the good, the bad, and the resting," J Neuroimmune Pharmacol 2009; 4: 389-398.
International Search Report and Written Opinion dated Jan. 28, 2008 in international application No. PCT/DK2007/000168, 5 pages.
International Search Report dated Aug. 29, 2003 in international application PCT/US2002/37178, 3 pages.
Japanese Office Action in Japanese Application No. 2014-535856, dated Jul. 5, 2016, 18 pages (with English translation).
Jepsen et al, "Locked nucleic acid: A potent nucleic acid analog in therapeutics and biotechnology," Oligonucleotides, 2004, 14(2): 130-146.
McGeer et al., "Reactive microglia express the MHC glycoprotein HLA-DR in chronic degenerative neurological disease," Clinical and Investigative Medicine, 1989, 12:B43.
Nagai et al., "Astrocytes expressing ALS-linked mutated SOD1 release factors selectively toxic to motor neurons," Nat Neurosci. May 2007; 10(5): 615-622.
Philips et al., "Neuroinflammation in amyotrophic lateral sclerosis: role of glial activation in motor neuron disease," Lancet Neurol 2011; 10: 253-263.
Schubert et al., "Detection by 4- parameter microscopic imaging and increase of rare mononuclear blood leukocyte types expressing the FcγRIII receptor (CD16 ) for immunoglobulin in human sporadic amyotrophic lateral sclerosis (ALS)," Neuroscience Letters, Sep. 1995, 198(1): 29-32.
Soreq et al., Nucleic Acid Therapeutics, 7th Annual Meeting of the Oligonucleotide Therapeutics Society, Sep. 2011, 21(5): A-57-A-58, 1002.
Troost et al., "Immunohistological alterations in muscle of patients with amyotrophic lateral sclerosis; mononuclear cell phenotypes and expression of MHC products," Clinical Neuropathology, 1992, 11(3): 115-120.
Weiler et al., "Ant1-m1RNA oligonucleotides (AMOs): ammunition to target miRNAs implicated in human disease?," Gene Therapy, Mar. 2006, 13(6): 496-502.
Australian Office Action in Australian Application No. 2012322788, dated Apr. 10, 2017, 5 pages.
Cardoso et al., "miR-155 modulates microglia-mediated immune response by down-regulating SOCS-1 and promoting cytokine and nitric oxide production," Immunology, Dec. 2011, 135:73-88.
Chinese Office Action in Application No. 201280061082, dated May 2, 2017, 4 pages (English translation).
Extended European Search Report in European Application No. 16193582.0, dated Apr. 24, 2017, 11 pages.

(56) References Cited

OTHER PUBLICATIONS

Japanese Office Action in Japanese Application No. 2014-535856, dated Mar. 14, 2017, 14 pages (with English translation).

\* cited by examiner

| Category | Functions Annotation | p-Value | Molecules | # Molecules |
|---|---|---|---|---|
| Genetic Disorder | Miyoshi myopathy | 1.29E-17 | let-7, mir-126, mir-132, mir-146, mir-155, mir-34, mir-379, mir-500 | 8 |
| | nemaline myopathy | 6.76E-17 | let-7, mir-126, mir-132, mir-146, mir-155, mir-34, mir-379, mir-500 | 8 |
| | limb girdle muscular dystrophy | 7.30E-16 | let-7, mir-126, mir-132, mir-146, mir-155, mir-34, mir-379, mir-500 | 8 |
| | facioscapulohumeral muscular dystrophy | 1.92E-15 | let-7, mir-126, mir-132, mir-146, mir-155, mir-34, mir-379 | 7 |
| | Duchenne muscular dystrophy | 7.15E-07 | mir-146, mir-155, mir-34, mir-379 | 4 |
| | prostatic carcinoma | 1.47E-06 | let-7, mir-126, mir-188, mir-34, mir-425, mir-8 | 6 |
| | lung squamous cell carcinoma | 3.05E-04 | let-7, mir-8 | 2 |
| | Down's syndrome | 8.71E-04 | let-7, mir-155 | 2 |
| | lung carcinoma | 1.76E-03 | let-7, mir-34, mir-8 | 3 |
| | non small cell lung adenocarcinoma | 3.57E-03 | mir-34 | 1 |
| | lung cancer | 4.43E-03 | let-7, mir-146, mir-34, mir-8 | 4 |
| | schizophrenia | 5.38E-03 | let-7, mir-132, mir-188, mir-500 | 4 |
| | squamous cell non small cell lung carcinoma | 5.94E-03 | mir-34 | 1 |
| | large cell lung carcinoma | 8.30E-03 | mir-34 | 1 |
| | Becker's muscular dystrophy | 1.54E-02 | mir-146 | 1 |
| | bronchiolo-alveolar adenocarcinoma | 2.70E-02 | mir-34 | 1 |
| Skeletal and Muscular Disorders | Miyoshi myopathy | 1.29E-17 | let-7, mir-126, mir-132, mir-146, mir-155, mir-34, mir-379, mir-500 | 8 |
| | nemaline myopathy | 6.76E-17 | let-7, mir-126, mir-132, mir-146, mir-155, mir-34, mir-379, mir-500 | 8 |
| | limb girdle muscular dystrophy | 7.30E-16 | let-7, mir-126, mir-132, mir-146, mir-155, mir-34, mir-379, mir-500 | 8 |
| | facioscapulohumeral muscular dystrophy | 1.92E-15 | let-7, mir-126, mir-132, mir-146, mir-155, mir-34, mir-379 | 7 |
| | polymyositis | 1.55E-12 | mir-132, mir-146, mir-155, mir-34, mir-379, mir-500 | 6 |
| | Duchenne muscular dystrophy | 7.15E-07 | mir-146, mir-155, mir-34, mir-379 | 4 |
| | Becker's muscular dystrophy | 1.54E-02 | mir-146 | 1 |

FIGURE 4 (CONT.)

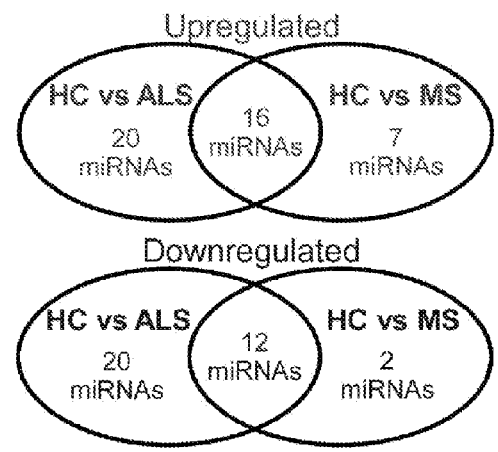
FIGURE 7A
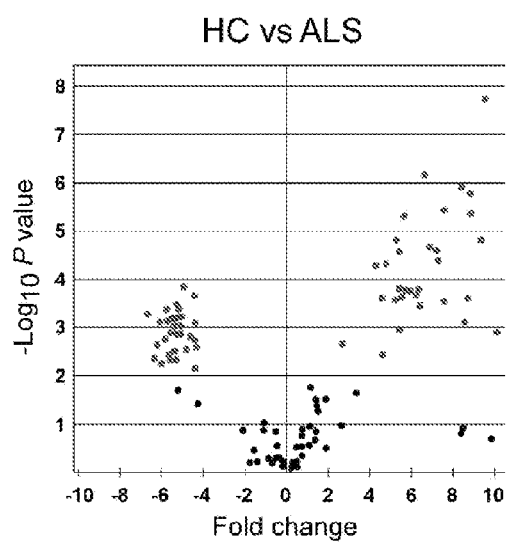 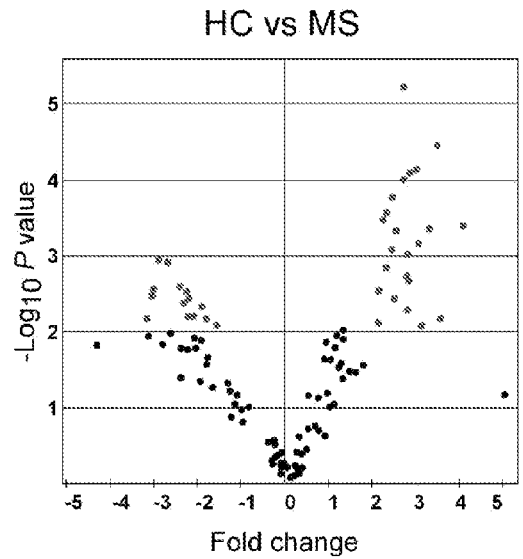
FIGURE 7B
FIGURE 7C

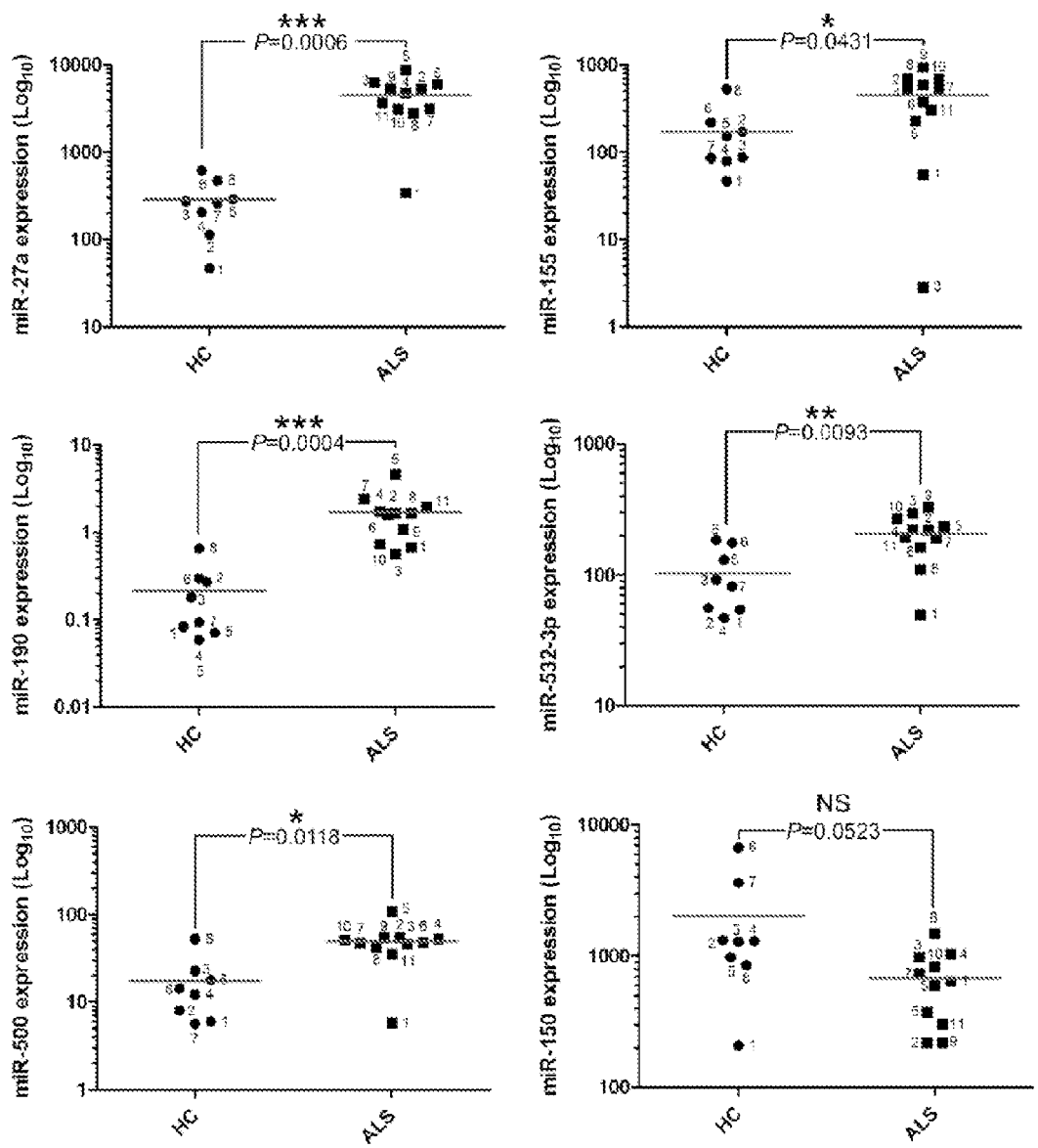
FIGURE 9
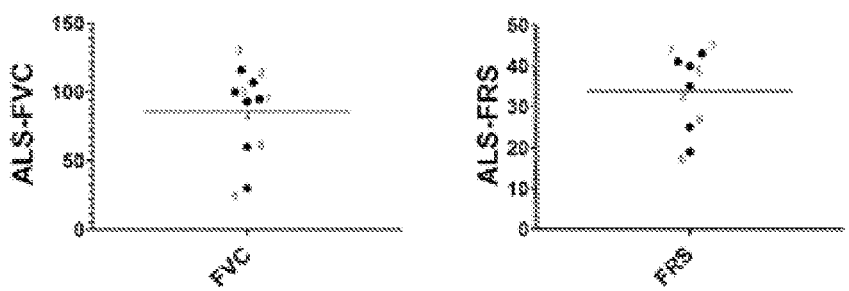
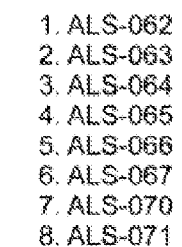
1. ALS-062
2. ALS-063
3. ALS-064
4. ALS-065
5. ALS-066
6. ALS-067
7. ALS-070
8. ALS-071
FIGURE 10A     FIGURE 10B

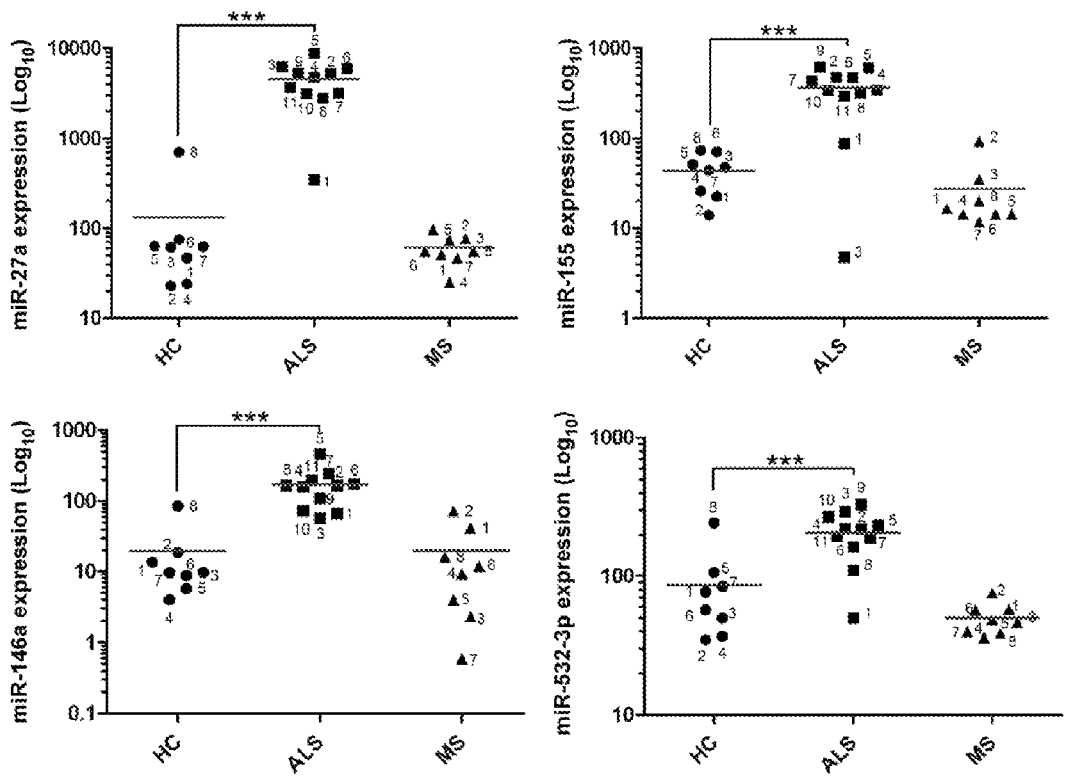
FIGURE 11
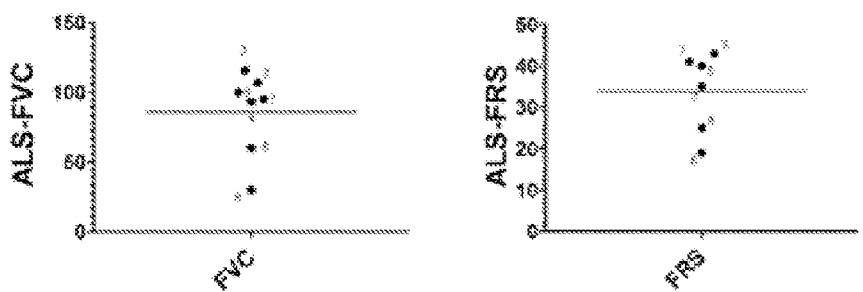
FIGURE 12A
1. ALS-062
2. ALS-063
3. ALS-064
4. ALS-065
5. ALS-066
6. ALS-067
7. ALS-070
8. ALS-071
FIGURE 12B

| Network | Total nodes | Seed nodes | P-value | zScore |
|---|---|---|---|---|
| 1 CREB1 | 30 | 29 | 1.60E-97 | 203.23 |
| 2 RelA (p65 NF-kB subunit) | 29 | 28 | 8.09E-94 | 199.58 |
| 3 SRF | 28 | 27 | 3.74E-90 | 195.86 |
| 4 SP1 | 28 | 27 | 3.74E-90 | 195.86 |
| 5 c-Rel (NF-kB subunit) | 28 | 27 | 3.74E-90 | 195.86 |
| 6 STAT3 | 27 | 26 | 1.59E-86 | 192.06 |
| 7 ikaros | 27 | 26 | 1.59E-86 | 192.06 |
| 8 E2A | 27 | 26 | 1.59E-86 | 192.06 |
| 9 AP1 | 27 | 26 | 1.59E-86 | 192.06 |
| 10 GCR-alpha | 25 | 25 | 2.42E-84 | 191.92 |
| 11 PU.1 | 26 | 25 | 6.30E-83 | 188.19 |
| 12 PPAR-gamma | 26 | 25 | 6.30E-83 | 188.19 |
| 13 NF-kB p50/p65 | 26 | 25 | 6.30E-83 | 188.19 |
| 14 IRF2 | 26 | 25 | 6.30E-83 | 188.19 |
| 15 IRF1 | 26 | 25 | 6.30E-83 | 188.19 |
| 16 HSF1 | 26 | 25 | 6.30E-83 | 188.19 |
| 17 HIF1A | 26 | 25 | 6.30E-83 | 188.19 |
| 18 Bcl-6 | 26 | 25 | 6.30E-83 | 188.19 |
| 19 AP-2A | 26 | 25 | 6.30E-83 | 188.19 |
| 20 Androgen receptor | 26 | 25 | 6.30E-83 | 188.19 |

FIGURE 21C

| | Biological Pathways | P-value |
|---|---|---|
| 1 | Chemotaxis | 6.3E-83 |
| 2 | Altern complement pathway | 6.3E-83 |
| 3 | Innate inflammatory response | 6.3E-83 |
| 4 | Neutrophil activation | 2.1E-09 |
| 5 | Integrin priming | 1.2E-08 |
| 6 | T helper cell differentiation | 4.3E-07 |
| 7 | Jak-STAT Pathway | 5.6E-07 |
| 8 | Leucocyte chemotaxis | 1.1E-06 |
| 9 | Regulation of angiogenesis | 2.4E-05 |
| 10 | Lymphocyte proliferation | 1.7E-04 |
| 11 | Blood vessel morphogenesis | 2.6E-04 |
| 12 | Leucocyte interactions | 6.3E-04 |
| 13 | Phagocytosis | 1.9E-03 |
| 14 | TREM1 signaling | 2.7E-03 |
| 15 | IL-1 signaling pathway | 5.2E-03 |
| 16 | CREM pathway | 7.2E-03 |
| 17 | IFN-gamma signaling | 9.9E-03 |

FIGURE 21F

| ID | Symbol | Fold Change | Symbol | Fold Change |
|---|---|---|---|---|
| hsa-miR-137 | miR-137 (human, mouse, rat) | -2.100 | AHR | ↑2.000 |
| hsa-miR-302c | miR-302a/miR-302b/miR-291a-3p (includes others) | -2.300 | AHR | ↑2.000 |
| hsa-miR-453 | miR-410*/miR-494*/miR-496* (includes others) | -1.900 | AHR | ↑2.000 |
| hsa-miR-19b | miR-19b/miR-19a | ↑3.100 | CASP10 | -1.500 |
| hsa-miR-24 | miR-24 | ↑3.000 | CASP10 | -1.500 |
| hsa-miR-361-5p | miR-361/miR-361-5p | ↑2.500 | CASP10 | -1.500 |
| hsa-miR-302c | miR-302a/miR-302b/miR-291a-3p (includes others) | -2.300 | CD44 | ↑1.600 |
| hsa-miR-513a-5p | miR-513a-5p | -2.500 | CD44 | ↑1.600 |
| hsa-miR-526a | miR-526a/miR-522*/miR-520c-5p (includes others) | -1.900 | CD44 | ↑1.600 |
| hsa-let-7a | let-7a/let-7f/let-7c (includes others) | ↑2.800 | CDKN1A | -1.400 |
| hsa-miR-106b | miR-20a/miR-106b/miR-17-5p (includes others) | ↑3.800 | CDKN1A | -1.400 |
| hsa-miR-21 | miR-21/miR-590-5p | ↑2.500 | CDKN1A | -1.400 |
| hsa-miR-423-5p | miR-423-5p/miR-423*/miR-3573-5p (includes others) | ↑1.600 | CDKN1A | -1.400 |
| hsa-miR-603 | miR-603/miR-3571 | -2.000 | CXCL3 | ↑5.400 |
| hsa-miR-146a | miR-146a/miR-146b/miR-146b-5p | ↑4.200 | CXCR4 | -4.200 |
| hsa-miR-101 | miR-101/miR-101a/miR-101b | ↑2.300 | FOS | -2.000 |
| hsa-miR-155 | miR-155 (human, mouse) | ↑3.000 | FOS | -2.000 |
| hsa-miR-221 | miR-222/miR-221/miR-1928 | ↑2.000 | FOS | -2.000 |
| hsa-miR-29c | miR-29b/miR-29c/miR-29a | ↑1.800 | FOS | -2.000 |
| hsa-miR-374a | miR-374/miR-374a/miR-374b | ↑3.200 | FOS | -2.000 |
| hsa-miR-513a-5p | miR-513a-5p | -2.500 | IL1RN | ↑2.100 |
| hsa-miR-603 | miR-603/miR-3571 | -2.000 | ITGAM | ↑1.500 |
| hsa-miR-16 | miR-16/miR-497/miR-195 (includes others) | ↑3.900 | LITAF | -1.600 |
| hsa-miR-106b | miR-20a/miR-106b/miR-17-5p (includes others) | ↑3.800 | LITAF | -1.600 |
| hsa-miR-27a | miR-27b/miR-27a | ↑4.200 | LITAF | -1.600 |
| hsa-miR-24 | miR-24 | ↑3.000 | LTB4R | -1.600 |
| hsa-miR-320c | miR-320d/miR-320b/miR-320c (includes others) | ↑2.000 | LTB4R | -1.600 |
| hsa-let-7a | let-7a/let-7f/let-7c (includes others) | ↑2.800 | MEF2D | -1.500 |
| hsa-miR-101 | miR-101/miR-101a/miR-101b | ↑2.300 | MEF2D | -1.500 |
| hsa-miR-19b | miR-19b/miR-19a | ↑3.100 | MEF2D | -1.500 |
| hsa-miR-106b | miR-20a/miR-106b/miR-17-5p (includes others) | ↑3.800 | MEF2D | -1.500 |
| hsa-miR-223 | miR-223 | ↑1.700 | MEF2D | -1.500 |
| hsa-miR-30b | miR-30c/miR-30a/miR-30d (includes others) | ↑3.600 | MEF2D | -1.500 |
| hsa-miR-374a | miR-374/miR-374a/miR-374b | ↑3.200 | MEF2D | -1.500 |
| hsa-miR-423-5p | miR-423-5p/miR-423*/miR-3573-5p (includes others) | ↑1.600 | MEF2D | -1.500 |
| hsa-miR-1260 | miR-1260b/miR-1260 | ↑2.500 | NCR1 | -3.400 |
| hsa-miR-532-3p | miR-532-3p | ↑2.800 | NCR1 | -3.400 |
| hsa-miR-101 | miR-101/miR-101a/miR-101b | ↑2.300 | NFE2L2 | -2.000 |

FIGURE 26

| hsa-miR-142-5p | miR-142-5p | ↑2.100 | NFE2L2 | -2.000 |
| hsa-miR-27a | miR-27b/miR-27a | ↑4.200 | NFE2L2 | -2.000 |
| hsa-miR-340 | miR-340-5p/miR-340 | ↑2.200 | NFE2L2 | -2.000 |
| hsa-miR-374a | miR-374/miR-374a/miR-374b | ↑3.200 | NFKBIZ | -1.900 |
| hsa-miR-142-5p | miR-142-5p | ↑2.100 | PLAUR | -2.500 |
| hsa-miR-340 | miR-340-5p/miR-340 | ↑2.200 | PLAUR | -2.500 |
| hsa-let-7a | let-7a/let-7f/let-7c (includes others) | ↑2.800 | PRDM1 | -2.300 |
| hsa-miR-223 | miR-223 | ↑1.700 | PRDM1 | -2.300 |
| hsa-miR-30b | miR-30c/miR-30a/miR-30d (includes others) | ↑3.600 | PRDM1 | -2.300 |
| hsa-miR-320c | miR-320d/miR-320b/miR-320c (includes others) | ↑2.000 | PRDM1 | -2.300 |
| hsa-miR-340 | miR-340-5p/miR-340 | ↑2.200 | PRDM1 | -2.300 |
| hsa-miR-374a | miR-374/miR-374a/miR-374b | ↑3.200 | PRDM1 | -2.300 |
| hsa-miR-1206 | miR-1206 | -2.200 | PTAFR | ↑2.100 |
| hsa-let-7a | let-7a/let-7f/let-7c (includes others) | ↑2.800 | PTGS2 | -2.500 |
| hsa-miR-101 | miR-101/miR-101a/miR-101b | ↑2.300 | PTGS2 | -2.500 |
| hsa-miR-146a | miR-146a/miR-146b/miR-146b-5p | ↑4.200 | PTGS2 | -2.500 |
| hsa-miR-16 | miR-16/miR-497/miR-195 (includes others) | ↑3.900 | PTGS2 | -2.500 |
| hsa-miR-26a | miR-26a/miR-26b | ↑4.400 | PTGS2 | -2.500 |
| hsa-miR-340 | miR-340-5p/miR-340 | ↑2.200 | PTGS2 | -2.500 |
| hsa-miR-374a | miR-374/miR-374a/miR-374b | ↑3.200 | PTGS2 | -2.500 |
| hsa-miR-664 | miR-664 (human, mouse, rat) | ↑1.900 | PTGS2 | -2.500 |
| hsa-miR-221 | miR-222/miR-221/miR-1928 | ↑2.000 | PTK2 | -1.900 |
| hsa-miR-340 | miR-340-5p/miR-340 | ↑2.200 | PTK2 | -1.900 |
| hsa-miR-137 | miR-137 (human, mouse, rat) | -2.100 | RAC1 | ↑1.700 |
| hsa-miR-302c | miR-302a/miR-302b/miR-291a-3p (includes others) | -2.300 | RUNX1 | ↑1.500 |
| hsa-miR-513a-5p | miR-513a-5p | -2.500 | RUNX1 | ↑1.500 |
| hsa-miR-548g | miR-548g | -2.100 | RUNX1 | ↑1.500 |
| hsa-miR-603 | miR-603/miR-3571 | -2.000 | SELL | ↑1.500 |
| hsa-let-7a | let-7a/let-7f/let-7c (includes others) | ↑2.800 | SOCS1 | -2.900 |
| hsa-miR-142-5p | miR-142-5p | ↑2.100 | SOCS1 | -2.900 |
| hsa-miR-155 | miR-155 (human, mouse) | ↑3.000 | SOCS1 | -2.900 |
| hsa-miR-19b | miR-19b/miR-19a | ↑3.100 | SOCS1 | -2.900 |
| hsa-miR-221 | miR-222/miR-221/miR-1928 | ↑2.000 | SOCS1 | -2.900 |
| hsa-miR-30b | miR-30c/miR-30a/miR-30d (includes others) | ↑3.600 | SOCS1 | -2.900 |
| hsa-miR-106b | miR-20a/miR-106b/miR-17-5p (includes others) | ↑3.800 | TAGAP | -2.300 |
| hsa-miR-21 | miR-21/miR-590-5p | ↑2.500 | TAGAP | -2.300 |
| hsa-miR-374a | miR-374/miR-374a/miR-374b | ↑3.200 | TAGAP | -2.300 |
| hsa-miR-526a | miR-526a/miR-522*/miR-520c-5p (includes others) | -1.900 | TLR2 | ↑1.700 |
| hsa-miR-603 | miR-603/miR-3571 | -2.000 | TLR4 | ↑1.600 |

FIGURE 26 (Cont.)

Legend

○ Complex
◊ Transcription Regulator
Y Transmembrane Receptor
○ Unknown
⊞ Mature Micro RNA
Y Cytokine/Growth Factor
⊗ Enzyme
Y G-protein Coupled Receptor
◎ Group/Complex/Other
V Growth factor
⋎ Kinase
⌒ Ligand-dependent Nuclear Receptor
◎ Peptidase
— Direct interaction
— — Indirect interaction
■ Upregulated
  Downregulated FIGURE 27, Continued

| # | Network | Total nodes | Seed nodes | p-value | zScore | pScore |
|---|---|---|---|---|---|---|
| 1 | SP1 | 45 | 44 | 3.6E-136 | 192.12 | 192.12 |
| 2 | AP-1 | 40 | 39 | 1.5E-119 | 180.61 | 180.61 |
| 3 | RelA (p65 NF-kB subunit) | 39 | 38 | 2.8E-116 | 178.22 | 178.22 |
| 4 | c-Rel (NF-kB subunit) | 33 | 32 | 6.8E-97 | 163.14 | 163.14 |
| 5 | STAT3 | 33 | 32 | 6.8E-97 | 163.14 | 163.14 |
| 6 | ETS1 | 33 | 32 | 6.8E-97 | 163.14 | 163.14 |
| 7 | NF-kB1 (p50) | 31 | 31 | 3.2E-95 | 163.07 | 163.07 |
| 8 | c-Jun | 32 | 31 | 1.0E-93 | 160.49 | 160.49 |
| 9 | CREB1 | 32 | 31 | 1.0E-93 | 160.49 | 160.49 |
| 10 | c-Myc | 30 | 30 | 5.0E-92 | 160.41 | 160.41 |
| 11 | STAT1 | 31 | 30 | 1.5E-90 | 157.8 | 157.8 |
| 12 | PU.1 | 31 | 30 | 1.5E-90 | 157.8 | 157.8 |
| 13 | p53 | 31 | 30 | 1.5E-90 | 157.8 | 157.8 |
| 14 | NF-kB | 29 | 29 | 7.4E-89 | 157.71 | 157.71 |
| 15 | EGR1 | 30 | 29 | 2.2E-87 | 155.06 | 155.06 |
| 16 | GCR-alpha | 29 | 28 | 3.1E-84 | 152.27 | 152.27 |
| 17 | C/EBPbeta | 29 | 28 | 3.1E-84 | 152.27 | 152.27 |
| 18 | HIF1A | 29 | 28 | 3.1E-84 | 152.27 | 152.27 |
| 19 | YY1 | 28 | 27 | 4.3E-81 | 149.43 | 149.43 |
| 20 | SP3 | 27 | 26 | 5.8E-78 | 146.53 | 146.53 |

FIGURE 29

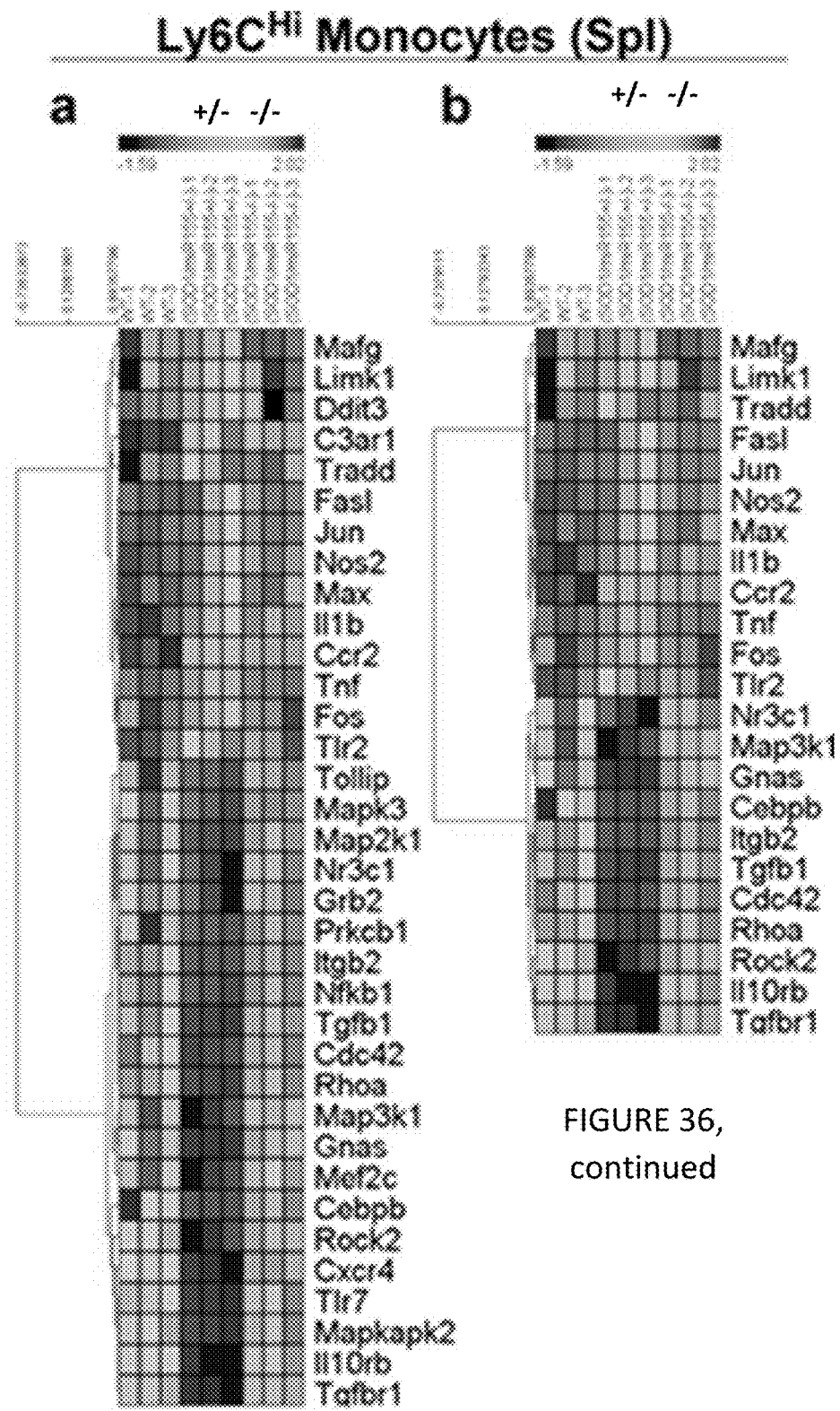
FIGURE 36, continued

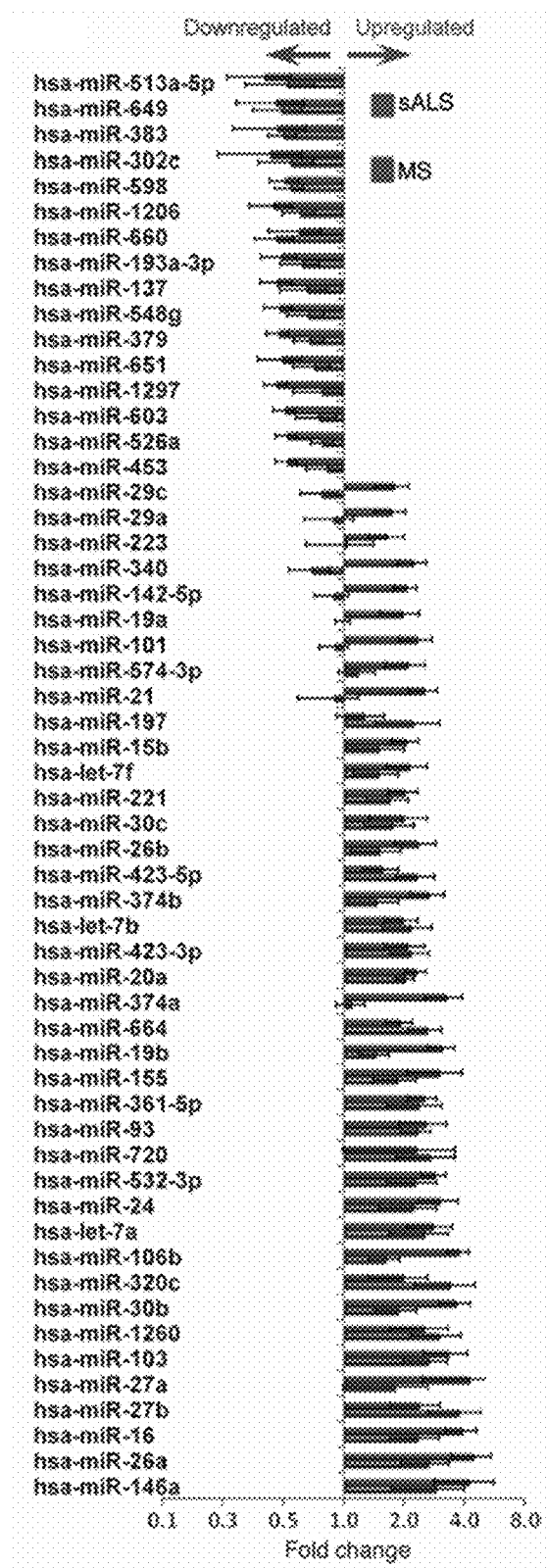
FIGURE 38, continued

SEQUENCE LISTING

<160> NUMBER OF SEQ ID NOS: 265

<210> SEQ ID NO 1
<211> LENGTH: 22
<212> TYPE: RNA
<213> ORGANISM: Homo sapiens

<400> SEQUENCE: 1
gugcaaaucc augcaaaacu ga                                            22

<210> SEQ ID NO 2
<211> LENGTH: 23
<212> TYPE: RNA
<213> ORGANISM: Homo sapiens

<400> SEQUENCE: 2
ugugcaaauc caugcaaaac uga                                           23

<210> SEQ ID NO 3
<211> LENGTH: 87
<212> TYPE: RNA
<213> ORGANISM: Homo sapiens

<400> SEQUENCE: 3
cacuguucua ugguuaguuu ugcagguuug cauccagcug ugugauauuc ugcugugcaa   60
auccaugcaa aacugacugu gguagug                                       87

<210> SEQ ID NO 4
<211> LENGTH: 96
<212> TYPE: RNA
<213> ORGANISM: Homo sapiens

<400> SEQUENCE: 4
acauugcuac uuacaauuag uuuugcaggu uugcauuuca gcguauauau guauaugugg   60
cugugcaaau ccaugcaaaa cugauuguga uaaugu                             96

<210> SEQ ID NO 5
<211> LENGTH: 21
<212> TYPE: RNA
<213> ORGANISM: Homo sapiens

<400> SEQUENCE: 5
uaaagugcug acagugcaga u                                             21

<210> SEQ ID NO 6
<211> LENGTH: 82
<212> TYPE: RNA
<213> ORGANISM: Homo sapiens

<400> SEQUENCE: 6
ccugccgggg cuaaagugcu gacagugcag auaguggucc ucuccgugcu accgcacugu   60
ggguacuugc ugcuccagca gg                                            82

<210> SEQ ID NO 7
<211> LENGTH: 22
<212> TYPE: RNA
<213> ORGANISM: Homo sapiens

<400> SEQUENCE: 7
uguaaacauc cuacacucag cu                                            22

```
<210> SEQ ID NO 8
<211> LENGTH: 88
<212> TYPE: RNA
<213> ORGANISM: Homo sapiens

<400> SEQUENCE: 8
accaaguuuc aguucaugua aacauccuac acucagcugu aauacaugga uuggcuggga      60
gguggauguu uacuucagcu gacuugga                                        88

<210> SEQ ID NO 9
<211> LENGTH: 22
<212> TYPE: RNA
<213> ORGANISM: Homo sapiens

<400> SEQUENCE: 9
uagcuuauca gacugauguu ga                                              22

<210> SEQ ID NO 10
<211> LENGTH: 72
<212> TYPE: RNA
<213> ORGANISM: Homo sapiens

<400> SEQUENCE: 10 ugucgguag cuuaucagac ugauguugac uguugaaucu cauggcaaca ccagucgaug       60
ggcugucuga ca                                                         72

<210> SEQ ID NO 11
<211> LENGTH: 21
<212> TYPE: RNA
<213> ORGANISM: Homo sapiens

<400> SEQUENCE: 11
cauaaaguag aaagcacuac u                                               21

<210> SEQ ID NO 12
<211> LENGTH: 87
<212> TYPE: RNA
<213> ORGANISM: Homo sapiens

<400> SEQUENCE: 12
gacagugcag ucacccauaa aguagaaagc acuacuaaca gcacuggagg guguaguguu      60
uccuacuuua uggaugagug uacugug                                         87

<210> SEQ ID NO 13
<211> LENGTH: 78
<212> TYPE: RNA
<213> ORGANISM: Homo sapiens

<400> SEQUENCE: 13
cugaggagca gggcuuagcu gcuugugagc agggccaca ccaagucgug uucacagugg       60
cuaaguuccg cccccccag                                                  78

<210> SEQ ID NO 14
<211> LENGTH: 22
<212> TYPE: RNA
<213> ORGANISM: Homo sapiens

<400> SEQUENCE: 14
uagcagcacg uaaauauugg cg                                              22
```

```
<210> SEQ ID NO 15
<211> LENGTH: 22
<212> TYPE: RNA
<213> ORGANISM: Homo sapiens

<400> SEQUENCE: 15
uagcagcacg uaaauauugg cg                                              22

<210> SEQ ID NO 16
<211> LENGTH: 89
<212> TYPE: RNA
<213> ORGANISM: Homo sapiens

<400> SEQUENCE: 16
gucagcagug ccuuagcagc acguaaauau uggcguuaag auucuaaaau uaucccagu       60 auuaacugug cugcugaagu aagguugac                                       89

<210> SEQ ID NO 17
<211> LENGTH: 81
<212> TYPE: RNA
<213> ORGANISM: Homo sapiens

<400> SEQUENCE: 17
guuccacucu agcagcacgu aaauauuggc guagugaaau auauuaaaa caccaauauu       60 acugugcugc uuuaguguga c                                               81

<210> SEQ ID NO 18
<211> LENGTH: 22
<212> TYPE: RNA
<213> ORGANISM: Homo sapiens

<400> SEQUENCE: 18
uuauaauaca accugauaag ug                                              22

<210> SEQ ID NO 19
<211> LENGTH: 72
<212> TYPE: RNA
<213> ORGANISM: Homo sapiens

<400> SEQUENCE: 19
uacaucggcc auuauaauac aaccugauaa guguuauagc acuuaucaga uuguauugua     60
auugucugug ua                                                         72

<210> SEQ ID NO 20
<211> LENGTH: 22
<212> TYPE: RNA
<213> ORGANISM: Homo sapiens

<400> SEQUENCE: 20
auauaauaca accugcuaag ug                                              22

<210> SEQ ID NO 21
<211> LENGTH: 72
<212> TYPE: RNA
<213> ORGANISM: Homo sapiens

<400> SEQUENCE: 21
acucggaugg auauaauaca accugcuaag uguccuagca cuuagcaggu uguauuauca     60
uuguccgugu cu                                                         72
```

```
<210> SEQ ID NO 22
<211> LENGTH: 21
<212> TYPE: RNA
<213> ORGANISM: Homo sapiens

<400> SEQUENCE: 22
uacaguacug ugauaacuga a                                                   21

<210> SEQ ID NO 23
<211> LENGTH: 21
<212> TYPE: RNA
<213> ORGANISM: Homo sapiens

<400> SEQUENCE: 23
uacaguacug ugauaacuga a                                                   21

<210> SEQ ID NO 24
<211> LENGTH: 75
<212> TYPE: RNA
<213> ORGANISM: Homo sapiens

<400> SEQUENCE: 24
ugcccuggcu caguuaucac agugcugaug cugucuauuc uaaagguaca guacugugau          60
aacugaagga uggca                                                          75

<210> SEQ ID NO 25
<211> LENGTH: 79
<212> TYPE: RNA
<213> ORGANISM: Homo sapiens

<400> SEQUENCE: 25
acuguccuuu uucgguuauc augguaccga ugcuguauau cugaaaggua caguacugug          60
auaacugaag aaugguggu                                                      79

<210> SEQ ID NO 26
<211> LENGTH: 22
<212> TYPE: RNA
<213> ORGANISM: Homo sapiens

<400> SEQUENCE: 26
uuauaaagca augagacuga uu                                                  22

<210> SEQ ID NO 27
<211> LENGTH: 95
<212> TYPE: RNA
<213> ORGANISM: Homo sapiens

<400> SEQUENCE: 27
uuguaccugg ugugauuaua aagcaaugag acugauuguc auaugucguu ugugggaucc          60
gucucaguua cuuuauagcc auaccuggua ucuua                                    95

<210> SEQ ID NO 28
<211> LENGTH: 22
<212> TYPE: RNA
<213> ORGANISM: Homo sapiens

<400> SEQUENCE: 28
uguaaacauc cuugacugga ag                                                  22
```

```
<210> SEQ ID NO 29
<211> LENGTH: 92
<212> TYPE: RNA
<213> ORGANISM: Homo sapiens

<400> SEQUENCE: 29
gggcagucuu ugcuacugua aacauccuug acuggaagcu guaaggguguu cagaggagcu      60 uucagucgga uguuuacagc ggcaggcugc ca                                    92

<210> SEQ ID NO 30
<211> LENGTH: 22
<212> TYPE: RNA
<213> ORGANISM: Homo sapiens

<400> SEQUENCE: 30
uagcaccauu ugaaaucggu ua                                               22

<210> SEQ ID NO 31
<211> LENGTH: 88
<212> TYPE: RNA
<213> ORGANISM: Homo sapiens

<400> SEQUENCE: 31
aucucuuaca caggcugacc gauuucuccu gguguucaga gucuguuuuu gucuagcacc      60
auuugaaauc gguuaugaug uaggggga                                         88

<210> SEQ ID NO 32
<211> LENGTH: 22
<212> TYPE: RNA
<213> ORGANISM: Homo sapiens

<400> SEQUENCE: 32
uagcaccauc ugaaaucggu ua                                               22

<210> SEQ ID NO 33
<211> LENGTH: 64
<212> TYPE: RNA
<213> ORGANISM: Homo sapiens

<400> SEQUENCE: 33
augacugauu ucuuuggug uucagaguca auauaauuuu cuagcaccau cugaaaucgg       60
uuau                                                                   64

<210> SEQ ID NO 34
<211> LENGTH: 22
<212> TYPE: RNA
<213> ORGANISM: Homo sapiens

<400> SEQUENCE: 34
ugucaguuug ucaaauaccc ca                                               22

<210> SEQ ID NO 35
<211> LENGTH: 110
<212> TYPE: RNA
<213> ORGANISM: Homo sapiens

<400> SEQUENCE: 35
ccuggccucc ugcagugcca cgcuccgugu auuugacaag cugaguugga cacuccaugu      60
gguagagugu caguuuguca aauaccccaa gugcggcaca ugcuuaccag                110
```

```
<210> SEQ ID NO 36
<211> LENGTH: 22
<212> TYPE: RNA
<213> ORGANISM: Homo sapiens

<400> SEQUENCE: 36
uucaaguaau ccaggauagg cu                                               22

<210> SEQ ID NO 37
<211> LENGTH: 22
<212> TYPE: RNA
<213> ORGANISM: Homo sapiens

<400> SEQUENCE: 37
uucaaguaau ccaggauagg cu                                               22

<210> SEQ ID NO 38
<211> LENGTH: 77
<212> TYPE: RNA
<213> ORGANISM: Homo sapiens

<400> SEQUENCE: 38
guggccucgu ucaaguaauc caggauaggc ugugcagguc ccaugggcc uauucuuggu       60 uacuugcacg gggacgc                                                     77

<210> SEQ ID NO 39
<211> LENGTH: 84
<212> TYPE: RNA
<213> ORGANISM: Homo sapiens

<400> SEQUENCE: 39
ggcuguggcu ggauucaagu aauccaggau aggcuguuuc caucugugag gccuauucuu       60
gauuacuugu uucuggaggc agcu                                             84

<210> SEQ ID NO 40
<211> LENGTH: 21
<212> TYPE: RNA
<213> ORGANISM: Homo sapiens

<400> SEQUENCE: 40
uucaaguaau ucaggauagg u                                                21

<210> SEQ ID NO 41
<211> LENGTH: 77
<212> TYPE: RNA
<213> ORGANISM: Homo sapiens

<400> SEQUENCE: 41
ccgggaccca guucaaguaa uucaggauag guugugugcu guccagccug uucuccauua       60
cuuggcucgg ggaccgg                                                     77

<210> SEQ ID NO 42
<211> LENGTH: 22
<212> TYPE: RNA
<213> ORGANISM: Homo sapiens

<400> SEQUENCE: 42
uggcucaguu cagcaggaac ag                                               22

<210> SEQ ID NO 43
<211> LENGTH: 22
<212> TYPE: RNA
```

<213> ORGANISM: Homo sapiens

<400> SEQUENCE: 43
uggcucaguu cagcaggaac ag                                                22

<210> SEQ ID NO 44
<211> LENGTH: 68
<212> TYPE: RNA
<213> ORGANISM: Homo sapiens

<400> SEQUENCE: 44
cuccggugcc uacugagcug auaucaguuc ucauuuuaca cacuggcuca guucagcagg       60
aacaggag                                                                68

<210> SEQ ID NO 45
<211> LENGTH: 73
<212> TYPE: RNA
<213> ORGANISM: Homo sapiens

<400> SEQUENCE: 45
cucugccucc cgugccuacu gagcugaaac acaguugguu uguguacacu ggcucaguuc       60
agcaggaaca ggg                                                          73

<210> SEQ ID NO 46
<211> LENGTH: 23
<212> TYPE: RNA
<213> ORGANISM: Homo sapiens

<400> SEQUENCE: 46
aacauucaac gcugucggug agu                                               23

<210> SEQ ID NO 47
<211> LENGTH: 23
<212> TYPE: RNA
<213> ORGANISM: Homo sapiens

<400> SEQUENCE: 47
aacauucaac gcugucggug agu                                               23

<210> SEQ ID NO 48
<211> LENGTH: 110
<212> TYPE: RNA
<213> ORGANISM: Homo sapiens

<400> SEQUENCE: 48
ugaguuuuga gguugcuuca gugaacauuc aacgcugucg gugaguuugg aauuaaaauc       60
aaaaccaucg accguugauu guacccuaug gcuaaccauc aucuacucca                 110

<210> SEQ ID NO 49
<211> LENGTH: 110
<212> TYPE: RNA
<213> ORGANISM: Homo sapiens

<400> SEQUENCE: 49
agaagggcua ucaggccagc cuucagagga cuccaaggaa cauucaacgc ugucggugag       60
uuugggauuu gaaaaaacca cugaccguug acuguaccuu ggggguccuua                110

<210> SEQ ID NO 50
<211> LENGTH: 23
<212> TYPE: RNA
<213> ORGANISM: Homo sapiens

```
<400> SEQUENCE: 50
agcagcauug uacagggcua uga                                              23

<210> SEQ ID NO 51
<211> LENGTH: 23
<212> TYPE: RNA
<213> ORGANISM: Homo sapiens

<400> SEQUENCE: 51
agcagcauug uacagggcua uga                                              23

<210> SEQ ID NO 52
<211> LENGTH: 23
<212> TYPE: RNA
<213> ORGANISM: Homo sapiens

<400> SEQUENCE: 52
ucauagcccu guacaaugcu gcu                                              23

<210> SEQ ID NO 53
<211> LENGTH: 23
<212> TYPE: RNA
<213> ORGANISM: Homo sapiens

<400> SEQUENCE: 53
ucauagcccu guacaaugcu gcu                                              23

<210> SEQ ID NO 54
<211> LENGTH: 78
<212> TYPE: RNA
<213> ORGANISM: Homo sapiens

<400> SEQUENCE: 54
uacugcccuc ggcuucuuua cagugcugcc uuguugcaua uggaucaagc agcauuguac      60
agggcuauga aggcauug                                                    78

<210> SEQ ID NO 55
<211> LENGTH: 78
<212> TYPE: RNA
<213> ORGANISM: Homo sapiens

<400> SEQUENCE: 55
uugugcuuuc agcuucuuua cagugcugcc uuguagcauu caggucaagc agcauuguac      60
agggcuauga aagaacca                                                    78

<210> SEQ ID NO 56
<211> LENGTH: 62
<212> TYPE: RNA
<213> ORGANISM: Homo sapiens

<400> SEQUENCE: 56
ucauagcccu guacaaugcu gcuugaucca uaugcaacaa ggcagcacug uaaagaagcc      60
ga                                                                     62

<210> SEQ ID NO 57
<211> LENGTH: 62
<212> TYPE: RNA
<213> ORGANISM: Homo sapiens

<400> SEQUENCE: 57
```
ucauagcccu guacaaugcu gcuugaccug aaugcuacaa ggcagcacug uaaagaagcu    60
ga                                                                  62

<210> SEQ ID NO 58
<211> LENGTH: 23
<212> TYPE: RNA
<213> ORGANISM: Homo sapiens

<400> SEQUENCE: 58
uuaaugcuaa ucgugauagg ggu                                           23

<210> SEQ ID NO 59
<211> LENGTH: 65
<212> TYPE: RNA
<213> ORGANISM: Homo sapiens

<400> SEQUENCE: 59
cuguuaaugc uaaucgugau aggguuuuu gccuccaacu gacuccuaca uauuagcauu     60
aacag                                                               65

<210> SEQ ID NO 60
<211> LENGTH: 22
<212> TYPE: RNA
<213> ORGANISM: Homo sapiens

<400> SEQUENCE: 60
caugccuuga guguaggacc gu                                            22

<210> SEQ ID NO 61
<211> LENGTH: 91
<212> TYPE: RNA
<213> ORGANISM: Homo sapiens

<400> SEQUENCE: 61
cgacuugcuu ucucuccucc augccuugag guaggaccg uuggcaucuu aauuacccuc     60
ccacacccaa ggcuugcaaa aaagcgagcc u                                  91

<210> SEQ ID NO 62
<211> LENGTH: 20
<212> TYPE: RNA
<213> ORGANISM: Homo sapiens

<400> SEQUENCE: 62
aaaagcuggg uugagagggu                                               20

<210> SEQ ID NO 63
<211> LENGTH: 20
<212> TYPE: RNA
<213> ORGANISM: Homo sapiens

<400> SEQUENCE: 63
aaaagcuggg uugagagggu                                               20

<210> SEQ ID NO 64
<211> LENGTH: 88
<212> TYPE: RNA
<213> ORGANISM: Homo sapiens

<400> SEQUENCE: 64
uuugcauuaa aaaugaggcc uucucuuccc aguucuuccc agaucagga aaagcugggu    60 ugagagggua gaaaaaaau gauguagg                                       88

<210> SEQ ID NO 65
<211> LENGTH: 50
<212> TYPE: RNA
<213> ORGANISM: Homo sapiens

<400> SEQUENCE: 65
cuucucuuuc caguucuucc cagaauuggg aaaagcuggg uugagagggu                50

<210> SEQ ID NO 66
<211> LENGTH: 21
<212> TYPE: RNA
<213> ORGANISM: Homo sapiens

<400> SEQUENCE: 66
uucacagugg cuaaguucug c                                              21

<210> SEQ ID NO 67
<211> LENGTH: 97
<212> TYPE: RNA
<213> ORGANISM: Homo sapiens

<400> SEQUENCE: 67
accucucuaa caaggugcag agcuuagcug auuggugaac agugauuggu uccgcuuug      60 uucacagugg cuaaguucug caccugaaga gaaggug                             97

<210> SEQ ID NO 68
<211> LENGTH: 23
<212> TYPE: RNA
<213> ORGANISM: Homo sapiens

<400> SEQUENCE: 68
uauucauuua uccccagccu aca                                            23

<210> SEQ ID NO 69
<211> LENGTH: 82
<212> TYPE: RNA
<213> ORGANISM: Homo sapiens

<400> SEQUENCE: 69
gaacauugaa acuggcuagg gaaaaugauu ggauagaaac uauuauucua uucauuuauc     60
cccagccuac aaaaugaaaa aa                                             82

<210> SEQ ID NO 70
<211> LENGTH: 23
<212> TYPE: RNA
<213> ORGANISM: Homo sapiens

<400> SEQUENCE: 70
ucuuggagua ggucauuggg ugg                                            23

<210> SEQ ID NO 71
<211> LENGTH: 94
<212> TYPE: RNA
<213> ORGANISM: Homo sapiens

<400> SEQUENCE: 71
ugacuccucc aggucuugga guaggucauu ggguggaucc ucuauuuccu uacgugggcc     60
acuggauggc uccuccaugu cuuggaguag auca                                94

<210> SEQ ID NO 72

```
<211> LENGTH: 22
<212> TYPE: RNA
<213> ORGANISM: Homo sapiens

<400> SEQUENCE: 72
uauugcacuu gucccggccu gu                                              22

<210> SEQ ID NO 73
<211> LENGTH: 22
<212> TYPE: RNA
<213> ORGANISM: Homo sapiens

<400> SEQUENCE: 73
uauugcacuu gucccggccu gu                                              22

<210> SEQ ID NO 74
<211> LENGTH: 78
<212> TYPE: RNA
<213> ORGANISM: Homo sapiens

<400> SEQUENCE: 74
cuuucuacac agguugggau cgguugcaau gcuguguuuc uguaugguau ugcacuuguc     60
ccggccuguu gaguuugg                                                  78

<210> SEQ ID NO 75
<211> LENGTH: 75
<212> TYPE: RNA
<213> ORGANISM: Homo sapiens

<400> SEQUENCE: 75
ucaucccugg gugggauuu guugcauuac uuguguucua uauaaaguau ugcacuuguc      60
ccggccugug gaaga                                                     75

<210> SEQ ID NO 76
<211> LENGTH: 22
<212> TYPE: RNA
<213> ORGANISM: Homo sapiens

<400> SEQUENCE: 76
cacccguaga accgaccuug cg                                              22

<210> SEQ ID NO 77
<211> LENGTH: 70
<212> TYPE: RNA
<213> ORGANISM: Homo sapiens

<400> SEQUENCE: 77
ggcacccacc cguagaaccg accuugcggg gccuucgccg cacacaagcu cgugucugug     60
gguccguguc                                                           70

<210> SEQ ID NO 78
<211> LENGTH: 22
<212> TYPE: RNA
<213> ORGANISM: Homo sapiens

<400> SEQUENCE: 78
ugagaacuga auuccauggg uu                                              22

<210> SEQ ID NO 79
<211> LENGTH: 99
<212> TYPE: RNA
<213> ORGANISM: Homo sapiens
```

<400> SEQUENCE: 79
ccgaugugua uccucagcuu ugagaacuga auuccauggg uugugucagu gucagaccuc    60
ugaaauucag uucuucagcu gggauaucuc ugucaucgu                          99

<210> SEQ ID NO 80
<211> LENGTH: 22
<212> TYPE: RNA
<213> ORGANISM: Homo sapiens

<400> SEQUENCE: 80
ucucccaacc cuuguaccag ug                                            22

<210> SEQ ID NO 81
<211> LENGTH: 84
<212> TYPE: RNA
<213> ORGANISM: Homo sapiens

<400> SEQUENCE: 81
cuccccaugg cccugucucc caacccuugu accagugcug ggcucagacc cugguacagg    60 ccuggggac agggaccugg ggac                                           84

<210> SEQ ID NO 82
<211> LENGTH: 22
<212> TYPE: RNA
<213> ORGANISM: Homo sapiens

<400> SEQUENCE: 82
cuggcccucu cugcccuucc gu                                            22

<210> SEQ ID NO 83
<211> LENGTH: 75
<212> TYPE: RNA
<213> ORGANISM: Homo sapiens

<400> SEQUENCE: 83
uggagugggg gggcaggagg ggcucaggga gaaagugcau acagcccug gcccucucug     60 cccuuccguc cccug                                                    75

<210> SEQ ID NO 84
<211> LENGTH: 22
<212> TYPE: RNA
<213> ORGANISM: Homo sapiens

<400> SEQUENCE: 84
ccucccacac ccaaggcuug ca                                            22

<210> SEQ ID NO 85
<211> LENGTH: 91
<212> TYPE: RNA
<213> ORGANISM: Homo sapiens

<400> SEQUENCE: 85
cgacuugcuu ucucuccucc augccuugag uguaggaccg uuggcaucuu aauuacccuc    60
ccacacccaa ggcuugcaaa aaagcgagcc u                                  91

<210> SEQ ID NO 86
<211> LENGTH: 18
<212> TYPE: RNA
<213> ORGANISM: Homo sapiens

```
<400> SEQUENCE: 86
aucccaccuc ugccacca                                                  18

<210> SEQ ID NO 87
<211> LENGTH: 73
<212> TYPE: RNA
<213> ORGANISM: Homo sapiens

<400> SEQUENCE: 87 accuuccag cucaucccac cucugccacc aaaacacuca ucgcgggguc agagggagug     60
ccaaaaaagg uaa                                                       73

<210> SEQ ID NO 88
<211> LENGTH: 23
<212> TYPE: RNA
<213> ORGANISM: Homo sapiens

<400> SEQUENCE: 88
ugaggggcag agagcgagac uuu                                            23

<210> SEQ ID NO 89
<211> LENGTH: 94
<212> TYPE: RNA
<213> ORGANISM: Homo sapiens

<400> SEQUENCE: 89
auaaaggaag uuaggcugag gggcagagag cgagacuuuu cuauuuucca aaagcucggu    60
cugaggcccc ucagucuugc uuccuaaccc gcgc                                94

<210> SEQ ID NO 90
<211> LENGTH: 22
<212> TYPE: RNA
<213> ORGANISM: Homo sapiens

<400> SEQUENCE: 90
uuaucagaau cuccagggu ac                                              22

<210> SEQ ID NO 91
<211> LENGTH: 72
<212> TYPE: RNA
<213> ORGANISM: Homo sapiens

<400> SEQUENCE: 91
ggagcuuauc agaaucucca gggguacuuu auaauuucaa aaagucccccc aggugugauu   60 cugauuugcu uc                                                        72

<210> SEQ ID NO 92
<211> LENGTH: 23
<212> TYPE: RNA
<213> ORGANISM: Homo sapiens

<400> SEQUENCE: 92
caaagugcug uucgugcagg uag                                            23

<210> SEQ ID NO 93
<211> LENGTH: 80
<212> TYPE: RNA
<213> ORGANISM: Homo sapiens

<400> SEQUENCE: 93 cuggggcuc caaagugcug uucgugcagg uagugugauu acccaaccua cugcugagcu     60
```

```
agcacuuccc gagcccccgg                                                80

<210> SEQ ID NO 94
<211> LENGTH: 23
<212> TYPE: RNA
<213> ORGANISM: Homo sapiens

<400> SEQUENCE: 94
agcuacauug ucugcugggu uuc                                            23

<210> SEQ ID NO 95
<211> LENGTH: 110
<212> TYPE: RNA
<213> ORGANISM: Homo sapiens

<400> SEQUENCE: 95
ugaacaucca ggucugggc augaaccugg cauacaaugu agauuucugu guucguuagg     60
caacagcuac auugucugcu ggguuucagg cuaccuggaa acauguucuc              110

<210> SEQ ID NO 96
<211> LENGTH: 23
<212> TYPE: RNA
<213> ORGANISM: Homo sapiens

<400> SEQUENCE: 96
uaaagugcuu auagugcagg uag                                            23

<210> SEQ ID NO 97
<211> LENGTH: 71
<212> TYPE: RNA
<213> ORGANISM: Homo sapiens

<400> SEQUENCE: 97
guagcacuaa agugcuuaua gugcagguag uguuuaguua ucuacugcau uaugagcacu    60
uaaaguacug c                                                         71

<210> SEQ ID NO 98
<211> LENGTH: 23
<212> TYPE: RNA
<213> ORGANISM: Homo sapiens

<400> SEQUENCE: 98
uguaaacauc cuacacucuc agc                                            23

<210> SEQ ID NO 99
<211> LENGTH: 23
<212> TYPE: RNA
<213> ORGANISM: Homo sapiens

<400> SEQUENCE: 99
uguaaacauc cuacacucuc agc                                            23

<210> SEQ ID NO 100
<211> LENGTH: 89
<212> TYPE: RNA
<213> ORGANISM: Homo sapiens

<400> SEQUENCE: 100
accaugcugu agugugugua aacaccuac acucucagcu gugagcucaa gguggcuggg     60
agaggguugu uuacuccuuc ugccaugga                                      89
```

```
<210> SEQ ID NO 101
<211> LENGTH: 72
<212> TYPE: RNA
<213> ORGANISM: Homo sapiens

<400> SEQUENCE: 101
agauacugua aacauccuac acucucagcu guggaaagua agaaagcugg gagaaggcug    60
uuuacucuuu cu                                                        72

<210> SEQ ID NO 102
<211> LENGTH: 22
<212> TYPE: RNA
<213> ORGANISM: Homo sapiens

<400> SEQUENCE: 102
uagcagcaca ucaugguuua ca                                             22

<210> SEQ ID NO 103
<211> LENGTH: 98
<212> TYPE: RNA
<213> ORGANISM: Homo sapiens

<400> SEQUENCE: 103
uugaggccuu aaaguacugu agcagcacau caugguuuac augcuacagu caagaugcga    60
aucauuauuu gcugcucuag aaauuuaagg aaauucau                            98

<210> SEQ ID NO 104
<211> LENGTH: 22
<212> TYPE: RNA
<213> ORGANISM: Homo sapiens

<400> SEQUENCE: 104
ugagguagua guuuguacag uu                                             22

<210> SEQ ID NO 105
<211> LENGTH: 84
<212> TYPE: RNA
<213> ORGANISM: Homo sapiens

<400> SEQUENCE: 105
aggcugaggu aguaguuugu acaguuugag ggucuaugau accacccggu acaggagaua    60
acuguacagg ccacugccuu gcca                                           84

<210> SEQ ID NO 106
<211> LENGTH: 22
<212> TYPE: RNA
<213> ORGANISM: Homo sapiens

<400> SEQUENCE: 106
ugagguagua gguugugugg uu                                             22

<210> SEQ ID NO 107
<211> LENGTH: 83
<212> TYPE: RNA
<213> ORGANISM: Homo sapiens

<400> SEQUENCE: 107
cggggugagg uaguagguug uggguuuca gggcagugau guugcccuc ggaagauaac     60 uauacaaccu acugccuucc cug                                            83
```

```
<210> SEQ ID NO 108
<211> LENGTH: 22
<212> TYPE: RNA
<213> ORGANISM: Homo sapiens

<400> SEQUENCE: 108
ugagguagua gguuguauag uu                                                  22

<210> SEQ ID NO 109
<211> LENGTH: 22
<212> TYPE: RNA
<213> ORGANISM: Homo sapiens

<400> SEQUENCE: 109
ugagguagua gguuguauag uu                                                  22

<210> SEQ ID NO 110
<211> LENGTH: 22
<212> TYPE: RNA
<213> ORGANISM: Homo sapiens

<400> SEQUENCE: 110
ugagguagua gguuguauag uu                                                  22

<210> SEQ ID NO 111
<211> LENGTH: 80
<212> TYPE: RNA
<213> ORGANISM: Homo sapiens

<400> SEQUENCE: 111
ugggaugagg uaguagguug uauaguuuua gggucacacc caccacuggg agauaacuau         60
acaaucuacu gucuuuccua                                                    80

<210> SEQ ID NO 112
<211> LENGTH: 72
<212> TYPE: RNA
<213> ORGANISM: Homo sapiens

<400> SEQUENCE: 112
agguugaggu aguagguugu auaguuuaga auuacaucaa gggagauaac uguacagccu         60
ccuagcuuuc cu                                                            72

<210> SEQ ID NO 113
<211> LENGTH: 74
<212> TYPE: RNA
<213> ORGANISM: Homo sapiens

<400> SEQUENCE: 113
gggugaggua guagguugua uaguuugggg cucugcccug cuaugggaua acauacaau          60 cuacugucuu uccu                                                          74

<210> SEQ ID NO 114
<211> LENGTH: 23
<212> TYPE: RNA
<213> ORGANISM: Homo sapiens

<400> SEQUENCE: 114
ugagugugug ugugugagug ugu                                                 23

<210> SEQ ID NO 115
<211> LENGTH: 96
<212> TYPE: RNA
```

<213> ORGANISM: Homo sapiens

<400> SEQUENCE: 115
gggaccugcg uggguscggg cgugugagug ugugugugug agugugsuguc gcuccggguc    60 cacgcucaug cacacaccca cacgcccaca cucagg    96

<210> SEQ ID NO 116
<211> LENGTH: 23
<212> TYPE: RNA
<213> ORGANISM: Homo sapiens

<400> SEQUENCE: 116
ugugcaaauc uaugcaaaac uga    23

<210> SEQ ID NO 117
<211> LENGTH: 82
<212> TYPE: RNA
<213> ORGANISM: Homo sapiens

<400> SEQUENCE: 117
gcaguccucu guuaguuuug cauaguugca cuacaagaag aauguaguug ugcaaaucua    60
ugcaaaacug augguggccu gc    82

<210> SEQ ID NO 118
<211> LENGTH: 22
<212> TYPE: RNA
<213> ORGANISM: Homo sapiens

<400> SEQUENCE: 118
ugagguagua gauuguauag uu    22

<210> SEQ ID NO 119
<211> LENGTH: 22
<212> TYPE: RNA
<213> ORGANISM: Homo sapiens

<400> SEQUENCE: 119
ugagguagua gauuguauag uu    22

<210> SEQ ID NO 120
<211> LENGTH: 87
<212> TYPE: RNA
<213> ORGANISM: Homo sapiens

<400> SEQUENCE: 120
ucagagugag guaguagauu guauaguugu ggguaguga uuuuacccug uucaggagau    60
aacuauacaa ucuauugccu ucccuga    87

<210> SEQ ID NO 121
<211> LENGTH: 83
<212> TYPE: RNA
<213> ORGANISM: Homo sapiens

<400> SEQUENCE: 121
ugugggauga gguaguagau uguauaguuu uagggucaua ccccaucuug gagauaacua    60
uacagucuac ugucuuuccc acg    83

<210> SEQ ID NO 122
<211> LENGTH: 22
<212> TYPE: RNA
<213> ORGANISM: Homo sapiens

```
<400> SEQUENCE: 122
cagugguuuu acccuauggu ag                                              22

<210> SEQ ID NO 123
<211> LENGTH: 100
<212> TYPE: RNA
<213> ORGANISM: Homo sapiens

<400> SEQUENCE: 123
ugugucucuc ucuguguccu gccagugguu uuacccuaug guagguuacg ucaugcuguu    60
cuaccacagg guagaaccac ggacaggaua ccggggcacc                         100

<210> SEQ ID NO 124
<211> LENGTH: 22
<212> TYPE: RNA
<213> ORGANISM: Homo sapiens

<400> SEQUENCE: 124
uguaaacauc cucgacugga ag                                              22

<210> SEQ ID NO 125
<211> LENGTH: 71
<212> TYPE: RNA
<213> ORGANISM: Homo sapiens

<400> SEQUENCE: 125
gcgacuguaa acauccucga cuggaagcug ugaagccaca gauggcuuuu cagucggaug    60
uuugcagcug c                                                          71

<210> SEQ ID NO 126
<211> LENGTH: 22
<212> TYPE: RNA
<213> ORGANISM: Homo sapiens

<400> SEQUENCE: 126
ugauauguuu gauauauuag gu                                              22

<210> SEQ ID NO 127
<211> LENGTH: 85
<212> TYPE: RNA
<213> ORGANISM: Homo sapiens

<400> SEQUENCE: 127
ugcaggccuc ugugugauau guuugauaua uuagguuguu auuuaaucca acuauauauc    60
aaacauauuc cuacaguguc uugcc                                           85

<210> SEQ ID NO 128
<211> LENGTH: 23
<212> TYPE: RNA
<213> ORGANISM: Homo sapiens

<400> SEQUENCE: 128
uaauccuugc uaccuggguig aga                                            23

<210> SEQ ID NO 129
<211> LENGTH: 18
<212> TYPE: RNA
<213> ORGANISM: Homo sapiens

<400> SEQUENCE: 129
```
aauccuugcu accugggu                                                          18

<210> SEQ ID NO 130
<211> LENGTH: 84
<212> TYPE: RNA
<213> ORGANISM: Homo sapiens

<400> SEQUENCE: 130 gcuccccuc ucuaauccuu gcuaccuggg ugagagugcu gucugaaugc aaugcaccug              60
ggcaaggauu cugagagcga gagc                                                   84

<210> SEQ ID NO 131
<211> LENGTH: 79
<212> TYPE: RNA
<213> ORGANISM: Homo sapiens

<400> SEQUENCE: 131
cccccucucu aauccuugcu accuggguga gagugcuuuc ugaaugcagu gcacccaggc            60
aaggauucug caagggga                                                          79

<210> SEQ ID NO 132
<211> LENGTH: 22
<212> TYPE: RNA
<213> ORGANISM: Homo sapiens

<400> SEQUENCE: 132
ugagguagua guuugugcug uu                                                     22

<210> SEQ ID NO 133
<211> LENGTH: 84
<212> TYPE: RNA
<213> ORGANISM: Homo sapiens

<400> SEQUENCE: 133
cuggcugagg uaguaguuug ugcuguuggu cggguuguga cauugcccgc uguggagaua            60
acugcgcaag cuacugccuu gcua                                                   84

<210> SEQ ID NO 134
<211> LENGTH: 21
<212> TYPE: RNA
<213> ORGANISM: Homo sapiens

<400> SEQUENCE: 134
aucacauugc cagggauuuc c                                                      21

<210> SEQ ID NO 135
<211> LENGTH: 73
<212> TYPE: RNA
<213> ORGANISM: Homo sapiens

<400> SEQUENCE: 135
ggccggcugg gguuccuggg gaugggauuu gcuuccuguc acaaaucaca uugccaggga            60
uuuccaaccg acc                                                               73

<210> SEQ ID NO 136
<211> LENGTH: 21
<212> TYPE: RNA
<213> ORGANISM: Homo sapiens

<400> SEQUENCE: 136
cauaaaguag aaagcacuac u                                                      21

<210> SEQ ID NO 137
<211> LENGTH: 87
<212> TYPE: RNA
<213> ORGANISM: Homo sapiens

<400> SEQUENCE: 137
gacagugcag ucacccauaa aguagaaagc acuacuaaca gcacuggagg guguaguguu        60
uccuacuuua uggaugagug uacugug                                            87

<210> SEQ ID NO 138
<211> LENGTH: 22
<212> TYPE: RNA
<213> ORGANISM: Homo sapiens

<400> SEQUENCE: 138
uagcagcaca uaaugguuug ug                                                 22

<210> SEQ ID NO 139
<211> LENGTH: 83
<212> TYPE: RNA
<213> ORGANISM: Homo sapiens

<400> SEQUENCE: 139
ccuuggagua aaguagcagc acauaauggu uuguggauuu ugaaaaggug caggccauau        60
ugugcugccu caaaaauaca agg                                                83

<210> SEQ ID NO 140
<211> LENGTH: 23
<212> TYPE: RNA
<213> ORGANISM: Homo sapiens

<400> SEQUENCE: 140
caacggaauc ccaaaagcag cug                                                23

<210> SEQ ID NO 141
<211> LENGTH: 92
<212> TYPE: RNA
<213> ORGANISM: Homo sapiens

<400> SEQUENCE: 141
cggcuggaca gcgggcaacg gaauccoaaa agcagcuguu gucccagag cauuccagcu         60 gcgcuuggau uucguccccu gcucuccugc cu                                      92

<210> SEQ ID NO 142
<211> LENGTH: 17
<212> TYPE: RNA
<213> ORGANISM: Homo sapiens

<400> SEQUENCE: 142
ucucgcuggg gccucca                                                       17

<210> SEQ ID NO 143
<211> LENGTH: 110
<212> TYPE: RNA
<213> ORGANISM: Homo sapiens

<400> SEQUENCE: 143
ccggaucuca cacgguggug uuaauaucuc gcuggggccu ccaaaauguu gugcccaggg        60
guguuagaga aaacaccaca cuuugagaug aauuaagagu ccuuuauuag                  110

```
<210> SEQ ID NO 144
<211> LENGTH: 22
<212> TYPE: RNA
<213> ORGANISM: Homo sapiens

<400> SEQUENCE: 144
aaaagcuggg uugagagggc ga                                              22

<210> SEQ ID NO 145
<211> LENGTH: 82
<212> TYPE: RNA
<213> ORGANISM: Homo sapiens

<400> SEQUENCE: 145
gcuucgcucc ccuccgccuu cucuucccgg uucuucccgg agucgggaaa agcuggguug     60
agagggcgaa aaaggaugag gu                                              82

<210> SEQ ID NO 146
<211> LENGTH: 24
<212> TYPE: RNA
<213> ORGANISM: Homo sapiens

<400> SEQUENCE: 146
acaaagugcu ucccuuuaga gugu                                            24

<210> SEQ ID NO 147
<211> LENGTH: 90
<212> TYPE: RNA
<213> ORGANISM: Homo sapiens

<400> SEQUENCE: 147
ucccaugcug ugacccucua gaggaagcac uuucuguuug uugucugaga aaaacaaag     60 ugcuucccuu uagaguguua ccguuuggga                                      90

<210> SEQ ID NO 148
<211> LENGTH: 22
<212> TYPE: RNA
<213> ORGANISM: Homo sapiens

<400> SEQUENCE: 148
uucccuuugu cauccuaugc cu                                              22

<210> SEQ ID NO 149
<211> LENGTH: 110
<212> TYPE: RNA
<213> ORGANISM: Homo sapiens

<400> SEQUENCE: 149
ggcuacaguc uuucuucaug ugacucgugg acuucccuuu gcauccuau gccugagaau     60 auaugaagga ggcugggaag gcaaagggac guucaauugu caucacuggc               110

<210> SEQ ID NO 150
<211> LENGTH: 21
<212> TYPE: RNA
<213> ORGANISM: Homo sapiens

<400> SEQUENCE: 150
gaaagcgcuu cucuuuagag g                                               21

<210> SEQ ID NO 151
<211> LENGTH: 87
```

```
<212> TYPE: RNA
<213> ORGANISM: Homo sapiens

<400> SEQUENCE: 151
ucucaugcug ugacccucua gagggaagca cuuucucuug ucuaaaagaa aagaaagcgc    60
uucucuuuag aggauuacuc uuugaga                                       87

<210> SEQ ID NO 152
<211> LENGTH: 22
<212> TYPE: RNA
<213> ORGANISM: Homo sapiens

<400> SEQUENCE: 152
uggaauguaa ggaagugugu gg                                            22

<210> SEQ ID NO 153
<211> LENGTH: 86
<212> TYPE: RNA
<213> ORGANISM: Homo sapiens

<400> SEQUENCE: 153
ugcuucccga ggccacaugc uucuuuauau ccccauaugg auuacuuugc uauggaaugu    60
aaggaagugu gugguuucgg caagug                                        86

<210> SEQ ID NO 154
<211> LENGTH: 22
<212> TYPE: RNA
<213> ORGANISM: Homo sapiens

<400> SEQUENCE: 154 uuccccuuugu cauccuaugc cu                                           22

<210> SEQ ID NO 155
<211> LENGTH: 110
<212> TYPE: RNA
<213> ORGANISM: Homo sapiens

<400> SEQUENCE: 155
ggcuacaguc uuucuucaug ugacucgugg acuucccuuu gucauccuau gccugagaau    60
auaugaagga ggcugggaag gcaaagggac guucaauugu caucacuggc               110

<210> SEQ ID NO 156
<211> LENGTH: 23
<212> TYPE: RNA
<213> ORGANISM: Homo sapiens

<400> SEQUENCE: 156
uuauugcuua agaauacgcg uag                                           23

<210> SEQ ID NO 157
<211> LENGTH: 102
<212> TYPE: RNA
<213> ORGANISM: Homo sapiens

<400> SEQUENCE: 157
gguccucuga cucucuucgg ugacggguau ucuuggugg auaauacgga uuacguuguu     60
auugcuuaag aauacgcgua gucgaggaga guaccagcgg ca                      102

<210> SEQ ID NO 158
<211> LENGTH: 22
<212> TYPE: RNA
```

<213> ORGANISM: Homo sapiens

<400> SEQUENCE: 158
cacacacugc aauuacuuuu gc    22

<210> SEQ ID NO 159
<211> LENGTH: 97
<212> TYPE: RNA
<213> ORGANISM: Homo sapiens

<400> SEQUENCE: 159
gauugaugcu guugguuugg ugcaaaagua auugcagugc uucccauuua aaaguaaugg    60
cacacacugc aauuacuuuu gcuccaacuu aauacuu    97

<210> SEQ ID NO 160
<211> LENGTH: 17
<212> TYPE: RNA
<213> ORGANISM: Homo sapiens

<400> SEQUENCE: 160
uucaaguaau ucaggug    17

<210> SEQ ID NO 161
<211> LENGTH: 77
<212> TYPE: RNA
<213> ORGANISM: Homo sapiens

<400> SEQUENCE: 161
uguuuaucuc uagggugau cuauuagaau uacuuaucg agccaaagua auucaaguaa    60
uucaggugua gugaaac    77

<210> SEQ ID NO 162
<211> LENGTH: 21
<212> TYPE: RNA
<213> ORGANISM: Homo sapiens

<400> SEQUENCE: 162
cugaccuaug aauugacagc c    21

<210> SEQ ID NO 163
<211> LENGTH: 110
<212> TYPE: RNA
<213> ORGANISM: Homo sapiens

<400> SEQUENCE: 163
gccgagaccg agugcacagg gcucugaccu augaauugac agccagugcu cucgucuccc    60
cucuggcugc caauuccaua ggucacaggu auguucgccu caaugccagc    110

<210> SEQ ID NO 164
<211> LENGTH: 22
<212> TYPE: RNA
<213> ORGANISM: Homo sapiens

<400> SEQUENCE: 164
cucuagaggg aagcacuuuc ug    22

<210> SEQ ID NO 165
<211> LENGTH: 22
<212> TYPE: RNA
<213> ORGANISM: Homo sapiens

<400> SEQUENCE: 165
cucuagaggg aagcacuuuc ug                                              22

<210> SEQ ID NO 166
<211> LENGTH: 85
<212> TYPE: RNA
<213> ORGANISM: Homo sapiens

<400> SEQUENCE: 166
cucaggcugu gacccucuag agggaagcac uuucuguugc uugaaagaag agaaagcgcu     60
uccuuuuaga ggauuacucu uugag                                          85

<210> SEQ ID NO 167
<211> LENGTH: 65
<212> TYPE: RNA
<213> ORGANISM: Homo sapiens

<400> SEQUENCE: 167
gugacccucu agagggaagc acuuucuguu gaaagaaaag aacaugcauc cuuucagagg     60
guuac                                                                65

<210> SEQ ID NO 168
<211> LENGTH: 22
<212> TYPE: RNA
<213> ORGANISM: Homo sapiens

<400> SEQUENCE: 168
gggggucccc ggugcucgga uc                                              22

<210> SEQ ID NO 169
<211> LENGTH: 96
<212> TYPE: RNA
<213> ORGANISM: Homo sapiens

<400> SEQUENCE: 169
cucgggaggg gcgggagggg ggucccccggu gcucggaucu cgagggugcu auuguucgg     60 uccgagccug ggucucccuc uuccccccaa cccccc                              96

<210> SEQ ID NO 170
<211> LENGTH: 22
<212> TYPE: RNA
<213> ORGANISM: Homo sapiens

<400> SEQUENCE: 170
auaauacaug guuaaccucu uu                                              22

<210> SEQ ID NO 171
<211> LENGTH: 97
<212> TYPE: RNA
<213> ORGANISM: Homo sapiens

<400> SEQUENCE: 171
aacuaugcaa ggauauuuga ggagagguua uccguguuau guucgcuuca uucaucauga     60
auaauacaug guuaaccucu uuugaauau cagacuc                              97

<210> SEQ ID NO 172
<211> LENGTH: 22
<212> TYPE: RNA
<213> ORGANISM: Homo sapiens

<400> SEQUENCE: 172

```
uuuugcaauua uguuccugaa ua                                              22

<210> SEQ ID NO 173
<211> LENGTH: 78
<212> TYPE: RNA
<213> ORGANISM: Homo sapiens

<400> SEQUENCE: 173
gcagaauuau uuuugcaaua uguuccugaa uauguaauau aaguguauug ggaucauuuu      60
gcauccauag uuuuguau                                                    78

<210> SEQ ID NO 174
<211> LENGTH: 22
<212> TYPE: RNA
<213> ORGANISM: Homo sapiens

<400> SEQUENCE: 174
aaaaguaauu gugguuuugg cc                                               22

<210> SEQ ID NO 175
<211> LENGTH: 97
<212> TYPE: RNA
<213> ORGANISM: Homo sapiens

<400> SEQUENCE: 175
cagacuauau auuuagguug gcgcaaaagu aauugugguu uuggccuuua uuucaaugg       60 caagaaccuc aguugcuuuu gugccaaccu aauacuu                              97

<210> SEQ ID NO 176
<211> LENGTH: 22
<212> TYPE: RNA
<213> ORGANISM: Homo sapiens

<400> SEQUENCE: 176
uuaugguuug ccugggacug ag                                               22

<210> SEQ ID NO 177
<211> LENGTH: 97
<212> TYPE: RNA
<213> ORGANISM: Homo sapiens

<400> SEQUENCE: 177
uagggugacc agccauuaug guuugccugg gacugaggaa uuugcuggga uaugucaguu      60
ccaggccaac caggcugguu ggucucccug aagcaac                              97

<210> SEQ ID NO 178
<211> LENGTH: 19
<212> TYPE: RNA
<213> ORGANISM: Homo sapiens

<400> SEQUENCE: 178
aaaaacugua auuacuuuu                                                   19

<210> SEQ ID NO 179
<211> LENGTH: 19
<212> TYPE: RNA
<213> ORGANISM: Homo sapiens

<400> SEQUENCE: 179
aaaaacugua auuacuuuu                                                   19
```

<210> SEQ ID NO 180
<211> LENGTH: 19
<212> TYPE: RNA
<213> ORGANISM: Homo sapiens

<400> SEQUENCE: 180
aaaaacugua auuacuuuu                                                    19

<210> SEQ ID NO 181
<211> LENGTH: 19
<212> TYPE: RNA
<213> ORGANISM: Homo sapiens

<400> SEQUENCE: 181
aaaaacugua auuacuuuu                                                    19

<210> SEQ ID NO 182
<211> LENGTH: 19
<212> TYPE: RNA
<213> ORGANISM: Homo sapiens

<400> SEQUENCE: 182
aaaaacugua auuacuuuu                                                    19

<210> SEQ ID NO 183
<211> LENGTH: 84
<212> TYPE: RNA
<213> ORGANISM: Homo sapiens

<400> SEQUENCE: 183
auuagguugg ugcaaaagua aucacaguuu uugacauuac uuucaaagac aaaaacugua       60
auuacuuuug gaccaaccua auag                                              84

<210> SEQ ID NO 184
<211> LENGTH: 98
<212> TYPE: RNA
<213> ORGANISM: Homo sapiens

<400> SEQUENCE: 184
uaauaacuau uagguuggug cgaacauaau ugcaguuuuu aucauuacuu uuaauggcaa       60
aaacuguaau uacuuuugca ccaaccuaau auuuagu                                98

<210> SEQ ID NO 185
<211> LENGTH: 87
<212> TYPE: RNA
<213> ORGANISM: Homo sapiens

<400> SEQUENCE: 185
auuagguugg ugcaaaccua auugcaauuu uugcaguuuu uuuaaguaau ugcaaaaacu       60
guaauuacuu uugcaccaac cuaauac                                           87

<210> SEQ ID NO 186
<211> LENGTH: 105
<212> TYPE: RNA
<213> ORGANISM: Homo sapiens

<400> SEQUENCE: 186
gaguucuaac guauuagguu ggugcaaaag uaauaguggu uuuugccauu aaaaguaaug       60
acaaaaacug uauuacuuuu uggaacaaua uuaauagaau uucag                      105

<210> SEQ ID NO 187

```
<211> LENGTH: 86
<212> TYPE: RNA
<213> ORGANISM: Homo sapiens

<400> SEQUENCE: 187
uauuagguug cugcaaaagu aaucauguuu uuuuccauug uaaguaaugg gaaaaacugu    60
aauuacuuuu guaccaaccu aauagc                                        86

<210> SEQ ID NO 188
<211> LENGTH: 22
<212> TYPE: RNA
<213> ORGANISM: Homo sapiens

<400> SEQUENCE: 188
uauacaaggg cagacucucu cu                                            22

<210> SEQ ID NO 189
<211> LENGTH: 83
<212> TYPE: RNA
<213> ORGANISM: Homo sapiens

<400> SEQUENCE: 189
ugcuacuuga agagagguaa uccuucacgc auuugcuuua cuugcaauga uuauacaagg    60
gcagacucuc ucugggagc aaa                                            83

<210> SEQ ID NO 190
<211> LENGTH: 23
<212> TYPE: RNA
<213> ORGANISM: Homo sapiens

<400> SEQUENCE: 190
uaagugcuuc cauguuucag ugg                                           23

<210> SEQ ID NO 191
<211> LENGTH: 68
<212> TYPE: RNA
<213> ORGANISM: Homo sapiens

<400> SEQUENCE: 191
ccuuugcuuu aacauggggg uaccugcugu gugaaacaaa aguaagugcu uccauguuuc    60
aguggagg                                                            68

<210> SEQ ID NO 192
<211> LENGTH: 23
<212> TYPE: RNA
<213> ORGANISM: Homo sapiens

<400> SEQUENCE: 192
aucaacagac auuaauuggg cgc                                           23

<210> SEQ ID NO 193
<211> LENGTH: 85
<212> TYPE: RNA
<213> ORGANISM: Homo sapiens

<400> SEQUENCE: 193
gcacauugua ggccucauua aauguuuguu gaaugaaaaa augaaucauc aacagacauu    60
aauugggcgc cugcucugug aucuc                                         85

<210> SEQ ID NO 194
<211> LENGTH: 22
```

<212> TYPE: RNA
<213> ORGANISM: Homo sapiens

<400> SEQUENCE: 194
uugagaauga ugaaucauua gg                                            22

<210> SEQ ID NO 195
<211> LENGTH: 97
<212> TYPE: RNA
<213> ORGANISM: Homo sapiens

<400> SEQUENCE: 195
auaaaauuuc caauuggaac cuaaugauuc aucagacuca gauauuuaag uuaacaguau     60
uugagaauga ugaaucauua gguuccgguc agaaauu                             97

<210> SEQ ID NO 196
<211> LENGTH: 22
<212> TYPE: RNA
<213> ORGANISM: Homo sapiens

<400> SEQUENCE: 196
uuuaggauaa gcuugacuuu ug                                            22

<210> SEQ ID NO 197
<211> LENGTH: 97
<212> TYPE: RNA
<213> ORGANISM: Homo sapiens

<400> SEQUENCE: 197
aaucuaucac ugcuuuuuag gauaagcuug acuuuguuc aaauaaaaau gcaaaggaa      60 aguguauccu aaaaggcaau gacaguuuaa uguguuu                             97

<210> SEQ ID NO 198
<211> LENGTH: 21
<212> TYPE: RNA
<213> ORGANISM: Homo sapiens

<400> SEQUENCE: 198
ugguagacua uggaacguag g                                             21

<210> SEQ ID NO 199
<211> LENGTH: 67
<212> TYPE: RNA
<213> ORGANISM: Homo sapiens

<400> SEQUENCE: 199
agagauggua gacuauggaa cguaggcguu augauuucug accuauguaa caugguccac     60
uaacucu                                                              67

<210> SEQ ID NO 200
<211> LENGTH: 22
<212> TYPE: RNA
<213> ORGANISM: Homo sapiens

<400> SEQUENCE: 200
ugggucuuug cgggcgagau ga                                            22

<210> SEQ ID NO 201
<211> LENGTH: 88
<212> TYPE: RNA
<213> ORGANISM: Homo sapiens -continued

```
<400> SEQUENCE: 201
cgaggauggg agcugagggc uggguucuuug cgggcgagau gaggguguucg gaucaacugg    60 ccuacaaagu cccaguucuc ggcccccg                                        88

<210> SEQ ID NO 202
<211> LENGTH: 24
<212> TYPE: RNA
<213> ORGANISM: Homo sapiens

<400> SEQUENCE: 202
uucuccaaaa gaaagcacuu ucug                                            24

<210> SEQ ID NO 203
<211> LENGTH: 24
<212> TYPE: RNA
<213> ORGANISM: Homo sapiens

<400> SEQUENCE: 203
uucuccaaaa gaaagcacuu ucug                                            24

<210> SEQ ID NO 204
<211> LENGTH: 83
<212> TYPE: RNA
<213> ORGANISM: Homo sapiens

<400> SEQUENCE: 204
ucucaugcag ucauucucca aagaaagca cuuucuguug ucgaaagca gagugccuuc       60 uuuuggagcg uuacuguuug aga                                             83

<210> SEQ ID NO 205
<211> LENGTH: 83
<212> TYPE: RNA
<213> ORGANISM: Homo sapiens

<400> SEQUENCE: 205
ucucaugcag ucauucucca aagaaagca cuuucuguug ucgaaagca gagugccuuc       60 uuuuggagcg uuacuguuug aga                                             83

<210> SEQ ID NO 206
<211> LENGTH: 22
<212> TYPE: RNA
<213> ORGANISM: Homo sapiens

<400> SEQUENCE: 206
uacgucaucg uugucaucgu ca                                              22

<210> SEQ ID NO 207
<211> LENGTH: 97
<212> TYPE: RNA
<213> ORGANISM: Homo sapiens

<400> SEQUENCE: 207
gcuugaugau gcugcugaug cuggcgguga ucccgauggu gugagcugga aaugggguugc    60 uacgucaucg uugucaucgu caucaucauc auccgag                              97

<210> SEQ ID NO 208
<211> LENGTH: 18
<212> TYPE: RNA
<213> ORGANISM: Homo sapiens

<400> SEQUENCE: 208
```

```
uucacaggga ggugucau                                                   18

<210> SEQ ID NO 209
<211> LENGTH: 18
<212> TYPE: RNA
<213> ORGANISM: Homo sapiens

<400> SEQUENCE: 209
uucacaggga ggugucau                                                   18

<210> SEQ ID NO 210
<211> LENGTH: 129
<212> TYPE: RNA
<213> ORGANISM: Homo sapiens

<400> SEQUENCE: 210
gggaugccac auucagccau ucagcguaca gugccuuuca cagggaggug ucauuuaugu      60
gaacuaaaau auaaauuuca ccuuucugag aaggguaaug uacagcaugc acugcauaug     120
ugguguccc                                                            129

<210> SEQ ID NO 211
<211> LENGTH: 127
<212> TYPE: RNA
<213> ORGANISM: Homo sapiens

<400> SEQUENCE: 211
ggaugccaca uucagccauu cagugugcag ugccuuucac agggaggugu cauuuaugug      60
aacuaaaaua uaaauuucac cuuucugaga aggguaaugu acagcaugca cugcauaugu     120
ggugucc                                                              127

<210> SEQ ID NO 212
<211> LENGTH: 21
<212> TYPE: RNA
<213> ORGANISM: Homo sapiens

<400> SEQUENCE: 212
augauccagg aaccugccuc u                                               21

<210> SEQ ID NO 213
<211> LENGTH: 96
<212> TYPE: RNA
<213> ORGANISM: Homo sapiens

<400> SEQUENCE: 213
gugacccugg gcaaguuccu gaagaucaga cacaucagau cccuuaucug uaaaaugggc      60
augauccagg aaccugccuc uacgguugcc uugggg                               96

<210> SEQ ID NO 214
<211> LENGTH: 22
<212> TYPE: RNA
<213> ORGANISM: Homo sapiens

<400> SEQUENCE: 214
aaaacuguaa uuacuuuugu ac                                              22

<210> SEQ ID NO 215
<211> LENGTH: 89
<212> TYPE: RNA
<213> ORGANISM: Homo sapiens
```

```
<400> SEQUENCE: 215
aguuauuaga uuagugcaaa aguaauugca guuuuugcau uacguucuau ggcaaaacug    60
uaauuacuuu uguaccaaca uaauacuuc                                     89

<210> SEQ ID NO 216
<211> LENGTH: 21
<212> TYPE: RNA
<213> ORGANISM: Homo sapiens

<400> SEQUENCE: 216
uguucaugua gauguuuaag c                                             21

<210> SEQ ID NO 217
<211> LENGTH: 59
<212> TYPE: RNA
<213> ORGANISM: Homo sapiens

<400> SEQUENCE: 217
caguguucau guagauguuu aagcucuugc aguagguuuu ugcaagcuag ugaacgcug     59

<210> SEQ ID NO 218
<211> LENGTH: 22
<212> TYPE: RNA
<213> ORGANISM: Homo sapiens

<400> SEQUENCE: 218
agaucagaag gugauugugg cu                                            22

<210> SEQ ID NO 219
<211> LENGTH: 73
<212> TYPE: RNA
<213> ORGANISM: Homo sapiens

<400> SEQUENCE: 219
cuccucagau cagaagguga uuguggcuuu ggguggauau uaaucagcca cagcacugcc    60
uggucagaaa gag                                                      73

<210> SEQ ID NO 220
<211> LENGTH: 22
<212> TYPE: RNA
<213> ORGANISM: Homo sapiens

<400> SEQUENCE: 220
aaaccugugu uguucaagag uc                                            22

<210> SEQ ID NO 221
<211> LENGTH: 97
<212> TYPE: RNA
<213> ORGANISM: Homo sapiens

<400> SEQUENCE: 221
ggccuagcca aauacuguau uuuugaucga cauuugguug aaaaauaucu auguauuagu    60
aaaccugugu uguucaagag uccacugugu uuugcug                            97

<210> SEQ ID NO 222
<211> LENGTH: 22
<212> TYPE: RNA
<213> ORGANISM: Homo sapiens

<400> SEQUENCE: 222
uugugucaau augcgaugau gu                                            22
```

<210> SEQ ID NO 223
<211> LENGTH: 97
<212> TYPE: RNA
<213> ORGANISM: Homo sapiens

<400> SEQUENCE: 223
uauuaugcca ugacauugug ucaauaugcg augaugmguu gugauggcac agcgucauca    60
cguggugacg caacaucaug acguaagacg ucacaac                             97

<210> SEQ ID NO 224
<211> LENGTH: 23
<212> TYPE: RNA
<213> ORGANISM: Homo sapiens

<400> SEQUENCE: 224
cuguaauaua aauuuaauuu auu                                            23

<210> SEQ ID NO 225
<211> LENGTH: 49
<212> TYPE: RNA
<213> ORGANISM: Homo sapiens

<400> SEQUENCE: 225
cuguaauaua aauuuaauuu auucucuauc auuaaaaaau guauuacag                49

<210> SEQ ID NO 226
<211> LENGTH: 22
<212> TYPE: RNA
<213> ORGANISM: Homo sapiens

<400> SEQUENCE: 226
uuuugcgaug uguuccuaau au                                             22

<210> SEQ ID NO 227
<211> LENGTH: 22
<212> TYPE: RNA
<213> ORGANISM: Homo sapiens

<400> SEQUENCE: 227
uuuugcgaug uguuccuaau au                                             22

<210> SEQ ID NO 228
<211> LENGTH: 91
<212> TYPE: RNA
<213> ORGANISM: Homo sapiens

<400> SEQUENCE: 228
aaacgauacu aaacuguuuu ugcgaugugu uccuaauaug cacuauaaau auauugggaa    60
cauuuugcau guauaguuuu guaucaauau a                                   91

<210> SEQ ID NO 229
<211> LENGTH: 100
<212> TYPE: RNA
<213> ORGANISM: Homo sapiens

<400> SEQUENCE: 229
ccaaagaaag augcuaaacu auuuuugcga uguguccua auauguaaua uaaauguauu    60
ggggacauuu ugcauucaua guuuuguauc aauaauaugg                         100

<210> SEQ ID NO 230

```
<211> LENGTH: 24
<212> TYPE: RNA
<213> ORGANISM: Homo sapiens

<400> SEQUENCE: 230
aauccuugga accuaggugu gagu                                              24

<210> SEQ ID NO 231
<211> LENGTH: 65
<212> TYPE: RNA
<213> ORGANISM: Homo sapiens

<400> SEQUENCE: 231
cuugaauccu uggaaccuag gugugagugc uauuucagug caacacaccu auucaaggau       60
ucaaa                                                                  65

<210> SEQ ID NO 232
<211> LENGTH: 22
<212> TYPE: RNA
<213> ORGANISM: Homo sapiens

<400> SEQUENCE: 232
ugggucuuug cgggcgagau ga                                                22

<210> SEQ ID NO 233
<211> LENGTH: 88
<212> TYPE: RNA
<213> ORGANISM: Homo sapiens

<400> SEQUENCE: 233
cgaggauggg agcugagggc ugggucuuug cgggcgagau gagggugucg gaucaacugg       60
ccuacaaagu cccaguucuc ggcccccg                                         88

<210> SEQ ID NO 234
<211> LENGTH: 19
<212> TYPE: RNA
<213> ORGANISM: Homo sapiens

<400> SEQUENCE: 234
gggcgccugu gaucccaac                                                    19

<210> SEQ ID NO 235
<211> LENGTH: 94
<212> TYPE: RNA
<213> ORGANISM: Homo sapiens

<400> SEQUENCE: 235
gcuaggcgug guggcgggcg ccugugaucc caacuacuca ggaggcuggg gcagcagaau       60
cgcuugaacc cgggaggcga agguugcagu gagc                                  94

<210> SEQ ID NO 236
<211> LENGTH: 21
<212> TYPE: RNA
<213> ORGANISM: Homo sapiens

<400> SEQUENCE: 236
cauaaaguag aaagcacuac u                                                 21

<210> SEQ ID NO 237
<211> LENGTH: 87
<212> TYPE: RNA
<213> ORGANISM: Homo sapiens
```

<400> SEQUENCE: 237
gacagugcag ucacccauaa aguagaaagc acuacuaaca gcacuggagg guguaguguu    60
uccuacuuua uggaugagug uacugug                                        87

<210> SEQ ID NO 238
<211> LENGTH: 22
<212> TYPE: RNA
<213> ORGANISM: Homo sapiens

<400> SEQUENCE: 238
uagcagcaca uaaugguuug ug                                             22

<210> SEQ ID NO 239
<211> LENGTH: 83
<212> TYPE: RNA
<213> ORGANISM: Homo sapiens

<400> SEQUENCE: 239
ccuuggagua aaguagcagc acauaauggu uuguggauuu ugaaaaggug caggccauau    60
ugugcugccu caaaaauaca agg                                            83

<210> SEQ ID NO 240
<211> LENGTH: 22
<212> TYPE: RNA
<213> ORGANISM: Homo sapiens

<400> SEQUENCE: 240
aaaaccgucu aguuacaguu gu                                             22

<210> SEQ ID NO 241
<211> LENGTH: 61
<212> TYPE: RNA
<213> ORGANISM: Homo sapiens

<400> SEQUENCE: 241
acagcuguaa uuagucaguu uucuguccug uccacacaga aaaccgucua guuacaguug    60
u                                                                    61

<210> SEQ ID NO 242
<211> LENGTH: 22
<212> TYPE: RNA
<213> ORGANISM: Homo sapiens

<400> SEQUENCE: 242
ucagugcauc acagaacuuu gu                                             22

<210> SEQ ID NO 243
<211> LENGTH: 99
<212> TYPE: RNA
<213> ORGANISM: Homo sapiens

<400> SEQUENCE: 243
caagcacgau uagcauuuga ggugaaguuc uguuauacac ucaggcugug gcucucugaa    60
agucagugca ucacagaacu uugucucgaa agcuuucua                           99

<210> SEQ ID NO 244
<211> LENGTH: 22
<212> TYPE: RNA
<213> ORGANISM: Homo sapiens

<400> SEQUENCE: 244
ugaaacauac acgggaaacc uc                                              22

<210> SEQ ID NO 245
<211> LENGTH: 81
<212> TYPE: RNA
<213> ORGANISM: Homo sapiens

<400> SEQUENCE: 245
gauacucgaa ggagagguug uccguguugu cuucucuuua uuuaugauga aacauacacg     60
ggaaaccucu uuuuaguau c                                                81

<210> SEQ ID NO 246
<211> LENGTH: 22
<212> TYPE: RNA
<213> ORGANISM: Homo sapiens

<400> SEQUENCE: 246
agaucgaccg uguuauauuc gc                                              22

<210> SEQ ID NO 247
<211> LENGTH: 70
<212> TYPE: RNA
<213> ORGANISM: Homo sapiens

<400> SEQUENCE: 247
uugaagggag aucgaccgug uuauauucgc uuuauugacu ucgaauaaua cagguugau      60 cuuuucucag                                                            70

<210> SEQ ID NO 248
<211> LENGTH: 23
<212> TYPE: RNA
<213> ORGANISM: Homo sapiens

<400> SEQUENCE: 248
uacccuguag auccgaauuu gug                                             23

<210> SEQ ID NO 249
<211> LENGTH: 110
<212> TYPE: RNA
<213> ORGANISM: Homo sapiens

<400> SEQUENCE: 249
gaucugucug ucuucuguau auacccugua gauccgaauu uguguaagga auuuuguggu     60
cacaaauucg uaucuagggg aauauguagu ugacauaaac acuccgcucu               110

<210> SEQ ID NO 250
<211> LENGTH: 22
<212> TYPE: RNA
<213> ORGANISM: Homo sapiens

<400> SEQUENCE: 250
uguaaacauc cccgacugga ag                                              22

<210> SEQ ID NO 251
<211> LENGTH: 70
<212> TYPE: RNA
<213> ORGANISM: Homo sapiens

<400> SEQUENCE: 251
guuguuguaa acauccccga cuggaagcug uaagacacag cuaagcuuuc agucagaugu     60
uugcugcuac                                                                  70

<210> SEQ ID NO 252
<211> LENGTH: 23
<212> TYPE: RNA
<213> ORGANISM: Homo sapiens

<400> SEQUENCE: 252
aaggagcuua caaucuagcu ggg                                                   23

<210> SEQ ID NO 253
<211> LENGTH: 88
<212> TYPE: RNA
<213> ORGANISM: Homo sapiens

<400> SEQUENCE: 253
aacugcccuc aaggagcuua caaucuagcu ggggguaaau gacuugcaca ugaacacaac           60
uagacuguga gcuucuagag ggcaggga                                              88

<210> SEQ ID NO 254
<211> LENGTH: 22
<212> TYPE: RNA
<213> ORGANISM: Homo sapiens

<400> SEQUENCE: 254
uucaccaccu ucuccaccca gc                                                    22

<210> SEQ ID NO 255
<211> LENGTH: 75
<212> TYPE: RNA
<213> ORGANISM: Homo sapiens

<400> SEQUENCE: 255
ggcugugccg gguagagagg gcagugggag guaagagcuc uucacccuuc accaccuucu           60
ccacccagca uggcc                                                            75

<210> SEQ ID NO 256
<211> LENGTH: 18
<212> TYPE: RNA
<213> ORGANISM: Homo sapiens

<400> SEQUENCE: 256
gucccuguuc aggcgcca                                                         18

<210> SEQ ID NO 257
<211> LENGTH: 23
<212> TYPE: RNA
<213> ORGANISM: Homo sapiens

<400> SEQUENCE: 257
agguuguccg uggugaguuc gca                                                   23

<210> SEQ ID NO 258
<211> LENGTH: 82
<212> TYPE: RNA
<213> ORGANISM: Homo sapiens

<400> SEQUENCE: 258
ugguacucgg agggagguug uccgugguga guucgcauua uuuaaugaug cccaauacac           60
ggucgaccuc uuuucgguau ca                                                    82

```
<210> SEQ ID NO 259
<211> LENGTH: 97
<212> TYPE: RNA
<213> ORGANISM: Homo sapiens

<400> SEQUENCE: 259
cugcuccuuc ucccauaccc auugcauauc ggaguuguga auucucaaaa caccuccugu      60
gugcauggau uacaggaggg ugagccuugu caucgug                              97

<210> SEQ ID NO 260
<211> LENGTH: 22
<212> TYPE: RNA
<213> ORGANISM: Homo sapiens

<400> SEQUENCE: 260
uacccauugc auaucggagu ug                                              22

<210> SEQ ID NO 261
<211> LENGTH: 21
<212> TYPE: RNA
<213> ORGANISM: Homo sapiens

<400> SEQUENCE: 261
accuccugug ugcauggauu a                                               21

<210> SEQ ID NO 262
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: LNA moiety
<220> FEATURE:
<221> NAME/KEY: modified_base
<222> LOCATION: (3)..(3)
<223> OTHER INFORMATION: LNA moiety
<220> FEATURE:
<221> NAME/KEY: modified_base
<222> LOCATION: (5)..(7)
<223> OTHER INFORMATION: LNA moiety
<220> FEATURE:
<221> NAME/KEY: modified_base
<222> LOCATION: (10)..(12)
<223> OTHER INFORMATION: LNA moiety
<220> FEATURE:
<221> NAME/KEY: modified_base
<222> LOCATION: (14)..(15)
<223> OTHER INFORMATION: LNA moiety

<400> SEQUENCE: 262
tcacaattag catta                                                      15

<210> SEQ ID NO 263
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: LNA moiety
```

```
<220> FEATURE:
<221> NAME/KEY: modified_base
<222> LOCATION: (3)..(3)
<223> OTHER INFORMATION: LNA moiety
<220> FEATURE:
<221> NAME/KEY: modified_base
<222> LOCATION: (5)..(7)
<223> OTHER INFORMATION: LNA moiety
<220> FEATURE:
<221> NAME/KEY: modified_base
<222> LOCATION: (10)..(12)
<223> OTHER INFORMATION: LNA moiety
<220> FEATURE:
<221> NAME/KEY: modified_base
<222> LOCATION: (14)..(15)
<223> OTHER INFORMATION: LNA moiety

<400> SEQUENCE: 263
tcaacattag actta                                                        15

<210> SEQ ID NO 264
<211> LENGTH: 17
<212> TYPE: RNA
<213> ORGANISM: Homo sapiens

<400> SEQUENCE: 264
ucccuguucg ggcgcca                                                      17

<210> SEQ ID NO 265
<211> LENGTH: 21
<212> TYPE: RNA
<213> ORGANISM: Homo sapiens

<400> SEQUENCE: 265
uucacagugg cuaaguuccg c                                                 21
```

MICRORNAS IN NEURODEGENERATIVE DISORDERS

CROSS-REFERENCE TO RELATED APPLICATIONS

This application is a U.S. National Phase Application under 35 U.S.C. § 371 of International Patent Application No. PCT/US2012/059671, filed on Oct. 11, 2012, which claims prior to U.S. Provisional Patent Application No. 61/545,968, filed Oct. 11, 2011, and U.S. Provisional Patent Application No. 61/601,205, filed Feb. 21, 2012, each of which is incorporated herein by reference in its entirety.

BACKGROUND OF THE INVENTION

Inflammation has been implicated in a number of neurodegenerative disorders (e.g., amyotrophic lateral sclerosis (ALS) and multiple sclerosis). For example, increased inflammatory responses have been observed in both human ALS patients and animal models of ALS (McGreer et al., *Muscle Nerve* 26:459-470, 2002; Beers et al., *Proc. Natl. Acad. Sci. U.S.A.* 105:15558-15563, 2008; Banerjee et al., *PLoS ONE* 3:e2740, 2008; Chiu et al., *Proc. Natl. Acad. Sci. U.S.A.* 105:17913-17918, 2008; Chiu et al., *Proc. Natl. Acad. Sci. U.S.A.* 106:20960-20965, 2009; Beers et al., *Proc. Natl. Acad. Sci. U.S.A.* 103:16021-16026, 2006; Henkel et al., *Ann. Neurol.* 55:221-235, 2004; Meissner et al., *Proc. Natl. Acad. Sci. U.S.A.* 107:13046-13050, 2010). It has been reported that both microglia and astrocytes are activated in the central nervous system in a mouse model of familial ALS (Alexianu et al., *Neurology* 57:1282-1289, 2001; Hall et al., *Glia* 23:249-256, 1998), and that natural killer cells and peripheral T-cells infiltrate the spinal cord during neurodegenerative disease progression in a mouse model of ALS (Chiu et al., *Proc. Natl. Acad. Sci. U.S.A.* 105:17913-17918, 2008).

In the peripheral nervous system, degeneration of peripheral motor axons is an early and significant pathological feature in ALS patients and in animal models of ALS, and is preceded by the recruitment and activation of macrophages (Chiu et al., *Proc. Natl. Acad. Sci. U.S.A.* 106:20960-20965, 2009). A specific monocyte subset ($Ly6C^{Hi}$) in mice participates in tissue damage and disease pathogenesis in a mouse models of multiple sclerosis (King et al., *Blood* 113:3190-3197, 2009), and these monocytes are recruited to inflamed tissues by CCL2 (Kim et al., *Immunity* 34:769-780, 2011; Getts et al., *J. Exp. Med.* 205:2319-2337, 2008).

SUMMARY OF THE INVENTION

The invention is based, at least in part, on the discovery that specific microRNAs and inflammatory marker genes are increased or decreased in the cerebrospinal fluid (CSF) and in $CD14^+CD16^-$ and $CD14^+CD16^+$ monocytes from subjects having neurodegenerative diseases compared to the expression level of these microRNAs and these inflammatory marker genes in the CSF and in $CD14^+CD16^-$ and $CD14^+CD16^+$ monocytes from healthy subjects. The specific microRNAs and inflammatory marker genes that have been identified as being increased or decreased in the CSF and/or in $CD14^+CD16^-$ and/or $CD14^+CD16^+$ monocytes in subjects having a neurodegenerative disease are listed in Tables 1-21. The inflammatory markers as described herein are listed in Tables 20 and 21.

Provided herein are methods of diagnosing a neurodegenerative disorder (e.g., amyotrophic lateral sclerosis or multiple sclerosis) in a subject that include determining a level of one or more microRNAs and/or one or more inflammatory markers listed in any one or more of Tables 1-21 in a monocyte (e.g., $CD14^+CD16^-$ and $CD14^+CD16^+$ monocyte) or in CSF from the subject, and comparing the level of the one or more microRNAs and/or one or more inflammatory markers to a reference level of the one or more microRNAs and/or one or more inflammatory markers (e.g., a threshold level or a level present in the CSF, or a $CD14^+CD16^-$ or a $CD14^+CD16^+$ monocyte from a healthy subject). In these methods, an increase or decrease in the level of the one or more microRNAs and/or the one or more inflammatory markers relative to the reference level indicates that the subject has a neurodegenerative disorder.

Also provided are methods of identifying a subject at risk of developing a neurodegenerative disorder (e.g., amyotrophic lateral sclerosis or multiple sclerosis) that include determining a level of one or more microRNAs and/or one or more inflammatory markers listed in any one or more of Tables 1-21 in a monocyte (e.g., $CD14^+CD16^-$ or $CD14^+CD16^+$ monocyte (e.g., a peripheral or blood-derived monocyte) or CSF from the subject, and comparing the level of the one or more microRNAs and/or the one or more inflammatory markers to a reference level of the one or more microRNAs and/or the one or more inflammatory markers (e.g., a threshold level or a level present in the CSF, or a $CD14^+CD16^-$ or $CD14^+CD16^+$ monocyte (e.g., a peripheral or blood-derived monocyte) from a healthy subject). In these methods, an increase or decrease in the level of the one or more microRNAs and/or the one or more inflammatory markers relative to the reference level indicates that the subject has an increased or decreased risk of developing a neurodegenerative disorder (e.g., relative to a person who does not show an increase or decrease in the level of the one or more microRNAs and/or the one or more inflammatory markers relative to a reference level).

Also provided are methods of predicting the rate of disease progression in a subject having a neurodegenerative disorder (e.g., amyotrophic lateral sclerosis or multiple sclerosis) that include determining a level of one or more microRNAs and/or one or more inflammatory markers listed in any one or more of Tables 1-21 in a monocyte (e.g., $CD14^+CD16^-$ or $CD14^+CD16^+$ monocyte (e.g., a peripheral or blood-derived monocyte) or CSF from the subject, and comparing the level of the one or more microRNAs and/or the one or more inflammatory markers to a reference level of the one or more microRNAs and/or the one or more inflammatory markers (e.g., a threshold level or a level present in the CSF or a $CD14^+CD16^-$ or $CD14^+CD16^+$ monocyte (e.g., a peripheral or blood-derived monocyte) from a healthy subject). In these methods, an increase or decrease in the level of the one or more microRNAs and/or the one or more inflammatory markers relative to the reference level indicates that the subject will have an increased or decreased rate of disease progression (e.g., relative to a person who does not show an increase or decrease in the level of the one or more microRNAs and/or the one or more inflammatory markers relative to a reference level).

Also provided are methods of selecting a subject for treatment of a neurodegenerative disorder (e.g., amyotrophic lateral sclerosis or multiple sclerosis) that include determining a level of one or more microRNAs and/or one or more inflammatory markers listed in any one or more of Tables 1-21 in a monocyte (e.g., a $CD14^+CD16^-$ or $CD14^+CD16^+$ monocyte (e.g., a periperhal or blood-derived monocyte) or CSF from the subject; comparing the level of the one or more microRNAs and/or the one or more inflammatory markers to a reference level of the one or more microRNAs and/or the one or more inflammatory markers (e.g., a threshold level or a level present in the CSF, or a CD14+CD16− or CD14+CD16+ monocyte (e.g., a peripheral or blood-derived monocyte) from a healthy subject); and selecting a subject having an increase or decrease in the level of the one or more microRNAs and/or the one or more inflammatory markers relative to the reference level for treatment of a neurodegenerative disorder.

Also provided are methods of determining the efficacy of treatment of a neurodegenerative disorder (e.g., amyotrophic lateral sclerosis or multiple sclerosis) in a subject that include determining a level of one or more microRNAs and/or one or more inflammatory markers listed in any one or more of Tables 1-21 in a monocyte (e.g., a CD14+CD16− or CD14+CD16+ monocyte (e.g., a peripheral or blood-derived monocyte)) or CSF from the subject at a first time point; determining a level of the one or more microRNAs and/or the one or more inflammatory markers in a monocyte (e.g., a CD14+CD16− or CD14+CD16+ monocyte (e.g., a peripheral or blood-derived monocyte) or CSF from the subject at a second time point following administration of at least one dose of a treatment; and comparing the level of the one or more microRNAs and/or the one or more inflammatory markers at the first time point to the level of the one or more microRNAs and/or the one or more inflammatory markers at the second time point. In these methods, a return or approach to levels in a healthy subject at the second time point (e.g., a decrease or increase in the level of the one or more microRNAs and/or the one or more inflammatory markers at the second time point compared to the levels at the first time point as described herein) indicates that the treatment was effective in the subject (e.g., the treatment was effective relative to a subject having the same neurodegenerative disorder and receiving the same treatment, but does not show a return or approach to levels in a healthy subject at the second time point (e.g., an increase or decrease in the level of the one or more microRNAs and/or the one or more inflammatory markers compared to a reference value as described herein), or does not show as significant of an increase or decrease in the level of the one or more microRNAs and/or the one or more inflammatory markers compared to a reference value as described herein).

Also provided are methods for selecting a subject for participation in a clinical study. These methods include determining a level of one or more microRNAs and/or one or more inflammatory markers listed in any one or more of Tables 1-21 in a monocyte (e.g., CD14+CD16− or CD14+CD16+ monocyte (e.g., a peripheral or blood-derived monocyte) or CSF from the subject; comparing the level of the one or more microRNAs and/or the one or more inflammatory markers to a reference level of the one or more microRNAs and/or the one or more inflammatory markers (e.g., a threshold level or a level present in the CSF, or a CD14+CD16− or CD14+CD16+ monocyte (e.g., a peripheral or blood-derived monocyte) from a healthy subject); and selecting a subject having an increase or a decrease in the level of the one or more microRNAs and/or the one or more of the inflammatory markers compared to the reference level for participation in a clinical study.

Also provided are methods of treating a neurodegenerative disorder (e.g., amyotrophic lateral sclerosis or multiple sclerosis) in a subject that include administering to a subject at least one agent (e.g., an inhibitory nucleic acid, e.g., an antagomir) that decreases the expression or activity of one or more of the microRNAs listed in Tables 1, 3, 5, 7, 9, 11, 12, 14, 16, or 18, or any of the inflammatory markers listed in Table 21. Also provided are methods of treating a neurodegenerative disorder (e.g., amyotrophic lateral sclerosis or multiple sclerosis) in a subject that include administering to a subject at least one agent (e.g., a nucleic acid containing a sense (protein-encoding) nucleic acid) that increases the expression or activity of one or more of the microRNAs listed in Tables 2, 4, 6, 8, 10, 13, 15, 17, or 19, and/or one or more of the inflammatory markers listed in Table 20.

Also provided are methods of treating a neurodegenerative disorder (e.g., ALS, such as sporadic ALS or familial ALS, or multiple sclerosis) in a subject that include administering to a subject having a neurodegenerative disorder (e.g., ALS, such as sporadic ALS or familial ALS, or multiple sclerosis) at least one inhibitory nucleic acid (e.g., siRNA, an antisense oligonucleotide, an antagomir, and/or a ribozyme) comprising a sequence that is complementary to a contiguous sequence present in hsa-miR-155 (e.g., a contiguous sequence present in the precursor or mature form of hsa-miR-155).

Also provided is an inhibitory nucleic acid comprising a sequence that is complementary to a contiguous sequence, e.g., a contiguous sequence of at least 5, 6, 7, 8, 9, 10, 11, 12, 13, 14, 15, 16, 17, 18, 19, 20, 21, 22, 23, 24, or 25 nucleotides, present in hsa-miR-155, hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-532-3p, hsa-miR-27b, hsa-miR-99b, hsa-miR-146a, hsa-miR-150, hsa-miR-328, hsa-miR-15b, or hsa-miR-19a, for use in treating amyotrophic lateral sclerosis (ALS) in a subject. Preferably the sequence is complementary to a contiguous sequence of at least 7 or 8 nucleotides present in hsa-miR-155.

Provided herein are methods of diagnosing amyotrophic lateral sclerosis (ALS) in a subject that include: determining a level of one or more microRNAs selected from the group consisting of: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14+CD16− monocyte from the subject; and comparing the level of the one or more of microRNA(s) in a CD14+CD16− monocyte from the subject with a reference level of the one or more microRNA(s); whereby an increase in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, and hsa-miR-532-3p and/or a decrease in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14+CD16− monocyte from the subject as compared to the reference level indicates that the subject has ALS.

Also provided are methods of diagnosing amyotrophic lateral sclerosis (ALS) in a subject that include: determining a level of one or more of hsa-miR-27b, hsa-miR-99b, hsa-miR-146a, hsa-miR-150, hsa-miR-328, and hsa-miR-532-3p in cerebrospinal fluid (CSF) in a subject; and comparing the level of one or more of hsa-miR-27b, hsa-miR-99b, hsa-miR-146a, hsa-miR-150, hsa-miR-328, and hsa-miR-532-3p in the CSF of the subject to a reference level of the one or more of hsa-miR-27b, hsa-miR-99b, hsa-miR-146a, hsa-miR-150, hsa-miR-328, and hsa-miR-532-3p, whereby an increase in the level of one or more of hsa-miR-27b, hsa-miR-99b, hsa-miR-146a, hsa-miR-150, hsa-miR-328, and hsa-miR-532-3p in the CSF of the subject compared to the reference level indicates that the subject has ALS.

Also provided are methods of diagnosing familial amyotrophic lateral sclerosis (ALS) in a subject that include: determining a level of hsa-miR-27b and a level of one or more of hsa-miR-99b, hsa-miR-146a, hsa-miR-150, hsa-miR-328, and hsa-miR-532-3p in cerebrospinal fluid (CSF) of a subject; and comparing the level of hsa-miR-27b in the CSF of the subject to a reference level of hsa-miR-27b, and the level of one or more of hsa-miR-99b, hsa-miR-146a, hsa-miR-150, hsa-miR-328, and hsa-miR-532-3p in the CSF of the subject to a reference level of one or more of hsa-miR-99b, hsa-miR-146a, hsa-miR-150, hsa-miR-328, and hsa-miR-532-3p; whereby an increase in the level of hsa-miR-27b in the CSF of the subject compared to the reference level of hsa-miR-27b, and a decrease or no significant change in the level of one or more of hsa-miR-99b, hsa-miR-146a, hsa-miR-150, hsa-miR-328, and hsa-miR-532-3p in the CSF of the subject compared to the reference level of one or more of hsa-miR-99b, hsa-miR-146a, hsa-miR-150, hsa-miR-328, and hsa-miR-532-3p indicates that the subject has familial ALS.

Also provided are methods of diagnosing sporadic amyotrophic lateral sclerosis (ALS) in a subject that include: determining a level of two or more microRNAs selected from the group consisting of hsa-miR-27b, hsa-miR-99b, hsa-miR-146a, hsa-miR-150, hsa-miR-328, and hsa-miR-532-3p in cerebrospinal fluid (CSF) of a subject; and comparing the level of the two or more microRNAs in the CSF of the subject to a reference level of the two or more microRNAs; whereby an increase in the level of the two or more microRNAs in the CSF of the subject compared to the reference level indicates that the subject has sporadic ALS.

Also provided are methods of identifying a subject at risk of developing amyotrophic lateral sclerosis (ALS) that include: determining a level of one or more microRNAs selected from the group consisting of: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14$^+$CD16$^-$ monocyte from the subject; and comparing the level of the one or more microRNAs in a CD14$^+$CD16$^-$ monocyte from the subject with a reference level of the one or more microRNAs; whereby an increase in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, and hsa-miR-532-3p and/or a decrease in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14$^+$CD16$^-$ monocyte from the subject as compared to the reference level indicates that the subject has an increased risk of developing ALS.

Also provided are methods of identifying a subject at risk of developing amyotrophic lateral sclerosis (ALS) in a subject that include: determining a level of one or more of hsa-miR-27b, hsa-miR-99b, hsa-miR-146a, hsa-miR-150, hsa-miR-328, and hsa-miR-532-3p in cerebrospinal fluid (CSF) in a subject; and comparing the level of one or more of hsa-miR-27b, hsa-miR-99b, hsa-miR-146a, hsa-miR-150, hsa-miR-328, and hsa-miR-532-3p in the CSF of the subject to a reference level of the one or more of hsa-miR-27b, hsa-miR-99b, hsa-miR-146a, hsa-miR-150, hsa-miR-328, and hsa-miR-532-3p, whereby an increase in the level of one or more of hsa-miR-27b, hsa-miR-99b, hsa-miR-146a, hsa-miR-150, hsa-miR-328, and hsa-miR-532-3p in the CSF of the subject compared to the reference level indicates that the subject has an increased risk of developing ALS.

Also provided are methods of identifying a subject at risk of developing familial amyotrophic lateral sclerosis (ALS) that include: determining a level of hsa-miR-27b and a level of one or more of hsa-miR-99b, hsa-miR-146a, hsa-miR-150, hsa-miR-328, and hsa-miR-532-3p in cerebrospinal fluid (CSF) of a subject; and comparing the level of hsa-miR-27b in the CSF of the subject to a reference level of hsa-miR-27b, and the level of one or more of hsa-miR-99b, hsa-miR-146a, hsa-miR-150, hsa-miR-328, and hsa-miR-532-3p in the CSF of the subject to a reference level of one or more of hsa-miR-99b, hsa-miR-146a, hsa-miR-150, hsa-miR-328, and hsa-miR-532-3p, whereby an increase in the level of hsa-miR-27b in the CSF of the subject compared to the reference level of hsa-miR-27b, and a decrease or no significant change in the level of one or more of hsa-miR-99b, hsa-miR-146a, hsa-miR-150, hsa-miR-328, and hsa-miR-532-3p in the CSF of the subject compared to the reference level of one or more of hsa-miR-99b, hsa-miR-146a, hsa-miR-150, hsa-miR-328, and hsa-miR-532-3p indicates that the subject has an increased risk of developing familial ALS.

Also provided are methods of identifying a subject at risk of developing sporadic amyotrophic lateral sclerosis (ALS) that include: determining a level of two or more microRNAs selected from the group consisting of hsa-miR-27b, hsa-miR-99b, hsa-miR-146a, hsa-miR-150, hsa-miR-328, and hsa-miR-532-3p in cerebrospinal fluid (CSF) of a subject; and comparing the level of the two or more microRNAs in the CSF of the subject with a reference level of the two or more microRNAs, whereby an increase in the level of the two or more microRNAs in the CSF of the subject compared to the reference level indicates that the subject has an increased risk of developing sporadic ALS.

Also provided are methods of predicting the rate of disease progression in a subject having amyotrophic lateral sclerosis (ALS) that include: determining a level of one or more microRNAs selected from the group consisting of:

hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, hsa-miR-580, hsa-miR-15b, and hsa-miR19a in a CD14$^+$CD16$^-$ from the subject; and comparing the level of the one or more microRNAs in a CD14$^+$CD16$^-$ monocyte from the subject to a reference level of the one or more microRNAs; whereby an increase in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-15b, and miR-19a and/or a decrease in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14$^+$CD16$^-$ monocyte from the subject as compared to the reference level indicates that the subject will have an increased rate of disease progression.

Also provided are methods of predicting the rate of disease progression in a subject having amyotrophic lateral sclerosis (ALS) that include: determining a level of one or more of hsa-miR-27b, hsa-miR-99b, hsa-miR-146a, hsa-miR-150, hsa-miR-328, and hsa-miR-532-3p in cerebrospinal fluid (CSF) in a subject; and comparing the level of one or more of hsa-miR-27b, hsa-miR-99b, hsa-miR-146a, hsa-miR-150, hsa-miR-328, and hsa-miR-532-3p in the CSF of the subject to a reference level of the one or more of hsa-miR-27b, hsa-miR-99b, hsa-miR-146a, hsa-miR-150, hsa-miR-328, and hsa-miR-532-3p, whereby an increase in the level of one or more of hsa-miR-27b, hsa-miR-99b, hsa-miR-146a, hsa-miR-150, hsa-miR-328, and hsa-miR-532-3p in the CSF of the subject compared to the reference level indicates that the subject will have an increased rate of disease progression. In some embodiments, an increase in the rate of disease progression is an increased rate of onset of one or more symptoms of ALS, an increase in the worsening of one or more symptoms of ALS, an increase in the frequency of one or more symptoms of ALS, an increase in the duration of one or more symptoms of ALS, or a decrease in the longevity of the subject.

Also provided are methods of selecting a subject for treatment of amyotrophic lateral sclerosis (ALS) that include: determining a level of one or more microRNAs selected from the group consisting of: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, hsa-miR-580, hsa-miR-15b, and hsa-miR-19a in a CD14$^+$CD16$^-$ monocyte from the subject; comparing the level of the one or more microRNAs in a CD14$^+$CD16$^-$ monocyte from the subject to a reference level of the one or more microRNAs; and selecting a subject having an increase in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-15b, and hsa-miR-19a and/or a decrease in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a CD14$^+$CD16$^-$ monocyte as compared to the reference level for treatment of ALS.

Also provided are methods for selecting a subject for treatment of amyotrophic lateral sclerosis (ALS) that include: determining a level of one or more of hsa-miR-27b, hsa-miR-99b, hsa-miR-146a, hsa-miR-150, hsa-miR-328, and hsa-miR-532-3p in cerebrospinal fluid (CSF) in a subject; and comparing the level of one or more of hsa-miR-27b, hsa-miR-99b, hsa-miR-146a, hsa-miR-150, hsa-miR-328, and hsa-miR-532-3p in the CSF of the subject to a reference level of the one or more of hsa-miR-27b, hsa-miR-99b, hsa-miR-146a, hsa-miR-150, hsa-miR-328, and hsa-miR-532-3p; and selecting a subject having an increase in the level of one or more of hsa-miR-27b, hsa-miR-99b, hsa-miR-146a, hsa-miR-150, hsa-miR-328, and hsa-miR-532-3p in the CSF compared to the reference level for treatment of ALS.

Also provided are methods for selecting a subject for treatment of familial amyotrophic lateral sclerosis (ALS) that include determining a level of hsa-miR-27b and a level of one or more of hsa-miR-99b, hsa-miR-146a, hsa-miR-150, hsa-miR-328, and hsa-miR-532-3p in cerebrospinal fluid (CSF) of a subject; and comparing the level of hsa-miR-27b in the CSF of the subject to a reference level of hsa-miR-27b, and the level of one or more of hsa-miR-99b, hsa-miR-146a, hsa-miR-150, hsa-miR-328, and hsa-miR-532-3p in the CSF of the subject to a reference level of one or more of hsa-miR-99b, hsa-miR-146a, hsa-miR-150, hsa-miR-328, and hsa-miR-532-3p; and selecting a subject having an increase in the level of hsa-miR-27b in the CSF compared to the reference level of hsa-miR-27b, and a decrease or no significant change in the level of one or more of hsa-miR-99b, hsa-miR-146a, hsa-miR-150, hsa-miR-328, and hsa-miR-532-3p in the CSF compared to the reference level of one or more of hsa-miR-99b, hsa-miR-146a, hsa-miR-150, hsa-miR-328, and hsa-miR-532-3p for treatment of familial ALS.

Also provided are methods for selecting a subject for treatment of sporadic amyotrophic lateral sclerosis (ALS) that include: determining a level of two or more microRNAs selected from the group consisting of hsa-miR-27b, hsa-miR-99b, hsa-miR-146a, hsa-miR-150, hsa-miR-328, and hsa-miR-532-3p in the cerebrospinal fluid (CSF) of a subject; comparing the level of the two or more microRNAs in the CSF of the subject to a reference level of the two or more microRNAs; and selecting a subject having an increase in the level of the two or more microRNAs in the CSF compared to the reference level for treatment of sporadic ALS.

In some embodiments of the methods described herein, the selected subject is further administered a treatment for ALS.

Also provided are methods of selecting a subject for participation in a clinical study that include: determining a level of one or more microRNAs selected from the group consisting of: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, hsa-miR-580, hsa-miR-15b, and hsa-miR-19a in a $CD14^+CD16^-$ monocyte from the subject; comparing the level of the one or more microRNAs in a $CD14^+CD16^-$ monocyte from the subject to a reference level of the one or more microRNAs; and selecting a subject having an increase in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-15b, and hsa-miR-19a and/or a decrease in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in a $CD14^+CD16^-$ monocyte as compared to the reference level for participation in a clinical study.

Also provided are methods of selecting a subject for participation in a clinical study that include: determining a level of one or more microRNAs selected from the group consisting of hsa-miR-27b, hsa-miR-99b, hsa-miR-146a, hsa-miR-150, hsa-miR-328, and hsa-miR-532-3p in the cerebrospinal fluid (CSF) of a subject; comparing the level of the one or more microRNAs in the CSF of the subject to a reference level of the one or more microRNAs; and selecting a subject having an increase in the level of the one or more microRNAs in the CSF compared to the reference level for participation in a clinical study.

Also provided are methods of determining the efficacy of treatment of amyotrophic lateral sclerosis in a subject that include: determining a level of one or more microRNAs selected from the group consisting of: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, hsa-miR-580, hsa-miR-15b, and hsa-miR-19a in a $CD14^+CD16^-$ monocyte from the subject at a first time point; determining a level of the one or more microRNAs in a $CD14^+/CD16^-$ monocyte from the subject at a second time point following administration of at least one dose of a treatment; and comparing the level of the one or more microRNAs at the first time point to the level of the one or more microRNAs at the second time point; whereby a decrease in the level of one or more of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-15b, and hsa-miR-19a and/or an increase in the level of one or more of hsa-miR-518f, hsa-miR-206, hsa-miR-204, hsa-miR-137, hsa-miR-453, hsa-miR-146a, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 at the second time point as compared to the level(s) at the first time point indicates that the treatment was effective in the subject.

Also provided are methods of determining the efficacy of treatment of amyotrophic lateral sclerosis (ALS) in a subject that include: determining a level of one or more of hsa-miR-27b, hsa-miR-99b, hsa-miR-146a, hsa-miR-150, hsa-miR-328, and hsa-miR-532-3p in cerebrospinal fluid of the subject at a first time point; determining a level of one or more of hsa-miR-27b, hsa-miR-99b, hsa-miR-146a, hsa-miR-150, hsa-miR-328, and hsa-miR-532-3p in CSF of the subject at a second time point following administration of at least one dose of a treatment; and comparing the level of one or more of hsa-miR-27b, hsa-miR-99b, hsa-miR-146a, hsa-miR-150, hsa-miR-328, and hsa-miR-532-3p at the first time point to the level of one or more of hsa-miR-27b, hsa-miR-99b, hsa-miR-146a, hsa-miR-150, hsa-miR-328, and hsa-miR-532-3p at the second time point; whereby a decrease in the level of one or more of hsa-miR-27b, hsa-miR-99b, hsa-miR-146a, hsa-miR-150, hsa-miR-328, and hsa-miR-532-3p at the second time point as compared to the level(s) at the first time point indicates that the treatment was effective in the subject.

In some embodiments of any of the methods described herein, the reference level is a threshold level. In some embodiments, the reference level is a level found in a $CD14^+CD16^-$ monocyte (e.g., a peripheral or blood-derived monocyte) from a control subject. In some embodiments, the reference level is a level found in the CSF of a control subject.

Some embodiments of the methods described herein further include obtaining a biological sample (e.g., a sample containing blood, plasma, serum, or cerebrospinal fluid) containing a $CD14^+CD16^-$ monocyte from the subject. In some embodiments, the method further comprises purifying a $CD14^+CD16^-$ monocyte from the biological sample.

Some embodiments of the methods described herein further include obtaining a sample containing CSF from the subject.

In some embodiments of any of the methods described herein, the microRNA or the one or more microRNA is a precursor microRNA. In some embodiments of any of the methods described herein, the microRNA or the one or more microRNA is a mature microRNA.

Also provided are methods of treating amyotrophic lateral sclerosis (ALS) in a subject that include administering to a subject having ALS at least one antagomir comprising a sequence that is complementary to a contiguous sequence (e.g., a contiguous sequence of at least 5, 6, 7, 8, 9, 10, 11, 12, 13, 14, 15, 16, 17, 18, 19, 20, 21, 22, 23, 24, or 25 nucleotides, preferably at least 7 or 8 nucleotides) present in any one of hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-155, hsa-miR-532-3p, hsa-miR-27b, hsa-miR-99b, hsa-miR-146a, hsa-miR-150 hsa-miR-328, has-miR-19a, hsa-miR-15b, hsa-miR-15b, and hsa-miR-19a.

Also provided are methods of treating amyotrophic lateral sclerosis (ALS) in a subject that include administering to a subject having ALS at least one inhibitory nucleic acid comprising a sequence that is complementary to a contiguous sequence present in hsa-miR-155. In some embodiments, the at least one inhibitory nucleic acid is an antagomir (e.g., an antagomir contains or has a sequence of SEQ ID NO: 262). In some embodiments, the at least one inhibitory nucleic acid is an antisense oligonucleotide. In some embodiments, the at least one inhibitory nucleic acid is a ribozyme. In some embodiments, the at least one inhibitory inhibitory nucleic acid is injected into the cerebrospinal fluid of a subject (e.g., intracranial injection or intrathecal injection). In some embodiments, the at least one inhibitory nucleic acid is complexed with one or more cationic polymers and/or cationic lipids. In some embodiments, the inhibitory nucleic acid is delivered using a lentivirus vector.

Also provided are methods of using at least one antagomir comprising a sequence that is complementary to a contiguous sequence present in any one of hsa-miR-155, hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-532-3p, hsa-miR-27b, hsa-miR-99b, hsa-miR-146a, hsa-miR-150, hsa-miR-328, hsa-miR-15b, and hsa-miR-19a in the manufacture of a medicament for treating amyotrophic lateral sclerosis in a subject. Also provided herein are antagomirs comprising a sequence that is complementary to a contiguous sequence present in any one of hsa-miR-155, hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, hsa-miR-103, hsa-miR-532-3p, hsa-miR-27b, hsa-miR-99b, hsa-miR-146a, hsa-miR-150, hsa-miR-328, hsa-miR-15b, and hsa-miR-19a for use in treating amyotrophic lateral sclerosis in a subject.

Also provided are methods of using at least one inhibitory nucleic acid (e.g., an antagomir) comprising a sequence that is complementary to a contiguous sequence present in hsa-miR-155 in the manufacture of a medicament for treating amyotrophic lateral sclerosis in a subject. Also provided herein are inhibitory nucleic acids (e.g., antagomirs) containing a sequence that is complementary to a contiguous sequence present in hsa-miR-155 for use in treating amyotrophic lateral sclerosis in a subject.

As used herein, "RNA" refers to a molecule comprising at least one or more ribonucleotide residues. A "ribonucleotide" is a nucleotide with a hydroxyl group at the 2' position of a beta-D-ribofuranose moiety. The term RNA, as used herein, includes double-stranded RNA, single-stranded RNA, isolated RNA, such as partially purified RNA, essentially pure RNA, synthetic RNA, recombinantly-produced RNA, as well as altered RNA that differs from naturally-occurring RNA by the addition, deletion, substitution and/or alteration of one or more nucleotides. Nucleotides of the RNA molecules can also comprise non-standard nucleotides, such as non-naturally occurring nucleotides or chemically synthesized nucleotides or deoxynucleotides.

A "mature microRNA" (mature miRNA) typically refers to a single-stranded RNA molecules of about 21-23 nucleotides in length, which regulates gene expression. miRNAs are encoded by genes from whose DNA they are transcribed, but miRNAs are not translated into protein; instead each primary transcript (pri-miRNA) is processed into a short stem-loop structure (precursor microRNA) before undergoing further processing into a functional mature miRNA. Mature miRNA molecules are partially complementary to one or more messenger RNA (mRNA) molecules, and their main function is to down-regulate gene expression. As used throughout, the term "microRNA" or "miRNA" includes both mature microRNA and precursor microRNA.

As used herein, the term "inflammatory marker" refers to any of the proteins or mRNAs listed in Tables 20 and 21. The proteins and mRNAs listed in Tables 20 and 21 have been implicated for a role in inflammation. Methods for detecting the levels or activity of the inflammatory markers are known in the art. Additional methods for detecting the levels or activity of the inflammatory markers are described herein.

By the term "reference level" is meant a control level of one of the microRNAs listed in Tables 1-19 or one of the inflammatory markers listed in Tables 20 and 21. A reference level may represent a threshold level of a specific microRNA or inflammatory marker. A reference level may also be a level of a particular microRNA or inflammatory marker present in the cerebrospinal fluid or in a monocyte (e.g., a $CD14^+CD16^-$ or $CD14^+CD16^+$ monocyte (e.g., a peripheral or blood-derived monocyte)) from a healthy subject (e.g., a subject that does not present with two or more symptoms of a neurodegenerative disorder, a subject that has not been diagnosed with a neurodegenerative disorder, and/or a subject that has no family history of neurodegenerative disease).

By the term "increase" is meant an observable, detectable, or significant increase in a level as compared to a reference level or a level measured at an earlier or later time point in the same subject.

By the term "decrease" is meant an observable, detectable, or significant decrease in a level as compared to a reference level or a level measured at an earlier or later time point in the same subject.

By the term "neurodegenerative disorder" is meant a neurological disorder characterized by a progressive loss of neuronal function and structure, and neuron death. Non-limiting examples of neurodegenerative disorders include Parkinson's disease (PD), Alzheimer's disease (AD), Huntington's disease (HD), brain stroke, brain tumors, cardiac ischemia, age-related macular degeneration (AMD), retinitis pigmentosa (RP), amyotrophic lateral sclerosis (ALS, e.g., familial ALS and sporadic ALS), and multiple sclerosis (MS). Methods for diagnosing a neurodegenerative disorder are described herein. Additional methods for diagnosing a neurodegenerative disorder are known in the art.

By the term "inhibitory RNA" is meant a nucleic acid molecule that contains a sequence that is complementary to a target nucleic acid (e.g., a target microRNA or target inflammatory marker, e.g., any of the microRNAs listed in Tables 1, 3, 5, 7, 9, 11, 12, 14, 16, or 18, or any of the inflammatory markers listed in Table 21) that mediates a decrease in the level or activity of the target nucleic acid (e.g., activity in $CD14^+CD16^-$ or $CD14^+CD16^+$ monocyte). Non-limiting examples of inhibitory RNAs include interfering RNA, shRNA, siRNA, ribozymes, antagomirs, and antisense oligonucleotides. Methods of making inhibitory RNAs are described herein. Additional methods of making inhibitory RNAs are known in the art.

As used herein, "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long.

As used herein, an "antagomir" refers to a small synthetic RNA having complementarity to a specific microRNA target, optionally with either mispairing at the cleavage site or one or more base modifications to inhibit cleavage.

As used herein, the phrase "post-transcriptional processing" refers to mRNA processing that occurs after transcription and is mediated, for example, by the enzymes Dicer and/or Drosha.

By the phrase "risk of developing disease" is meant the relative probability that a subject will develop a neurodegenerative disorder in the future as compared to a control subject or population (e.g., a healthy subject or population). Provided herein are methods for determining a subject's risk of developing a neurodegenerative disease in the future that include determining the level of one or more of the microRNAs listed in Tables 1-19 and/or one or more of the inflammatory markers listed in Tables 20-21.

By the phrase "rate of disease progression" is meant one or more of the rate of onset of symptoms of a neurodegenerative disorder in a subject, the rate of the increasing intensity (worsening) of symptoms of a neurodegenerative disorder in a subject, the frequency of one or more symptoms of a neurodegenerative disorder in a subject, the duration of one or more symptoms of a neurodegenerative disorder in a subject, or the longevity of subject. For example, an increased rate of disease progression can include one or more of: an increased rate of onset of symptoms of a neurodegenerative disorder in a subject, an increased frequency of one or more symptoms of a neurodegenerative disorder in a subject, an increase in the duration of one or more symptoms of a neurodegenerative disorder in a subject, or a decrease in the longevity of a subject. Methods of predicting the rate of disease progression in a subject having a neurodegenerative disorder are described herein.

By the term "purifying" is meant a partial isolation of a substance from its natural environment (e.g., partial removal of contaminating biomolecules or cells). For example, a monocyte (e.g., a $CD14^+CD16^-$ or $CD14^+CD16^+$ monocyte) can be purified from other cell types present in a sample of peripheral blood (e.g., using fluorescence-assisted cell sorting).

The term "treating" includes reducing the number of symptoms or reducing the severity, duration, or frequency of one or more symptoms of disease (e.g., a neurodegenerative disease) in a subject. The term treating can also include reducing the risk of developing a neurodegenerative disorder in a subject, delaying the onset of symptoms of a neurodegenerative disorder in a subject, or increasing the longevity of a subject having a neurodegenerative disorder.

By the term "cationic polymer" is meant a polymeric material that is positively-charged at a physiological pH (e.g., a pH of approximately 6.5 to 8.0) that is capable of condensing nucleic acids into nanoparticles. Non-limiting examples of cationic polymers include poly-L-lysine and poly(ethylenimine). Additional examples of cationic polymers are known in the art.

By the term "cationic lipids" is meant a lipid that has at least one positive charge at a physiological pH (e.g., a pH of approximately 6.5 to 8.0) that is able to form a complex with a nucleic acid. Non-limiting examples of cationic lipids include 1,2-dioleoyl-3-trimethylammonium propone (DOTAP), N-methyl-4-(dioleyl)methylpyridinium, and 3β-[N—(N',N'-dimethylaminoethane)-carbamoyl] cholesterol. Additional examples of cationic lipids are known in the art and are commercially available (e.g., Lipofectamine™ 2000; Life Technologies Corporation, Carlsbad, Calif.).

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 7A is a Venn diagram of the unique or similar dysregulated (upregulated or downregulated) microRNAs in CD14$^+$CD16$^-$ monocytes from ALS and MS subjects as compared to the expression of the microRNAs in CD14$^+$CD16$^-$ monocytes from healthy controls.

FIG. 7B is a volcano plot showing the significantly dysregulated microRNAs in CD14$^+$CD16$^-$ from ALS subjects as compared to the expression of the microRNAs in CD14$^+$CD16$^-$ from healthy controls.

FIG. 7C is a volcano plot showing the significantly dysregulated microRNAs in CD14$^+$CD16$^-$ from MS subjects as compared to the expression of the microRNAs in CD14$^+$CD16$^-$ from healthy controls.

FIG. 9 is a set of six graphs showing the expression of six different microRNAs in CD14$^+$CD16$^-$ from healthy subjects (8 subjects) and subjects having ALS (11 subjects) (as determined by real-time PCR). A two-tiled Mann-Whitney t-test was used to calculate the P values (*, P<0.05; , P<0.01; *, P<0.001).

FIG. 10A is two graphs showing the clinical scoring (forced vital capacity (FVC) score and Functional Rating Scale (FRS)) of eight different ALS patients. A comparison of the microRNA expression in CD14$^+$CD16$^-$ monocytes from these eight patients to microRNA expression in CD14$^+$CD16$^-$ monocytes from healthy controls and MS subjects are shown in FIG. 10C.

FIG. 10B is a list of the eight different ALS patients described in FIGS. 10A and 10C.

FIG. 11 is four graphs showing the real-time PCR analysis of the expression of four upregulated microRNAs in CD14$^+$CD16$^-$ from sporadic ALS (n=11) subjects as compared to healthy controls (n=8), and subjects with MS (n=8). The data shown were generated using one-way ANOVA and the Dunett's multiple comparison test (***, p<0.001).

FIG. 12A is two graphs showing the clinical scoring (forced vital capacity (FVC) score and Functional Rating Scale (FRS)) of eight different ALS patients. A comparison of the microRNA expression in CD14$^+$CD16$^-$ monocytes from these eight patients to microRNA expression in CD14$^+$CD16$^-$ monocytes from healthy controls and MS subjects are shown in FIG. 10C.

FIG. 12B is a list of the eight different ALS patients described in FIGS. 12A and 12C.

FIG. 21C is a list of the major biological networks activated in Ly6C$^{Hi}$ spleen-derived monocytes one month prior to disease onset in SOD1$^{G93A}$ mice.

FIG. 21F is a list of the major biological pathways activated in CD39$^+$ microglia the spinal cords of SOD1 mice at the onset of disease

FIG. 26 is a table of the results of the microRNA-mRNA target analysis performed on the data gathered from $CD14^+CD16^-$ blood monocytes from ALS subjects (IPA; Ingenuity). The results show 32 miRNAs targeting 27 mRNAs.

DETAILED DESCRIPTION OF THE INVENTION

Figure 1A:
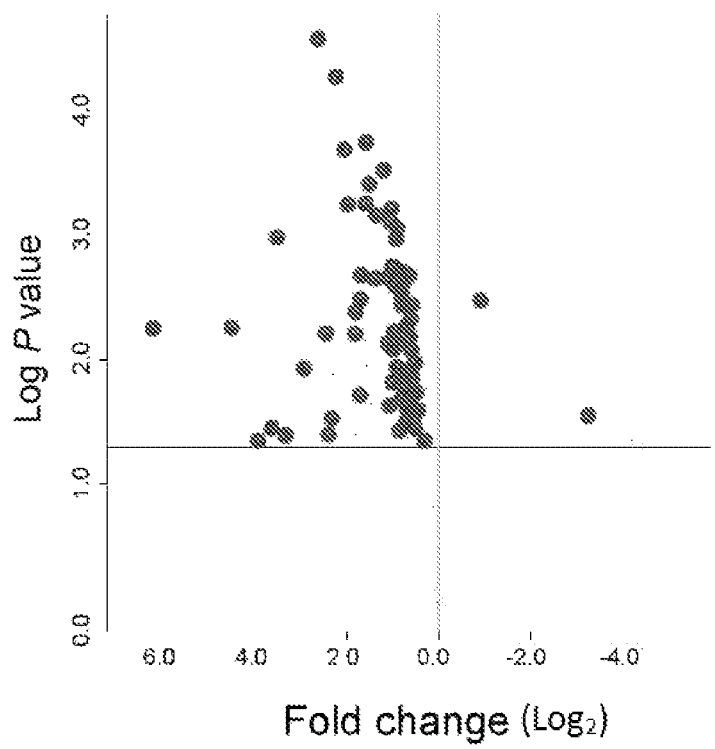
FIG. 1A is a volcano plot of significantly dysregulated microRNAs in $CD39^+$ microglia in $SOD^{G93A}$ mice compared to the expression of microRNAs in $CD39^+$ microglia from non-transgenic littermates at a presymptomatic (60 days) time point (Presymptomatic), at the time of onset of symptoms (Onset), and at the end-stage of the disease (End-Stage). The x-axis represents changes in expression ($\log_2$-fold change based on ddCT values) and the y-axis shows the statistical significance of the change in log-odds.

The invention is based, at least in part, on the discovery that specific microRNAs and inflammatory markers are dysregulated in CD14$^+$CD16$^-$ monocytes and/or CD14$^+$CD16$^+$ monocytes (e.g., peripheral or blood-derived monocytes) from patients having a neurodegenerative disease, and that specific microRNAs are present in increased or decreased levels in the cerebrospinal fluid of patients having a neurodegenerative disorder (e.g., ALS (e.g., sporadic ALS and familial ALS) and MS) compared to healthy individuals. The invention is also based on the discovery that hsa-miR-155 plays a significant role in the development of disease in a mouse model of ALS. In view of this discovery, methods for diagnosing a neurodegenerative disorder, identifying a subject at risk (e.g., increased risk or decreased risk) of developing a neurodegenerative disorder, predicting the rate of disease progression in a subject having a neurodegenerative disorder, selecting a subject for treatment of a neurodegenerative disorder, selecting a treatment for a subject having a neurological disorder, determining the efficacy of treatment of a neurodegenerative disorder, and selecting a subject for participation in a clinical study are provided herein. These methods include measuring a level of one or more (e.g., at least 2, 3, 4, 5, 6, 7, 8, 9, or 10) microRNAs listed in one or more of Tables 1-19 and/or one or more inflammatory markers listed in Tables 20-21.

Also provided are methods of treating a neurodegenerative disorder (e.g., ALS or MS) that include administering to a subject an agent (e.g., a nucleic acid) that decreases the level or activity of one or more of the microRNAs listed in Tables 1, 3, 5, 7, 9, 11, 12, 14, 16, or 18 (e.g., hsa-miR-155), and/or increases the level or activity of one or more of the microRNAs listed in Tables 2, 4, 6, 8, 10, 13, 15, 17, or 19. Also provided are methods of treating a neurological disorder (e.g., ALS or MS) that include administering to a subject an agent (e.g., a nucleic acid) that decreases the expression (e.g., protein or mRNA) and/or activity of one or more of the inflammatory markers listed in Table 21 and/or increases the expression (e.g., protein or mRNA) and/or activity of one or more of the genes listed in Table 20.

Also provided are nucleic acids that contain a sequence complementary to a sequence present in any one of the microRNAs listed in Tables 1-19 or a sequence present in an mRNA that encodes any of the genes listed in Tables 20 and 21 (e.g., a primer or probe). Also provided are nucleic acids that contain a sequence that is complementary to a sequence present in any one of the microRNAs listed in Tables 1, 3, 5, 7, 9, 11, 12, 14, 16, or 18 (the target microRNA), or a sequence present in a mRNA encoded by any of the genes listed in Table 21 (the target mRNA), that decrease the expression or activity of the target microRNA or target mRNA (e.g., an inhibitory RNA, e.g., any of the inhibitory nucleic acids described herein). Also provided are compositions that contain a nucleic acid that includes the sequence of any one of the microRNAs listed in Tables 2, 4, 6, 8, 10, 13, 15, 17, and 19 (the target microRNA), or a sequence present in an mRNA encoded by any of the genes listed in Table 20 (the target mRNA), that increase the expression or activity of the target microRNA or target mRNA. Also included are compositions that contain at least one antibody that specifically binds to any one of the proteins listed in Table 20 and Table 21. Also included are compositions that contain at least one protein listed in Table 20 and Table 21. Also provided are kits that contain one or more of the above nucleic acids, proteins, or antibodies (in any combination).

Neurodegenerative Disorders

Neurodegenerative disorders are a class of neurological diseases that are characterized by the progressive loss of the structure and function of neurons and neuronal cell death. Inflammation has been implicated for a role in several neurodegenerative disorders. Progressive loss of motor and sensory neurons and the ability of the mind to refer sensory information to an external object is affected in different kinds of neurodegenerative disorders. Non-limiting examples of neurodegenerative disorders include Parkinson's disease, Alzheimer's disease, Huntington's disease, amyotrophic lateral sclerosis (ALS, e.g., familial ALS and sporadic ALS), and multiple sclerosis (MS).

A health care professional may diagnose a subject as having a neurodegenerative disorder by the assessment of one or more symptoms of a neurodegenerative disorder in the subject. Non-limiting symptoms of a neurodegenerative disorder in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disorder. A health care professional may diagnose a subject as having a neurodegenerative disorder upon presentation of a subject to a health care facility (e.g., a clinic or a hospital). In some instances, a health care professional may diagnose a subject as having a neurodegenerative disorder while the subject is admitted in an assisted care facility. Typically, a physician diagnoses a neurodegenerative disorder in a subject after the presentation of one or more symptoms.

Provided herein are additional methods for diagnosing a neurodegenerative disorder in a subject (e.g., a subject presenting with one or more symptoms of a neurodegenerative disorder or a subject not presenting a symptom of a neurodegenerative disorder (e.g., an undiagnosed and/or asymptomatic subject). Also provided herein are prognostic methods and methods of treating a neurodegenerative disorder in a subject (e.g., methods of decreasing the rate of onset or the progression of symptoms (e.g., ataxia) of a neurodegenerative disorder in a subject).

Markers

Any combination of one or more of the markers described herein can be used in any of the methods described herein, e.g., used in methods for diagnosing a neurodegenerative disorder in a subject, identifying a subject at risk (e.g., increased or decreased risk) of developing a neurodegenerative disorder, predicting the rate of disease progression in a subject having a neurodegenerative disorder, selecting a subject for treatment of a neurodegenerative disorder, determining the efficacy of treatment in a subject having a neurodegenerative disorder, or selecting a subject for participation in a clinical study.

MicroRNA markers increased in monocytes (CD14+ CD16− or CD14+CD16+ monocytes) or the CSF in subjects having a neurodegenerative disorder relative to healthy controls (CD14+CD16− or CD14+CD16+ monocytes, or the CSF in healthy controls) are listed in Table 1.

TABLE 1

List of microRNAs increased in CD14+CD16− monocytes, CD14+CD16− monocytes, or CSF from patients having neurodegenerative disorders compared to healthy controls

| MiRNA | Mature miRNA sequence | Precursor miRNA sequence |
|---|---|---|
| hsa-miR-19b | gugcaaauccaugcaaaac uga (SEQ ID NO: 1) | CACUGUUCUAUGGUUAGUUUUGCAGGUUUGC AUCCAGCUGUGUGAUAUUCUGCUGUGCAAAUC CAUGCAAAACUGACUGUGGUAGUG (SEQ ID NO: 3) |
| | ugugcaaauccaugcaaaa cuga (SEQ ID NO: 2) | ACAUUGCUACUUACAAUUAGUUUUGCAGGUU UGCAUUUCAGCGUAUAUAUGUAUAUGUGGCU GUGCAAAUCCAUGCAAAACUGAUUGUGAUAA UGU (SEQ ID NO: 4) |
| hsa-miR-106b | uaaagugcugacagugca gau (SEQ ID NO: 5) | CCUGCCGGGGCUAAAGUGCUGACAGUGCAGAU AGUGGUCCUCUCCGUGCUACCGCACUGUGGGU ACUUGCUGCUCCAGCAGG (EQ ID NO: 6) |
| hsa-miR-30b | uguaaacauccuacacuca gcu (SEQ ID NO: 7) | ACCAAGUUUCAGUUCAUGUAAACAUCCUACAC UCAGCUGUAAUACAUGGAUUGGCUGGGAGGU GGAUGUUUACUUCAGCUGACUUGGA (SEQ ID NO: 8) |
| hsa-miR-21 | uagcuuaucagacugaug uuga (SEQ ID NO: 9) | UGUCGGGUAGCUUAUCAGACUGAUGUUGACU GUUGAAUCUCAUGGCAACACCAGUCGAUGGGC UGUCUGACA (SEQ ID NO: 10) |
| hsa-miR-142-5p | cauaaaguagaaagcacua cu (SEQ ID NO: 11) | GACAGUGCAGUCACCCAUAAAGUAGAAAGCAC UACUAACAGCACUGGAGGGUGUAGUGUUUCC UACUUUAUGGAUGAGUGUACUGUG (SEQ ID NO: 12) |
| hsa-miR-27a | uucacaguggcuaaguuc cgc (SEQ ID NO: 265) | CUGAGGAGCAGGGCUUAGCUGCUUGUGAGCA GGGUCCACACCAAGUCGUGUUCACAGUGGCUA AGUUCCGCCCCCCAG (SEQ ID NO: 13) |
| hsa-miR-16 | uagcagcacguaaauauu ggcg (SEQ ID NO: 14) | GUCAGCAGUGCCUUAGCAGCACGUAAAUAUUG GCGUUAAGAUUCUAAAAUUAUCUCCAGUAUU AACUGUGCUGCUGAAGUAAGGUUGAC (SEQ ID NO: 16) |
| | uagcagcacguaaauauu ggcg (SEQ ID NO: 15) | GUUCCACUCUAGCAGCACGUAAAUAUUGGCGU AGUGAAAUAUAUUAAACACCAAUAUUACU GUGCUGCUUUAGUGUGAC (SEQ ID NO: 17) |
| hsa-miR-374a | uuauaauacaaccugauaa gug (SEQ ID NO: 18) | UACAUCGGCCAUUAUAAUACAACCUGAUAAGU GUUAUAGCACUUAUCAGAUUGUAUUGUAAUU GUCUGUGUA (SEQ ID NO: 19) |
| hsa-miR-374b | auauaauacaaccugcuaa gug (SEQ ID NO: 20) | ACUCGGAUGGAUAUAAUACAACCUGCUAAGU GUCCUAGCACUUAGCAGGUUGUAUUAUCAUU GUCCGUGUCU (SEQ ID NO: 21) |
| hsa-miR-101 | uacaguacugugauaacu gaa (SEQ ID NO: 22) | UGCCCUGGCUCAGUUAUCACAGUGCUGAUGCU GUCUAUUCUAAAGGUACAGUACUGUGAUAAC UGAAGGAUGGCA (SEQ ID NO: 24) |
| | uacaguacugugauaacu gaa (SEQ ID NO: 23) | ACUGUCCUUUUUCGGUUAUCAUGGUACCGAUG CUGUAUAUCUGAAAGGUACAGUACUGUGAUA ACUGAAGAAUGGGUGGU (SEQ ID NO: 25) |
| hsa-miR-340 | uuauaaagcaaugagacu gauu (SEQ ID NO: 26) | UUGUACCGGGUGUGAUUAUAAAGCAAUGAGA CUGAUUGUCAUAUGUCGUUUGUGGGAUCCGU CUCAGUUACUUUAUAGCCAUACCUGGUAUCUU A (SEQ ID NO: 27) |
| hsa-miR-30e | uguaaacauccuugacug gaag (SEQ ID NO: 28) | GGGCAGUCUUUGCUACUGUAAACAUCCUUGAC UGGAAGCUGUAAGGUGUUCAGAGGAGCUUUC AGUCGGAUGUUUACAGCGGCAGGCUGCCA (SEQ ID NO: 29) |

TABLE 1 -continued

List of microRNAs increased in CD14⁺CD16⁻ monocytes, CD14⁺CD16⁻ monocytes, or CSF from patients having neurodegenerative disorders compared to healthy controls

| MiRNA | Mature miRNA sequence | Precursor miRNA sequence |
|---|---|---|
| hsa-miR-29c | uagcaccauuugaaaucg guua (SEQ ID NO: 30) | AUCUCUUACACAGGCUGACCGAUUUCUCCUGG UGUUCAGAGUCUGUUUUUGUCUAGCACCAUU UGAAAUCGGUUAUGAUGUAGGGGGA (SEQ ID NO: 31) |
| hsa-miR-29a | uagcaccaucugaaaucg guua (SEQ ID NO: 32) | AUGACUGAUUUCUUUUGGUGUUCAGAGUCAA UAUAAUUUCUAGCACCAUCUGAAAUCGGUU AU (SEQ ID NO: 33) |
| hsa-miR-223 | ugucaguuugucaaauac ccca (SEQ ID NO: 34) | CCUGGCCUCCUGCAGUGCCACGCUCCGUGUAU UUGACAAGCUGAGUUGGACACUCCAUGUGGU AGAGUGUCAGUUUGUCAAAUACCCCAAGUGCG GCACAUGCUUACCAG (SEQ ID NO: 35) |
| hsa-miR-26a | uucaaguaauccaggaua ggcu (SEQ ID NO: 36) uucaaguaauccaggaua ggcu (SEQ ID NO: 37) | GUGGCCUCGUUCAAGUAAUCCAGGAUAGGCUG UGCAGGUCCCAAUGGGCCUAUUCUUGGUUACU UGCACGGGACGC (SEQ ID NO: 38) GGCUGUGGCUGGAUUCAAGUAAUCCAGGAUA GGCUGUUUCCAUCUGUGAGGCCUAUUCUUGAU UACUUGUUUCUGGAGGCAGCU (SEQ ID NO: 39) |
| hsa-miR-26b | uucaaguaauucaggaua ggu (SEQ ID NO: 40) | CCGGGACCCAGUUCAAGUAAUUCAGGAUAGGU UGUGUGCUGUCCAGCCUGUUCUCCAUUACUUG GCUCGGGACCGG (SEQ ID NO: 41) |
| hsa-miR-24 | uggcucaguucagcagga acag (SEQ ID NO: 42) uggcucaguucagcagga acag (SEQ ID NO: 43) | CUCCGGUGCCUACUGAGCUGAUAUCAGUUCUC AUUUUACACACUGGCUCAGUUCAGCAGGAACA GGAG (SEQ ID NO: 44) CUCUGCCUCCCGUGCCUACUGAGCUGAAACAC AGUGGUUUGUGUACACUGGCUCAGUUCAGC AGGAACAGGG (SEQ ID NO: 45) |
| hsa-miR-181a | aacauucaacgcugucgg ugagu (SEQ ID NO: 46) aacauucaacgcugucgg ugagu (SEQ ID NO: 47) | UGAGUUUUGAGGUUGCUUCAGUGAACAUUCA ACGCUGUCGGUGAGUUUGGAAUUAAAAUCAA AACCAUCGACCGUUGAUUGUACCCUAUGGCUA ACCAUCAUCUACUCCA (SEQ ID NO: 48) AGAAGGGCUAUCAGGCCAGCCUUCAGAGGACU CCAAGGAACAUUCAACGCUGUCGGUGAGUUUG GGAUUUGAAAAAACCACUGACCGUUGACUGU ACCUUGGGUCCUUA (SEQ ID NO: 49) |
| hsa-miR-103 | agcagcauuguacagggc uauga (SEQ ID NO: 50) agcagcauuguacagggc uauga (SEQ ID NO: 51) ucauagcccuguacaaug cugcu (SEQ ID NO: 52) ucauagcccuguacaaug cugcu (SEQ ID NO: 53) | UACUGCCCUCGGCUUCUUUACAGUGCUGCCUU GUUGCAUAUGGAUCAAGCAGCAUUGUACAGG GCUAUGAAGGCAUUG (SEQ ID NO: 54) UUGUGCUUUCAGCUUCUUUACAGUGCUGCCUU GUAGCAUUCAGGUCAAGCAGCAUUGUACAGG GCUAUGAAAGAACCA (SEQ ID NO: 55) UCUAGCCCUGUACAAUGCUGCUUGAUCCAUA UGCAACAAGGCAGCACUGUAAAGAAGCCGA (SEQ ID NO: 56) UCAUAGCCCUGUACAAUGCUGCUUGACCUGAA UGCUACAAGGCAGCACUGUAAAGAAGCUGA (SEQ ID NO: 57) |
| hsa-miR-155 | uuaaugcuaaucgugaua ggggu (SEQ ID NO: 58) | CUGUUAAUGCUAAUCGUGAUAGGGGUUUUUG CCUCCAACUGACUCCUACAUAUUAGCAUUAAC AG (SEQ ID NO: 59) |
| hsa-miR-532-3p | caugccuugaguguagga ccgu (SEQ ID NO: 60) | CGACUUGCUUUCUCUCCUCCAUGCCUUGAGUG UAGGACCGUUGGCAUCUUAAUUACCCUCCCAC ACCCAAGGCUUGCAAAAAAGCGAGCCU (SEQ ID NO: 61) |
| hsa-miR-320c | aaaagcuggguugagagg gu (SEQ ID NO: 62) aaaagcuggguugagagg gu (SEQ ID NO: 63) | UUUGCAUUAAAAAUGAGGCCUUCUCUUCCCAG UUCUUCCCAGAGUCAGGAAAAGCUGGGUUGA GAGGGUAGAAAAAAAAAUGAUGUAGG (SEQ ID NO: 64) CUUCUCUUUCCAGUUCUUCCCAGAAUUGGGAA AAGCUGGGUUGAGAGGGU (SEQ ID NO: 65) |

TABLE 1-continued

List of microRNAs increased in CD14⁺CD16⁻ monocytes, CD14⁺CD16⁻ monocytes, or CSF from patients having neurodegenerative disorders compared to healthy controls

| MiRNA | Mature miRNA sequence | Precursor miRNA sequence |
|---|---|---|
| hsa-miR-27b | uucacaguggcuaaguuc ugc (SEQ ID NO: 66) | ACCUCUCUAACAAGGUGCAGAGCUUAGCUGAU UGGUGAACAGUGAUUGGUUUCCGCUUUGUUC ACAGUGGCUAAGUUCUGCACCUGAAGAGAAG GUG (SEQ ID NO: 67) |
| hsa-miR-664 | uauucauuuauccccagc cuaca (SEQ ID NO: 68) | GAACAUUGAAACUGGCUAGGGAAAAUGAUUG GAUAGAAACUAUUAUUCUAUUCAUUUAUCCCC AGCCUACAAAAUGAAAAAA (SEQ ID NO: 69) |
| hsa-miR-432-5p | ucuuggaguaggucauug ggugg (SEQ ID NO: 70) | UGACUCCUCCAGGUCUUGGAGUAGGUCAUUGG GUGGAUCCUCUAUUUCCUUACGUGGGCCACUG GAUGGCUCCUCCAUGUCUUGGAGUAGAUCA (SEQ ID NO: 71) |
| hsa-miR-92a | uauugcacuugucccggc cugu (SEQ ID NO: 72) uauugcacuugucccggc cugu (SEQ ID NO: 73) | CUUUCUACACAGGUUGGGAUCGGUUGCAAUGC UGUGUUUCUGUAUGGUAUUGCACUUGUCCCG GCCUGUUGAGUUUGG (SEQ ID NO: 74) UCAUCCCUGGGUGGGGAUUUGUUGCAUUACU UGUGUUCUAUAUAAAGUAUUGCACUUGUCCC GGCCUGUGGAAGA (SEQ ID NO: 75) |
| hsa-miR-99b | cacccguagaaccgaccuu gcg (SEQ ID NO: 76) | GGCACCCACCCGUAGAACCGACCUUGCGGGGC CUUCGCCGCACACAAGCUCGUGUCUGUGGGUC CGUGUC (SEQ ID NO: 77) |
| hsa-miR-146a | ugagaacugaauuccaug gguu (SEQ ID NO: 78) | CCGAUGUGUAUCCUCAGCUUUGAGAACUGAAU UCCAUGGGUUGUGUCAGUGUCAGACCUCUGAA AUUCAGUUCUUCAGCUGGGAUAUCUCUGUCAU CGU (SEQ ID NO: 79) |
| hsa-miR-150 | ucucccaacccuuguacca gug (SEQ ID NO: 80) | CUCCCCAUGGCCCUGUCUCCCAACCCUUGUAC CAGUGCUGGGCUCAGACCCUGGUACAGGCCUG GGGGACAGGGACCUGGGGAC (SEQ ID NO: 81) |
| hsa-miR-328 | cuggcccucucugccuu ccgu (SEQ ID NO: 82) | UGGAGUGGGGGGCAGGAGGGGCUCAGGGAG AAAGUGCAUACAGCCCCUGGCCCUCUCUGCCC UUCCGUCCCCUG (SEQ ID NO: 83) |
| hsa-miR-532-3p | ccucccacacccaaggcuu gca (SEQ ID NO: 84) | CGACUUGCUUUCUCUCCUCCAUGCCUUGAGUG UAGGACCGUUGGCAUCUUUAAUUACCCUCCCAC ACCCAAGGCUUGCAAAAAAGCGAGCCU (SEQ ID NO: 85) |
| hsa-miR-1260 | aucccaccucugccacca (SEQ ID NO: 86) | ACCUUUCCAGCUCAUCCCACCUCUGCCACCAA AACACUCAUCGCGGGGUCAGAGGGAGUGCCAA AAAAGGUAA (SEQ ID NO: 87) |
| hsa-miR-423 | ugaggggcagagagcgag acuuu (SEQ ID NO: 88) | AUAAAGGAAGUUAGGCUGAGGGGCAGAGAGC GAGACUUUCUAUUUUCCAAAAGCUCGGUCUG AGGCCCCUCAGUCUUGCUUCCUAACCCGCGC (SEQ ID NO: 89) |
| hsa-miR-361-5p | uuaucagaaucuccaggg guac (SEQ ID NO: 90) | GGAGCUUAUCAGAAUCUCCAGGGGUACUUUA UAAUUUCAAAAAGUCCCCCAGGUGUGAUUCUG AUUUGCUUC (SEQ ID NO: 91) |
| hsa-miR-93 | caaagugcuguucgugca gguag (SEQ ID NO: 92) | CUGGGGGCUCCAAAGUGCUGUUCGUGCAGGUA GUGUGAUUACCCAACCUACUGCUGAGCUAGCA CUUCCCGAGCCCCCGG (SEQ ID NO: 93) |
| hsa-miR-221 | agcuacauugucugcugg guuuc (SEQ ID NO: 94) | UGAACAUCCAGGUCUGGGGCAUGAACCUGGCA UACAAUGUAGAUUUCUGUGUUCGUUAGGCAA CAGCUACAUUGUCUGCUGGGUUUCAGGCUACC UGGAAACAUGUUCUC (SEQ ID NO: 95) |
| hsa-miR-20a | uaaagugcuuauagugca gguag (SEQ ID NO: 96) | GUAGCACUAAAGUGCUUAUAGUGCAGGUAGU GUUUAGUUAUCUACUGCAUUAUGAGCACUUA AAGUACUGC (SEQ ID NO: 97) |
| hsa-miR-30c | uguaaacauccuacacucu cagc (SEQ ID NO: 98) | ACCAUGCUGUAGUGUGUAAACAUCCUACAC UCUCAGCUGUGAGCUCAAGGUGGCUGGGAGA GGGUUGUUUACUCCUUCUGCCAUGGA (SEQ ID NO: 100) |

TABLE 1 -continued

List of microRNAs increased in CD14+CD16− monocytes, CD14+CD16−
monocytes, or CSF from patients having neurodegenerative disorders
compared to healthy controls

| MiRNA | Mature miRNA sequence | Precursor miRNA sequence |
|---|---|---|
| | uguaaacauccuacacucu cagc (SEQ ID NO: 99) | AGAUACUGUAAACAUCCUACACUCUCAGCUGU GGAAAGUAAGAAAGCUGGGAGAAGGCUGUUU ACUCUUUCU (SEQ ID NO: 101) |
| hsa-miR-15b | uagcagcacaucaugguu uaca (SEQ ID NO: 102) | UUGAGGCCUUAAAGUACUGUAGCAGCACAUCA UGGUUUACAUGCUACAGUCAAGAUGCGAAUC AUUAUUUGCUGCUCUAGAAAUUUAAGGAAAU UCAU (SEQ ID NO: 103) |
| hsa-let-7g | ugagguaguaguuuguac aguu (SEQ ID NO: 104) | AGGCUGAGGUAGUAGUUUGUACAGUUUGAGG GUCUAUGAUACCACCCGGUACAGGAGAUAACU GUACAGGCCACUGCCUUGCCA (SEQ ID NO: 105) |
| hsa-let-7b | ugagguaguagguugugu gguu (SEQ ID NO: 106) | CGGGGUGAGGUAGUAGGUUGUGUGGUUUCAG GGCAGUGAUGUUGCCCCUCGGAAGAUAACUAU ACAACCUACUGCCUUCCCUG (SEQ ID NO: 107) |
| hsa-let-7a | ugagguaguagguuguau aguu (SEQ ID NO: 108) ugagguaguagguuguau aguu (SEQ ID NO: 109) ugagguaguagguuguau aguu (SEQ ID NO: 110) | UGGGAUGAGGUAGUAGGUUGUAUAGUUUUAG GGUCACACCCACCACUGGGAGAUAACUAUACA AUCUACUGUCUUUCCUA (SEQ ID NO: 111) AGGUUGAGGUAGUAGGUUGUAUAGUUUAGAA UUACAUCAAGGGAGAUAACUGUACAGCCUCCU AGCUUUCCU (SEQ ID NO: 112) GGGUGAGGUAGUAGGUUGUAUAGUUUGGGGC UCUGCCCUGCUAUGGGAUAACUAUACAAUCUA CUGUCUUUCCU (SEQ ID NO: 113) |
| hsa-miR-574-3p | ugaguguguguguga gugugu (SEQ ID NO: 114) | GGGACCUGCGUGGGUGCGGGCGUGUGAGUGU GUGUGUGUGAGUGUGUGUCGCUCCGGGUCCAC GCUCAUGCACACACCCACACGCCCACACUCAG G (SEQ ID NO: 115) |
| hsa-miR-19a | ugugcaaaucuaugcaaa acuga (SEQ ID NO: 116) | GCAGUCCUCUGUUAGUUUUGCAUAGUUGCACU ACAAGAAGAAUGUAGUUGUGCAAAUCUAUGC AAAACUGAUGGUGGCCUGC (SEQ ID NO: 117) |
| hsa-let-7f | ugagguaguagauuguau aguu (SEQ ID NO: 118) ugagguaguagauuguau aguu (SEQ ID NO: 119) | UCAGAGUGAGGUAGUAGAUUGUAUAGUUGUG GGGUAGUGAUUUUACCCUGUUCAGGAGAUAA CUAUACAAUCUAUUGCCUUCCCUGA (SEQ ID NO: 120) UGUGGGAUGAGGUAGUAGAUUGUAUAGUUUU AGGGUCAUACCCCAUCUUGGAGAUAACUAUAC AGUCUACUGUCUUUCCACG (SEQ ID NO: 121) |
| hsa-miR-140-5p | cagugguuuuacccuaug guag (SEQ ID NO: 122) | UGUGUCUCUCUCUGUGUCCUGCCAGUGGUUUU ACCCUAUGGUAGGUUACGUCAUGCUGUUCUAC CACAGGGUAGAACCACGGACAGGAUACCGGGG CACC (SEQ ID NO: 123) |
| hsa-miR-30a | uguaaacauccucgacug gaag (SEQ ID NO: 124) | GCGACUGUAAACAUCCUCGACUGGAAGCUGUG AAGCCACAGAUGGGCUUUCAGUCGGAUGUUU GCAGCUGC (SEQ ID NO: 125) |
| hsa-miR-190 | ugauauguuugauauauu aggu (SEQ ID NO: 126) | UGCAGGCCUCUGUGUGAUAUGUUUGAUAUAU UAGGUUGUUAUUUAAUCCAACUAUAUAUCAA ACAUAUUCCUACAGUGUCUUGCC (SEQ ID NO: 127) |
| hsa-miR-500 | uaauccuugcuaccuggg ugaga (SEQ ID NO: 128) aauccuugcuaccugggu (SEQ ID NO: 129) | GCUCCCCCUCUCUAAUCCUUGCUACCUGGGUG AGAGUGCUGUCUGAAUGCAAUGCACCUGGGCA AGGAUUCUGAGAGCGAGAGC (SEQ ID NO: 130) CCCCCUCUCUAAUCCUUGCUACCUGGGUGAGA GUGCUUUCUGAAUGCAGUGCACCCAGGCAAGG AUUCUGCAAGGGGGA (SEQ ID NO: 131) |
| hsa-let-7i | ugagguaguaguuugugc uguu (SEQ ID NO: 132) | CUGGCUGAGGUAGUAGUUUGUGCUGUUGGUC GGGUUGUGACAUUGCCCGCUGUGGAGAUAAC UGCGCAAGCUACUGCCUUGCUA (SEQ ID NO: 133) |
| hsa-miR-23a | aucacauugccagggauu ucc (SEQ ID NO: 134) | GGCCGGCUGGGGUUCCUGGGGAUGGGAUUUG CUUCCUGUCACAAAUCACAUUGCCAGGGAUUU CCAACCGACC (SEQ ID NO: 135) |

TABLE 1 -continued

List of microRNAs increased in CD14⁺CD16⁻ monocytes, CD14⁺CD16⁻ monocytes, or CSF from patients having neurodegenerative disorders compared to healthy controls

| MiRNA | Mature miRNA sequence | Precursor miRNA sequence |
|---|---|---|
| hsa-miR-142-3p | cauaaaguagaaagcacua cu (SEQ ID NO: 136) | GACAGUGCAGUCACCCAUAAAGUAGAAAGCAC UACUAACAGCACUGGAGGGUGUAGUGUUUCC UACUUUAUGGAUGAGUGUACUGUG (SEQ ID NO: 137) |
| hsa-miR-15a | uagcagcacauaaugguu ugug (SEQ ID NO: 138) | CCUUGGAGUAAAGUAGCAGCACAUAAUGGUU UGUGGAUUUUGAAAAGGUGCAGGCCAUAUUG UGCUGCCUCAAAAAUACAAGG (SEQ ID NO: 139) |
| hsa-miR-191 | caacggaaucccaaaagca gcug (SEQ ID NO: 140) | CGGCUGGACAGCGGGCAACGGAAUCCCAAAAG CAGCUGUUGUCUCCAGAGCAUUCCAGCUGCGC UUGGAUUUCGUCCCCUGCUCUCCUGCCU (SEQ ID NO: 141) |
| hsa-miR-720 | ucucgcuggggccucca (SEQ ID NO: 142) | CCGGAUCUCACACGGUGGUGUUAAUAUCUCGC UGGGGCCUCCAAAAUGUUGUGCCCAGGGGUGU UAGAGAAAACACCACACUUUGAGAUGAAUUA AGAGUCCUUUAUUAG (SEQ ID NO: 143) |
| hsa-miR-320a | aaaagcuggguugagagg gcga (SEQ ID NO: 144) | GCUUCGCUCCCCUCCGCCUUCUCUUCCCGGUU CUUCCCGGAGUCGGGAAAAGCUGGGUUGAGA GGGCGAAAAAGGAUGAGGU (SEQ ID NO: 145) |
| hsa-miR-520g | acaaagugcuucccuuua gagugu (SEQ ID NO: 146) | UCCCAUGCUGUGACCCUCUAGAGGAAGCACUU UCUGUUUGUUGUCUGAGAAAAAACAAAGUGC UUCCCUUUAGAGUGUUACCGUUUGGGA (SEQ ID NO: 147) |
| hsa-miR-204 | uucccuuugucauccuau gccu (SEQ ID NO: 148) | GGCUACAGUCUUUCUUCAUGUGACUCGUGGAC UUCCCUUUGUCAUCCUAUGCCUGAGAAUAUAU GAAGGAGGCUGGGAAGGCAAAGGGACGUUCA AUUGUCAUCACUGGC (SEQ ID NO: 149) |
| hsa-miR-708 | aaggagcuuacaaucuag cuggg (SEQ ID NO: 252) | AACUGCCCUCAAGGAGCUUACAAUCUAGCUGG GGGUAAAUGACUUGCACAUGAACACAACUAG ACUGUGAGCUUCUAGAGGGCAGGGA (SEQ ID NO: 253) |
| hsa-miR-197 | uucaccaccuucuccaccc agc (SEQ ID NO: 254) | GGCUGUGCCGGGUAGAGAGGGCAGUGGGAGG UAAGAGCUCUUCACCCUUCACCACCUUCUCCA CCCAGCAUGGCC (SEQ ID NO: 255) |
| hsa-miR-1274a | GUCCCUGUUCAG GCGCCA (SEQ ID NO: 256) | |
| hsa-miR-1274b | UCCCUGUUCGGG CGCCA (SEQ ID NO: 264) | |

MicroRNA markers decreased in CD14⁺CD16⁻ or CD14⁺CD16⁺ monocytes in subjects having a neurodegenerative disorder relative to healthy controls (CD14⁺CD16⁻ or CD14⁺CD16⁺ monocytes in healthy controls) are listed in Table 2.

TABLE 2

List of microRNAs decreased in CD14⁺CD16⁻ or CD14⁺CD16⁺ monocytes from subjects having a neurodegenerative disease compared to healthy controls

| miRNA | Mature miRNA sequence | Precursor miRNA sequence |
|---|---|---|
| hsa-miR-518f | gaaagcgcuucucuuuaga gg (SEQ ID NO: 150) | UCUCAUGCUGUGACCCUCUAGAGGGAAGCACU UUCUCUUGUCUAAAAGAAAAGAAAGCGCUUC UCUUUAGAGGAUUACUCUUUGAGA (SEQ ID NO: 151) |

TABLE 2 -continued

List of microRNAs decreased in CD14+CD16− or CD14+CD16+ monocytes from subjects having a neurodegenerative disease compared to healthy controls

| miRNA | Mature miRNA sequence | Precursor miRNA sequence |
|---|---|---|
| hsa-miR-206 | uggaauguaaggaagugug ugg (SEQ ID NO: 152) | UGCUUCCCGAGGCCACAUGCUUCUUUAUAUCC CCAUAUGGAUUACUUUGCUAUGGAAUGUAAG GAAGUGUGUGGUUUCGGCAAGUG (SEQ ID NO: 153) |
| hsa-miR-204 | uucccuuugucauccuaug ccu (SEQ ID NO: 154) | GGCUACAGUCUUUCUUCAUGUGACUCGUGGAC UUCCCUUUGUCAUCCUAUGCCUGAGAAUAUAU GAAGGAGGCUGGGAAGGCAAAGGGACGUUCA AUUGUCAUCACUGGC (SEQ ID NO: 155) |
| hsa-miR-137 | uuauugcuuaagaauacgc guag (SEQ ID NO: 156) | GGUCCUCUGACUCUCUUCGGUGACGGGUAUUC UUGGGUGGAUAAUACGGAUUACGUUGUUAUU GCUUAAGAAUACGCGUAGUCGAGGAGAGUAC CAGCGGCA (SEQ ID NO: 157) |
| hsa-miR-453 | AGGUUGUCCGUG GUGAGUUCGCA (SEQ ID NO: 257) | UGGUACUCGGAGGGAGGUUGUCCGUGGUGAG UUCGCAUUAUUUAAUGAUGCCCAAUACACGGU CGACCUCUUUUCGGUAUCA (SEQ ID NO: 258) |
| hsa-miR-603 | cacacacugcaauuacuuu ugc (SEQ ID NO: 158) | GAUUGAUGCUGUUGGUUUGGUGCAAAAGUAA UUGCAGUGCUUCCCAUUUAAAAGUAAUGGCAC ACACUGCAAUUACUUUUGCUCCAACUUAAUAC UU (SEQ ID NO: 159) |
| hsa-miR-1297 | uucaaguaauucaggug (SEQ ID NO: 160) | UGUUUAUCUCUAGGGUUGAUCUAUUAGAAUU ACUUAUCUGAGCCAAAGUAAUUCAAGUAAUU CAGGUGUAGUGAAAC (SEQ ID NO: 161) |
| hsa-miR-192 | cugaccuaugaauugacag cc (SEQ ID NO: 162) | GCCGAGACCGAGUGCACAGGGCUCUGACCUAU GAAUUGACAGCCAGUGCUCUCGUCUCCCCUCU GGCUGCCAAUUCCAUAGGUCACAGGUAUGUUC GCCUCAAUGCCAGC (SEQ ID NO: 163) |
| hsa-miR-526a | cucuagagggaagcacuuu cug (SEQ ID NO: 164) | CUCAGGCUGUGACCCUCUAGAGGGAAGCACUU UCUGUUGCUUGAAAGAAGAGAAAGCGCUUCC UUUUAGAGGAUUACUCUUUGAG (SEQ ID NO: 166) |
| | cucuagagggaagcacuuu cug (SEQ ID NO: 165) | GUGACCCUCUAGAGGGAAGCACUUUCUGUUGA AAGAAAAGAACAUGCAUCCUUUCAGAGGGUU AC (SEQ ID NO: 167) |
| hsa-miR-615-5p | gggggucccccggugcucgg auc (SEQ ID NO: 168) | CUCGGGAGGGGCGGGAGGGGGGUCCCCGGUGC UCGGAUCUCGAGGGUGCUUAUUGUUCGGUCCG AGCCUGGGUCUCCCUCUUCCCCCCAACCCCCC (SEQ ID NO: 169) |
| hsa-miR-655 | auaauacaugguuaaccuc uuu (SEQ ID NO: 170) | AACUAUGCAAGGAUAUUUGAGGAGAGGUUAU CCGUGUUAUGUUCGCUUCAUUCAUCAUGAAUA AUACAUGGUUAACCUCUUUUUGAAUAUCAGA CUC (SEQ ID NO: 171) |
| hsa-miR-450b-5p | uuuugcaauauguuccuga aua (SEQ ID NO: 172) | GCAGAAUUAUUUUUGCAAUAUGUUCCUGAAU AUGUAAAUAAGUGUAUUGGGAUCAUUUUGC AUCCAUAGUUUUGUAU (SEQ ID NO: 173) |
| hsa-miR-548b-3p | aaaaguaauugugguuuug gcc (SEQ ID NO: 174) | CAGACUAUAUAUUUAGGUUGGCGCAAAAGUA AUUGUGGUUUUGGCCUUUAUUUUCAAUGGCA AGAACCUCAGUUGCUUUUUGUGCCAACCUAAUA CUU (SEQ ID NO: 175) |
| hsa-miR-584 | uuauggguuugccugggacu gag (SEQ ID NO: 176) | UAGGGUGACCAGCCAUUAUGGUUUGCCUGGG ACUGAGGAAUUUGCUGGGAUAUGUCAGUUCC AGGCCAACCAGGCUGGUUGGUCUCCCUGAAGC AAC (SEQ ID NO: 177) |
| hsa-miR-548f | aaaaacuguaauuacuuuu (SEQ ID NO: 178) | AUUAGGUUGGUGCAAAAGUAAUCACAGUUUU UGACAUUACUUUCAAAGACAAAAACUGUAAU UACUUUUGGACCAACCUAAUAG (SEQ ID NO: 183) |
| | aaaaacuguaauuacuuuu (SEQ ID NO: 179) | UAAUAACUAUUAGGUUGGUGCGAACAUAAUU GCAGUUUUUAUCAUUACUUUUAAUGGCAAAA ACUGUAAUUACUUUUGCACCAACCUAAUAUUU UAGU (SEQ ID NO: 184) |

TABLE 2 -continued

List of microRNAs decreased in CD14⁺CD16⁻ or CD14⁺CD16⁺ monocytes from subjects having a neurodegenerative disease compared to healthy controls

| miRNA | Mature miRNA sequence | Precursor miRNA sequence |
|---|---|---|
| | aaaaacuguaauuacuuuu (SEQ ID NO: 180) | AUUAGGUUGGUGCAAACCUAAUUGCAAUUUU UGCAGUUUUUUAAGUAAUUGCAAAAACUGU AAUUACUUUUGCACCAACCUAAUAC (SEQ ID NO: 185) |
| | aaaaacuguaauuacuuuu (SEQ ID NO: 181) | GAGUUCUAACGUAUUAGGUUGGUGCAAAAGU AAUAGUGGUUUUUGCCAUUAAAAGUAAUGAC AAAAACUGUAAUUACUUUUGGAACAAUAUUA AUAGAAUUUCAG (SEQ ID NO: 186) |
| | aaaaacuguaauuacuuuu (SEQ ID NO: 182) | UAUUAGGUUGCUGCAAAAGUAAUCAUGUUUU UUUCCAUUGUAAGUAAUGGGAAAAACUGUAA UUACUUUUGUACCAACCUAAUAGC (SEQ ID NO: 187) |
| hsa-miR-300 | uauacaagggcagacucuc ucu (SEQ ID NO: 188) | UGCUACUUGAAGAGAGGUAAUCCUUCACGCAU UUGCUUUACUUGCAAUGAUUAUACAAGGGCA GACUCUCUCUGGGGAGCAAA (SEQ ID NO: 189) |
| hsa-miR-302c | uaagugcuuccauguuuca gugg (SEQ ID NO: 190) | CCUUUGCUUUAACAUGGGGGUACCUGCUGUGU GAAACAAAAGUAAGUGCUUCCAUGUUUCAGU GGAGG (SEQ ID NO: 191) |
| hsa-miR-328 | cuggcccucucugcccuuc cgu (SEQ ID NO: 82) | UGGAGUGGGGGGGCAGGAGGGGCUCAGGGAG AAAGUGCAUACAGCCCCUGGCCCUCUCUGCCC UUCCGUCCCCUG (SEQ ID NO: 83) |
| hsa-miR-421 | aucaacagacauuaauugg gcgc (SEQ ID NO: 192) | GCACAUUGUAGGCCUCAUUUAAAUGUUUGUUG AAUGAAAAAAUGAAUCAUCAACAGACAUUAA UUGGGCGCCUGCUCUGUGAUCUC (SEQ ID NO: 193) |
| hsa-miR-580 | uugagaaugaugaaucauu agg (SEQ ID NO: 194) | AUAAAAUUUCCAAUUGGAACCUAAUGAUUCA UCAGACUCAGAUAUUUAAGUUAACAGUAUUU GAGAAUGAUGAAUCAUUAGGUUCCGGUCAGA AAUU (SEQ ID NO: 195) |
| hsa-miR-651 | uuuaggauaagcuugacuu uug (SEQ ID NO: 196) | AAUCUAUCACUGCUUUUUAGGAUAAGCUUGA CUUUUGUUCAAAUAAAAAUGCAAAAGGAAAG UGUAUCCUAAAAGGCAAUGACAGUUUAAUGU GUUU (SEQ ID NO: 197) |
| hsa-miR-379 | ugguagacuauggaacgua gg (SEQ ID NO: 198) | AGAGAUGGUAGACUAUGGAACGUAGGCGUUA UGAUUUCUGACCUAUGUAACAUGGUCCACUAA CUCU (SEQ ID NO: 199) |
| hsa-miR-193a-3p | ugggucuuugcgggcgaga uga (SEQ ID NO: 200) | CGAGGAUGGGAGCUGAGGGCUGGGUCUUUGC GGGCGAGAUGAGGGUGUCGGAUCAACUGGCC UACAAAGUCCCAGUUCUCGGCCCCCG (SEQ ID NO: 201) |
| hsa-miR-515-3p | uucuccaaaagaaagcacu uucug (SEQ ID NO: 202) | UCUCAUGCAGUCAUUCUCCAAAAGAAAGCACU UUCUGUUGUCUGAAAGCAGAGUGCCUUCUUU UGGAGCGUUACUGUUUGAGA (SEQ ID NO: 204) |
| | uucuccaaaagaaagcacu uucug (SEQ ID NO: 203) | UCUCAUGCAGUCAUUCUCCAAAAGAAAGCACU UUCUGUUGUCUGAAAGCAGAGUGCCUUCUUU UGGAGCGUUACUGUUUGAGA (SEQ ID NO: 205) |
| hsa-miR-598 | uacgucaucguugucaucg uca (SEQ ID NO: 206) | GCUUGAUGAUGCUGCUGAUGCUGGCGGUGAU CCCGAUGGUGUGAGCUGGAAAUGGGGUGCUA CGUCAUCGUUGUCAUCGUCAUCAUCAUCAUCC GAG (SEQ ID NO: 207) |
| hsa-miR-513a-5p | uucacagggaggugucau (SEQ ID NO: 208) | GGGAUGCCACAUUCAGCCAUUCAGCGUACAGU GCCUUUCACAGGGAGGUGUCAUUUAUGUGAA CUAAAAUAUAAAUUUCACCUUUCUGAGAAGG GUAAUGUACAGCAUGCACUGCAUAUGUGGUG UCCC (SEQ ID NO: 210) |
| | uucacagggaggugucau (SEQ ID NO: 209) | GGAUGCCACAUUCAGCCAUUCAGUGUGCAGUG CCUUUCACAGGGAGGUGUCAUUUAUGUGAAC UAAAAUAUAAAUUUCACCUUUCUGAGAAGGG UAAUGUACAGCAUGCACUGCAUAUGUGGGUGU CC (SEQ ID NO: 211) |

TABLE 2 -continued

List of microRNAs decreased in CD14⁺CD16⁻ or CD14⁺CD16⁺ monocytes from subjects having a neurodegenerative disease compared to healthy controls

| miRNA | Mature miRNA sequence | Precursor miRNA sequence |
|---|---|---|
| hsa-miR-640 | augauccaggaaccugccucu (SEQ ID NO: 212) | GUGACCCUGGGCAAGUUCCUGAAGAUCAGACACAUCAGAUCCCUUAUCUGUAAAAUGGGCAUGAUCCAGGAACCUGCCUCUACGGUUGCCUUGGGG (SEQ ID NO: 213) |
| hsa-miR-548g | aaaacuguaauuacuuuuguac (SEQ ID NO: 214) | AGUUAUUAGAUUAGUGCAAAAGUAAUUGCAGUUUUUGCAUUACGUUCUAUGGCAAAACUGUAAUUACUUUUGUACCAACAUAAUACUUC (SEQ ID NO: 215) |
| hsa-miR-1206 | uguucauguagauguuuaagc (SEQ ID NO: 216) | CAGUGUUCAUGUAGAUGUUUAAGCUCUUGCAGUAGGUUUUUGCAAGCUAGUGAACGCUG (SEQ ID NO: 217) |
| hsa-miR-383 | agaucagaaggugauugugcu (SEQ ID NO: 218) | CUCCUCAGAUCAGAAGGUGAUUGUGGCUUUGGGUGGAUAUUAAUCAGCCACAGCACUGCCUGGUCAGAAAGAG (SEQ ID NO: 219) |
| hsa-miR-649 | aaaccuguguuguucaagaguc (SEQ ID NO: 220) | GGCCUAGCCAAAUACUGUAUUUUUGAUCGACAUUUGGUUGAAAAAUAUCUAUGUAUUAGUAAACCUGUGUUGUUCAAGAGUCCACUGUGUUUUGCUG (SEQ ID NO: 221) |
| hsa-miR-592 | uugugucaauaugcgaugaugu (SEQ ID NO: 222) | UAUUAUGCCAUGACAUUGUGUCAAUAUGCGAUGAUGUGUUGUGAUGGCACAGCGUCAUCACGUGGUGACGCAACAUCAUGACGUAAGACGUCACAAC (SEQ ID NO: 223) |
| hsa-miR-2054 | cuguaauauaaauuuaauuauu (SEQ ID NO: 224) | CUGUAAUAUAAAUUUAAUUUAUUCUCUAUCAUUAAAAAAUGUAUUACAG (SEQ ID NO: 225) |
| hsa-miR-450a | uuuugcgauguguccuaauau (SEQ ID NO: 226) | AAACGAUACUAAACUGUUUUUGCGAUGUGUUCCUAAUAUGCACUAUAAAUAUAUUGGGAACAUUUUGCAUGUAUAGUUUUGUAUCAAUAUA (SEQ ID NO: 228) |
| | uuuugcgauguguccuaauau (SEQ ID NO: 227) | CCAAAGAAAGAUGCUAAACUAUUUUUGCGAUGUGUUCCUAAUAUGUAAAUAUAAAUGUAUUGGGGACAUUUUGCAUUCAUAGUUUUGUAUCAAUAAUAUGG (SEQ ID NO: 229) |
| hsa-miR-362-3p | aauccuuggaaccuaggugugagu (SEQ ID NO: 230) | CUUGAAUCCUUGGAACCUAGGUGUGAGUGCUAUUUCAGUGCAACACACCUAUUCAAGGAUUCAAA (SEQ ID NO: 231) |
| hsa-miR-193a-3p | ugggucuuugcgggcgagauga (SEQ ID NO: 232) | CGAGGAUGGGAGCUGAGGGCUGGGUCUUUGCGGGCGAGAUGAGGGUGUCGGAUCAACUGGCCUACAAAGUCCCAGUUCUCGGCCCCCG (SEQ ID NO: 233) |
| hsa-miR-566 | gggcgccugugaucccaac (SEQ ID NO: 234) | GCUAGGCGUGGUGGCGGGCGCCUGUGAUCCCAACUACUCAGGAGGCUGGGGCAGCAGAAUCGCUUGAACCCGGGAGGCGAAGGUUGCAGUGAGC (SEQ ID NO: 235) |
| hsa-miR-142-3p | cauaaaguagaaagcacuacu (SEQ ID NO: 236) | GACAGUGCAGUCACCCAUAAAGUAGAAAGCACUACUAACAGCACUGGAGGGUGUAGUGUUUCCUACUUUAUGGAUGAGUGUACUGUG (SEQ ID NO: 237) |
| hsa-miR-15a | uagcagcacauaauggUUUgug (SEQ ID NO: 238) | CCUUGGAGUAAAGUAGCAGCACAUAAUGGUUUGUGGAUUUUGAAAAGGUGCAGGCCAUAUUGUGCUGCCUCAAAAAUACAAGG (SEQ ID NO: 239) |
| hsa-miR-1537 | aaaaccgucuaguuacaguugu (SEQ ID NO: 240) | ACAGCUGUAAUUAGUCAGUUUUCUGUCCUGUCCACACAGAAAACCGUCUAGUUACAGUUGU (SEQ ID NO: 241) |
| hsa-miR-148b | ucagugcaucacagaacuuugu (SEQ ID NO: 242) | CAAGCACGAUUAGCAUUUGAGGUGAAGUUCUGUUAUACACUCAGGCUGUGGCUCUCUGAAAGUCAGUGCAUCACAGAACUUUGUCUCGAAAGCUUUCUA (SEQ ID NO: 243) |

TABLE 2-continued

List of microRNAs decreased in CD14⁺CD16⁻ or CD14⁺CD16⁺ monocytes from subjects having a neurodegenerative disease compared to healthy controls

| miRNA | Mature miRNA sequence | Precursor miRNA sequence |
|---|---|---|
| hsa-miR-494 | ugaaacauacacgggaaaccuc (SEQ ID NO: 244) | GAUACUCGAAGGAGAGGUUGUCCGUGUUGUC UUCUCUUUAUUUAUGAUGAAACAUACACGGG AAACCUC AGUAUC (SEQ ID NO: 245) |
| hsa-miR-369-3p | agaucgaccguguuauauucgc (SEQ ID NO: 246) | UUGAAGGGAGAUCGACCGUGUUAUAUUCGCU UUAUUGACUUCGAAUAAUACAUGGUUGAUCU UUUCUCAG (SEQ ID NO: 247) |
| hsa-miR-10a | uacccuguagauccgaauugug (SEQ ID NO: 248) | GAUCUGUCUGUCUUCUGUAUAUACCCUGUAGA UCCGAAUUUGUGUAAGGAAUUUUGUGGUCAC AAAUUCGUAUCUAGGGGAAUAUGUAGUUGAC AUAAACACUCCGCUCU (SEQ ID NO: 249) |
| hsa-miR-30d | uguaaacauccccgacuggaag (SEQ ID NO: 250) | GUUGUUGUAAACAUCCCCGACUGGAAGCUGUA AGACACAGCUAAGCUUUCAGUCAGAUGUUUGC UGCUAC (SEQ ID NO: 251) |
| hsa-miR-660 | uacccauugcauaucggaguug (SEQ ID NO: 260) accuccugugugcauggauua (SEQ ID NO: 261) | CUGCUCCUUCUCCCAUACCCAUUGCAUAUCGG AGUUGUGAAUUCUCAAAACACCUCCUGUGUGC AUGGAUUACAGGAGGGUGAGCCUUGUCAUCG UG (SEQ ID NO: 259) |

MicroRNA markers increased in monocytes (CD14⁺CD16⁻ or CD14⁺CD16⁺ monocytes) or the CSF in subjects having ALS relative to healthy controls (CD14⁺CD16⁻ or CD14⁺CD16⁺ monocytes, or the CSF in healthy controls) are listed in Table 3.

TABLE 3

List of microRNAs increased in CD14⁺CD16⁻ or CD14⁺CD16⁺ monocytes, or in the CSF in subjects having ALS relative to healthy controls.

| | | |
|---|---|---|
| hsa-miR-19b | hsa-miR-26b | hsa-let-7a |
| hsa-miR-106b | hsa-miR-24 | hsa-miR-574-3p |
| hsa-miR-30b | hsa-miR-181a | hsa-miR-19a |
| hsa-miR-21 | hsa-miR-103 | hsa-let-7f |
| hsa-miR-142-5p | hsa-miR-155 | hsa-miR-140-5p |
| hsa-miR-27a | hsa-miR-532-3p | hsa-miR-30a |
| hsa-miR-16 | hsa-miR-1260 | hsa-miR-190 |
| hsa-miR-374a | hsa-miR-423 | hsa-miR-500 |
| hsa-miR-374b | hsa-miR-361-5p | hsa-let-7i |
| hsa-miR-101 | hsa-miR-93 | hsa-miR-23a |
| hsa-miR-340 | hsa-miR-221 | hsa-miR-142-3p |
| hsa-miR-30e | hsa-miR-20a | hsa-miR-15a |
| hsa-miR-29c | hsa-miR-30c | hsa-let-7b |
| hsa-miR-29a | hsa-miR-15b | hsa-miR-26a |
| hsa-miR-223 | hsa-let-7g | |

MicroRNA markers decreased in monocytes (CD14⁺CD16⁻ or CD14⁺CD16⁺ monocytes) in subjects having ALS relative to healthy controls (CD14⁺CD16⁻ or CD14⁺CD16⁺ monocytes in healthy controls) are listed in Table 4.

TABLE 4

List of microRNAs decreased in CD14⁺CD16⁻ or CD14⁺CD16⁺ monocytes in subjects having ALS compared to healthy controls.

| | | | |
|---|---|---|---|
| hsa-miR-518f | hsa-miR-655 | hsa-miR-421 | hsa-miR-383 |
| hsa-miR-206 | hsa-miR-450b-5p | hsa-miR-651 | hsa-miR-649 |
| hsa-miR-204 | hsa-miR-548b-3p | hsa-miR-379 | hsa-miR-592 |
| hsa-miR-137 | hsa-miR-584 | hsa-miR-193a-3p | hsa-miR-2054 |
| hsa-miR-453 | hsa-miR-548f | hsa-miR-515-3p | hsa-miR-566 |

TABLE 4-continued

List of microRNAs decreased in CD14⁺CD16⁻ or CD14⁺CD16⁺ monocytes in subjects having ALS compared to healthy controls.

| | | | |
|---|---|---|---|
| hsa-miR-603 | hsa-miR-300 | hsa-miR-598 | hsa-miR-494 |
| hsa-miR-1297 | hsa-miR-302c | hsa-miR-513a-5p | hsa-miR-142-3p |
| hsa-miR-192 | hsa-miR-328 | hsa-miR-640 | hsa-miR-1206 |
| hsa-miR-526a | hsa-miR-421 | hsa-miR-548g | hsa-miR-580 |
| hsa-miR-615-5p | | | |
| hsa-miR-660 | | | |

MicroRNA markers increased in CD14⁺CD16⁻ monocytes from ALS patients relative to CD14⁺CD16⁻ monocytes from healthy controls are listed in Table 5.

TABLE 5

List of microRNAs increased in CD14⁺CD16⁻ monocytes from ALS patients relative to CD14⁺CD16⁻ monocytes from healthy controls.

| | | | |
|---|---|---|---|
| hsa-miR-1260 | hsa-let-7g | hsa-miR-26a | hsa-miR-500 |
| hsa-miR-30a | hsa-let-7b | hsa-miR-16 | hsa-miR-150 |
| hsa-miR-423 | hsa-let-7a | hsa-miR-374b | hsa-miR-30e |
| hsa-miR-361-5p | hsa-miR-574-3p | hsa-miR-140-5p | hsa-miR-29c |
| hsa-miR-93 | hsa-miR-26b | hsa-miR-101 | hsa-miR-29a |
| hsa-miR-103 | hsa-miR-532-3p | hsa-miR-142-5p | hsa-miR-223 |
| hsa-miR-24 | hsa-miR-19a | hsa-miR-374a | hsa-mIR-423 |
| hsa-miR-221 | hsa-let-7f | hsa-miR-340 | hsa-miR-1260 |
| hsa-miR-20a | hsa-miR-27a | hsa-miR-21 | hsa-miR-30a |
| hsa-miR-30c | hsa-miR-106b | hsa-miR-155 | hsa-miR-30b |
| hsa-miR-181a | hsa-miR-19b | hsa-miR-146a | hsa-miR-190 |
| hsa-miR-15b | | | |

MicroRNAs that are decreased in CD14⁺CD16⁻ monocytes from ALS patients relative to CD14⁺CD16⁻ monocytes from healthy controls are listed in Table 6.

TABLE 6

List of microRNAs decreased in CD14⁺CD16⁻ monocytes from ALS patients relative to CD14⁺CD16⁻ monocytes from healthy controls.

| | | | |
|---|---|---|---|
| hsa-miR-328 | hsa-miR-513a-5p | hsa-miR-302c | hsa-miR-453 |
| hsa-miR-651 | hsa-miR-640 | hsa-miR-2054 | hsa-miR-204 |

TABLE 6-continued

List of microRNAs decreased in CD14+CD16− monocytes from ALS patients relative to CD14+CD16− monocytes from healthy controls.

| | | | |
|---|---|---|---|
| hsa-miR-379 | hsa-miR-548g | hsa-miR-584 | hsa-miR-518f |
| hsa-miR-300 | hsa-miR-1206 | hsa-miR-655 | hsa-miR-206 |
| hsa-miR-548f | hsa-miR-450b-5p | hsa-miR-421 | hsa-miR-192 |
| hsa-miR-193a-3p | hsa-miR-548b-3p | hsa-miR-615-5p | hsa-miR-566 |
| hsa-miR-137 | hsa-miR-383 | hsa-miR-526a | hsa-miR-598 |
| hsa-miR-580 | hsa-miR-649 | hsa-miR-603 | |
| hsa-miR-515-3p | hsa-miR-592 | hsa-miR-1297 | |
| hsa-miR-660 | | | |

MicroRNA markers uniquely increased in CD14+CD16− monocytes from ALS patients relative to CD14+CD16− monocytes from both MS subjects and healthy controls are listed in Table 7.

TABLE 7

List of microRNAs uniquely increased in CD14+CD16− monocytes from ALS patients relative to CD14+CD16− monocytes from both MS subjects and healthy controls

| | | | |
|---|---|---|---|
| hsa-miR-19b | hsa-miR-16 | hsa-miR-29c | hsa-miR-181a |
| hsa-miR-106b | hsa-miR-374a | hsa-miR-29a | hsa-miR-103 |
| hsa-miR-30b | hsa-miR-374b | hsa-miR-223 | hsa-miR-155 |
| hsa-miR-21 | hsa-miR-101 | hsa-miR-26a | hsa-miR-532-3p |
| hsa-miR-142-5p | hsa-miR-340 | hsa-miR-26b | hsa-miR-24 |
| hsa-miR-27a | hsa-miR-30e | | |

MicroRNA markers uniquely decreased in CD14+CD16− monocytes from ALS patients relative to CD14+CD16− monocytes from both MS subjects and healthy controls are listed in Table 8.

TABLE 8

List of microRNAs uniquely decreased in CD14+CD16− monocytes from ALS patients relative to CD14+CD16− monocytes from both MS subjects and healthy controls

| | | | |
|---|---|---|---|
| hsa-miR-518f | hsa-miR-603 | hsa-miR-655 | hsa-miR-300 |
| hsa-miR-206 | hsa-miR-1297 | hsa-miR-450b-5p | hsa-miR-302c |
| hsa-miR-204 | hsa-miR-192 | hsa-miR-548b-3p | hsa-miR-328 |
| hsa-miR-137 | hsa-miR-526a | hsa-miR-584 | hsa-miR-421 |
| hsa-miR-453 | hsa-miR-615-5p | hsa-miR-548f | hsa-miR-580 |

MicroRNA markers increased in CD14+CD16+ monocytes from ALS patients relative to CD14+CD16+ monocytes from healthy controls are listed in Table 9.

TABLE 9

List of microRNAs increased in CD14+CD16+ monocytes from ALS patients relative to CD14+CD16+ monocytes from healthy controls

| | | | |
|---|---|---|---|
| hsa-miR-708 | hsa-miR-24 | hsa-miR-26a | hsa-miR-21 |
| hsa-miR-142-5p | hsa-miR-103 | hsa-miR-30b | hsa-miR-142-3p |
| hsa-miR-15b | hsa-miR-23a | hsa-miR-16 | hsa-miR-340 |
| hsa-miR-223 | hsa-miR-29a | hsa-miR-15a | hsa-let-7i |

MicroRNA markers decreased in CD14+CD16+ monocytes from ALS patients relative to CD14+CD16+ monocytes from healthy controls are listed in Table 10.

TABLE 10

List of microRNAs decreased in CD14+CD16+ monocytes from ALS patients relative to CD14+CD16+ monocytes from healthy controls hsa-miR-598
hsa-miR-494
hsa-miR-142-3p MicroRNA markers uniquely increased in CSF from subjects having sporadic ALS or familial ALS compared to CSF from healthy controls are listed in Table 11.

TABLE 11

List of microRNAs uniquely increased in CSF from subjects having sporadic ALS or familial ALS compared to CSF from healthy controls

| miRNA | Form of ALS |
|---|---|
| hsa-miR-27b | Familial and sporadic ALS |
| hsa-miR-99b | Sporadic ALS |
| hsa-miR-146a | Sporadic ALS |
| hsa-miR-150 | Sporadic ALS |
| hsa-miR-328 | Familial and Sporadic ALS |
| hsa-miR-532-3p | Familial and Sporadic ALS |

MicroRNA markers increased in monocytes (CD14+CD16− or CD14+CD16+ monocytes) in subjects having MS relative to healthy controls (CD14+CD16− or CD14+CD16+ in healthy controls) are listed in Table 12.

TABLE 12

List of microRNAs increased in CD14+CD16− or CD14+CD16+ monocytes in subjects having MS relative to CD14+CD16− or CD14+CD16+ monocytes in healthy controls.

| | | | | |
|---|---|---|---|---|
| hsa-miR-320c | hsa-miR-1260 | hsa-miR-19b | hsa-miR-340 | hsa-let-320a |
| hsa-miR-27b | hsa-miR-720 | hsa-miR-106b | hsa-miR-26b | hsa-miR-520g |
| hsa-miR-664 | hsa-miR-1274a | hsa-let-7g | hsa-miR-1260 | hsa-miR-204 |
| hsa-miR-432-5p | hsa-miR-423 | hsa-miR-181a | hsa-miR-361-5p | hsa-miR-29a |
| hsa-miR-92a | hsa-miR-197 | hsa-miR-140-5p | hsa-miR-374b | hsa-miR-23a |
| hsa-miR-24 | hsa-miR-30a | hsa-miR-142-5p | hsa-let-7a | hsa-miR-142-3p |
| hsa-miR-93 | hsa-miR-221 | hsa-miR-19a | hsa-miR-532-3p | hsa-miR-103 |
| hsa-miR-20a | hsa-miR-361-5p | hsa-let-7b | hsa-miR-155 | hsa-miR-15a |
| hsa-miR-let-7a | hsa-miR-103 | hsa-miR-221 | hsa-miR-27a | hsa-miR-21 |
| hsa-miR-30c | hsa-miR-16 | hsa-miR-15b | hsa-miR-146a | hsa-miR-223 |
| hsa-miR-181a | hsa-miR-30b | hsa-miR-574-3p | hsa-let-7i | hsa-miR-1274b |
| hsa-miR-423 | hsa-miR-26a | hsa-let-7f | hsa-let-191 | |

MicroRNA markers decreased in monocytes (CD14+CD16− or CD14+CD16+ monocytes) in subjects having MS relative to healthy controls (CD14+CD16− or CD14+CD16+ monocytes in healthy controls) are listed in Table 13.

TABLE 13

List of microRNAs decreased in CD14+CD16− or CD14+CD16+ monocytes in subjects having MS compared to CD14+CD16− or CD14+CD16+ monocytes in healthy controls

| | | | |
|---|---|---|---|
| hsa-miR-649 | hsa-miR-362-3p | hsa-miR-603 | hsa-miR-15a |
| hsa-miR-383 | hsa-miR-450b-5p | hsa-miR-584 | hsa-miR-1537 |
| hsa-miR-1206 | hsa-miR-302c | hsa-miR-204 | hsa-miR-148b |
| hsa-miR-548g | hsa-miR-548f | hsa-miR-526a | hsa-miR-369-3p |
| hsa-miR-640 | hsa-miR-328 | hsa-miR-453 | hsa-miR-615-5p |
| hsa-miR-592 | hsa-miR-580 | hsa-miR-2054 | hsa-miR-10a |
| hsa-miR-598 | hsa-miR-421 | hsa-miR-655 | hsa-miR-30d |
| hsa-miR-515-3p | hsa-miR-1297 | hsa-miR-518f | hsa-miR-494 |
| hsa-miR-513a-5p | hsa-miR-548b-3p | hsa-miR-206 | hsa-miR-142-3p |
| hsa-miR-651 | hsa-miR-615-5p | hsa-miR-192 | hsa-miR-651 |
| hsa-miR-379 | hsa-miR-137 | hsa-miR-450a | |
| hsa-miR-193a-3p | hsa-miR-300 | hsa-miR-566 | |

MicroRNA markers increased in CD14+CD16− monocytes from MS patients relative to CD14+CD16− monocytes from MS patients are listed in Table 14.

TABLE 14

List of microRNAs increased in CD14+CD16− monocytes from MS patients relative to CD14+CD16− monocytes from healthy controls.

| | | | |
|---|---|---|---|
| hsa-miR-720 | hsa-miR-20a | hsa-let-7g | hsa-miR-26b |
| hsa-miR-1274a | hsa-miR-93 | hsa-miR-181a | hsa-miR-21 |
| hsa-miR-320c | hsa-miR-361-5p | hsa-miR-140-5p | hsa-miR-374b |
| hsa-miR-27b | hsa-miR-423 | hsa-miR-142-5p | hsa-let-7a |
| hsa-miR-664 | hsa-miR-24 | hsa-miR-19a | hsa-miR-532-3p |
| hsa-miR-1260 | hsa-miR-103 | hsa-let-7b | hsa-miR-155 |
| hsa-miR-423 | hsa-miR-16 | hsa-miR-15b | hsa-miR-27a |
| hsa-miR-197 | hsa-miR-30b | hsa-miR-574-3p | hsa-miR-146a |
| hsa-miR-30a | hsa-miR-26a | hsa-let-7f | hsa-miR-92a |
| hsa-miR-30c | hsa-miR-19b | hsa-miR-340 | hsa-miR-1274b |
| hsa-miR-221 | hsa-miR-106b | hsa-miR-101 | |

MicroRNA markers decreased in CD14+CD16− monocytes from MS patients relative to CD14+CD16− monocytes from healthy patients are listed in Table 15.

TABLE 15

List of microRNAs decreased in CD14+CD16− monocytes from MS patients relative to CD14+CD16− monocytes from healthy controls.

| | | | |
|---|---|---|---|
| hsa-miR-649 | hsa-miR-193a-3p | hsa-miR-615-5p | hsa-miR-206 |
| hsa-miR-383 | hsa-miR-450a | hsa-miR-137 | hsa-miR-192 |
| hsa-miR-1206 | hsa-miR-362-3p | hsa-miR-300 | hsa-miR-566 |
| hsa-miR-548g | hsa-miR-450b-5p | hsa-miR-603 | hsa-miR-142-3p |
| hsa-miR-640 | hsa-miR-302c | hsa-miR-584 | hsa-miR-15a |
| hsa-miR-592 | hsa-miR-548f | hsa-miR-204 | hsa-miR-1537 |
| hsa-miR-598 | hsa-miR-328 | hsa-miR-526a | hsa-miR-148b |
| hsa-miR-515-3p | hsa-miR-580 | hsa-miR-453 | hsa-miR-379 |
| hsa-miR-513a-5p | hsa-miR-421 | hsa-miR-2054 | hsa-miR-548b-3p |
| hsa-miR-651 | hsa-miR-1297 | hsa-miR-655 | hsa-miR-518f |

MicroRNA markers uniquely increased in CD14+CD16− monocytes from MS patients relative to CD14+CD16− monocytes from both ALS subjects and healthy controls are listed in Table 16.

TABLE 16

List of microRNAs uniquely increased in CD14+CD16− monocytes from MS patients relative to CD14+CD16− monocytes from both ALS subjects and healthy controls

| | | |
|---|---|---|
| hsa-miR-320c | hsa-miR-664 | hsa-miR-92a |
| hsa-miR-27b | hsa-miR-432-5p | |

MicroRNA markers uniquely decreased in CD14+CD16− monocytes from MS patients relative to CD14+CD16− monocytes from both ALS subjects and healthy controls are listed in Table 17.

TABLE 17

List of microRNAs uniquely decreased in CD14+CD16− monocytes from MS patients relative to CD14+CD16− monocytes from both ALS subjects and healthy controls

| | | |
|---|---|---|
| hsa-miR-142-3p | hsa-miR-1537 | hsa-miR-148b |
| hsa-miR-15a | hsa-miR-362-3p | |

MicroRNA markers increased in CD14+CD16+ monocytes from MS patients compared to CD14+CD16+ monocytes from healthy controls are shown in Table 18.

TABLE 18

List of microRNAs increased in CD14+CD16+ monocytes from MS patients compared to CD14+CD16+ monocytes from healthy controls

| | | | |
|---|---|---|---|
| hsa-let-7i | hsa-miR-520g | hsa-miR-24 | hsa-miR-21 |
| hsa-miR-191 | hsa-miR-204 | hsa-miR-30b | hsa-miR-16 |
| hsa-miR-1260 | hsa-miR-340 | hsa-miR-142-3p | hsa-miR-142-5p |
| hsa-miR-720 | hsa-miR-15b | hsa-miR-103 | hsa-miR-223 |
| hsa-miR-1274a | hsa-miR-29a | hsa-miR-15a | |
| hsa-miR-320a | hsa-miR-23a | hsa-miR-26a | |

MicroRNA markers decreased in CD14+CD16+ monocytes from MS patients relative to CD14+CD16+ monocytes from healthy controls are listed in Table 19.

TABLE 19

List of microRNAs decreased in CD14+CD16+ monocytes from MS patients relative to CD14+CD16+ monocytes from healthy controls

| | | |
|---|---|---|
| hsa-miR-369-3p | hsa-miR-10a | hsa-miR-598 |
| hsa-miR-615-5p | hsa-miR-30d | hsa-miR-494 |

Inflammatory markers decreased in CD14+CD16− monocytes from patients having neurodegenerative disorders relative to CD14+CD16− monocytes from healthy controls are listed in Table 20.

TABLE 20

List of inflammatory markers decreased in CD14+CD16− monocytes from patients having neurodegenerative disorders relative to CD14+CD16− monocytes from healthy controls

| Marker | Protein sequence (NCBI Accession No.; Version No.) | mRNA sequence (NCBI Accession No.; Version No.) |
|---|---|---|
| BCL6 | NP_001128210; NP_001128210.1 | NM_001134738; NM_001134738.1 |
|  | NP_001124317; NP_001124317.1 | NM_001130845; NM_001130845.1 |
| IL1RAP | NP_001161401; NP_001161401.1 | NM_001167929; NM_001167929.1 |
|  | NP_001161402; NP_001161402.1 | NM_001167930; NM_001167930.1 |
|  | NP_001161403; NP_001161403.1 | NM_001167931; NM_001167931.1 |
| PLCB1 | NP_056007; NP_056007.1 | NM_015192; NM_015192.2 |
|  | NP_877398; NP_877398.1 | NM_182734; NM_182734.1 |
| MAFK | AAC14426; AAC14426.1 | AF059194; AF059194.1 |
| NFE2L2 | NP_006155; NP_006155.2 | NM_006164; NM_006164.3 |
|  | NP_001138884; NP_001138884.1 | NM_001145412; NM_001145412.1 |
|  | NP_001138885; NP_001138885.1 | NM_001145413; NM_001145413.1 |
| DDIT3 | NP_001181982; NP_001181982.1 | NM_001195053; NM_001195053.1 |
|  | NP_001181983; NP_001181983.1 | NM_001195054; NM_001195054.1 |
|  | NP_001181984TN; NP_001181984.1 | NM_001195055; NM_001195055.1 |
|  | NP_001181985; NP_001181985.1 | NM_001195056; NM_001195056.1 |
|  | NP_004074; NP_004074.2 | NM_004083; NM_004083.5 |
| GNAQ | NP_002063; NP_002063.2 | NM_002072; NM_002072.3 |
| RAPGEF2 | NP_055062; NP_055062.1 | NM_014247; NM_014247.2 |
| MAFG | NP_002350; NP_002350.1 | NM_002359; NM_002359.3 |
|  | NP_116100; NP_116100.2 | NM_032711; NM_032711.3 |
| PTK2N | NP_722560; NP_722560.1 | NM_153831; NM_153831.3 |
|  | NP_005598; NP_005598.3 | NM_005607; NM_005607.4 |
|  | NP_001186578; NP_001186578.1 | NM_001199649; NM_001199649.1 |
| MKNK1 | NP_003675; NP_003675.2 | NM_003684; NM_003684.4 |
|  | NP_945324; NP_945324.1 | NM_198973; NM_198973.2 |
|  | NP_001129025; NP_001129025.1 | NM_001135553; NM_001135553.1 |
| RIPK1 | NP_003795; NP_003795.2 | NM_003804; NM_003804.3 |
| IL15 | NP_751915; NP_751915.1 | NM_172175; NM_172175.2 |
|  | NP_000576; NP_000576.1 | NM_000585; NM_000585.4 |
| MAP3K1 | NP_005912; NP_005912.1 | NM_005921; NM_005921.1 |
| PPP1R12B | NP_001184060; NP_001184060.1 | NM_001197131; NM_001197131.1 |
|  | NP_001161330; NP_001161330.1 | NM_001167858; NM_001167858.1 |
|  | NP_001161329; NP_001161329.1 | NM_001167857; NM_001167857.1 |
|  | NP_115287; NP_115287.1 | NM_032104; NM_032104.2 |
|  | NP_115286; NP_115286.1 | NM_032103; NM_032103.2 |
|  | NP_002472; NP_002472.2 | NM_002481; NM_002481.3 |
| MAPK14 | NP_620582; NP_620582.1 | NM_139013; NM_139013.2 |
|  | NP_001306; NP_001306.1 | NM_001315; NM_001315.2 |
|  | NP_620583; NP_620583.1 | NM_139014; NM_139014.2 |
|  | NP_620581; NP_620581.1 | NM_139012; NM_139012.2 |
| CXCR4 | NP_001008540; NP_001008540.1 | NM_001008540; NM_001008540.1 |
|  | NP_003458; NP_003458.1 | NM_003467; NM_003467.2 |
| MEF2A | NP_001165365; NP_001165365.1 | NM_001171894; NM_001171894.1 |
|  | NP_001124400; NP_001124400.1 | NM_001130928; NM_001130928.1 |
|  | NP_001124399; NP_001124399.1 | NM_001130927; NM_001130927.1 |
|  | NP_001124398; NP_001124398.1 | NM_001130926; NM_001130926.1 |
|  | NP_005578; NP_005578.2 | NM_005587; NM_005587.2 |
| TGFB1 | NP_000651; NP_000651.3 | NM_000660; NM_000660.4 |
| NR3C1 | NP_001191194; NP_001191194.1 | NM_001204265; NM_001204265.1 |
|  | NP_001019265; NP_001019265.1 | NM_001024094; NM_001024094.1 |
|  | NP_001018661; NP_001018661.1 | NM_001020825; NM_001020825.1 |
|  | NP_001018087; NP_001018087.1 | NM_001018077; NM_001018077.1 |
|  | NP_001018086; NP_001018086.1 | NM_001018076; NM_001018076.1 |
|  | NP_001018085; NP_001018085.1 | NM_001018075; NM_001018075.1 |
|  | NP_001018084; NP_001018084.1 | NM_001018074; NM_001018074.1 |
|  | NP_000167; NP_000167.1 | NM_000176; NM_000176.2 |
| MAP3K5 | NP_005914; NP_005914.1 | NM_005923; NM_005923.3 |
| CDC42 | NP_426359; NP_426359.1 | NM_044472; NM_044472.2 |
|  | NP_001782; NP_001782.1 | NM_001791; NM_001791.3 |
|  | NP_001034891; NP_001034891.1 | NM_001039802; NM_001039802.1 |
| RAF1 | NP_002871; NP_002871.1 | NM_002880; NM_002880.3 |
| CFB | NP_001701; NP_001701.2 | NM_001710; NM_001710.5 |
| ITGB2 | NP_000202; NP_000202.2 | NM_000211; NM_000211.3 |
|  | NP_001120963; NP_001120963.1 | NM_001127491; NM_001127491.1 |
| ATF2 | NP_001871; NP_001871.2 | NM_001880; NM_001880.2 |
| CREB1 | NP_004370; NP_004370.1 | NM_004379; NM_004379.3 |
|  | NP_604391; NP_604391.1 | NM_134442; NM_134442.3 |
| MAP2K6 | NP_002749; NP_002749.2 | NM_002758; NM_002758.3 |

TABLE 20-continued

List of inflammatory markers decreased in CD14⁺CD16⁻ monocytes from patients having neurodegenerative disorders relative to CD14⁺CD16⁻ monocytes from healthy controls

| Marker | Protein sequence (NCBI Accession No.; Version No.) | mRNA sequence (NCBI Accession No.; Version No.) |
|---|---|---|
| MAP3K7 | NP_663306; NP_663306.1 | NM_145333; NM_145333.1 |
| | NP_663305; NP_663305.1 | NM_145332; NM_145332.1 |
| | NP_663304; NP_663304.1 | NM_145331; NM_145331.1 |
| | NP_003179; NP_003179.1 | NM_003188; NM_003188.2 |
| RPS6KA5 | NP_004746; NP_004746.2 | NM_004755; NM_004755.2 |
| | NP_872198; NP_872198.1 | NM_182398; NM_182398.1 |
| TRADD | NP_003780; NP_003780.1 | NM_003789; NM_003789.3 |
| C5 | NP_001726; NP_001726.2 | NM_001735; NM_001735.2 |
| NCR1 | NP_004820; NP_004820.1 | NM_004829; NM_004829.5 |
| | NP_001138929; NP_001138929.1 | NM_001145457; NM_001145457.1 |
| | NP_001138930; NP_001138930.1 | NM_001145458; NM_001145458.1 |
| | NP_001229285; NP_001229285.1 | NM_001242356; NM_001242356.1 |
| | NP_001229286; NP_001229286.1 | NM_001242357; NM_001242357.1 |
| SOCS1 | NP_003736; NP_003736.1 | NM_003745; NM_003745.1 |
| TAGAP | NP_687034; NP_687034.1 | NM_152133; NM_152133.1 |
| | NP_473455; NP_473455.2 | NM_054114; NM_054114.3 |
| | NP_620165; NP_620165.1 | NM_138810; NM_138810.2 |
| PTGS2 | NP_000954; NP_000954.1 | NM_000963; NM_000963.2 |
| PRDM1 | NP_001189; NP_001189.2 | NM_001198; NM_001198.3 |
| | NP_878911; NP_878911.1 | NM_182907; NM_182907.2 |
| PLAUR | NP_002650; NP_002650.1 | NM_002659; NM_002659.3 |
| | NP_001005376; NP_001005376.1 | NM_00100537; NM_001005376.2 |
| FOS | NP_005243; NP_005243.1 | NM_005252; NM_005252.3 |
| NFKBIZ | NP_113607; NP_113607.1 | NM_031419; NM_031419.3 |
| | NP_001005474; NP_001005474.1 | NM_001005474; NM_001005474.2 |
| LILRA5 | NP_067073; NP_067073.1 | NM_021250; NM_021250.2 |
| | NP_871714; NP_871714.1 | NM_181985; NM_181985.2 |
| | NP_870994; NP_870994.1 | NM_181879; NM_181879.2 |
| | NP_871715; NP_871715.1 | NM_181986; NM_181986.2 |
| RIPK2 | NP_003812; NP_003812.1 | NM_003821; NM_003821.5 |
| LCP2 | NP_005556; NP_005556.1 | NM_005565; NM_005565.3 |
| LITAF | NP_004853; NP_004853.2 | NM_004862; NM_004862.3 |
| | NP_037531; NP_037531.2 | NM_013399; NM_013399.2 |
| | NP_001129945; NP_001129945.1 | NM_001136473; NM_001136473.1 |
| | | NR_024320; NR_024320.1 |
| TNFRSF8 | NP_001234; NP_001234.2 | NM_001243; NM_001243.3 |
| | NP_694421; NP_694421.1 | NM_152942; NM_152942.2 |
| MEF2D | NP_005911; NP_005911.1 | NM_005920; NM_005920.2 |
| CDKN1A | NP_000380; NP_000380.1 | NM_000389; NM_000389.2 |
| | NP_510867; NP_510867.1 | NM_078467; NM_078467.2 |
| | NP_001207707; NP_001207707.1 | NM_001220778; NM_001220778.1 |
| | NP_001207706; NP_001207706.1 | NM_001220777; NM_001220777.1 |
| CD83 | NP_004224; NP_004224.1 | NM_004233; NM_004233.3 |
| | NP_001035370; NP_001035370.1 | NM_001040280; NM_001040280.1 |
| | NP_001238830; NP_001238830.1 | NM_001251901; NM_001251901.1 |
| CASP10 | NP_116759; NP_116759.2 | NM_032977; NM_032977.3 |
| | NP_116756; NP_116756.2 | NM_032974; NM_032974.4 |
| | NP_001221; NP_001221.2 | NM_001230; NM_001230.4 |
| | NP_116758; NP_116758.1 | NM_032976; NM_032976.3 |
| | NP_001193471; NP_001193471.1 | NM_001206542; NM_001206542.1 |
| | NP_001193453; NP_001193453.1 | NM_001206524; NM_001206524.1 |
| LTB4R | NP_858043; NP_858043.1 | NM_181657; NM_181657.3 |
| | NP_001137391; NP_001137391.1 | NM_001143919; NM_001143919.2 |

Inflammatory markers uniquely increased in CD14⁺CD16⁻ monocytes from patients having neurodegenerative disorders relative to CD14⁺CD16⁻ monocytes from healthy controls are listed in Table 21.

TABLE 21

List of inflammatory markers increased in CD14⁺CD16⁻ monocytes from patients having neurodegenerative disorders relative to CD14⁺CD16⁻ monocytes from healthy controls

| Marker | Protein sequence (NCBI Accession No.; Version No.) | mRNA sequence (NCBI Accession No.; Version No.) |
|---|---|---|
| CSF1 | NP_000748; NP_000748.3 | NM_000757; NM_000757.5 |
| | NP_757351; NP_757351.1 | NM_172212; NM_172212.2 |
| | NP_757349; NP_757349.1 | NM_172210; NM_172210.2 |

TABLE 21-continued

List of inflammatory markers increased in CD14+CD16−
monocytes from patients having neurodegenerative disorders
relative to CD14+CD16− monocytes from healthy controls

| Marker | Protein sequence (NCBI Accession No.; Version No.) | mRNA sequence (NCBI Accession No.; Version No.) |
|---|---|---|
| IL10 | NP_000563; NP_000563.1 | NM_000572; NM_000572.2 |
| IL1A | NP_000566; NP_000566.3 | NM_000575; NM_000575.3 |
| HLA-DRA | NP_061984; NP_061984.2 | NM_019111; NM_019111.4 |
| RAC1 | NP_061485; NP_061485.1 | NM_018890; NM_018890.3 |
|  | NP_008839; NP_008839.2 | NM_006908; NM_006908.4 |
| GRB2 | NP_987102; NP_987102.1 | NM_203506; NM_203506.2 |
|  | NP_002077; NP_002077.1 | NM_002086; NM_002086.4 |
| PLA2G4A | NP_077734; NP_077734.1 | NM_024420; NM_024420.2 |
| GNAS | NP_001070956; NP_001070956.1 | NM_001077488; NM_001077488.2 |
|  | NP_001070957; NP_001070957.1 | NM_001077489; NM_001077489.2 |
|  | NP_001070958; NP_001070958.1 | NM_001077490; NM_001077490.1 |
|  | NP_057676; NP_057676.1 | NM_016592; NM_016592.2 |
|  | NP_536351; NP_536351.1 | NM_080426; NM_080426.2 |
|  | NP_536350; NP_536350.2 | NM_080425; NM_080425.2 |
|  | NP_000507; NP_000507.1 | NM_000516; NM_000516.4 |
| GNB1 | NP_002065; NP_002065.1 | NM_002074; NM_002074.3 |
| TGFB3 | NP_003230; NP_003230.1 | NM_003239; NM_003239.2 |
| IL6R | NP_000556; NP_000556.1 | NM_000565; NM_000565.3 |
|  | NP_852004; NP_852004.1 | NM_181359; NM_181359.2 |
|  | NP_001193795; NP_001193795.1 | NM_001206866; NM_001206866.1 |
| CXCL3 | NP_002081; NP_002081.2 | NM_002090; NM_002090.2 |
| IL18 | NP_001553; NP_001553.1 | NM_001562; NM_001562.3 |
|  | NP_001230140; NP_001230140.1 | NM_001243211; NM_001243211.1 |
| IL1RN | NP_776214; NP_776214.1 | NM_173842; NM_173842.2 |
|  | NP_000568; NP_000568.1 | NM_000577; NM_000577.4 |
|  | NP_776213; NP_776213.1 | NM_173841; NM_173841.2 |
|  | NP_776215; NP_776215.1 | NM_173843; NM_173843.2 |
| KEAP1 | NP_036421; NP_036421.2 | NM_012289; NM_012289.3 |
|  | NP_987096; NP_987096.1 | NM_203500; NM_203500.1 |
| LIMK1 | NP_002305; NP_002305.1 | NM_002314; NM_002314.3 |
|  | NP_001191355; NP_001191355.1 | NM_001204426; NM_001204426.1 |
| MYC | NP_002458; NP_002458.2 | NM_002467; NM_002467.4 |
| NFKB1 | NP_003989; NP_003989.2 | NM_003998; NM_003998.2 |
| SHC1 | NP_892113; NP_892113.4 | NM_183001; NM_183001.4 |
|  | NP_001123512; NP_001123512.1 | NM_001130040; NM_001130040.1 |
|  | NP_001123513; NP_001123513.1 | NM_001130041; NM_001130041.1 |
|  | NP_001189788; NP_001189788.1 | NM_001202859; NM_001202859.1 |
|  | NP_003020; NP_003020.2 | NM_003029; NM_003029.4 |
| TLR2 | NP_003255; NP_003255.2 | NM_003264; NM_003264.3 |
| TLR4 | NP_612564; NP_612564.1 | NM_138554; NM_138554.3 |
| TNFSF14 | NP_003798; NP_003798.2 | NM_003807; NM_003807.3 |
|  | NP_742011; NP_742011.2 | NM_172014; NM_172014.2 |
| AHR | NP_001612; NP_001612.1 | NM_001621; NM_001621.4 |
| BCL3 | NP_005169; NP_005169.1 | NM_005178; NM_005178.4 |
| CD44 | NP_000601; NP_000601.3 | NM_000610; NM_000610.3 |
|  | NP_001001389; NP_001001389.1 | NM_001001389; NM_001001389.1 |
|  | NP_001001390; NP_001001390.1 | NM_001001390; NM_001001390.1 |
|  | NP_001001391; NP_001001391.1 | NM_001001391; NM_001001391.1 |
|  | NP_001001392; NP_001001392.1 | NM_001001392; NM_001001392.1 |
|  | NP_001189484; NP_001189484.1 | NM_001202555; NM_001202555.1 |
|  | NP_001189485; NP_001189485.1 | NM_001202556; NM_001202556.1 |
|  | NP_001189486; NP_001189486.1 | NM_001202557; NM_001202557.1 |
| CD81 | NP_004347; NP_004347.1 | NM_004356; NM_004356.3 |
| CD82 | NP_002222; NP_002222.1 | NM_002231; NM_002231.3 |
|  | NP_001020015; NP_001020015.1 | NM_001024844; NM_001024844.1 |
| FCER1A | NP_001992; NP_001992.1 | NM_002001; NM_002001.2 |
| FCER1G | NP_004097; NP_004097.1 | NM_004106; NM_004106.1 |
| IL4R | NP_000409; NP_000409.1 | NM_000418; NM_000418.2 |
|  | NP_001008699; NP_001008699.1 | NM_001008699; NM_001008699.1 |
| IL7R | NP_002176; NP_002176.1 | NM_002185; NM_002185.2 |
| ITGAM | NP_000623; NP_000623.2 | NM_000632; NM_000632.3 |
|  | NP_001139280; NP_001139280.1 | NM_001145808; NM_001145808.1 |
| JAK3 | NP_000206; NP_000206.2 | NM_000215; NM_000215.3 |
| KLRB1 | NP_002249; NP_002249.1 | NM_002258; NM_002258.2 |
| LILRB4 | NP_001074907; NP_001074907.1 | NM_001081438; NM_001081438.1 |
|  | NP_006838; NP_006838.3 | NM_006847; NM_006847.3 |
| PTAFR | NP_000943; NP_000943.1 | NM_000952; NM_000952.4 |
|  | NP_001158193; NP_001158193.1 | NM_001164721; NM_001164721.1 |
|  | NP_001158194; NP_001158194.1 | NM_001164722; NM_001164722.2 |
|  | NP_001158195; NP_001158195.1 | NM_001164723; NM_001164723.2 |
| RUNX1 | NP_001745; NP_001745.2 | NM_001754; NM_001754.4 |
|  | NP_001001890; NP_001001890.1 | NM_001001890; NM_001001890.2 |
|  | NP_001116079; NP_001116079.1 | NM_001122607; NM_001122607.1 |

TABLE 21-continued

List of inflammatory markers increased in CD14+CD16−
monocytes from patients having neurodegenerative disorders
relative to CD14+CD16− monocytes from healthy controls

| Marker | Protein sequence (NCBI Accession No.; Version No.) | mRNA sequence (NCBI Accession No.; Version No.) |
|---|---|---|
| SELL | NP_000646; NP_000646.2 | NM_000655; NM_000655.4 |
| TNFSF8 | NP_001235; NP_001235.1; | NM_001244; NM_001244.3 |
|  | NP_001239219; NP_001239219.1 | NM_001252290; NM_001252290.1 |
| TRAF3 | NP_663777; NP_663777.1 | NM_145725; NM_145725.1 |
|  | NP_001186356; NP_001186356.1 | NM_001199427; NM_001199427.1 |
|  | NP_003291; NP_003291.2 | NM_003300; NM_003300.3 |
|  | NP_663778; NP_663778.1 | NM_145726; NM_145726.2 |
| CCL2 | NP_002973; NP_002973.1 | NM_002982; NM_002982.3 |
| CCL4 | NP_002975; NP_002975.1 | NM_002984; NM_002984.2 |
| CCR1 | NP_001286; NP_001286.1 | NM_001295; NM_001295.2 |
| TLR1 | NP_003254; NP_003254.2 | NM_003263; NM_003263.3 |
|  | AAC34137; AAC34137.1 | U88540; U88540.1 |
|  | AAI09094; AAI09094.1 | BC109093; BC109093.1 |
|  | AAI09095; AAI09095.1 | BC109094; BC109094.1 |
|  | AAH89403; AAH89403.1 | BC089403; BC089403.1 |
|  | AAY85642; AAY85642.1 | DQ012263; DQ012263.1 |
|  | AAY85640; AAY85640.1 | DQ012261; DQ012261.1 |
|  | AAY85638; AAY85638.1 | DQ012259; DQ012259.1 |
|  | AAY85636; AAY85636.1 | DQ012257; DQ012257.1 |
|  | AAY85634; AAY85634.1 | DQ012255; DQ012255.1 |
|  | AAY85643; AAY85643.1 | DQ012264; DQ012264.1 |
|  | AAY85641; AAY85641.1 | DQ012262; DQ012262.1 |
|  | AAY85639; AAY85639.1 | DQ012260; DQ012260.1 |
|  | AAY85637; AAY85637.1 | DQ012258; DQ012258.1 |
|  | AAY85635; AAY85635.1 | DQ012256; DQ012256.1 |
|  | AAY85633; AAY85633.1 | DQ012254; DQ012254.1 |
| TLR5 | NP_003259; NP_003259.2 | NM_003268; NM_003268.5 |
|  | AAC34136; AAC34136.1 | U88881; U88881.1 |
|  | BAG55042; BAG55042.1 | AB445645; AB445645.1 |
|  | AAI09120; AAI09120.1 | BC109119; BC109119.1 |
|  | AAI09119; AAI09119.1 | BC109118; BC109118.1 |
|  | BAB43955; BAB43955.1 | AB060695; AB060695.1 |

Diagnostic Methods

Provided herein are methods of diagnosing a neurodegenerative disorder. These methods include determining a level of one or more (e.g., at least two, three, four, five or six) microRNAs listed in Tables 1-19 and/or one or more (e.g., at least two, three, four, five or six) inflammatory markers listed in Tables 20-21 in cerebrospinal fluid or a CD14+CD16− or CD14+CD16+ monocyte (e.g., peripheral or blood-derived monocyte) from the subject, and comparing the level of the one or more microRNAs and/or the one or more inflammatory markers with a reference level of the one or more microRNAs and/or one or more inflammatory markers. An increase or decrease in the level of the one or more microRNAs and/or the level of the one or more inflammatory markers as compared to the reference level(s) indicates that the subject has a neurodegenerative disease as outlined in detail below.

In some embodiments, a subject can be diagnosed as having a neurodegenerative disorder if the level of one or more or more (e.g., at least two, three, four, five or six) microRNAs listed in Table 1 in the CSF or a CD14+CD16− or CD14+CD16+ monocyte (e.g., peripheral or blood-derived monocyte) from the subject is increased compared to a reference level of the one or more microRNAs listed in Table 1, and/or if the level of one or more (e.g., at least two, three, four, five or six) microRNAs listed in Table 2 in the CSF or a CD14+CD16− or CD14+CD16+ monocyte (e.g., peripheral or blood-derived monocyte) from the subject is decreased compared to a reference level of the one or more microRNAs listed in Table 2.

In some embodiments, a subject can be diagnosed as having a neurodegenerative disorder if the level of one or more (e.g., at least two, three, four, five or six) microRNAs listed in Tables 3 and 12 in a CD14+CD16− or CD14+CD16+ monocyte from the subject is increased compared to a reference level of the one or more (e.g., at least two, three, four, five or six) microRNAs listed in Tables 3 and 12, and/or if the level of one or more microRNAs listed in Tables 4 and 13 in a CD14+CD16− or CD14+CD16+ monocyte from the subject is decreased compared to a reference level of the one or more microRNAs listed in Tables 4 and 13.

In some embodiments, a subject can be diagnosed as having a neurodegenerative disorder if the level of one or more (e.g., at least two, three, four, five or six) microRNAs listed in Table 5 and Table 14, and/or one or more inflammatory markers (e.g., at least two, three, four, five or six) in Table 21 in a CD14+CD16− monocyte from the subject is increased compared to a reference level of the one or more microRNAs listed in Table 5 and Table 14 and/or a reference level of the one or more inflammatory markers listed in Table 21; and/or if the level of one or more (e.g., at least two, three, four, five or six) microRNAs listed in Table 6 and Table 15, and/or one or more (e.g., at least two, three, four, five or six) inflammatory markers in Table 20 in a CD14+CD16− monocyte from the subject is decreased compared to a reference level of the one or more microRNAs listed in Table 6 and Table 15 and/or a reference level of the one or more inflammatory markers listed in Table 20.

In some embodiments, a subject can be diagnosed as having amyotrophic lateral sclerosis if the level of one or more (e.g., at least two, three, four, five or six) microRNAs listed in Tables 5 and 7, and/or one or more (e.g., at least two, three, four, five or six) inflammatory markers listed in Table 21 in a CD14$^+$CD16$^-$ monocyte from the subject is increased compared to a reference level of the one or more microRNAs listed in Tables 5 and 7, and/or a reference level of the one or more inflammatory markers in Table 21; and/or if the level of one or more (e.g., at least two, three, four, five or six) microRNAs listed in Tables 6 and 8, and/or one or more (e.g., at least two, three, four, five or six) inflammatory markers listed in Table 20 in a CD14$^+$CD16$^-$ monocyte from the subject is decreased compared to a reference level of the one or more microRNAs listed in Tables 6 and 8, and/or a reference level of one or more inflammatory markers listed in Table 20.

In some embodiments, a subject can be diagnosed as having amyotrophic lateral sclerosis if the level of one or more (e.g., at least two, three, four, five or six) microRNAs listed in Table 9 in a CD14$^+$CD16$^+$ monocyte from the subject is increased compared to a reference level of the one or more microRNAs listed in Table 9, and/or if the level of one or more (e.g., one, two, or three) microRNAs listed in Table 10 in a CD14$^+$CD16$^+$ monocyte from the subject is decreased as compared to a reference level of the one or more microRNAs listed in Table 10.

In some embodiments, a subject can be diagnosed as having amyotrophic lateral sclerosis if the level of one or more (e.g., at least two, three, four, five or six) of hsa-miR-27b, hsa-miR-99b, hsa-miR-146a, hsa-miR-150, hsa-miR-328, and hsa-miR-532-3p are increased in cerebrospinal fluid of the subject compared to a reference level of hsa-miR-27b, hsa-miR-99b, hsa-miR-146a, hsa-miR-150, hsa-miR-328, and hsa-miR-532-3p.

In some embodiments, a subject can be diagnosed as having familial ALS if the level of hsa-miR-27b in the cerebrospinal fluid from the subject is increased compared to a reference level of hsa-miR-27b and the level of one or more (e.g., one, two, three, four, or five) of hsa-miR-99b, hsa-miR-146a, hsa-miR-150, hsa-miR-328, and hsa-miR-532-3p in the cerebrospinal fluid from the subject is decreased or not significantly changed compared to a reference level of one or more of hsa-miR-99b, hsa-miR-146a, hsa-miR-150, hsa-miR-328, and hsa-miR-532-3p.

In embodiments, a subject can be diagnosed as having sporadic ALS if the level of two or more (e.g., two, three, four, five, or six) microRNAs selected from hsa-27b, hsa-miR-99b, hsa-miR-146a, hsa-miR-150, hsa-miR-328, and hsa-miR-532-3p in the cerebrospinal fluid from the subject is increased compared to a reference level of the one or more microRNAs. In embodiments, a subject can be diagnosed as having sporadic ALS if the level of one or more (e.g., two, three, four or five) microRNAs selected from hsa-miR-99b, hsa-miR-146a, hsa-miR-150, hsa-miR-328, and hsa-miR-532-3p in the cerebrospinal fluid from the subject is increased compared to a reference level of the one or more microRNAs.

In some embodiments, a subject can be diagnosed as having multiple sclerosis if the level of one or more (e.g., at least two, three, four, five, or six) microRNAs in Table 14 and Table 16, and/or one or more (e.g., at least two, three, four, five, or six) inflammatory markers in Table 21 in a CD14$^+$CD16$^-$ from the subject is increased compared to a reference level of the one or more microRNAs listed in Table 14 and Table 16 and/or the reference level of the one or more inflammatory markers listed in Table 21; and/or if the level of one or more (e.g., at least two, three, four, five, or six) microRNAs in Table 15 and Table 17, and/or one or more (e.g., at least two, three, four, five, or six) inflammatory markers in Table 20 in a CD14$^+$CD16$^-$ from the subject is decreased compared to a reference level of the one or more microRNAs listed in Table 15 and Table 17, and/or the reference level of the one or more inflammatory markers listed in Table 20.

In some embodiments, a subject can be diagnosed as having multiple sclerosis if the level of one or more (e.g., at least two, three, four, five, or six) microRNAs in Table 18 in CD14$^+$CD16$^+$ monocyte from the subject is increased compared to a reference level of the one or more microRNAs in Table 18 and/or if the level of one or more (e.g., at least two, three, four, five, or six) microRNAs in Table 19 in a CD14$^+$CD16$^+$ monocyte from the subject is decreased compared to a reference level of the one or more microRNAs listed in Table 19.

The levels of the one or more microRNAs (both the mature and precursor microRNAs) described in Tables 1-19 can be determined using molecular biology methods known in the art. For example, levels of any of the microRNAs described herein can be measured using techniques that include the use of a polymerase chain reaction (PCR) and suitable primers, e.g., quantitative real-time PCR (qRT-PCR). Primers for each of the mature and precursor microRNAs described herein can be designed using methods known in the art. Likewise, the levels of an mRNA encoding any of the inflammatory markers in Tables 20 and 21 can be determined using techniques that include the use of a PCR and suitable primers. For example, a primer can contain at least 7 (e.g., at least 8, 9, 10, 11, 12, 13, 14, 15, 16, 17, 18, 19, or 20) contiguous nucleotides that are complementary to a sequence present in the target microRNA or the target inflammatory marker mRNA. Primers can include one or more of the modifications described herein (e.g., one or more modifications in the backbone, one or more modifications in the nucleobase(s), and one or more modifications in the sugar(s)). The primers can also include a label (e.g., a radioisotope or a fluorophore). The primers can also be conjugated to secondary molecules or agents in order to improve the stability of the primers (as described herein).

The levels of a protein encoded by the inflammatory marker genes listed in Tables 20 and 21 can be detected using a number of techniques known in the art which utilize antibodies that specifically bind to one of the proteins listed in Tables 20 and 21 (e.g., immunoblotting).

Any of the methods described herein may further include obtaining or collecting a sample from a subject (e.g., a biological sample containing cerebrospinal fluid or peripheral blood). In some embodiments, the methods (e.g., any of the methods described herein) further include purifying a monocyte (e.g., a CD14$^+$CD16$^-$ monocyte or a CD14$^+$CD16$^+$ monocyte from a biological sample from the subject). Methods of purifying a CD14$^+$CD16$^-$ monocyte or a CD14$^+$CD16$^-$ monocyte can be performed using a variety of methods known in the art, e.g., antibody-based methods, such as fluorescence-assisted cell sorting (FACS).

Any of the methods described herein can be performed on patients presenting to a health care facility (e.g., a hospital, clinic, or an assisted care facility). The subjects may present with one or more symptoms of a neurodegenerative disorder (e.g., any of the symptoms of a neurodegenerative disorder described herein). The subject can also present with no symptoms (an asymptomatic subject) or just one symptom of a neurodegenerative disorder. The subject can have a familial history of a neurodegenerative disorder (e.g., familial ALS).

The diagnostic methods described herein can be performed by any health care professional (e.g., a physician, a laboratory technician, a nurse, a physician's assistant, and a nurse's assistant). The diagnostic methods described herein can be used in combination with any additional diagnostic testing methods known in the art (e.g., the observation or assessment of one or more symptoms of a neurodegenerative disorder in a subject).

Methods of Selecting a Subject for Treatment

Also provided are methods of selecting a subject for treatment of a neurodegenerative disorder. These methods include determining a level of one or more (e.g., at least two, three, four, five, or six) of the microRNAs listed in Tables 1-19 and/or the level of one or more (e.g., at least two, three, four, five, or six) inflammatory markers listed in Tables 20 and 21 in cerebrospinal fluid or a CD14$^+$CD16$^-$ or CD14$^+$CD16$^+$ monocyte from the subject; comparing the level of the one or more microRNAs in cerebrospinal fluid or a CD14$^+$CD16$^-$ or CD14$^+$CD16$^+$ monocyte from the subject to a reference level of the one or more microRNAs and/or a reference level of the one or more inflammatory markers; and selecting a subject having an increase in the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a CD14$^+$CD16$^-$ or CD14$^+$CD16$^+$ monocyte from the subject compared to a reference level of the one or more microRNAs listed in Tables 1, 3, 5, 7, 9, 11, 12, 14, 16, or 18, and/or a reference level of the one or more inflammatory markers listed in Table 21; and/or a decrease in the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject compared to a reference level of the one or more microRNAs listed in Tables 2, 4, 6, 8, 10, 13, 15, 17, and 19, and/or a reference level of one or more inflammatory markers listed in Table 20 for treatment of a neurodegenerative disorder.

A subject may be selected for treatment on the basis of the relative expression of one or more (e.g., at least two, three, four, five, or six) microRNAs listed in Tables 1-19 and/or one or more (e.g., at least two, three, four, five, or six) inflammatory markers listed in Tables 20 and 21 as described in the above section describing diagnostic methods. For example, an increase in the level of one or more (e.g., at least two, three, four, five, or six) microRNAs listed in Tables 1, 3, 5, 7, 9, 11, 12, 14, 16, or 18 and/or the level of one or more (e.g., at least two, three, four, five, or six) inflammatory markers listed in Table 21 (compared to a reference level), as used to diagnose a subject as having a neurodegenerative disorder, may likewise be used to select a subject for treatment of a neurodegenerative disorder. Similarly, a decrease in the level of one or more (e.g., at least two, three, four, five, or six) microRNAs listed in Tables 2, 4, 6, 8, 10, 13, 15, 17, and 19 and/or the level of one or more (e.g., at least two, three, four, five, or six) inflammatory markers listed in Table 20 (compared to a reference level), as used to diagnose a subject as having a neurodegenerative disorder, may likewise be used to select a subject for treatment of a neurodegenerative disorder.

The levels of the one or more microRNAs (both the mature and precursor microRNAs) described in Tables 1-19 can be determined using molecular biology methods known in the art. For example, levels of any of the microRNAs described herein can be measured using techniques that include the use of a polymerase chain reaction (PCR) and suitable primers, e.g., quantitative real-time PCR (qRT-PCR). Primers for each of the mature and precursor microRNAs described herein can be designed using methods known in the art. Likewise, the levels of an mRNA encoding any of the inflammatory markers in Tables 20 and 21 can be determined using techniques that include the use of a PCR and suitable primers. For example, a primer can contain at least 7 (e.g., at least 8, 9, 10, 11, 12, 13, 14, 15, 16, 17, 18, 19, or 20) contiguous nucleotides that are complementary to a sequence present in the target microRNA or the target inflammatory marker mRNA. Primers can include one or more of the modifications described herein (e.g., one or more modifications in the backbone, one or more modifications in the nucleobase(s), and one or more modifications in the sugar(s)). The primers can also include a label (e.g., a radioisotope or a fluorophore). The primers can also be conjugated to secondary molecules or agents in order to improve the stability of the primers (as described herein). The methods can be performed by any health care professional (e.g., a physician, a nurse, a physician's assistant, a laboratory technician, or a nurse's assistant).

The subjects may present with one or more symptoms (e.g., at least two, three, or four) of a neurodegenerative disorder (e.g., any of the symptoms of a neurodegenerative disorder described herein). The subject can also present with no symptoms or just one symptom of a neurodegenerative disorder. The subject can have a familial history of a neurodegenerative disorder (e.g., familial ALS). The subject can be previously diagnosed as having a neurodegenerative disorder.

Treatments of neurodegenerative disorders that can be administered to the subject include riluzole, corticosteroids, beta-interferon, glatiramer, fingolimod, natalizumab, mitoxantrone, muscle relaxants, and amantadine. Additional treatments of neurodegenerative disorders include physical therapy and plasmapheresis.

Methods of Identifying a Subject at Risk of Developing a Neurodegenerative Disorder Also provided are methods of identifying a subject at risk of developing a neurodegenerative disorder. These methods include determining a level of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a CD14$^+$CD16$^-$ or CD14$^+$CD16$^+$ monocyte from the subject; comparing the level of the one or more microRNAs in the cerebrospinal fluid or a CD14$^+$CD16$^-$ or CD14$^+$CD16$^+$ monocyte from the subject to a reference level of the one or more microRNAs and/or a reference level of the one or more inflammatory markers. A subject is identified as having an increased risk of developing a neurological disorder if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a CD14$^+$CD16$^-$ or CD14$^+$CD16$^+$ monocyte from the subject is increased compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject is decreased compared to a reference level of the one or more microRNAs listed in Tables 2, 4, 6, 8, 10, 13, 15, 17, and 19, and/or a reference level of one or more inflammatory markers listed in Table 20.

In some embodiments, a subject is identified having a decreased risk of developing a neurological disorder if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a $CD14^+CD16^-$ or $CD14^+CD16^+$ monocyte from the subject is decreased or not significantly changed compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a $CD14^+CD16^-$ or $CD14^+CD16^+$ monocyte from the subject is increased or not significantly changed compared to a reference level of the one or more microRNAs listed in Tables 2, 4, 6, 8, 10, 13, 15, 17, and 19, and/or a reference level of one or more inflammatory markers listed in Table 20.

In some embodiments, a subject may be identified as having an increased or decreased risk of developing a neurodegenerative disorder on the basis of the relative expression of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a $CD14^+CD16^-$ or $CD14^+CD16^+$ monocyte from the subject as compared to a reference value as described in the above section describing diagnostic methods. For example, an increase in the level of one or more (e.g., at least two, three, four, five, or six) microRNAs listed in Tables 1, 3, 5, 7, 9. 11, 12, 14, 16, and 18 and/or the level of one or more (e.g., at least two, three, four, five, or six) inflammatory markers listed in Table 21 in the cerebrospinal fluid or a $CD14^+CD16^-$ or $CD14^+CD16^+$ monocyte from the subject (compared to a reference level), as used to diagnose a subject as having a neurodegenerative disorder, may likewise be used to identify a subject at increased risk of developing a neurodegenerative disorder. Similarly, a decrease in the level of one or more (e.g., at least two, three, four, five, or six) microRNAs listed in Tables 2, 4, 6, 8, 10, 13, 15, 17, and 19 or the level of one or more (e.g., at least two, three, four, five, or six) inflammatory markers listed in Table 20 in the cerebrospinal fluid or a $CD14^+CD16^-$ or $CD14^+CD16^+$ monocyte (compared to a reference level), as used to diagnose a subject as having a neurodegenerative disorder, may likewise be used to identify a subject at increased risk of developing a neurodegenerative disorder.

In some embodiments, an increase in the level of one or more (e.g., at least two, three, four, five, or six) microRNAs listed in Tables 2, 4, 6, 8, 10, 13, 15, 17, or 19 and/or the level of one or more (e.g., at least two, three, four, five, or six) inflammatory markers listed in Table 20 in the cerebrospinal fluid or a $CD14^+CD16^-$ or $CD14^+CD16^+$ monocyte from the subject (compared to a reference level), when a decrease in the level of the one or more microRNAs or a decrease in the level of the one or more inflammatory markers indicates a diagnosis of a neurodegenerative disease (as detailed in the section describing diagnostic methods above), indicates that the subject is at decreased risk of developing a neurodegenerative disorder. In some embodiments, a decrease in the level of one or more (e.g., at least two, three, four, five, or six) microRNAs listed in Tables 1, 3, 5, 7, 9, 11, 12, 14, 16, and 18, or the level of one or more (e.g., at least two, three, four, five, or six) inflammatory markers listed in Table 21 in the cerebrospinal fluid or a $CD14^+CD16^-$ or $CD14^+CD16^+$ monocyte from the subject (compared to a reference level), when an increase in the level of one or more microRNAs or an increase in the level of the one or more inflammatory markers indicates a diagnosis of a neurodegenerative disorder (as detailed in the section describing diagnostic methods above), indicates that the subject is at decreased risk of developing a neurodegenerative disorder.

In any of the methods described herein, the increased or decreased risk is relative to a subject that does not have an increase or decrease in the levels of one or more (e.g., at least two, three, four, five, or six) microRNA listed in Tables 1-19 and/or does not have an increase or decrease in the levels of one or more (e.g., at least two, three, four, five, or six) inflammatory markers listed in Tables 20 and 21 (e.g., a subject that is not diagnosed as having a neurodegenerative disorder using any of the methods described herein).

The levels of any of the microRNAs in Tables 1-19 or the levels of any of the inflammatory markers listed in Tables 20 and 21 may be performed using standard molecular biology methods (e.g., the PCR-based and antibody-based methods described herein). The methods can be performed by any health care professional (e.g., a physician, a nurse, a physician's assistant, a laboratory technician, or a nurse's assistant).

The subjects may present with one or more symptoms of a neurodegenerative disorder (e.g., any of the symptoms of a neurodegenerative disorder described herein). The subject can also present with no symptoms or just one symptom of a neurodegenerative disorder. The subject can have a family history of a neurodegenerative disorder (e.g., familial ALS).

Subjects identified as having an increased risk of developing a neurodegenerative disease may be administered a treatment for a neurodegenerative disorder or may be administered a new or alternative treatment for a neurodegenerative disorder. Subjects identified as having an increased risk of developing a neurodegenerative disorder can also undergo more aggressive therapeutic treatment (e.g., increased periodicity of clinic or hospital visits).

Methods of Predicting the Rate of Disease Progression

Also provided are methods of predicting the rate of disease progression in a subject having a neurodegenerative disorder. These methods include determining a level of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a $CD14^+CD16^-$ or $CD14^+CD16^+$ monocyte from the subject; comparing the level of the one or more microRNAs and/or the one or more inflammatory markers to a reference level of the one or more microRNAs and/or a reference level of the one or more inflammatory markers. A subject is predicted to have an increased rate of disease progression if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a $CD14^+CD16^-$ or $CD14^+CD16^+$ monocyte from the subject is increased compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject is decreased compared to a reference level of the one or more microRNAs listed in Tables 2, 4, 6, 8, 10, 13, 15, 17, and 19, and/or a reference level of one or more inflammatory markers listed in Table 20.

In some embodiments, a subject is predicted to have a slower or average rate of disease progression if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a CD14$^+$CD16$^-$ or CD14$^+$CD16$^+$ monocyte from the subject is decreased or not significantly changed compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject is increased or not significantly changed compared to a reference level of the one or more microRNAs listed in Tables 2, 4, 6, 8, 10, 13, 15, 17, and 19, and/or a reference level of one or more inflammatory markers listed in Table 20.

In some embodiments, a subject may be predicted to have an increased or decreased rate of disease progression on the basis of the relative expression of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a CD14$^+$CD16$^-$ or CD14$^+$CD16$^+$ monocyte from the subject as compared to a reference value as described in the above section describing diagnostic methods. For example, an increase in the level of one or more (e.g., at least two, three, four, five, or six) microRNAs listed in Tables 1, 3, 5, 7, 9, 11, 12, 14, 16, and 18, and/or the level of one or more (e.g., at least two, three, four, five, or six) inflammatory markers listed in Table 21 in the cerebrospinal fluid or a CD14$^+$CD16$^-$ or CD14$^+$CD16$^+$ monocyte from the subject (compared to a reference level), as used to diagnose a subject as having a neurodegenerative disorder, may likewise be used to predict an increased rate of disease progression. Similarly, a decrease in the level of one or more (e.g., at least two, three, four, five, or six) microRNAs listed in Tables 2, 4, 6, 8, 10, 13, 15, 17, and 19 and/or the level of one or more (e.g., at least two, three, four, five, or six) inflammatory markers listed in Table 20 in the cerebrospinal fluid or a CD14$^+$CD16$^-$ or CD14$^+$CD16$^+$ monocyte (compared to a reference level), as used to diagnose a subject as having a neurodegenerative disorder, may likewise be used to predict an increased rate of disease progression.

In some embodiments, an increase in the level of one or more (e.g., at least two, three, four, five, or six) microRNAs listed in Tables 2, 4, 6, 8, 10, 13, 15, 17, and 19, and/or the level of one or more (e.g., at least two, three, four, five, or six) inflammatory markers in Table 20 in the cerebrospinal fluid or a CD14$^+$CD16$^-$ or CD14$^+$CD16$^+$ monocyte from the subject (compared to a reference level), when a decrease in the level of the one or more microRNAs and/or a decrease in the level of the one or more inflammatory markers indicates a diagnosis of a neurodegenerative disease (as detailed in the section describing diagnostic methods above), can be used to predict a decreased or average rate of disease progression. In some embodiments, a decrease in the level of one or more (e.g., at least two, three, four, five, or six) microRNAs listed in Tables 1, 3, 5, 7, 9, 11, 12, 14, 16, or 18, and/or the level of one or more (e.g., at least two, three, four, five, or six) inflammatory markers listed in Table 21 in the cerebrospinal fluid or a CD14$^+$CD16$^-$ or CD14$^+$CD16$^+$ monocyte from the subject (compared to a reference level), when an increase in the level of the one or more microRNAs and/or an increase in the level of the one or more inflammatory markers indicates a diagnosis of a neurodegenerative disorder (as detailed in the section describing diagnostic methods above), can be used to predict a decreased or average rate of disease progression.

In some embodiments, the rate of disease progression is the rate of onset of one or more (e.g., one, two, three, or four) symptoms (e.g., ataxia) of a neurodegenerative disorder, the rate of increasing intensity (worsening) of symptoms of a neurodegenerative disorder, the frequency of one or more symptoms of a neurodegenerative disorder, the duration of one or more symptoms of a neurodegenerative disorder, or the longevity of the subject. For example, an increase in the rate of disease progression can be manifested by one or more of: an increase in the rate of onset of one or more (new) symptoms of a neurodegenerative disorder, an increase in the rate of increasing intensity (worsening) of one or more symptoms of a neurodegenerative disorder, an increase in the duration of one or more symptoms of a neurodegenerative disorder, and a decrease in the longevity of the subject.

The rate of disease progression determined using the methods described herein can be compared to the rate of disease progression in subjects that do not have an increase or a decrease in the level of the one or more (e.g., at least two, three, four, five, or six) microRNAs listed in Tables 1-19 and/or do not have an increase or a decrease in the level of the one or more (e.g., at least two, three, four, five, or six) inflammatory markers listed in Tables 20 and 21 in their CSF or in a CD14$^+$CD16$^-$ or CD14$^+$CD16$^+$ monocyte. In some embodiments, the rate of disease progression can be compared to the average rate of disease progression for all subjects diagnosed as having the same neurodegenerative disease.

The levels of any of the microRNAs in Tables 1-19 or the levels of any of the inflammatory markers listed in Tables 20 and 21 may be performed using standard molecular biology methods (e.g., the PCR-based and antibody-based methods described herein). The methods can be performed by any health care professional (e.g., a physician, a nurse, a physician's assistant, a laboratory technician, or a nurse's assistant).

The subjects may present with one or more (e.g., one, two, three, or four) symptoms of a neurodegenerative disorder (e.g., any of the symptoms of a neurodegenerative disorder described herein). The subject can also present with no symptoms or just one symptom of a neurodegenerative disorder. The subject can have a family history of a neurodegenerative disorder (e.g., familial ALS). In some embodiments, the subject can already be diagnosed as having a neurodegenerative disorder.

Some embodiments of these methods further include administering a treatment to a subject predicted to have an increased rate of disease progression. In some embodiments, a subject predicted to have an increased rate of disease progression is administered a more aggressive treatment (e.g., increased periodicity of clinic visits).

Methods of Selecting a Subject for Participation in a Clinical Study

Also provided are methods for selecting a subject for participation in a clinical study. These methods include determining a level of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a CD14$^+$CD16$^-$ or CD14$^+$CD16$^+$ monocyte from the subject; comparing the level of the one or more microRNAs and/or the level of the one or more inflammatory markers to a reference level of the one or more microRNAs and/or a reference level of the one or more inflammatory markers, and selecting a subject having an increase or decrease in the level of the one or more microRNAs and/or one or more inflammatory markers in the cerebrospinal fluid or a CD14$^+$CD16$^-$ or CD14$^+$CD16$^+$ monocyte from the subject compared to the reference level (as described in detail below) for participation in a clinical study. In some embodiments, a subject is selected for participation in a clinical study if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a CD14$^+$CD16$^-$ or CD14$^+$CD16$^+$ monocyte from the subject is increased compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject is decreased compared to a reference level of the one or more microRNAs listed in Tables 2, 4, 6, 8, 10, 13, 15, 17, and 19, and/or a reference level of one or more inflammatory markers listed in Table 20.

In some embodiments, a subject is selected for participation in a clinical study if the level of one or more (e.g., at least two, three, four, five, or six) microRNAs listed in Tables 1, 3, 5, 7, 9, 11, 12, 14, 16, or 18, and/or one or more (e.g., at least two, three, four, five, or six) inflammatory markers listed in Table 21 in cerebrospinal fluid or a CD14$^+$CD16$^-$ or CD14$^+$CD16$^+$ monocyte from the subject is decreased or not significantly changed compared to a reference level of the one or more microRNAs listed in Tables 1, 3, 5, 7, 9, 11, 12, 14, 16, or 18, and/or a reference level of the one or more inflammatory markers listed in Table 21; and/or the level of one or more (e.g., at least two, three, four, five, or six) microRNAs listed in Tables 2, 4, 6, 8, 10, 13, 15, 17, and 19, and/or a one or more (e.g., at least two, three, four, five, or six) inflammatory markers listed in Table 20 in cerebrospinal fluid or a CD14$^+$CD16$^-$ or CD14$^+$CD16$^+$ monocyte from the subject is increased or not significantly changed compared to a reference level of the one or more microRNAs listed in Tables 2, 4, 6, 8, 10, 13, 15, 17, and 19, and/or a reference level of one or more inflammatory markers listed in Table 20.

In some embodiments, a subject can be selected for participation in a clinical study on the basis of the relative expression of one or more (e.g., at least two, three, four, five, or six) microRNAs listed in Tables 1-19 and/or one or more (e.g., at least two, three, four, five, or six) inflammatory markers listed in Tables 20 and 21 in the cerebrospinal fluid or a CD14$^+$CD16$^-$ or CD14$^+$CD16$^+$ monocyte from the subject as compared to a reference value as described in the above section describing diagnostic methods. For example, an increase in the level of one or more (e.g., at least two, three, four, five, or six) microRNAs listed in Tables 1, 3, 5, 7, 9, 11, 12, 14, 16, and 18, and/or the level of one or more (e.g., at least two, three, four, five, or six) inflammatory markers listed in Table 21 in the cerebrospinal fluid or a CD14$^+$CD16$^-$ or CD14$^+$CD16$^+$ monocyte from the subject (compared to a reference level), as used to diagnose a subject as having a neurodegenerative disorder, may likewise be used to select a subject for participation in a clinical study. Similarly, a decrease in the level of one or more (e.g., at least two, three, four, five, or six) microRNAs listed in Tables 2, 4, 6, 8, 10, 13, 15, 17, or 19 and/or the level of one or more (e.g., at least two, three, four, five, or six) inflammatory markers listed in Table 20 in the cerebrospinal fluid or a CD14$^+$CD16$^-$ or CD14$^+$CD16$^+$ monocyte (compared to a reference level), as used to diagnose a subject as having a neurodegenerative disorder, may likewise be used to select a subject for participation in a clinical study.

In some embodiments, an increase or no significant change in the level of one or more (e.g., at least two, three, four, five, or six) microRNAs listed in Tables 2, 4, 6, 8, 10, 13, 15, 17, and 19 and/or the level of one or more (e.g., at least two, three, four, five, or six) inflammatory markers listed in Table 20 in the cerebrospinal fluid or a CD14$^+$CD16$^-$ or CD14$^+$CD16$^+$ monocyte from the subject (compared to a reference level), when a decrease in the level of the one or more microRNAs and/or a decrease in the level of the one or more inflammatory markers indicates a diagnosis of a neurodegenerative disease (as detailed in the section describing diagnostic methods above), can be used to select a subject for participation in a clinical study (e.g., as a control subject). In some embodiments, a decrease or no significant change in the level of one or more (e.g., at least two, three, four, five, or six) microRNAs listed in Tables 1, 3, 5, 7, 9, 11, 12, 14, 16, or 18 and/or the level of one or more (e.g., at least two, three, four, five, or six) inflammatory markers listed in Table 21 in the cerebrospinal fluid or a CD14$^+$CD16$^-$ or CD14$^+$CD16$^+$ monocyte from the subject (compared to a reference level), when an increase in the level of the one or more microRNAs and/or an increase in the level of the one or more inflammatory markers indicates a diagnosis of a neurodegenerative disorder (as detailed in the section describing diagnostic methods above), can be used to select a subject for participation in a clinical study.

The levels of any of the microRNAs in Tables 1-19 or the levels of any of the inflammatory markers listed in Tables 20 and 21 may be performed using standard molecular biology methods (e.g., the PCR-based and antibody-based methods described herein). The methods can be performed by any health care professional (e.g., a physician, a nurse, a physician's assistant, a laboratory technician, or a nurse's assistant).

In some embodiments, the subject may present with one or more symptoms of a neurodegenerative disorder (e.g., any of the symptoms of a neurodegenerative disorder described herein). In some embodiments, the subject can also present with no symptoms or just one symptom of a neurodegenerative disorder. In some embodiments, the subject can have a familial history of a neurodegenerative disorder (e.g., familial ALS). In some embodiments, the subject can already be diagnosed as having a neurodegenerative disorder.

Methods of Treatment

Also provided are methods of treating a neurodegenerative disorder that include administering to a subject at least one (e.g., at least two, three, four, five, or six) agent (e.g., a nucleic acid) that decreases the level or activity of one or more (e.g., at least two, three, four, five, or six) of the microRNAs listed in Tables 1, 3, 5, 7, 9, 11, 12, 14, 16, or 18 (e.g., an inhibitory nucleic acid, e.g., an antagomir), and/or increases the level or activity of one or more (e.g., at least two, three, four, five, or six) of the microRNAs listed in Tables 2, 4, 6, 8, 10, 13, 15, 17, or 19 (e.g., a sense nucleic acid). Also provided are methods of treating a neurodegenerative disorder (e.g., ALS or MS) that include administering to a subject at least one (e.g., at least two, three, four, five, or six) agent (e.g., a nucleic acid) that decreases the expression (e.g., protein or mRNA) or activity of one or more (e.g., at least two, three, four, five, or six) of the inflammatory markers listed in Table 21 (e.g., an inhibitory nucleic acid or antibody) and/or increases the expression (e.g., protein or mRNA) and/or activity of one or more (e.g., at least two, three, four, five, or six) of the genes listed in Table 20 (e.g., a sense nucleic acid). In some embodiments, the subject is first identified or selected for treatment using any of the diagnostic methods described herein or any of the methods of predicting a subject at risk of developing a neurodegenerative disorder described herein.

In some embodiments, the subject is administered at least one inhibitory nucleic acid comprising a sequence that is complementary to a contiguous sequence present in hsa-miR-155 (e.g., a contiguous sequence present in mature or precursor hsa-miR-155). In non-limiting embodiments, the inhibitory nucleic acid can be an antisense oligonucleotide, a ribozyme, an siRNA, or an antagomir. In some embodiments, the at least one inhibitory nucleic acid is injected into the cerebrospinal fluid of a subject. In some embodiments, the injection is intracranial injection or intrathecal injection. In some embodiments, the at least one inhibitory nucleic acid is complexed with one or more cationic polymers and/or cationic lipids (e.g., any of the cationic polymers described herein or known in the art). Antagomirs to decrease the expression and/or activity of a specific target miRNA (e.g., hsa-miR-155) can be designed using methods known in the art (see, e.g., Krutzfeld et al., *Nature* 438:685-689, 2005). Additional exemplary methods for designing and making antagomirs and other types of inhibitory nucleic acids are described herein.

In some embodiments, the inhibitory nucleic acid that decreases miR-155 levels is the antogmir-155 LNA sequence +TC+AC+A+A+TTA+G+C+AT+T+A (SEQ ID NO: 262) (wherein the + indicates the presence of an LNA moiety). Methods for designing antagomirs to target microRNA molecules are described in Obad et al., *Nature Genetics* 43:371-378, 2011. Additional inhibitory nucleic acids for decreasing the levels or expression of hsa-miR-155 are described in Worm et al., *Nucleic Acids Res.* 37:5784-5792, 2009, and Murugaiyan et al., *J. Immunol.* 187:2213-2221, 2011.

A subject can be administered at least one (e.g., at least 2, 3, 4, or 5) dose of the agent (e.g., one or more inhibitory nucleic acids). The agent (e.g., one or more inhibitory nucleic acids) can be administered to the subject at least once a day (e.g., twice a day, three times a day, and four times a day), at least once a week (e.g., twice a week, three times a week, four times a week), and/or at least once a month. A subject can be treated (e.g., periodically administered the agent) for a prolonged period of time (e.g., at least one month, two months, six months, one year, two years, three years, four years, or five years). As described in detail herein, the dosage of the agent to be administered to the subject can be determined by a physician by consideration of a number of physiological factors including, but not limited to, the sex of the subject, the weight of the subject, the age of the subject, and the presence of other medical conditions. The agent can be administered to the subject orally, intravenously, intraarterially, subcutaneously, intramuscularly, intracranially, or via injection into the cerebrospinal fluid. Likewise, the agent may be formulated as a solid (e.g., for oral administration) or a physiologically acceptable liquid carrier (e.g., saline) (e.g., for intravenous, intraarterial, subcutaneous, intramuscular, cerebrospinal (intrathecal), or intracranial administration). In some embodiments, the agent (e.g., one or more inhibitory nucleic acids) can be administered by injection or can be administered by infusion over a period of time.

The agents to be administered to a subject for treatment of a neurodegenerative disorder are described below, and can be used in any combination (e.g., at least one, two, three, four, or five of any combination of the agents or classes of agents described below).

Inhibitory Nucleic Acids

Inhibitory agents useful in the methods of treatment described herein include inhibitory nucleic acid molecules that decrease the expression or activity of any of the microRNAs (e.g., mature microRNA or precursor microRNA) listed in Tables 1, 3, 5, 7, 9, 11, 12, 14, 16, or 18 (e.g., hsa-miR-155), or decrease the expression or activity of any of the mRNAs encoding an inflammatory marker listed in Table 21 (the target mRNA).

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds, such as siRNA compounds, modified bases/locked nucleic acids (LNAs), antagomirs, peptide nucleic acids (PNAs), and other oligomeric compounds, or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010/040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29, or 30 nucleotides in length, or any range therewithin.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides, and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino, and 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide—the modified oligos survive intact for a longer time than unmodified oligonucleotides. Specific examples of modified oligonucleotides include those comprising modified backbones, for example, phosphorothioates, phosphotriesters, methyl phosphonates, short-chain alkyl or cycloalkyl intersugar linkages, or short-chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al., Ace. Chem. Res. 28:366-374, 1995); morpholino backbone structures (see U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 254: 1497, 1991). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050 (each of which is incorporated by reference).

Morpholino-based oligomeric compounds are described in Braasch et al., Biochemistry 41(14):4503-4510, 2002; Genesis, volume 30, issue 3, 2001; Heasman, J., Dev. Biol., 243:209-214, 2002; Nasevicius et al., Nat. Genet. 26: 216-220, 2000; Lacerra et al., Proc. Natl. Acad. Sci. U.S.A. 97:9591-9596, 2000; and U.S. Pat. No. 5,034,506. Cyclohexenyl nucleic acid oligonucleotide mimetics are described in Wang et al., J. Am. Chem. Soc. 122, 8595-8602, 2000.

Modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439 (each of which is herein incorporated by reference).

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$, where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy[2'-0-$CH_2CH_2OCH_3$, also known as 2'-O-(2-methoxyethyl)] (Martin et al., Helv. Chim. Acta 78:486, 1995). Other preferred modifications include 2'-methoxy(2'-0-$CH_3$), 2'-propoxy(2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics, such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC, and gentobiosyl HMC, as well as synthetic nucleobases, e.g., 2-aminoadenine, 2-(methylamino)adenine, 2-(imidazolylalkyl)adenine, 2-(aminoaklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. See Kornberg, A., DNA Replication, W. H. Freeman & Co., San Francisco, 1980, pp 75-77; and Gebeyehu et al., Nucl. Acids Res. 15:4513, 1987. A "universal" base known in the art, e.g., inosine, can also be included. 5-Me-C substitutions have been shown to increase nucleic acid duplex stability by 0.6-1.2<0>C (Sanghvi, Y. S., in Crooke, S. T. and Lebleu, B., Eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science 254:1497-1500, 1991.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C), and uracil (U). Modified nucleobases comprise other synthetic and natural nucleobases, such as 5-methylcytosine (5-me-C), 5-hydroxymethyl cytosine, xanthine, hypoxanthine, 2-aminoadenine, 6-methyl, and other alkyl derivatives of adenine and guanine, 2-propyl and other alkyl derivatives of adenine and guanine, 2-thiouracil, 2-thiothymine, and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine, and 7-deazaadenine, and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., Ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines, and N2, N-6 and 0-6 substituted purines, comprising 2-aminopropyladenine, 5-propynyluracil, and 5-propynylcytosine. 5-methylcytosine substitutions have been shown to increase nucleic acid duplex stability by 0.6-1.2<0>C (Sanghvi, Y. S., Crooke, S. T. and Lebleu, B., Eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and U.S. Pat. No. 5,681,941 (each of which is herein incorporated by reference).

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. U.S.A. 86:6553-6556, 1989), cholic acid (Manoharan et al., Bioorg. Med. Chem. Lett. 4:1053-1060, 1994), a thioether, e.g., hexyl-S-tritylthiol (Manoharan et al, Ann. N.Y. Acad. Sci. 660:306-309, 1992; Manoharan et al., Bioorg. Med. Chem. Lett. 3:2765-2770, 1993), a thiocholesterol (Oberhauser et al., Nucl. Acids Res. 20, 533-538, 1992), an aliphatic chain, e.g., dodecandiol or undecyl residues (Kabanov et al., FEBS Lett. 259:327-330, 1990; Svinarchuk et al., Biochimie 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett. 36:3651-3654, 1995; Shea et al., Nucl. Acids Res. 18:3777-3783, 1990), a polyamine or a polyethylene glycol chain (Mancharan et al., Nucleosides & Nucleotides 14:969-973, 1995), or adamantane acetic acid (Manoharan et al., Tetrahedron Lett. 36:3651-3654, 1995), a palmityl moiety (Mishra et al., Biochim. Biophys. Acta 1264: 229-237, 1995), or an octadecylamine or hexylamino-carbonyl-t oxycholesterol moiety (Crooke et al., J. Pharmacol. Exp. Ther. 277:923-937, 1996). See also U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941 (each of which is herein incorporated by reference).

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism, or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941 (each of which is incorporated by reference).

The inhibitory nucleic acids useful in the present methods are sufficiently complementary to the target miRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miRNA, then the bases are considered to be complementary to each other at that position. In some embodiments, 100% complementarity is not required. In some embodiments, 100% complementarity is required. Routine methods can be used to design an inhibitory nucleic acid that binds to the target sequence with sufficient specificity.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments of 5, 6, 7, 8, 9, 10 or more nucleotides in length comprising a stretch of at least five (5) consecutive nucleotides within the seed sequence, or immediately adjacent thereto, are considered to be suitable for targeting as well. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the inhibitory nucleic acid contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the inhibitory nucleic acid contains about 5 to about 30 nucleotides). One having skill in the art armed with the sequences provided herein will be able, without undue experimentation, to identify further preferred regions to target. In some embodiments, an inhibitory nucleic acid contain a sequence that is complementary to at least 5, 6, 7, 8, 9, 10, 11, 12, 13, 14, 15, 16, 17, 18, 19, 20, 21, 22, 23, 24, or 25 contiguous nucleotides present in the target (e.g., the target miRNA, e.g., mature or precursor hsa-miR-155, or the target mRNA).

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a miRNA molecule or an mRNA molecule, then the inhibitory nucleic acid and the miRNA or mRNA are considered to be complementary to each other at that position. The inhibitory nucleic acids and the miRNA or mRNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the inhibitory nucleic acid and the miRNA target. For example, if a base at one position of an inhibitory nucleic acid is capable of hydrogen bonding with a base at the corresponding position of a miRNA or a mRNA, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridisable when binding of the sequence to the target miRNA or mRNA molecule interferes with the normal function of the target miRNA or mRNA to cause a loss of expression or activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci. U.S.A.* 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an miRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., *J. Mol. Biol.* 215:403-410, 1990; Zhang and Madden, *Genome Res.* 7:649-656, 1997). Antisense and other compounds of the invention that hybridize to an miRNA or a mRNA are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to the target microRNA or the target inflammatory marker mRNA. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O, 4'-C-methylene-β-D-ribofuranosyl nucleotide. LNA bases form standard Watson-Crick base pairs but the locked configuration increases the rate and stability of the base pairing reaction (Jepsen et al., *Oligonucleotides* 14:130-146, 2004). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., miRNAs and mRNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the miRNA or the mRNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., *Nuc. Acids. Res.* 34:e60, 2006; McTigue et al., *Biochemistry* 43:5388-405, 2004; and Levin et al., *Nucl. Acids. Res.* 34:e142, 2006. For example, "gene walk" methods, similar to those used to design antisense oligos, can be used to optimize the inhibitory activity of the LNA; for example, a series of oligonucleotides of 10-30 nucleotides spanning the length of a target miRNA or mRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the miRNA. For example, a specific functional region can be targeted, e.g., a region comprising a seed sequence. Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., *J. Mol. Biol.* 215:403-410, 1990; Zhang and Madden, *Genome Res.* 7:649-656, 1997), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 2010/0267018; 2010/0261175; and 2010/0035968; Koshkin et al., *Tetrahedron* 54:3607-3630, 1998; Obika et al., *Tetrahedron Lett.* 39:5401-5404, 1998; Jepsen et al., *Oligonucleotides* 14:130-146, 2004; Kauppinen et al., *Drug Disc. Today* 2(3):287-290, 2005; and Ponting et al., *Cell* 136(4):629-641, 2009, and references cited therein.

See also U.S. Ser. No. 61/412,862, which is incorporated by reference herein in its entirety.

Antagomirs

In some embodiments, the antisense is an antagomir. Antagomirs are chemically-modified antisense oligonucleotides that target a microRNA (e.g., target hsa-miR-155). For example, an antagomir for use in the methods described herein can include a nucleotide sequence sufficiently complementary to hybridize to a miRNA target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., *Nature* 438:685-689, 2005; Czech, *N. Engl. J. Med.* 354:1194-1195, 2006; Robertson et al., *Silence* 1:10, 2010; Marquez and McCaffrey, *Human Gene Ther.* 19(1):27-38, 2008; van Rooij et al., *Circ. Res.* 103(9):919-928, 2008; and Liu et al., *Int. J. Mol. Sci.* 9:978-999, 2008.

Antagomirs useful in the present methods can also be modified with respect to their length or otherwise the number of nucleotides making up the antagomir. In general, the antagomirs are about 20-21 nucleotides in length for optimal function, as this size matches the size of most mature microRNAs. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

siRNA

In some embodiments, the nucleic acid sequence that is complementary to a target miRNA or a target mRNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., *Science* 296:550-553, 2002; Lee et al., *Nature Biotechnol.*, 20, 500-505, 2002; Miyagishi and Taira, *Nature Biotechnol.* 20:497-500, 2002; Paddison et al., *Genes & Dev.* 16:948-958, 2002; Paul,

*Nature Biotechnol.* 20, 505-508, 2002; Sui, *Proc. Natl. Acad. Sci. U.S.A.,* 99(6):5515-5520, 2002; Yu et al., *Proc. Natl. Acad. Sci. U.S.A.* 99:6047-6052, 2002.

The target RNA cleavage reaction guided by siRNAs is highly sequence specific. In general, siRNA containing a nucleotide sequences identical to a portion of the target nucleic acid (i.e., a target region comprising the seed sequence of a target miRNA or mRNA) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, *Ann. Rep. Med. Chem.* 30:285-294, 1995; Christoffersen and Marr, *J. Med. Chem.* 38:2023-2037, 1995). Enzymatic nucleic acid molecules can be designed to cleave specific miRNA or mRNA targets within the background of cellular RNA. Such a cleavage event renders the miRNA or mRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its activity. After an enzymatic nucleic acid has bound and cleaved its RNA target, it is released from that RNA to search for another target and can repeatedly bind and cleave new targets.

Several approaches such as in vitro selection (evolution) strategies (Orgel, *Proc. R. Soc. London,* B 205:435, 1979) have been used to evolve new nucleic acid catalysts capable of catalyzing a variety of reactions, such as cleavage and ligation of phosphodiester linkages and amide linkages, (Joyce, *Gene,* 82, 83-87, 1989; Beaudry et al., *Science* 257, 635-641, 1992; Joyce, *Scientific American* 267, 90-97, 1992; Breaker et al., *TIBTECH* 12:268, 1994; Bartel et al., *Science* 261:1411-1418, 1993; Szostak, *TIBS* 17, 89-93, 1993; Kumar et al., *FASEB J.,* 9:1183, 1995; Breaker, *Curr. Op. Biotech.,* 1:442, 1996). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Sense Nucleic Acids

Agents useful in the methods of treatment described herein include sense nucleic acid molecules that increase the expression or activity of any of the microRNAs (e.g., mature microRNA or precursor microRNA) listed in Tables 2, 4, 6, 8, 10, 13, 15, 17, and 19, or increase the expression or activity of any of the mRNAs encoding an inflammatory marker listed in Table 21. A sense nucleic acid can be contain a sequence that is at least 80% (e.g., at least 90%, 95%, 96%, 97%, 98%, 99%, or 100%) identical to the sequence of any one of the microRNAs (e.g., mature microRNA or precursor microRNA) listed in Tables 2, 4, 6, 8, 10, 13, 15, 17, and 19, or the sequence of any one of the mRNAs listed in Table 21. Sense nucleic acids can contain one or more of any of the modifications (e.g., backbone modifications, nucleobase modifications, sugar modifications, or one or more conjugated molecules) described herein without limitation. Methods of making and administering sense nucleic acids are known in the art. Additional methods of making and using sense nucleic acids are described herein.

Making and Using Inhibitory Nucleic Acids and Sense Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g., in vitro, bacterial, fungal, mammalian, yeast, insect, or plant cell expression systems.

Nucleic acid sequences of the invention (e.g., any of the inhibitory nucleic acids or sense nucleic acids described herein) can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, herpes virus, adenovirus, adeno-associated virus, pox virus, or alphavirus. The recombinant vectors (e.g., viral vectors) capable of expressing the nucleic acids of the invention can be delivered as described herein, and persist in target cells (e.g., stable transformants). For example, such recombinant vectors (e.g., a recombinant vector that results in the expression of an antisense oligomer that is complementary to hsa-miR-155) can be administered into (e.g., injection or infusion into) the cerebrospinal fluid of the subject (e.g., intracranial injection, intraparenchymal injection, intraventricular injection, and intrathecal injection, see, e.g., Bergen et al., *Pharmaceutical Res.* 25:983-998, 2007). A number of exemplary recombinant viral vectors that can be used to express any of the nucleic acids described herein are also described in Bergen et al. (supra). Additional examples of recombinant viral vectors are known in the art.

The nucleic acids provided herein (e.g., the inhibitory nucleic acids) can be further be complexed with one or more cationic polymers (e.g., poly-L-lysine and poly(ethylenimine), cationic lipids (e.g., 1,2-dioleoyl-3-trimethylammonium propone (DOTAP), N-methyl-4-(dioleyl)methylpyridinium, and 3β-[N—(N',N'-dimethylaminoethane)-carbamoyl] cholesterol), and/or nanoparticles (e.g., cationic polybutyl cyanoacrylate nanoparticles, silica nanoparticles, or polyethylene glycol-based nanoparticles) prior to administration to the subject (e.g., injection or infusion into the cerebrospinal fluid of the subject). Additional examples of cationic polymers, cationic lipids, and nanoparticles for the therapeutic delivery of nucleic acids are known in the art. The therapeutic delivery of nucleic acids has also been shown to be achieved following intrathecal injection of polyethyleneimine/DNA complexes (Wang et al., *Mol. Ther.* 12:314-320, 2005). The methods for delivery of nucleic acids described herein are non-limiting. Additional methods for the therapeutic delivery of nucleic acids to a subject are known in the art.

In some embodiments, the inhibitory nucleic acids (e.g., one or more inhibitory nucleic acids targeting hsa-miR-155) can be administered systemically (e.g., intravenously, intaarterially, intramuscularly, subcutaneously, or intraperitoneally) or intrathecally (e.g., epidural administration). In some embodiments, the inhibitory nucleic acid is administered in a composition (e.g., complexed with) one or more cationic lipids. Non-limiting examples of cationic lipids that can be used to administer one or more inhibitory nucleic acids (e.g., any of the inhibitory nucleic acids described herein) include: Lipofectamine, the cationic lipid molecules described in WO 97/045069, and U.S. Patent Application Publication Nos. 2012/0021044, 2012/0015865, 2011/0305769, 2011/0262527, 2011/0229581, 2010/0305198, 2010/0203112, and 2010/0104629 (each of which is herein incorporated by reference). Nucleic acid sequences used to practice this invention can be synthesized in vitro by well-known chemical synthesis techniques, as described in, e.g., Adams, *J. Am. Chem. Soc.* 105:661, 1983; Belousov, *Nucleic Acids Res.* 25:3440-3444, 1997; Frenkel, *Free Radic. Biol. Med.* 19:373-380, 1995; Blommers, *Biochemistry* 33:7886-7896, 1994; Narang, *Meth. Enzymol.* 68:90, 1994; Brown, *Meth. Enzymol.* 68:109, 1979; Beaucage, *Tetra. Lett.* 22:1859, 1981; and U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., *Drug Disc. Today* 2(3):287-290, 2005; Koshkin et al., *J. Am. Chem. Soc.*, 120(50):13252-13253, 1998). For additional modifications see US 2010/0004320, US 2009/0298916, and US 2009/0143326 (each of which is incorporated by reference).

Techniques for the manipulation of nucleic acids used to practice this invention, such as, e.g., subcloning, labeling probes (e.g., random-primer labeling using Klenow polymerase, nick translation, amplification), sequencing, hybridization, and the like are well described in the scientific and patent literature, see, e.g., Sambrook et al., *Molecular Cloning; A Laboratory Manual* 3d ed. (2001); *Current Protocols in Molecular Biology*, Ausubel et al., Eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, Ed. Elsevier, N.Y. (1993).

Antibodies and Recombinant Proteins

One or more antibodies that specifically bind to a protein encoded by any of the inflammatory marker genes listed in Table 21 can also be administered to a subject to treat a neurodegenerative disease. Antibodies that specifically bind to a protein listed in Table 21 are either commercially available or can be generated using standard methods known in the art. For example, a polyclonal antibody that specifically binds to a protein listed in Table 21 can be generated by immunizing a mammal with the purified protein and isolating antibodies from the mammal that specifically bind to the purified protein. The antibodies used can be a monoclonal or polyclonal antibody. The antibodies administered can be a immunoglobulin G or immunoglobulin M. The antibodies administered can be chimeric (e.g., a humanized antibody) or a human antibody. The antibodies used can also be an antibody fragment (e.g., a Fab, F(ab')$_2$, Fv, and single chain Fv (scFv) fragment).

One or more inflammatory marker proteins listed in Table 20 can also be administered to a subject for the treatment of a neurodegenerative disorder. Several methods are known in the art for the production of a recombinant protein using molecular biology and cell culture techniques. For example, an inflammatory marker protein encoded by a mRNA sequence listed in Table 20 can be transfected into a bacterial, yeast, or mammalian cell (using a protein expression plasmid or viral vector) that allows for the expression of the inflammatory by the transfected cell. The transfected cells or the culture medium can be collected, and the recombinant inflammatory marker protein purified using methods known in the art. The inflammatory marker proteins administered to the subject can contain a sequence having at least 80% (e.g., at least 85%, 90%, 95%, 96%, 97%, 98%, 99%, or 100%) identity to any of the amino acid sequences listed in Table 20. The inflammatory marker proteins administered to the subject can further contain a modification (e.g., a polyethylene glycol or an HIV tat protein, or any other moiety that increases the cellular permeability of the inflammatory marker protein).

Pharmaceutical Compositions

The methods described herein can include the administration of pharmaceutical compositions and formulations comprising any one or more (e.g., two, three, four, or five)

of the inhibitory nucleic acids (e.g., one or more inhibitory nucleic acids targeting hsa-miR-155), sense nucleic acids, inflammatory marker proteins, or antibodies described herein.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions. In some embodiments, one or more cationic lipids, cationic polymers, or nanoparticles can be included in compositions containing the one or more inhibitory nucleic acids (e.g., compositions containing one or more inhibitory nucleic acids targeting hsa-miR-155).

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents, and preserving agents. A formulation can be admixtured with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., inhibitory nucleic acids or sense nucleic acids described herein) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth, and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long-chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil, or coconut oil, or in a mineral oil such as liquid paraffin; or a mixture of these. See e.g., U.S. Pat. No. 5,716,928, describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an antioxidant such as ascorbic acid. As an example of an injectable oil vehicle, see Minto, *J. Pharmacol. Exp. Ther.* 281:93-102, 1997.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate, and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi, *J. Clin. Pharmacol.* 35:1187-1193, 1995; Tjwa, *Ann. Allergy Asthma Immunol.* 75:107-111, 1995). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao, *J. Biomater Sci. Polym. Ed.* 7:623-645, 1995; as biodegradable and injectable gel formulations, see, e.g., Gao, *Pharm. Res.* 12:857-863, 1995; or, as microspheres for oral administration, see, e.g., Eyles, *J. Pharm. Pharmacol.* 49:669-674, 1997.

In some embodiments, the pharmaceutical compounds can be parenterally administered, such as by intravenous (IV) administration or administration into a body cavity, a lumen of an organ, or into the cranium (e.g., intracranial injection or infusion) or the cerebrospinal fluid of a subject. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid or a sense nucleic acid can be made by lyophilizing a solution comprising a pharmaceutical of the invention and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US2004/0028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to reduce the number of symptoms or reduce the severity, duration, or frequency of one or more symptoms of a neurodegenerative disorder in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones, *J. Steroid Biochem. Mol. Biol.* 58:611-617, 1996; Groning, *Pharmazie* 51:337-341, 1996; Fotherby, *Contraception* 54:59-69, 1996; Johnson, *J. Pharm. Sci.* 84:1144-1146, 1995; Rohatagi, *Pharmazie* 50:610-613, 1995; Brophy, *Eur. J. Clin. Pharmacol.* 24:103-108, 1983; *Remington: The Science and Practice of Pharmacy*, 21st ed., 2005). The state of the art allows the clinician to determine the dosage regimen for each individual patient, active agent, and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, and the like. The formulations should provide a sufficient quantity of active agent to effectively treat, prevent or ameliorate conditions, diseases, or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Various studies have reported successful mammalian dosing using complementary nucleic acid sequences. For example, Esau C., et al., *Cell Metabolism*, 3(2):87-98, 2006, reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., *Nature* 438, 685-689, 2005, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen et al., *Nature* 452, 896-899, 2008, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., any of the treatments of a neurodegenerative disorder described herein.

Kits

Also provided herein are kits containing one or more (e.g., at least 2, 3, 4, 5, 6, 7, 8, 9, 10, 12, 14, 16, 18, or 20) of any of the probes, inhibitory nucleic acids, sense nucleic acids, inflammatory marker proteins, or antibodies described herein (in any combination). In some embodiments, the kits can include instructions for performing any of the methods described herein.

In some embodiments, the kit can contain at least two primers (e.g., at least 4, 6, 8, 10, 12, 14, 16, 18, 20, 22, 24, 26, 28, 30, 32, 36, 38, or 40) for amplifying a sequence present within any of the microRNAs listed in Tables 1-19 (e.g., mature microRNA or precursor microRNA) or for amplifying a sequence present within any of the mRNAs listed in Tables 20 and 21.

In some embodiments, the kits contain two or more sets of primer (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 pairs of primers) that amplify a sequence present within one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 pairs of primers) of the microRNAs listed in any one of Tables 1-11 (e.g., one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109) of the microRNAs from Tables 1 and 2; Tables 3 and 4; Tables 5 and 6; Tables 7 and 8; Tables 9 and 10; and Table 11) and/or that amplify a sequence present within one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95) of the mRNAs listed in Table 20 and/or Table 21 (e.g., ALS diagnostic kits).

In some embodiments, the kits contain two or more sets of primer (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 pairs of primers) that amplify a sequence present within one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 pairs of primers) of the microRNAs listed in any one of Tables 1-11 (e.g., one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109) of the microRNAs from Tables 1 and 2; Tables 3 and 4; Tables 5 and 6; Tables 7 and 8; Tables 9 and 10; and Table 11) and/or that amplify a sequence present within one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95) of the mRNAs listed in Table 20 and/or Table 21 (e.g., ALS diagnostic kits).

In some embodiments, the kits contain two or more antisense oligonucleotides (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 pairs of primers) that collectively are capable of hybridizing to one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109) of the microRNAs listed in any one of Tables 1, 2, and 12-19 (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 microRNAs from Tables 1 and 2; Tables 12 and 13; Tables 14 and 15; Tables 16 and 17; and Tables 18 and 19) and/or that are collectively capable of hybridizing to one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95) of the mRNAs listed in Table 20 and/or Table 21 (e.g., MS diagnostic kits).

In some embodiments, the kits contain two or more antisense oligonucleotides (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 antisense oligonucleotides) that collectively are capable of hybridizing to one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109) of the microRNAs listed in any one of Tables 1, 2, and 12-19 (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 microRNAs from Tables 1 and 2; Tables 12 and 13; Tables 14 and 15; Tables 16 and 17; and Tables 18 and 19) and/or that are collectively capable of hybridizing to one or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95) of the mRNAs listed in Table 20 and/or Table 21 (e.g., MS diagnostic kits).

In some embodiments, the kit can contain at least two antisense molecules (e.g., at least 4, 6, 8, 10, 12, 14, 16, 20, 22, 24, 26, 28, 30, 32, 34, 36, 38, or 40) for hybridizing with a sequence present within any of the microRNAs listed in Tables 1-19 (e.g., mature microRNA or precursor microRNA) or a sequence within any of the mRNAs listed in Tables 20 and 21.

In some embodiments, the kits can contain at least one inhibitory nucleic acid and/or at least one sense nucleic acid (e.g., any of the inhibitory nucleic acids or sense nucleic acids described herein). In some embodiments, the kit contains at least one inhibitory nucleic acid (e.g., at least one inhibitory nucleic acid targeting hsa-miR-155) formulated for intrathecal or intracranial injection or infusion.

In some embodiments, the kits can contain at least one (e.g., at least two, three, four, five, or six) antibody that specifically binds to any one of the proteins encoded by any of the inflammatory marker genes listed in Table 20 or Table 21 (e.g., any of the variety of antibodies or antibody fragments described herein). In some embodiments, the antibodies can be labeled (e.g., labeled with a fluorophore, a radioisotope, an enzyme, biotin, or avidin).

In some embodiments, the kit further contains at least one additional therapeutic agent (e.g., one or more of KNS760704, SB509, ceftriaxone, minocycline, rilutek, and riluzole). In some embodiments, the kit further contains instructions for administering the at least one agent (e.g., one or more inhibitory nucleic acids) to a subject having or diagnosed as having a neurodegenerative disease (e.g., sporadic ALS and/or familial ALS, or MS).

The invention is further described in the following examples, which do not limit the scope of the invention described in the claims.

EXAMPLES

Example 1. MicroRNA Deregulation in Ly6C$^{Hi}$ Monocytes, Ly6C$^{Low}$ Monocytes, and CD39$^+$ Microglia in a Mouse Model of ALS (SOD1$^{G93A}$ Mice)

Figure 1B:
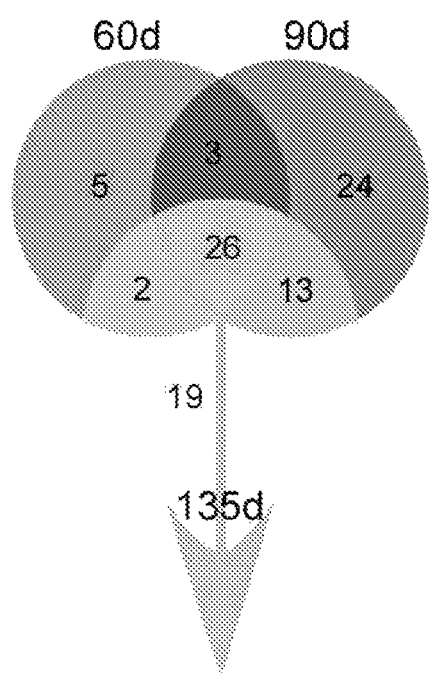
FIG. 1B is a Venn diagram of significantly dysregulated microRNAs in $CD39^+$ microglia in $SOD^{G93A}$ mice compared to the expression of the microRNAs in $CD39^+$ microglia from non-transgenic littermates across all disease stages. The numbers represent significantly dysregulated microRNAs at each disease stage.
Figure 1C:
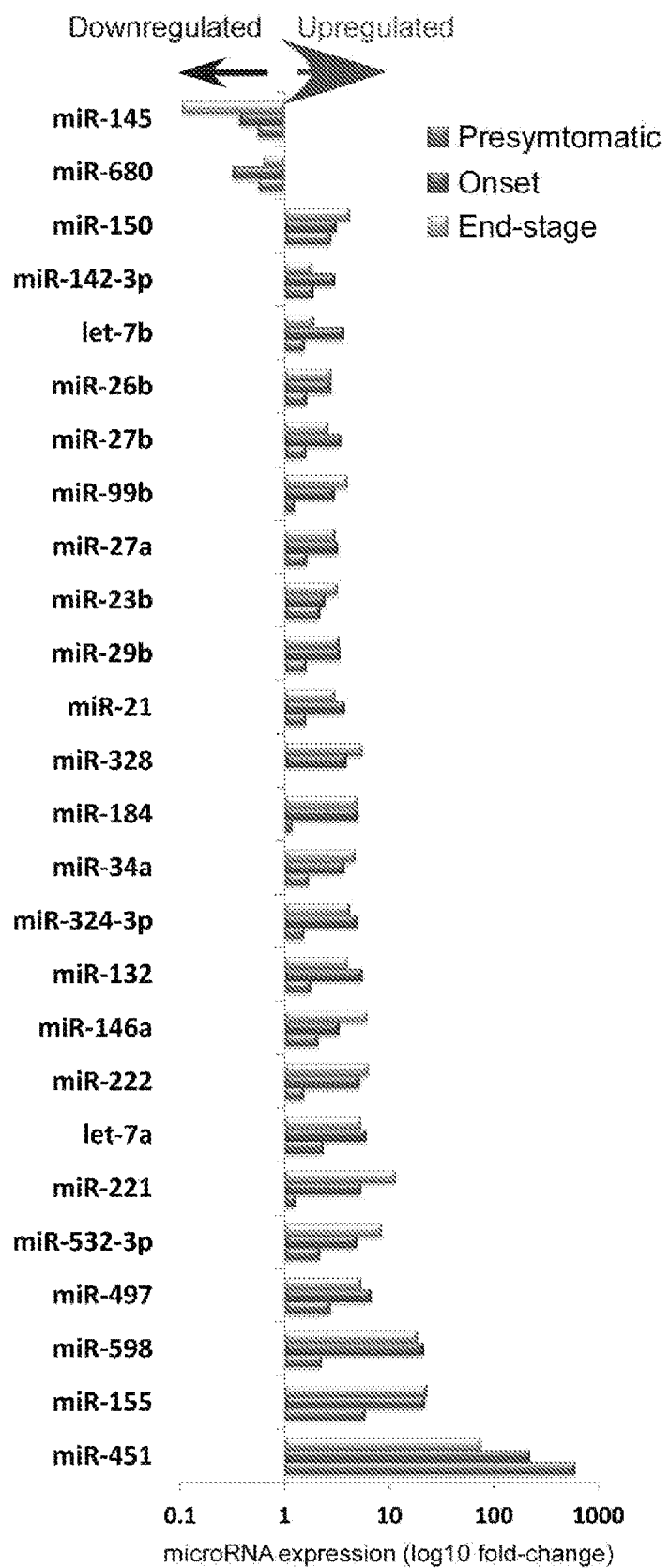
FIG. 1C is a summary of significantly dysregulated microRNAs in $CD39^+$ microglia in $SOD^{G93A}$ mice compared to the expression of the microRNAs in $CD39^+$ microglia from non-transgenic littermates. These data were validated in singleplex TaqMan PCR.
Figure 2A:
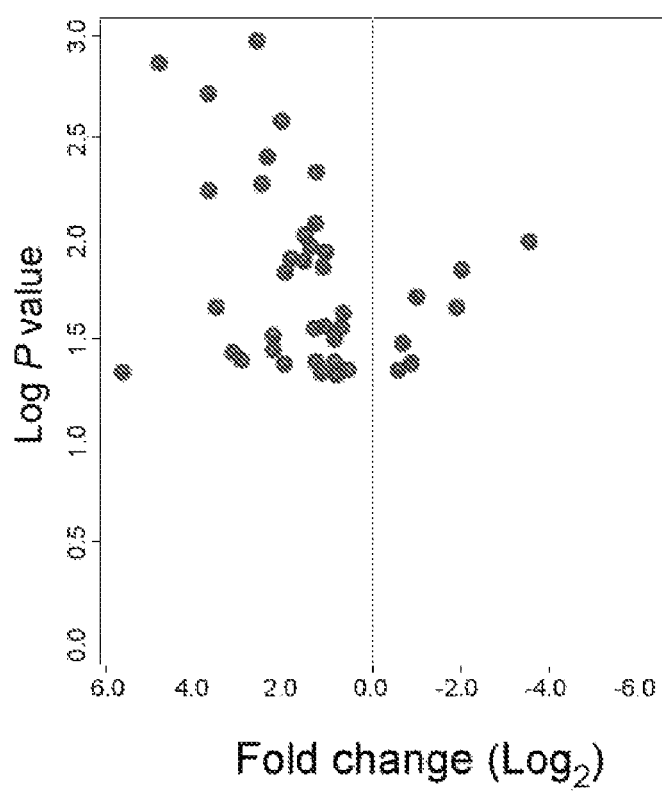
FIG. 2A is a volcano plot of significantly dysregulated microRNAs in Ly6C$^{Hi}$ monocytes in SOD$^{G93A}$ mice compared to the expression of the microRNAs in Ly6C$^{Hi}$ monocytes from non-transgenic littermates at a presymptomatic (60 days) time point (Presymptomatic), at the time of onset of symptoms (Onset), and at the end-stage of disease (End-Stage). The x-axis represents changes in expression (log$_2$-fold change based on ddCT values) and the y-axis shows statistical significance of the change in log-odds.
Figure 2B:
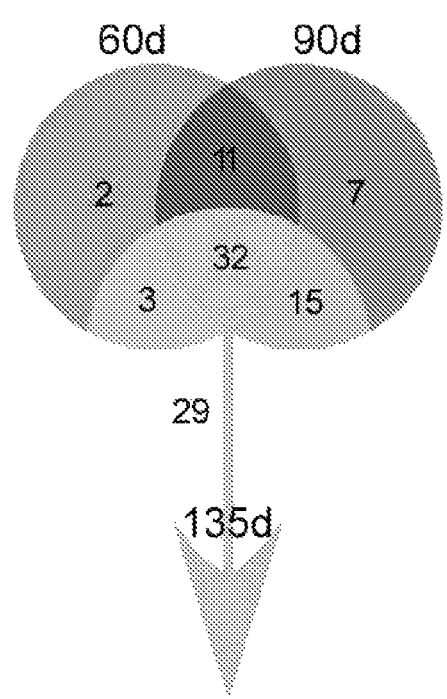
FIG. 2B is a Venn diagram of significantly dysregulated microRNAs in Ly6C$^{Hi}$ monocytes in SOD$^{G93A}$ mice compared to the expression of the microRNAs in Ly6C$^{Hi}$ monocytes from non-transgenic littermates across all disease stages (presymptomatic, onset of symptoms, and the end-stage of disease). The numbers represent significantly dysregulated microRNAs at each disease stage.
Figure 2C:
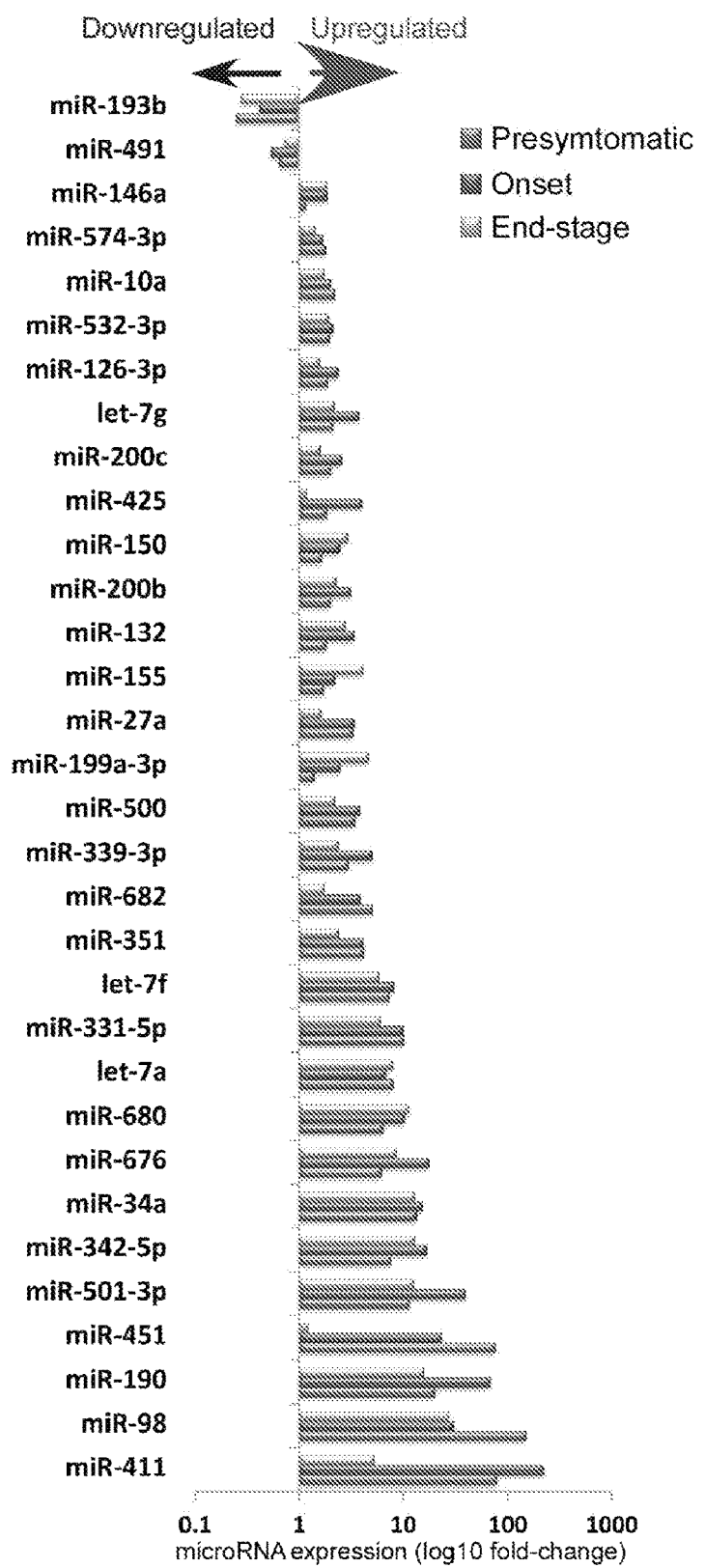
FIG. 2C is a summary of significantly dysregulated microRNAs in Ly6C$^{Hi}$ monocytes in SOD$^{G93A}$ mice compared to the expression of the microRNAs in Ly6C$^{Hi}$ monocytes from non-transgenic littermates. These data were validated in singleplex TaqMan PCR.
Figure 3A:
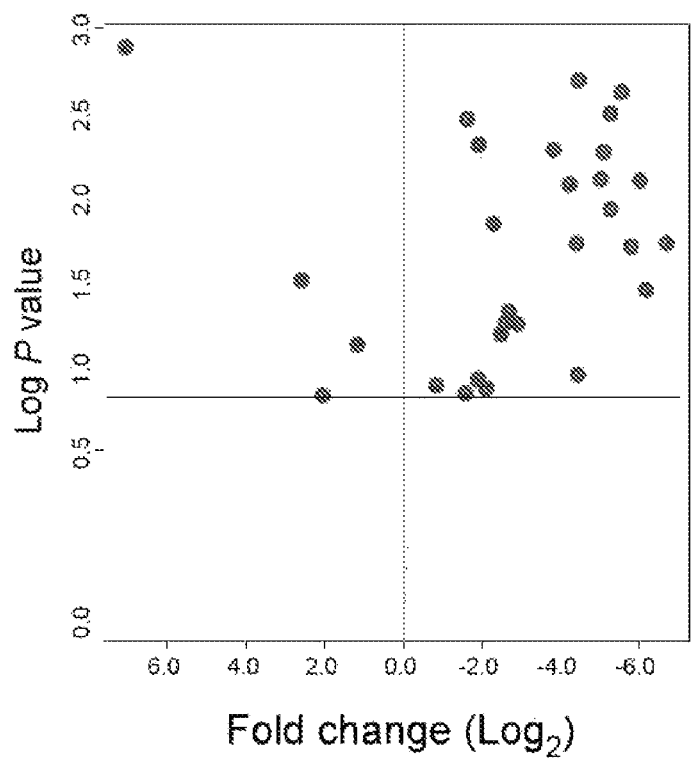
FIG. 3A is a volcano plot of significantly dysregulated microRNAs in Ly6C$^{Low}$ monocytes in SOD$^{G93A}$ mice compared to the expression of the microRNAs in Ly6C$^{Low}$ monocytes from non-transgenic littermates at a presymptomatic (60 days) time point, at the time of onset of symptoms (Onset), and at the end-stage of disease (End-Stage). The x-axis represents changes in expression (log$_2$-fold change based on ddCT values) and the y-axis shows statistical significance of the change in log-odds.
Figure 3B:
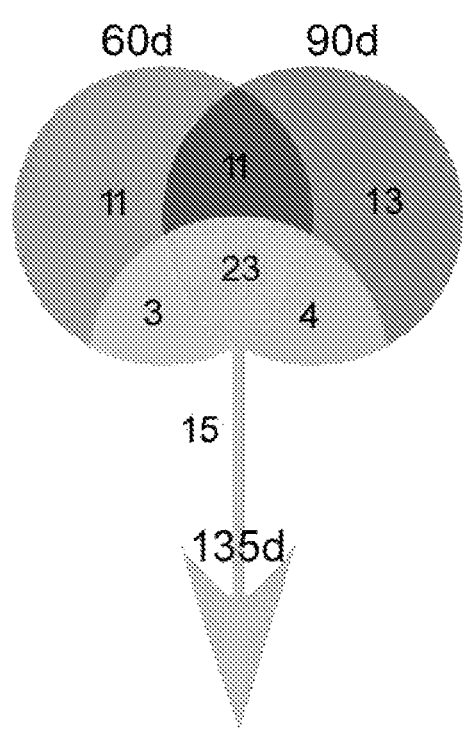
FIG. 3B is a Venn diagram of significantly dysregulated microRNAs in Ly6C$^{Low}$ monocytes in SOD$^{G93A}$ mice compared to the expression of the microRNAs in Ly6C$^{Low}$ monocytes from non-transgenic littermates across all disease stages. The numbers represent significantly dysregulated microRNAs at each disease stage.
Figure 3C:
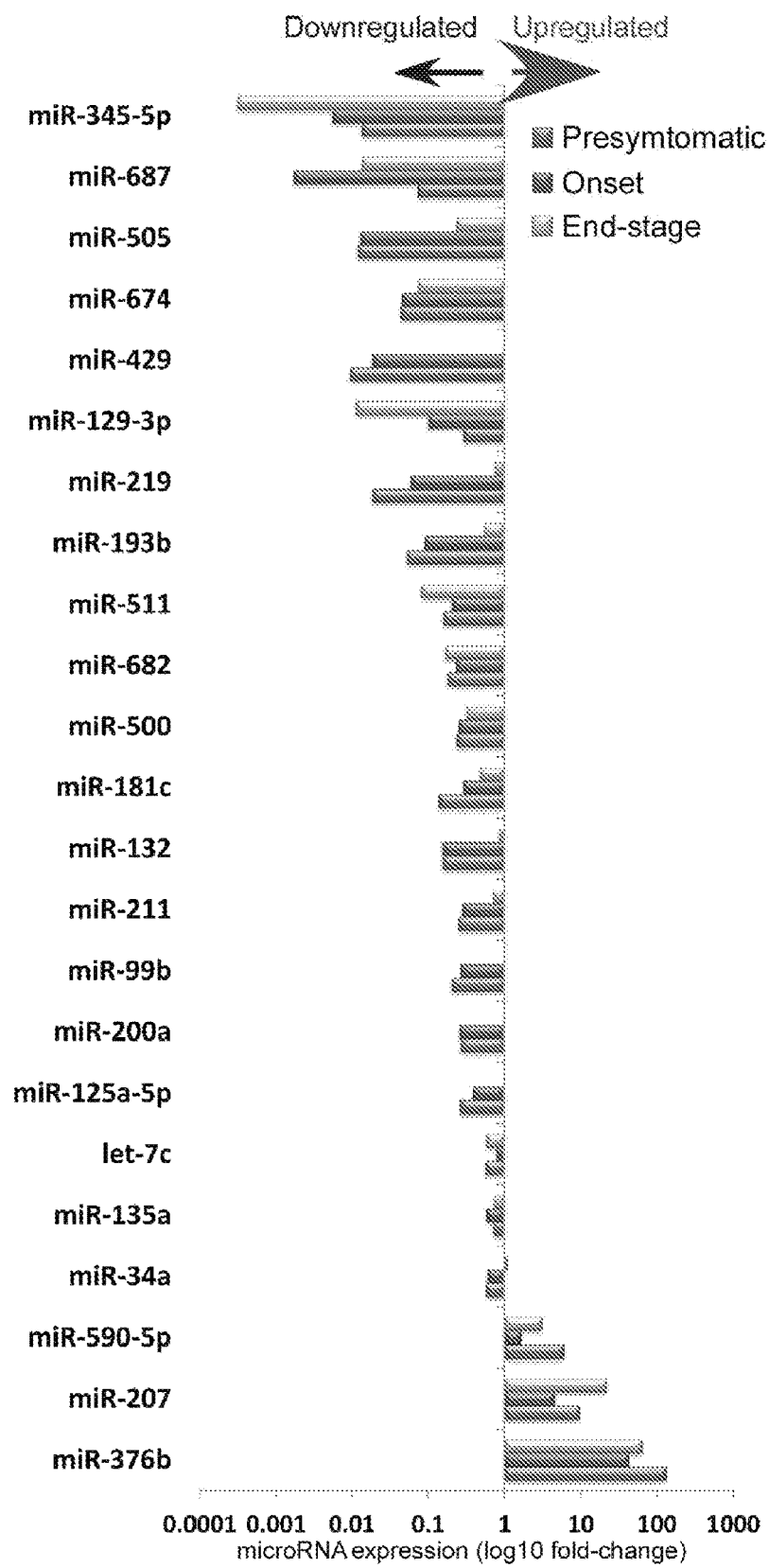
FIG. 3C is a summary of significantly dysregulated microRNAs in Ly6C$^{Low}$ monocytes in SOD$^{G93A}$ mice compared to the expression of the microRNAs in Ly6C$^{Low}$ monocytes from non-transgenic littermates. These data were validated in singleplex TaqMan PCR.

Lys6C$^{Hi}$/CCR2$^+$ monocytes participate in tissue damage and disease pathogenesis in a variety of conditions, including an animal model of MS (King et al., *Blood* 113:3190-3197, 2009). Experiments were to performed to compare the microRNA expression profile in CD39$^+$ microglia (FIG. 1A-1C), Ly6C$^{Hi}$ monocytes (FIGS. 2A-2C), and Ly6C$^{Low}$ monocytes (FIGS. 3A-3C), in the mouse SOD1$^{G93A}$ model of ALS at the presymptomatic stage (60 days), at the time of onset of symptoms, and at the end stage of disease to the expression in the same cells in non-transgenic litermates.

These data were gathered using rodent TaqMan Low Density Arrays (TaqMan MicroRNA Assays containing 364 mouse microRNA assays (n=2 arrays for each group; pool of 5-6 mice per group). The microarray data were normalized using quantile (R software) to remove variation between samples. MicroRNA expression level was normalized using dCT against U6 miRNA (internal control) and geometric mean across all samples. After the normalization step, analysis of variants between groups (ANOVA) was used to define significantly altered microRNAs across all disease stages in SOD1 mice (using a false discovery rate of ≤0.1).

Figure 4:
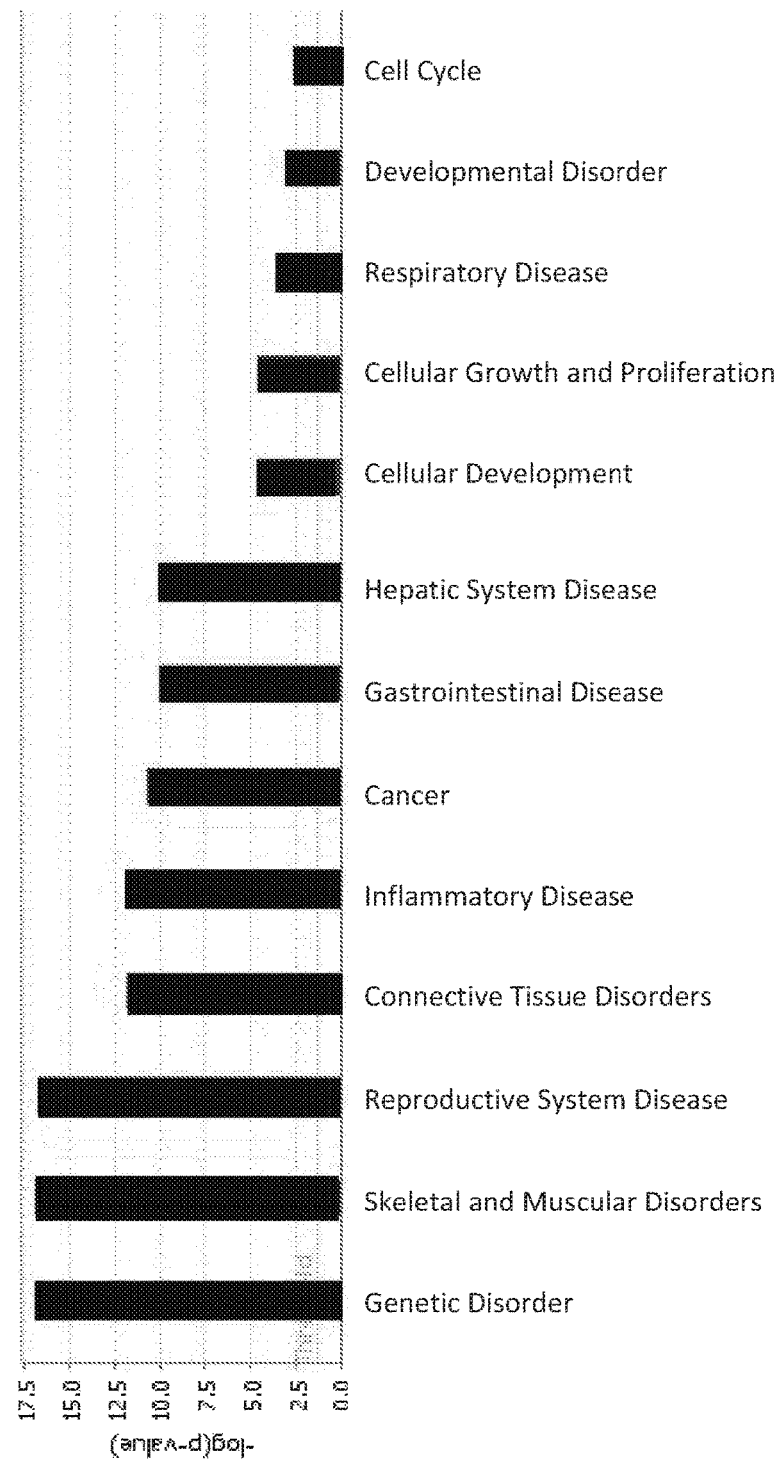
FIG. 4 is a graph and a table showing the results of Ingenuity pathway analysis of the 32 dysregulated microRNAs in Ly6C$^{Hi}$ monocytes (as compared to non-transgenic littermate controls) across all disease stages in SOD1 mice. The graph shows patterns observed in skeletal diseases, muscular diseases, and myopathic disorders.

MicroRNA profiling of spleen-derived Ly6C$^{Hi}$ and Ly6C$^{Low}$ monocytes of the SOD1 mice during all stages of the disease showed 32 significantly dysregulated microRNAs in Ly6C$^{Hi}$ splenic monocytes and 23 dysregulated microRNAs in Ly6C$^{Low}$ splenic monocytes. All of the dysregulated microRNAs in the monocyte subsets were observed one month prior to clinical onset and during disease progression. The majority of these microRNAs were not overlapping between Lys6C$^{Hi}$ monocytes and Ly6C$^{Low}$ monocytes, suggesting that these different monocyte subsets have different functions during disease progression. Inflammation-related microRNAs such as let-7a, miR-27a, miR-34a, miR-132, miR-146a, miR-451, and miR-155 were significantly upregulated in the Ly6C$^{Hi}$ monocytes in the spleen during disease progression in the SOD1 mice (FIG. 2). Ingenuity pathway analysis of the microRNA profile of Ly6C$^{Hi}$ monocytes in SOD1 mice identified patterns of microRNA expression observed in primary muscular disorders (FIG. 4).

The data from microRNA expression profiling of CD39$^+$ microglia in the SOD1 mouse show that 24 microRNAs were upregulated and two microRNAs were downregulated compared to the same cells in non-transgenic litermates. These microRNAs were different from the microRNAs dysregulated in Ly6C$^{Hi}$ monocytes, with the exception of 6 microRNAs (let-7a, miR-27a, miR-34a, miR-132, miR-146a, and miR-155). These data demonstrate differences between resident microglia identified by CD39 and infiltrating Ly6C monocytes, and identify a unique microRNA pattern in microglia in SOD1 mice.

Figure 5:
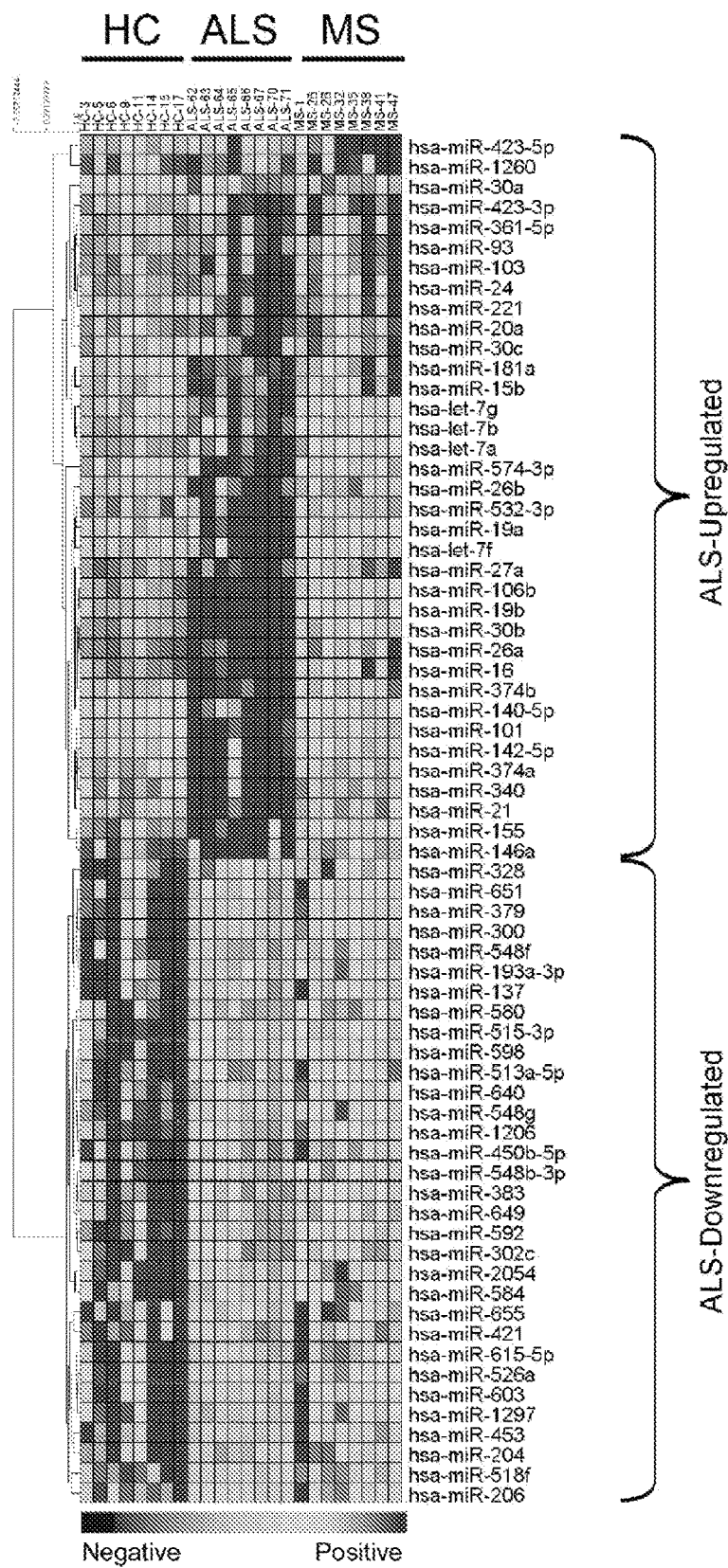
FIG. 5 is a heatmap showing the nCounter expression profiling of blood-derived CD14$^+$CD16$^-$ monocytes for 664 microRNAs in sporadic ALS (8 subjects) and relapsing-remitting multiple sclerosis (8 subjects) compared to the expression of the microRNAs in CD14$^+$CD16$^-$ monocytes from healthy controls (8 subjects). The heatmap shows the results of analysis of variance (ANOVA) using Dunnett's post hoc test (P<0.01). The microRNAs upregulated or downregulated in CD14$^+$CD16$^-$ monocytes from ALS subjects (as compared to expression of these microRNAs in CD14$^+$CD16$^-$ monocytes from healthy controls) are indicated. Each row of the heatmap represents an individual gene and each column an individual.
Figure 6:
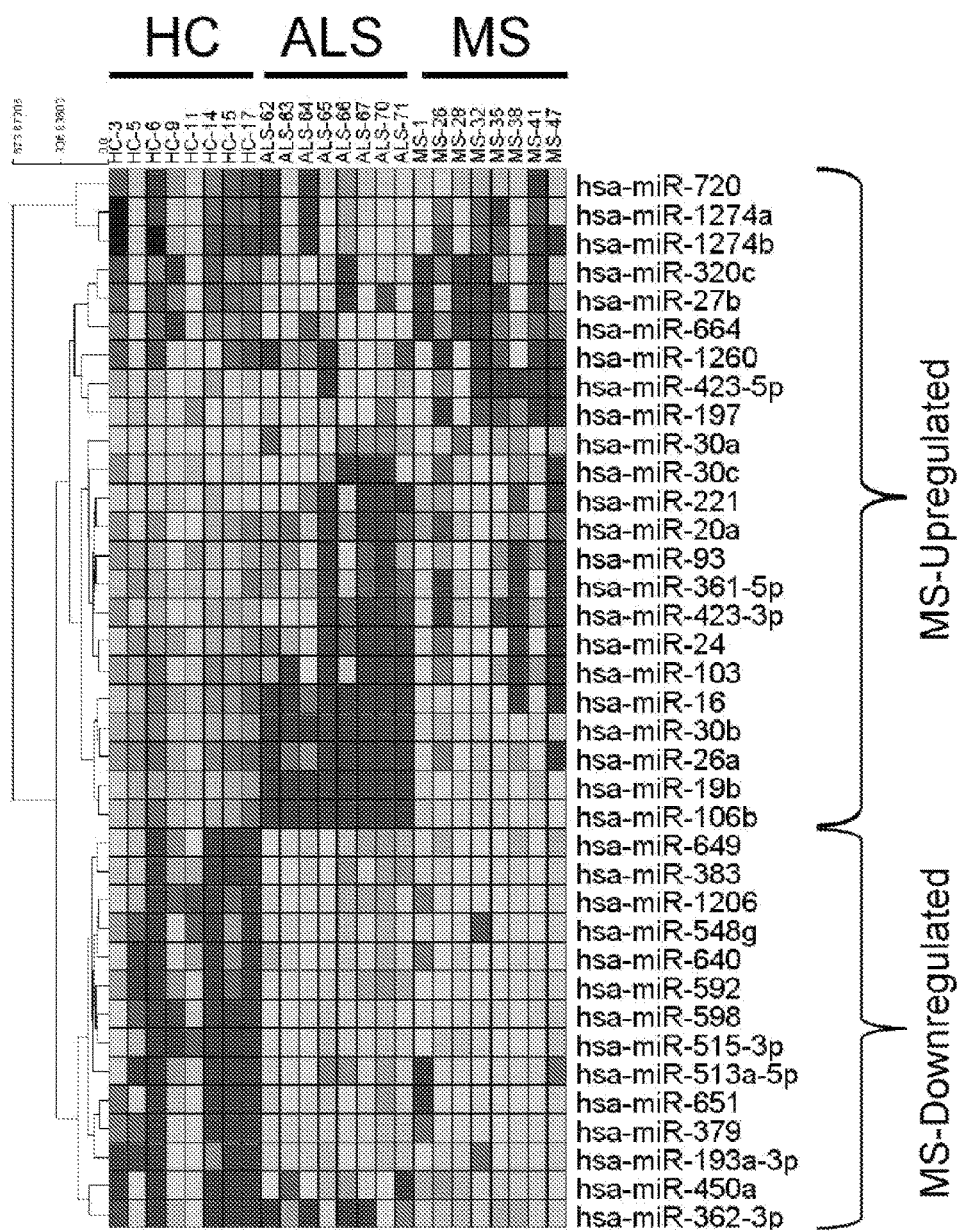
FIG. 6 is a heatmap showing the nCounter expression profiling of blood-derived CD14$^+$CD16$^-$ monocytes for 664 microRNAs in sporadic ALS (8 subjects) and relapsing-remitting multiple sclerosis (8 subjects) compared to the expression of these microRNAs in CD14$^+$CD16$^-$ monocytes from healthy controls (8 subjects). The heatmap shows the results of ANOVA using Dunnett's post hoc test (P<0.01). The microRNAs upregulated or downregulated in CD14$^+$CD16$^-$ monocytes from MS subjects (as compared to the expression of the microRNAs in CD14$^+$CD16$^-$ monocytes from healthy controls) are indicated. Each row of the heatmap represents an individual gene and each column an individual.
Figure 8:
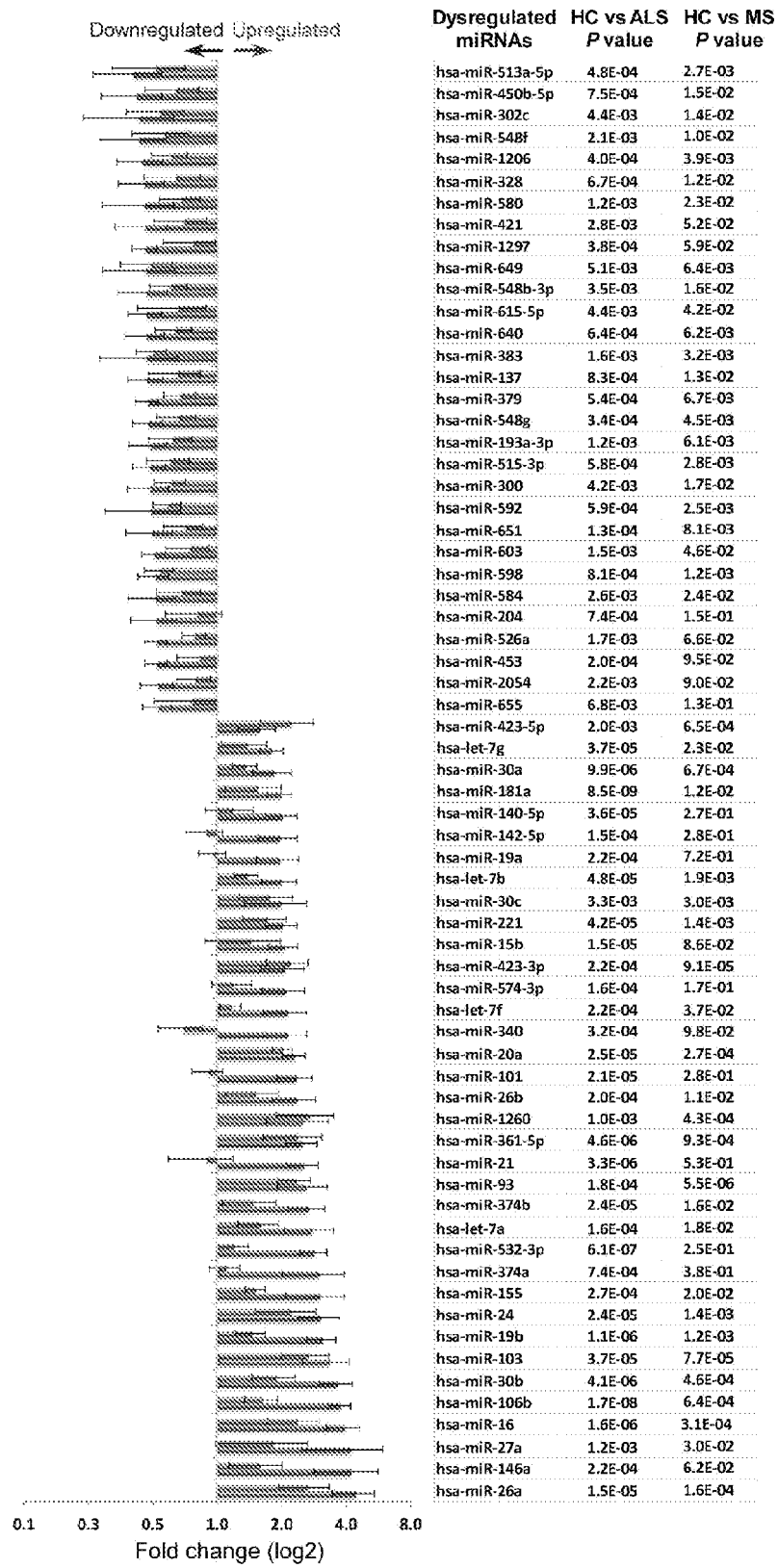
FIG. 8 is a summary of the significantly dysregulated microRNAs in CD14$^+$CD16$^-$ monocytes from ALS and MS subjects compare d to the expression of the microRNAs in CD14$^+$CD16$^-$ monocytes from healthy controls. The bars show the relative expression of dysregulated microRNAs in CD14$^+$CD16$^-$ monocytes from ALS and MS subjects compared to the expression of the microRNAs in CD14$^+$CD16$^-$ monocytes from healthy controls.
Figure 33:
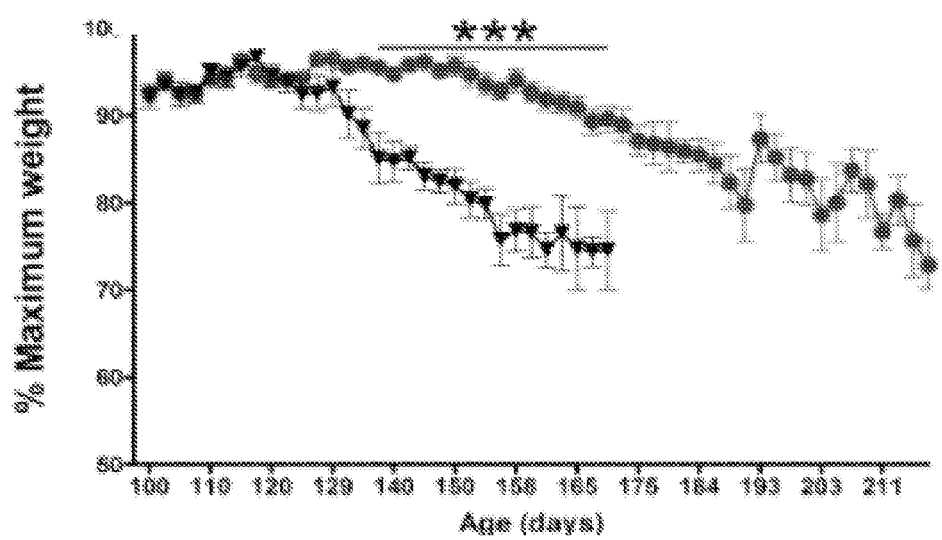
FIG. 33 is a graph of the weight loss of SOD1/miR-155$^{-/-}$ (circles) and SOD1/miR-155$^{+/-}$ (triangles) mice. Statistical analysis was performed using 2-way ANOVA, Bonferri post-hoc test. ***P<0.001.

Example 2. MicroRNAs Dysregulated in CD14$^+$CD16$^-$ Monocytes in Subjects with ALS and MS In view of the unique microRNA profiles observed in mouse monocytes, microRNA expression profiling was performed on human blood-derived CD14$^+$CD16$^-$ monocytes (Ly6C$^{Hi}$ analog) from ALS subjects and MS subjects. In these experiments, nCounter expression profiling of 664 microRNAs in blood-derived CD14$^+$CD16$^-$ monocytes from subjects having sporadic ALS (n=8), subjects having relapsing-remitting MS (n=8), and healthy controls (n=8). The microRNA expression level was normalized against a geometric mean of five house-keeping genes (ACTB, B2M, GAPDH, RPL19, and RPLP0). A heatmap comparing the microRNA expression in monocytes from ALS or MS subjects compared to the expression in healthy controls was generated using ANOVA with Dunnett's post hoc test (p<0.01) (FIGS. 5, 6, and 33, respectively). FIG. 7A depicts the number of microRNAs uniquely upregulated in CD14$^+$CD16$^-$ monocytes from ALS and MS subjects, as well as the number of microRNAs upregulated in CD14$^+$CD16$^-$ monocytes from both ALS and MS subjects. FIG. 7A also depicts the number of microRNAs uniquely downregulated in CD14$^+$CD16$^-$ monocytes from ALS and MS subjects, as well as the number of microRNAs downregulated in CD14$^+$CD16$^-$ monocytes from both ALS and MS subjects. FIG. 7B is a volcano plot showing the significantly deregulated microRNAs in CD14$^+$CD16$^-$ monocytes from ALS subjects compared to the expression of the microRNAs in CD14$^+$CD16$^-$ monocytes from healthy controls. FIG. 7C is a volcano plot showing the significantly deregulated microRNAs in CD14$^+$CD16$^-$ monocytes from MS subjects compared to the expression of the microRNAs in CD14$^+$CD16$^-$ monocytes from healthy controls. FIG. 8 provides a summary of the microRNAs deregulated in CD14$^+$CD16$^-$ monocytes from ALS and MS subjects compared to the expression of the microRNAs in CD14$^+$CD16$^-$ monocytes from healthy controls.

Figure 10C:
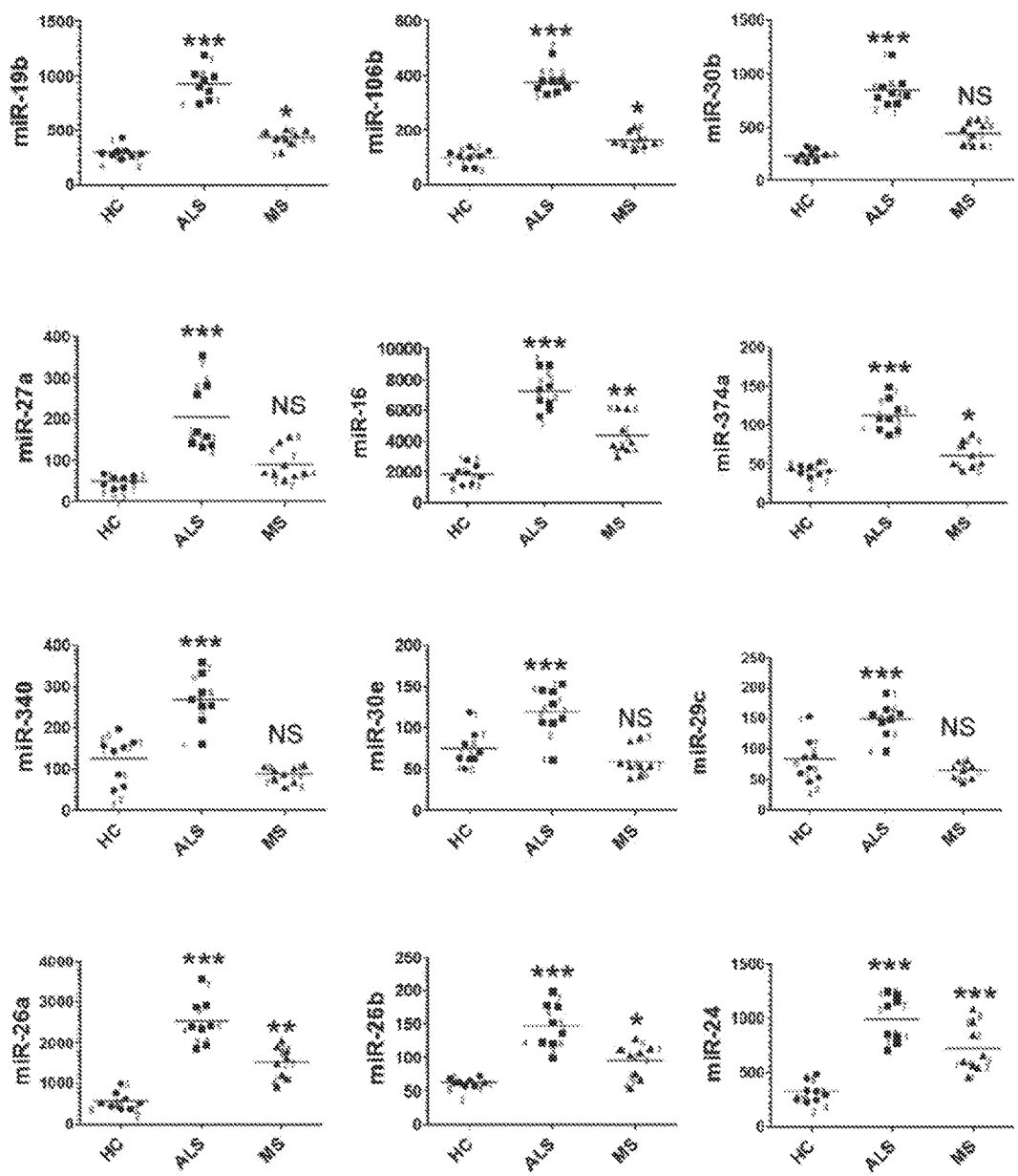
FIG. 10C is twenty graphs showing the expression of twenty upregulated microRNAs in CD14$^+$CD16$^-$ monocytes from sporadic ALS subjects (8 subjects), healthy subjects, and subjects having MS (determined using real-time PCR). A two-tiled Mann-Whitney t-test was used to calculate the P values.
Figure 10C:
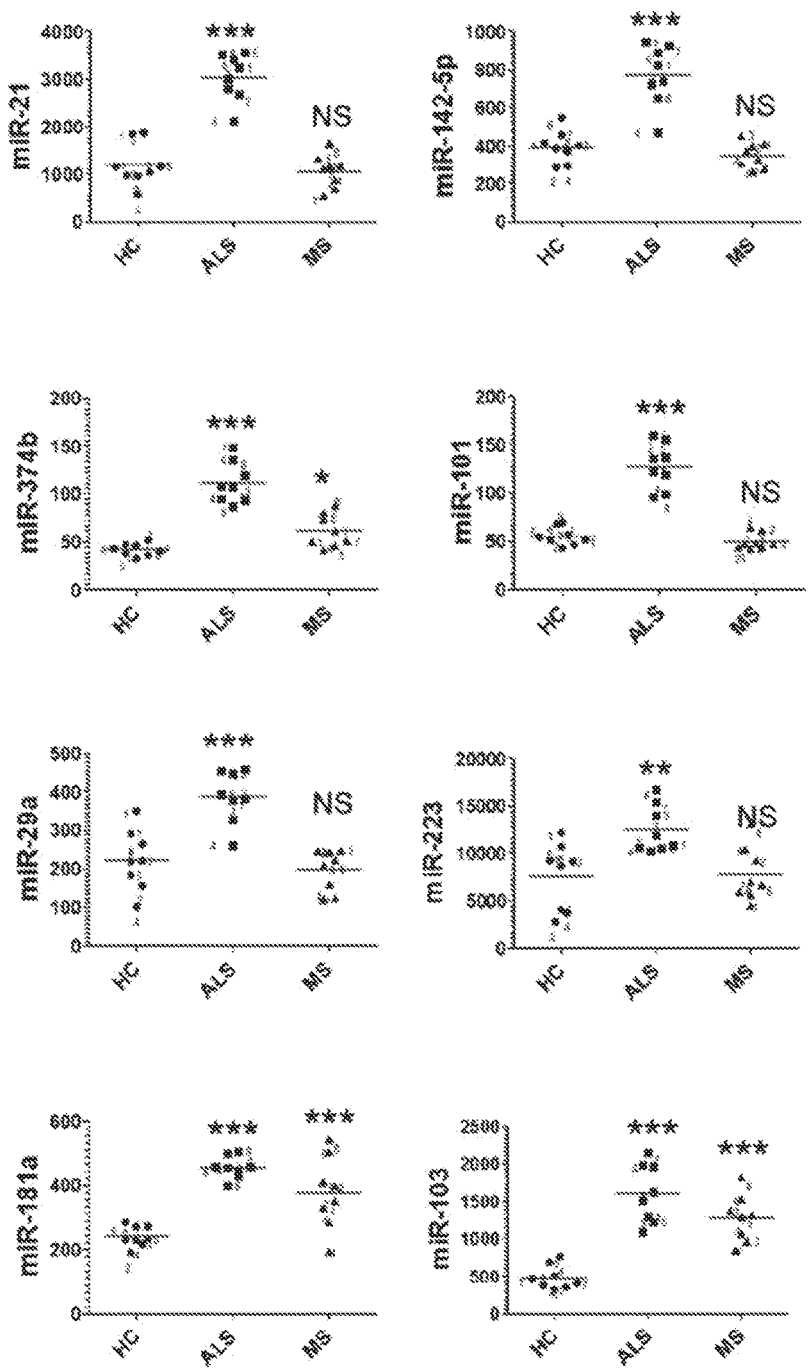
Figure 12C:
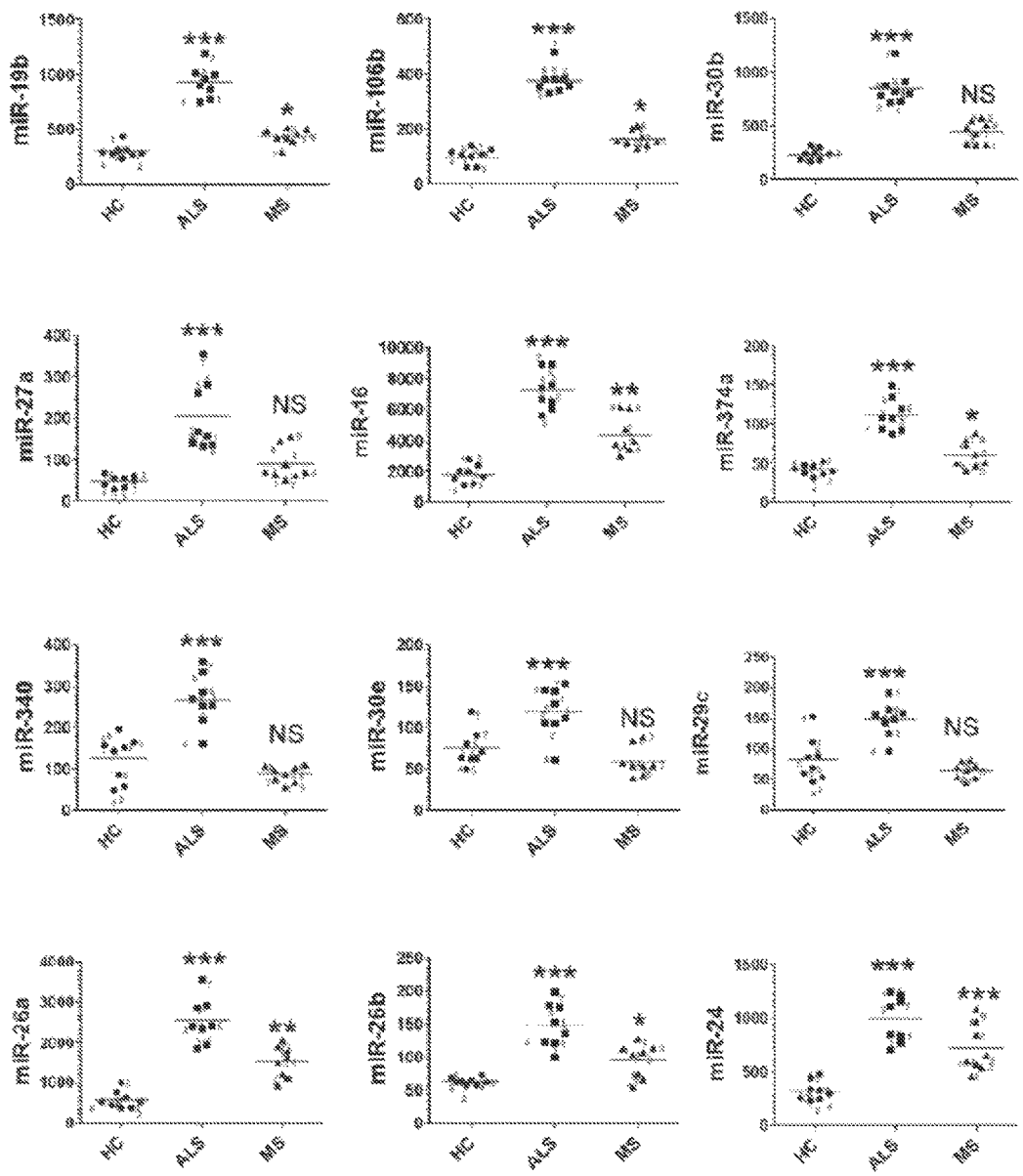
FIG. 12C is twenty graphs showing the expression of twenty downregulated microRNAs in CD14$^+$CD16$^-$ monocytes from sporadic ALS subjects as compared to healthy subjects, and subjects having MS-relapsing remitting (MS- RR) (determined using real-time PCR). A two-tiled Mann-Whitney t-test was used to calculate the P values (*, $P<0.05$; , $P<0.01$; *, $P<0.001$).
Figure 12C:
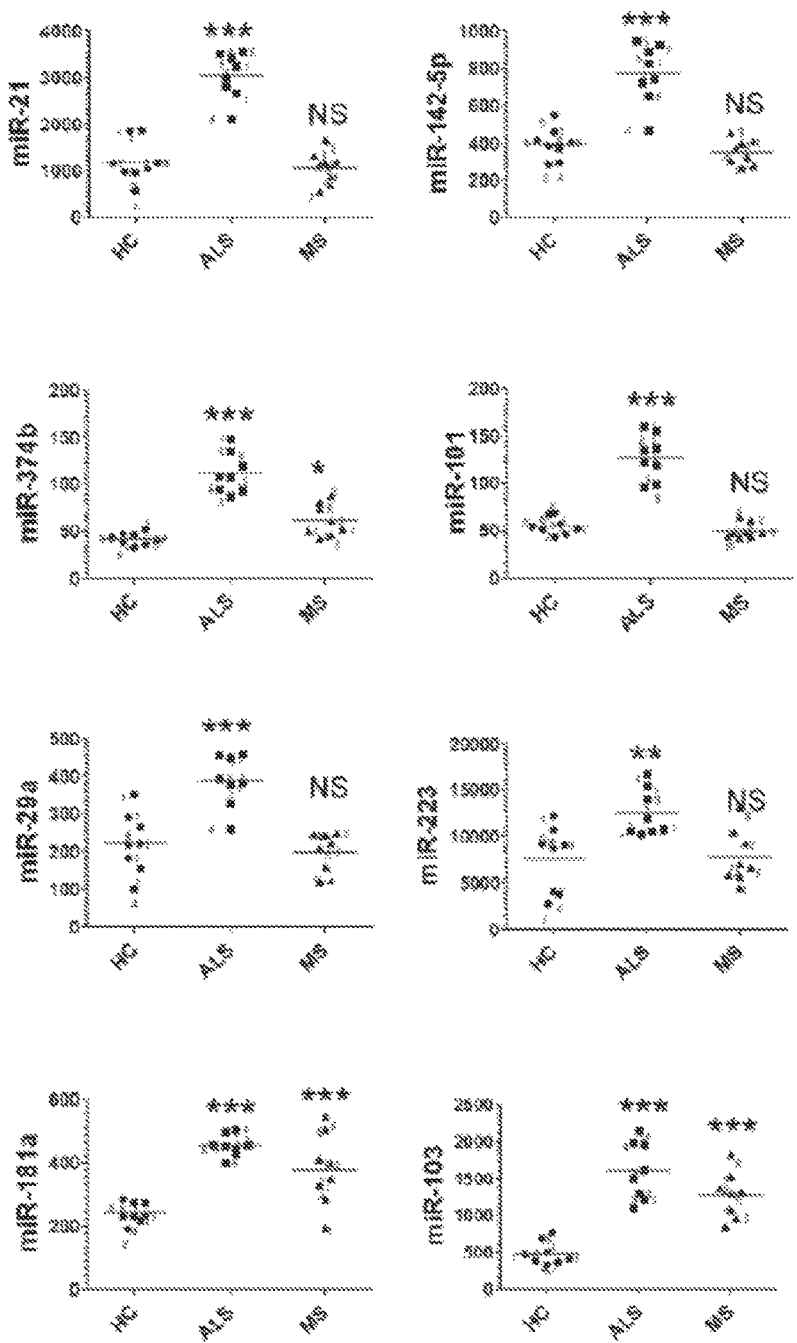

The dysregulation of specific microRNAs in CD14$^+$CD16$^-$ monocytes from ALS and MS subjects (as compared to healthy controls) were confirmed using real-time PCR. For example, real-time PCR was used to confirm the upregulation of hsa-miR-27a, hsa-miR-190, hsa-miR-500, hsa-miR-155, and hsa-miR-532-3p in CD14$^+$CD16$^-$ monocytes from ALS subjects (n=11) compared to the expression of these microRNAs in CD14$^+$CD16$^-$ monocytes from healthy controls (n=8) (two-tiled Mann-Whitney t-test) (FIG. 9). Additional real-time PCR experiments were performed to confirm the unique upregulation of microRNAs in CD14$^+$CD16$^-$ monocytes from ALS subjects (n=8; clinical scoring of these subjects is shown in FIGS. 10A and 10B) as compared to the expression of these microRNAs in CD14$^+$CD16$^-$ monocytes from both MS subjects and healthy controls (FIG. 10C). The data in FIG. 10C show that 20 different microRNAs are uniquely upregulated in CD14$^+$CD16$^-$ monocytes as compared the expression of these microRNAs in CD14$^+$CD16$^-$ monocytes from MS subjects and healthy controls: hsa-miR-19b, hsa-miR-106b, hsa-miR-30b, hsa-miR-21, hsa-miR-142-5p, hsa-miR-27a, hsa-miR-16, hsa-miR-374a, hsa-miR-374b, hsa-miR-101, hsa-miR-340, hsa-miR-30e, hsa-miR-29c, hsa-miR-29a, hsa-miR-223, hsa-miR-26a, hsa-miR-26b, hsa-miR-24, hsa-miR-181a, and hsa-miR-103. The unique upregulation of hsa-miR-27a, hsa-miR-155, hsa-miR-146a, and hsa-miR-532-3p in CD14$^+$CD16$^-$ monocytes from ALS subjects as compared to the expression of these microRNAs in CD14$^+$CD16$^-$ monocytes from MS subjects and healthy controls was also confirmed in a second set of real-time PCR experiments (FIG. 11) (microRNA expression was normalized against dCT using U6 miRNA). Additional real-time PCR experiments were performed to confirm the unique down-regulation of hsa-miR-518f, hsa-miR-206, hsa-miR-204, hsa-miR-137, hsa-miR-453, hsa-miR-603, hsa-miR-1297, hsa-miR-192, hsa-miR-526a, hsa-miR-615-5p, hsa-miR-655, hsa-miR-450b-5p, hsa-miR-548b-3p, hsa-miR-584, hsa-miR-548f, hsa-miR-300, hsa-miR-302c, hsa-miR-328, hsa-miR-421, and hsa-miR-580 in CD14$^+$CD16$^-$ monocytes from ALS subjects compared to the expression of these microRNAs in CD14$^+$CD16$^-$ monocytes from both MS subjects and healthy controls (FIG. 12).

Figure 13:
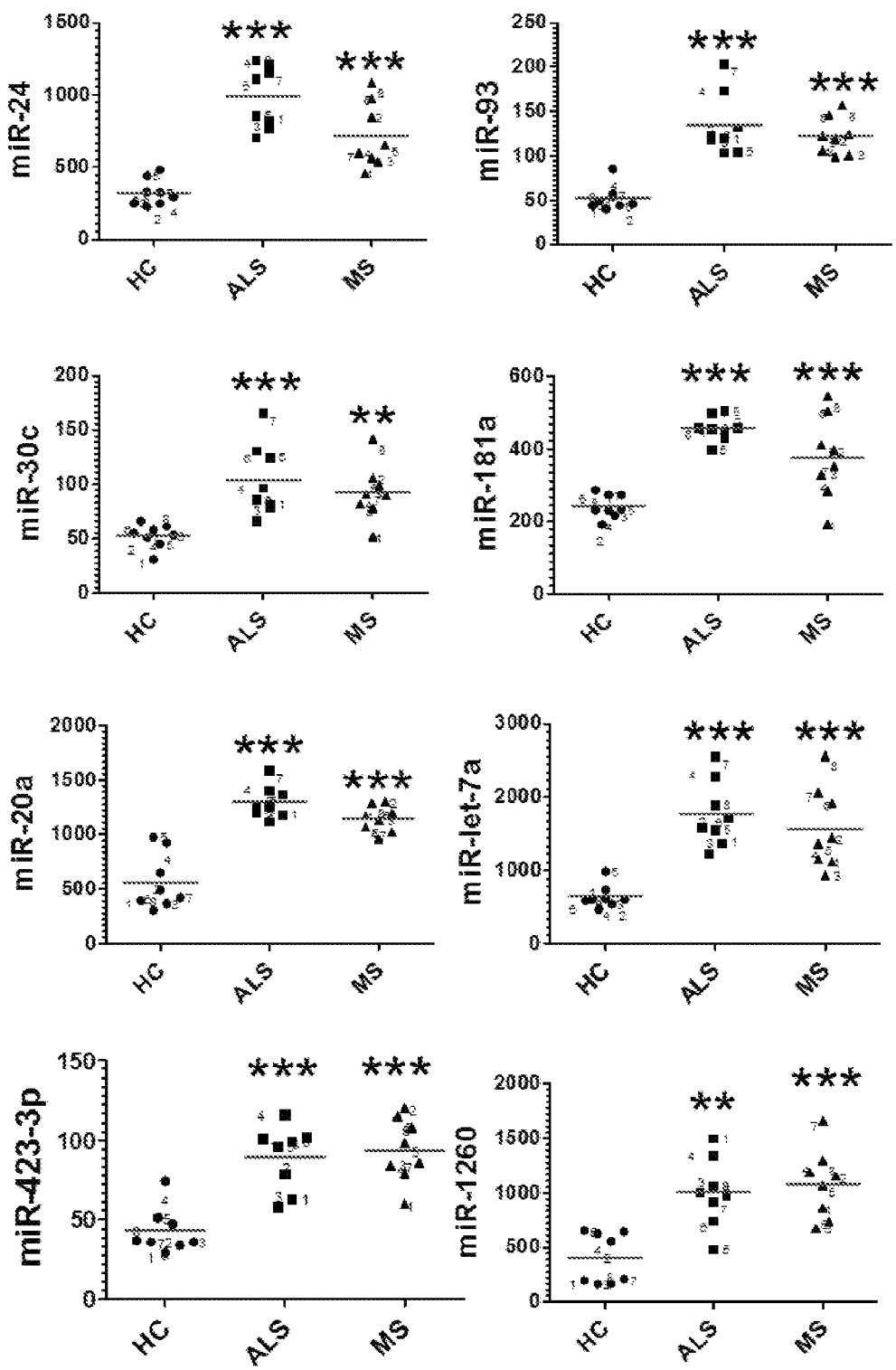
FIG. 13 is eight graphs showing the expression of eight upregulated microRNAs in CD14$^+$CD16$^-$ from sporadic ALS and MS-RR as compared to healthy subjects, subjects (8 subjects in each group) (determined using real-time PCR). The data shown were generated using one-way ANOVA and the Dunett's multiple comparison test (, $P<0.01$; *, $p<0.001$).
Figure 14:
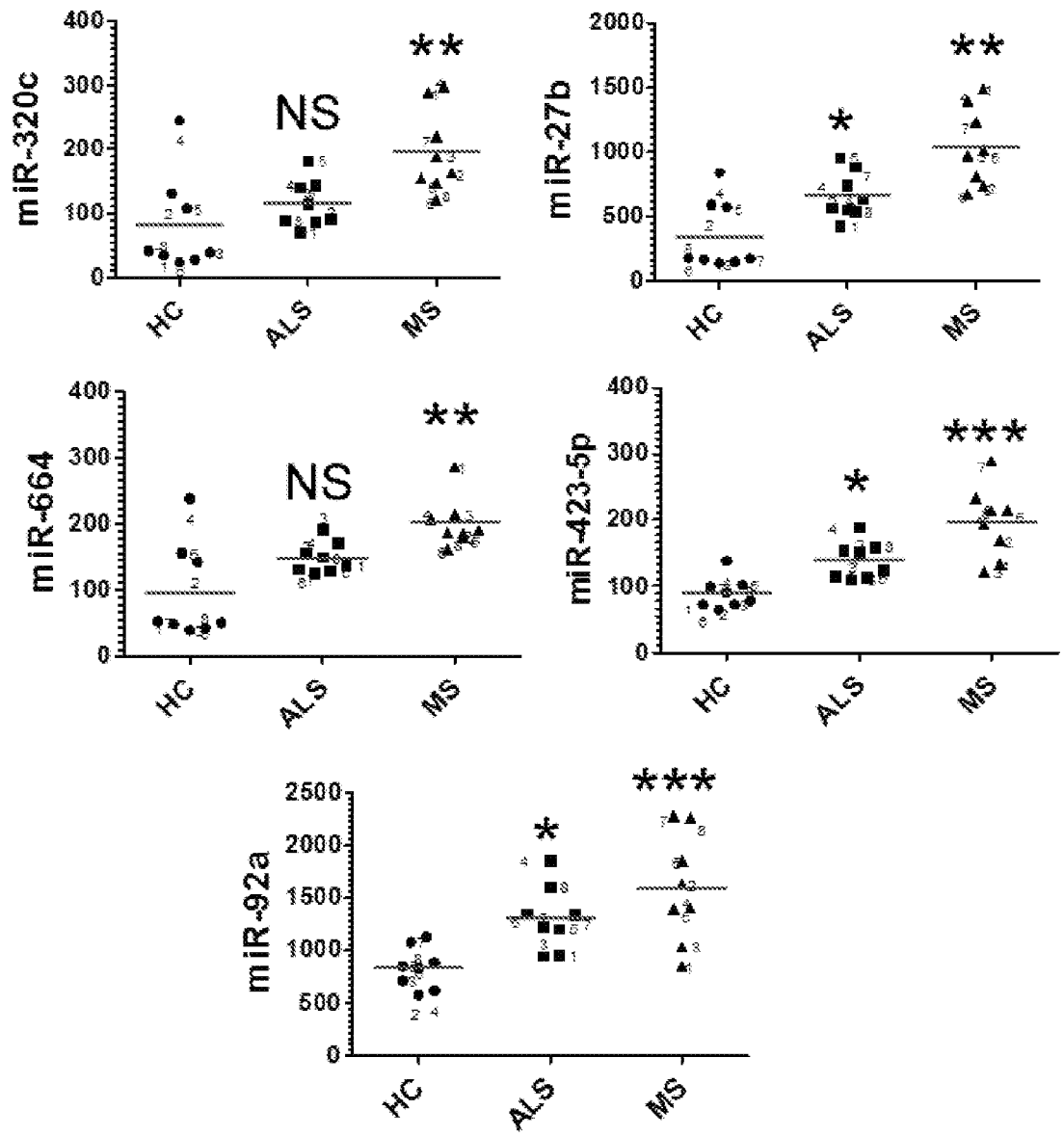
FIG. 14 is five different graphs showing the expression of five upregulated microRNAs in CD14$^+$CD16$^-$ monocytes from MS-RR subjects as compared to healthy subjects and subjects having ALS (8 subjects) (determined using real-time PCR). A two-tiled Mann-Whitney t-test was used to calculate the P values (*, $P<0.05$; , $P<0.01$; *, $P<0.001$).

A further set of real-time PCR experiments were performed to verify the upregulation of hsa-miR-24, hsa-miR-93, hsa-miR-20a, hsa-let-7a, hsa-miR-30c, hsa-miR-181a, hsa-miR-432-3p, and hsa-miR-1260 in CD14$^+$CD16$^-$ monocytes from both ALS and MS subjects as compared to the expression of these microRNAs in CD14$^+$CD16$^-$ monocytes from healthy controls (FIG. 13). An additional set of real-time PCR experiments were performed to verify the upregulation of hsa-miR-320c, hsa-miR-27b, hsa-miR-664, hsa-miR-423-5p, and hsa-miR-92a in CD14$^+$CD16$^-$ monocytes from MS subjects as compared to healthy controls (FIG. 14). These data also show confirm that hsa-miR-664 is uniquely upregulated in CD14$^+$CD16$^-$ monocytes from MS subjects as compared the expression of this microRNA in CD14$^+$CD16$^-$ monocytes from both ALS subjects and healthy controls (FIG. 14).

Figure 15:
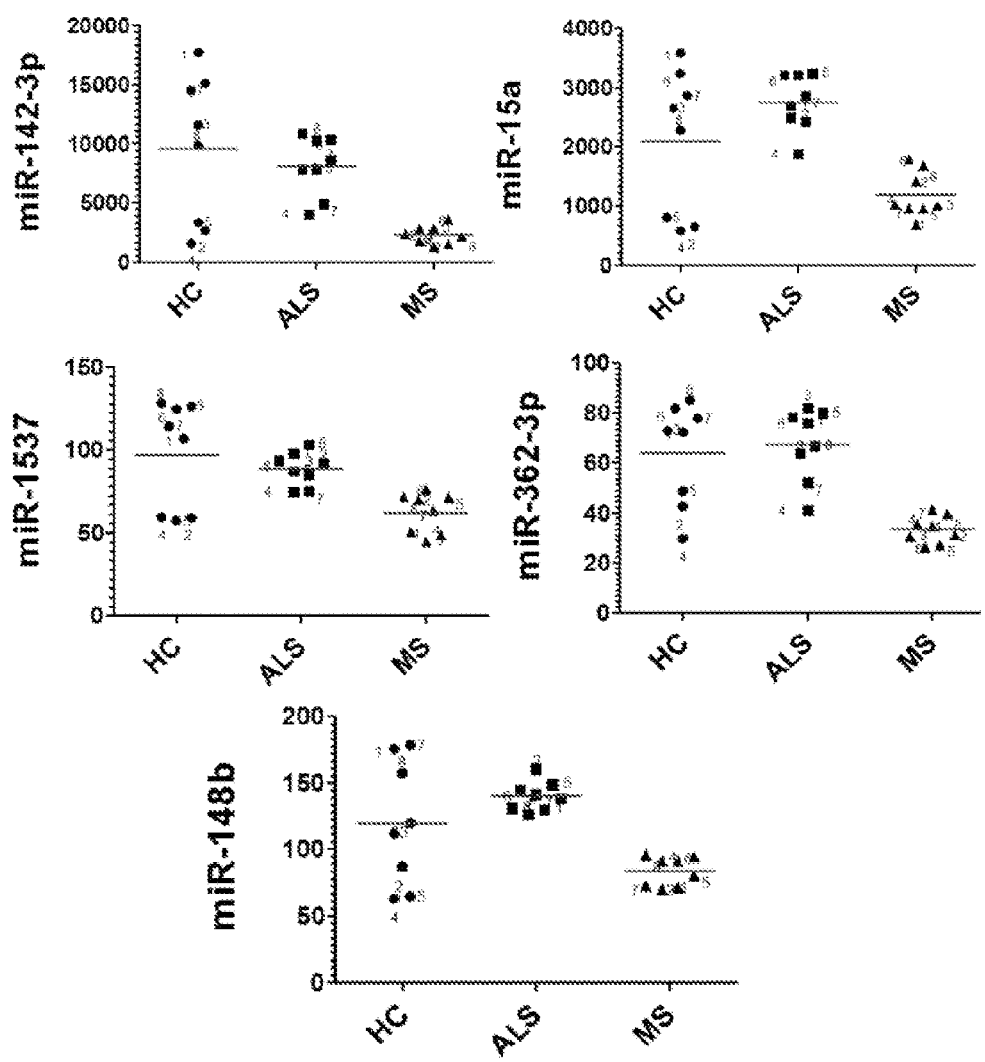
FIG. 15 is five graphs showing the expression of five downregulated microRNAs in CD14$^+$CD16$^-$ from MS-RR subjects as compared to healthy subjects, and subjects having sporadic ALS (determined by real-time PCR). A two-tiled Mann-Whitney t-test was used to calculate the P values (*, $P<0.05$).

In addition, the unique downregulation of hsa-miR-142-3p, hsa-miR-15a, hsa-miR-1537, hsa-miR-362-3p, and hsa-miR-148b in CD14$^+$CD16$^-$ monocytes from MS subjects compared to the expression of these microRNAs in CD14$^+$CD16$^-$ monocytes from ALS subjects and healthy controls was confirmed using real-time PCR (FIG. 15).

Figure 16:
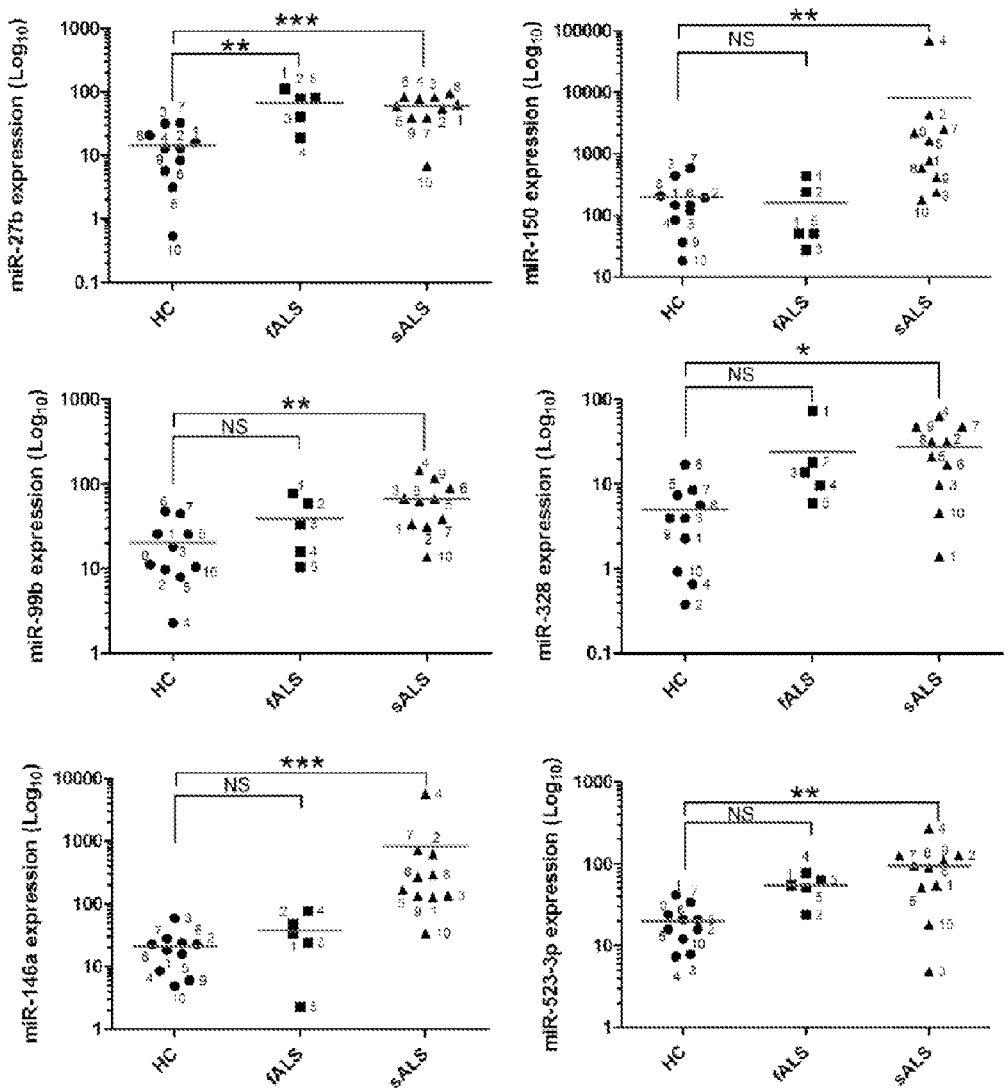
FIG. 16 is six graphs showing the expression of six upregulated microRNAs in the cerebrospinal fluid (CSF) from healthy subjects, subjects with familial ALS (n=5), and subjects with sporadic ALS (n=10). The data were analyzed using ANOVA with Bonfferoni's multiple comparison test. *, $p<0.05$; , $p<0.01$; and *, $p<0.001$.

Example 3. Abnormal MicroRNA Levels in Cerebrospinal Fluid from Subjects Having Sporadic ALS and Familial ALS MicroRNA expression profiling was also performed using cerebrospinal fluid (CSF) from subjects having sporadic ALS and familial ALS. The levels of microRNAs in the CSF from both sporadic ALS (n=10) and familial ALS (n=5) subjects was compared to the levels of microRNAs in the CSF of healthy controls (n=10). The resulting data show that hsa-miR-27b is increased in the CSF of subjects having both sporadic and familial ALS as compared to the level of this microRNA in the CSF of healthy controls, and that hsa-miR-99b, hsa-miR-146a, hsa-miR-150, hsa-miR-328, and hsa-miR-532-3p are uniquely upregulated in CSF from subjects having sporadic ALS compared to the levels of these microRNAs in CSF from healthy controls or subjects having familial ALS (FIG. 16).

Figure 17:
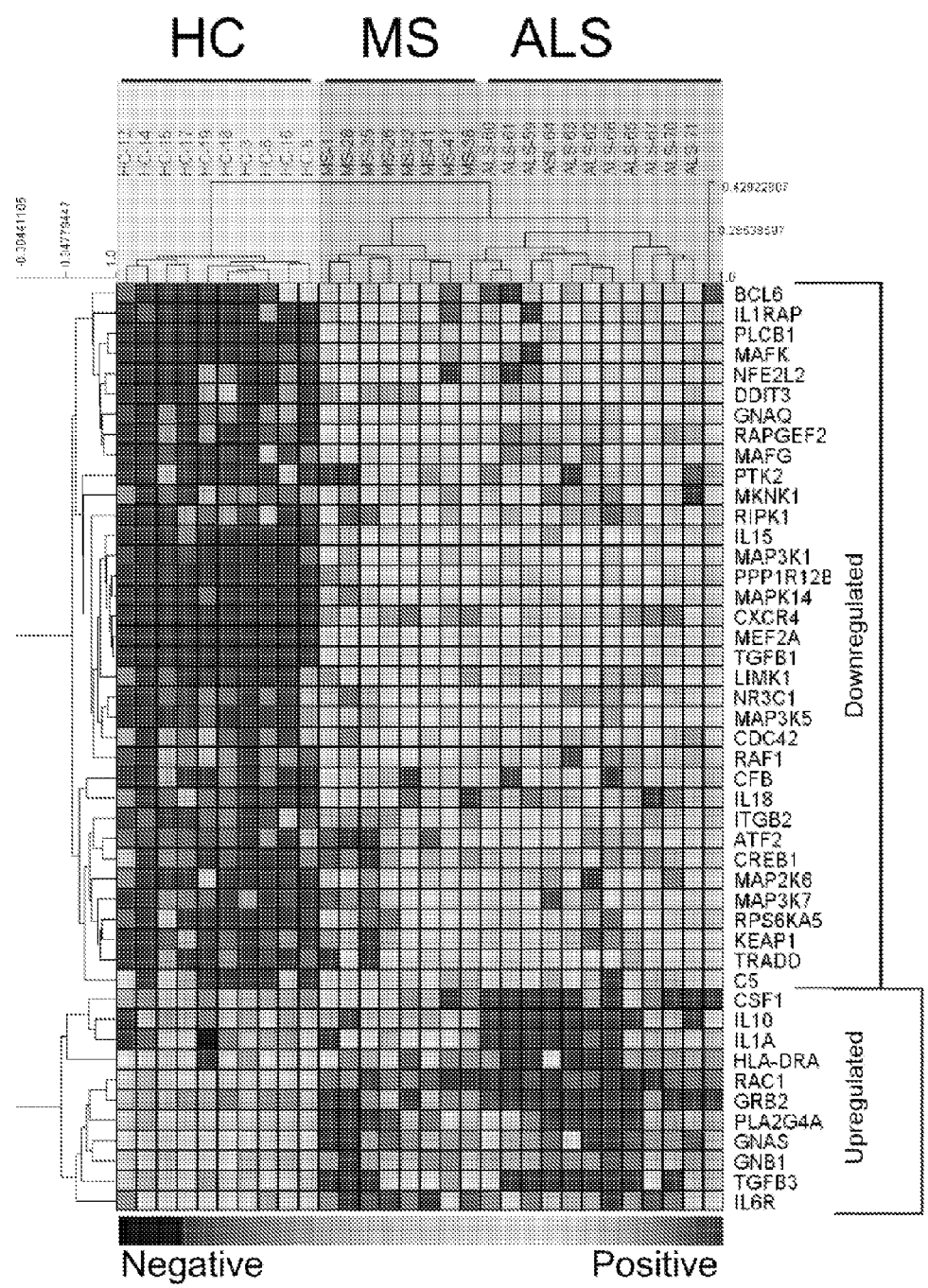
FIG. 17 is a heatmap showing the nCounter expression profiles of 179 inflammation related genes ("inflammatory marker genes") in CD14$^+$CD16$^-$ monocytes from ALS subjects (n=8) and MS subjects (n=11) compared to the levels of these inflammatory marker genes in CD14$^+$CD16$^-$ monocytes from healthy controls (n=10). Data analysis was performed using ANOVA with Dunnett's post hoc test (p<0.01). Each row of the heatmap represents an individual gene and each column represents an individual subject.
Figure 18A:
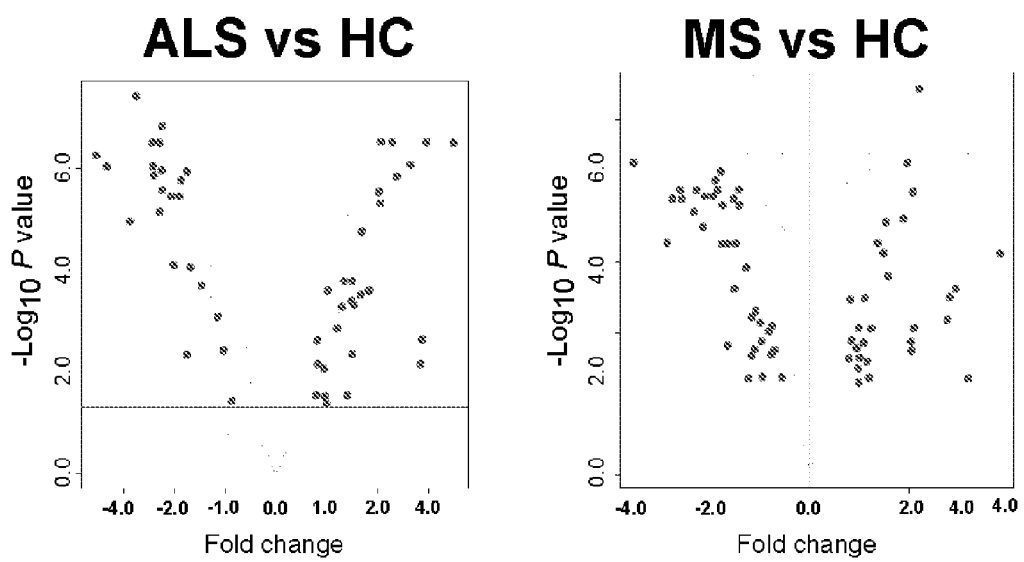
FIG. 18A is two volcano plots showing the significantly dysregulated inflammatory marker genes in CD14$^+$CD16$^-$ monocytes from ALS subjects (left graph) and MS subjects (right graph) compared to the level of the inflammatory marker genes in CD14$^+$CD16$^-$ monocytes from healthy controls.
Figure 18B:
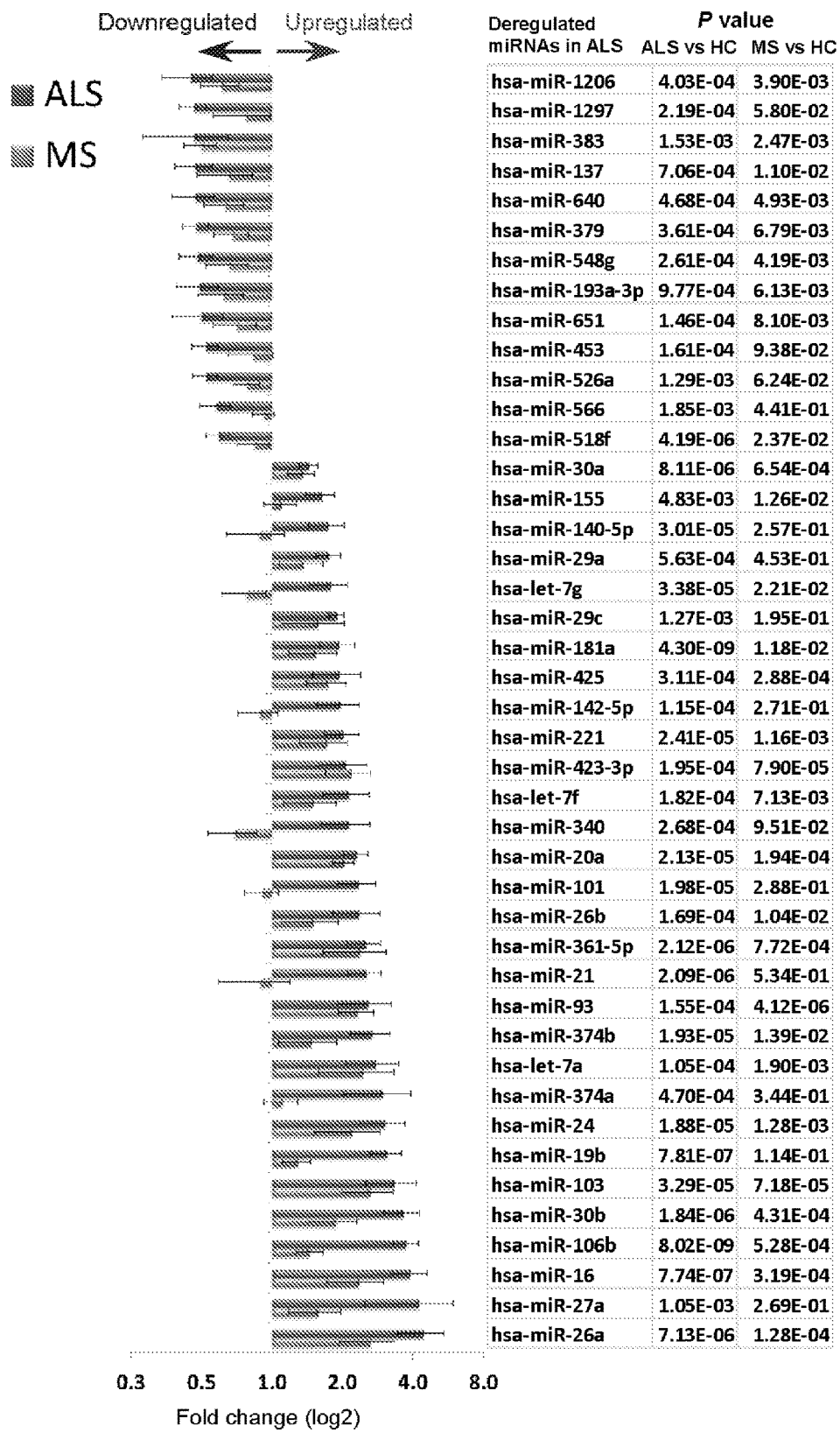
FIG. 18B is a summary of the significantly dysregulated inflammatory marker genes in CD14$^+$CD16$^-$ from ALS and MS subjects compared to the level of the inflammatory marker genes in CD14$^+$CD16$^-$ from healthy controls. The bars show the relative expression of dysregulated inflammatory marker genes in CD14$^+$CD16$^-$ monocytes from ALS and MS subjects compared to the expression of these genes in CD14$^+$CD16$^-$ from healthy controls.

Example 4. Inflammation-Related Genes are Also Dysregulated in CD14$^+$CD16$^-$ Monocytes from Subjects Having ALS and MS Expression profiling analysis of 179 inflammation-related genes ("inflammatory marker genes") was performed using CD14$^+$CD16$^-$ monocytes from ALS subjects (n=8), MS subjects (n=11), and healthy controls (n=10). A heatmap showing the change in expression of different inflammatory marker genes in CD14$^+$CD16$^-$ monocytes from ALS or MS subjects, as compared to the expression of these genes in CD14$^+$CD16$^-$ monocytes from healthy subjects is shown in FIG. 17). A volcano plot of inflammatory marker genes dysregulated in CD14$^+$CD16$^-$ monocytes from ALS and MS subjects compared to the expression of these genes in CD14$^+$CD16$^-$ monocytes from healthy controls is shown in FIG. 18A (left graph and right graph, respectively). A list of the inflammatory marker genes upregulated or downregulated in CD14$^+$CD16$^-$ monocytes from ALS and MS subjects compared to the expression of these genes in CD14$^+$CD16$^-$ monocytes from healthy controls is shown in FIG. 18B.

Figure 19:
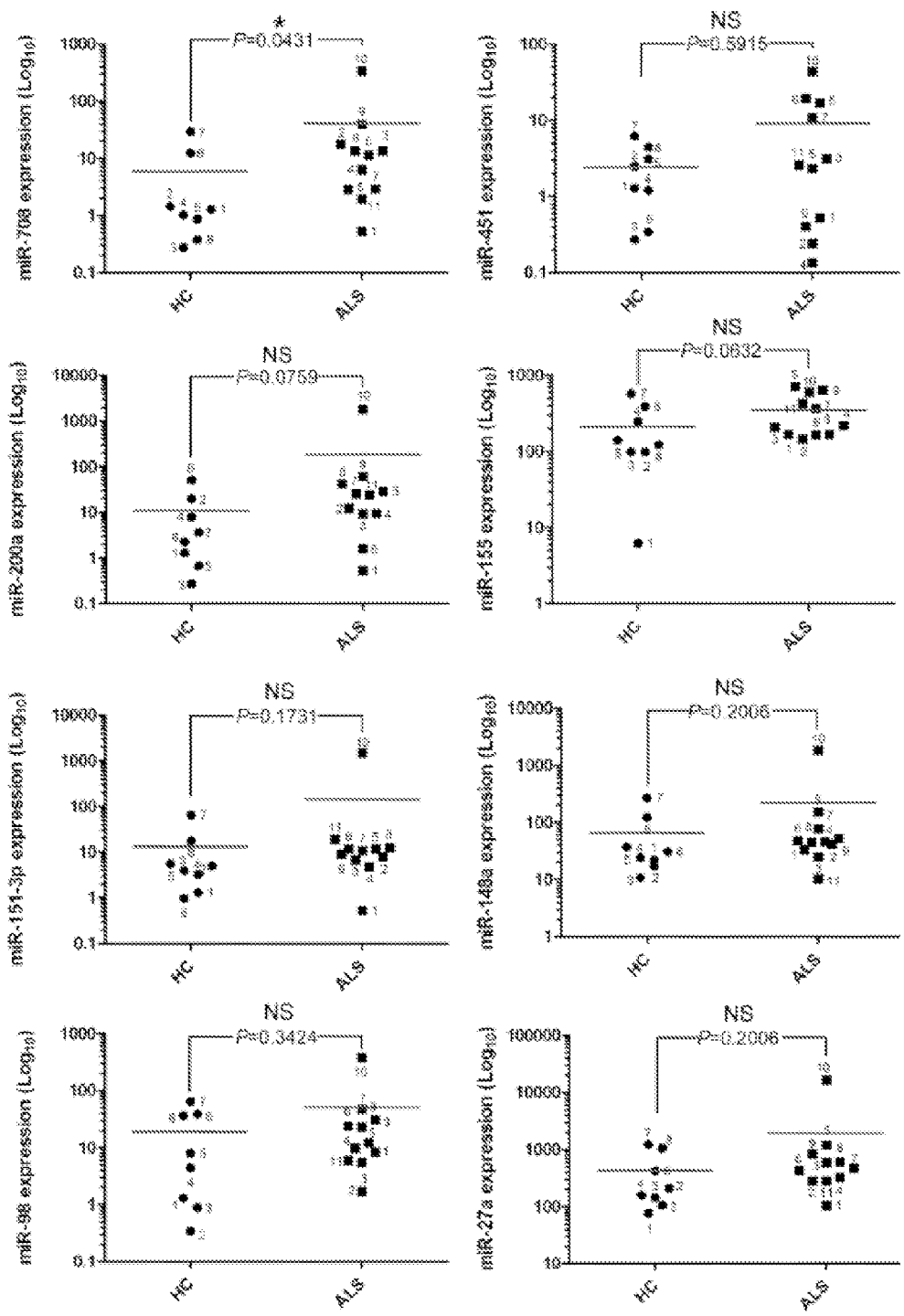
FIG. 19 is eight graphs showing the expression of eight different microRNAs in CD14$^+$CD16$^+$ monocytes from healthy controls (n=8) and ALS subjects (n=11) (determined using real-time PCR). The data were analyzed using the two-tiled Mann-Whitney t-test (*, $P<0.05$).
Figure 20A:
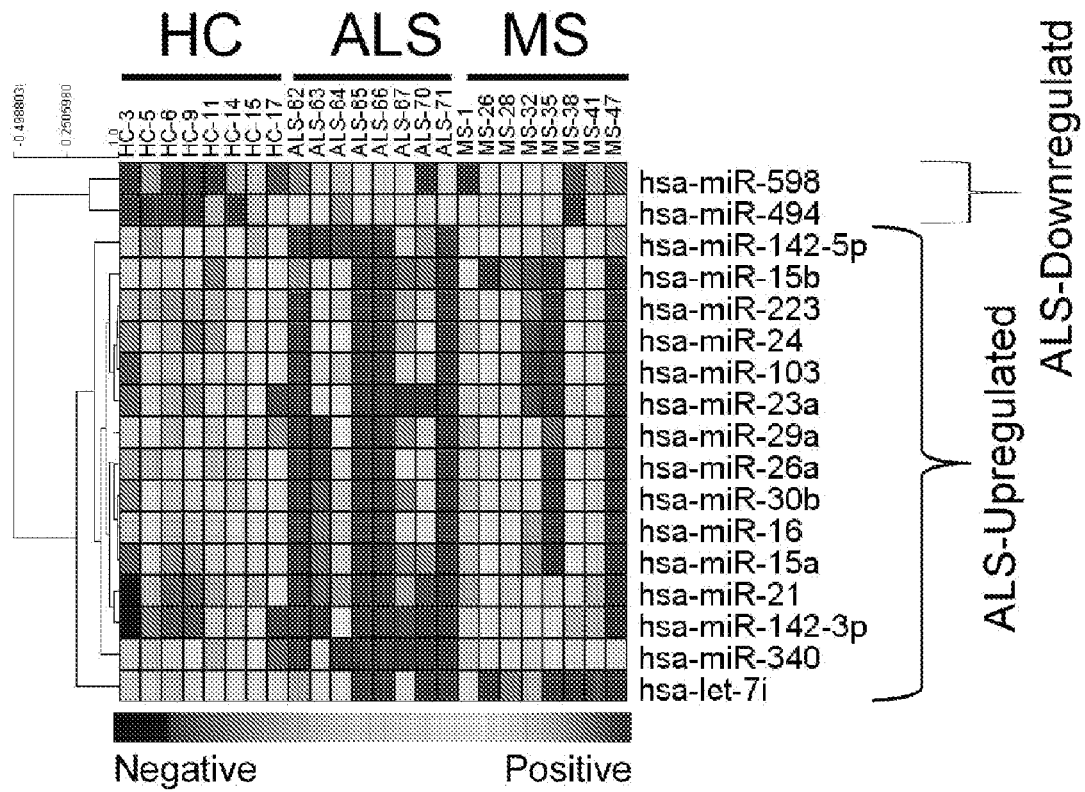
FIG. 20A is a heatmap showing the nCounter expression profiles of microRNAs in CD14$^+$CD16$^+$ monocytes from ALS subjects (n=8) and MS subjects (n=8) compared to the expression of these microRNAs in CD14$^+$CD16$^+$ monocytes from healthy controls (n=8). Data analysis was performed using ANOVA with Dunnett's post hoc test (p<0.01). Each row of the heatmap represents an individual gene and each column represents an individual subject. MicroRNAs upregulated or downregulated in CD14$^+$CD16$^+$ monocytes from ALS subjects relative to CD14$^+$CD16$^+$ monocytes from healthy subjects are indicated.
Figure 20B:
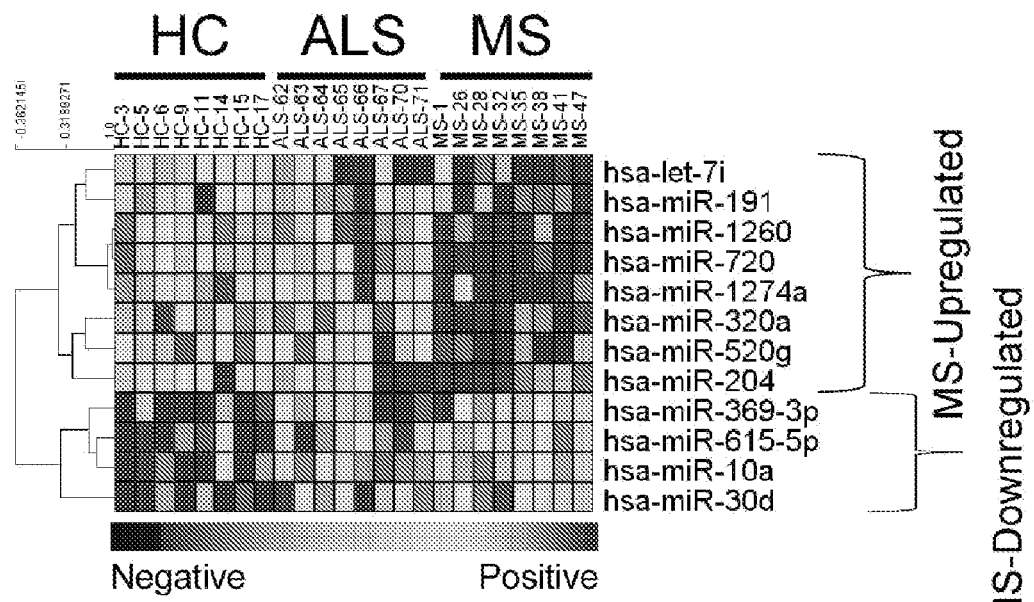
FIG. 20B is a heatmap showing the nCounter expression profiles of microRNAs in CD14$^+$CD16$^+$ monocytes from ALS subjects (n=8) and MS subjects (n=8) compared to the expression of the microRNAs in CD14$^+$CD16$^+$ monocytes from healthy controls (n=8). Data analysis was performed using ANOVA with Dunnett's post hoc test (p<0.01). Each row of the heatmap represents an individual gene and each column represents an individual subject. MicroRNAs upregulated or downregulated in CD14$^+$CD16$^+$ monocytes from MS subjects relative to the expression of the microRNAs in CD14$^+$CD16$^+$ monocytes from healthy subjects are indicated.
Figure 20C:
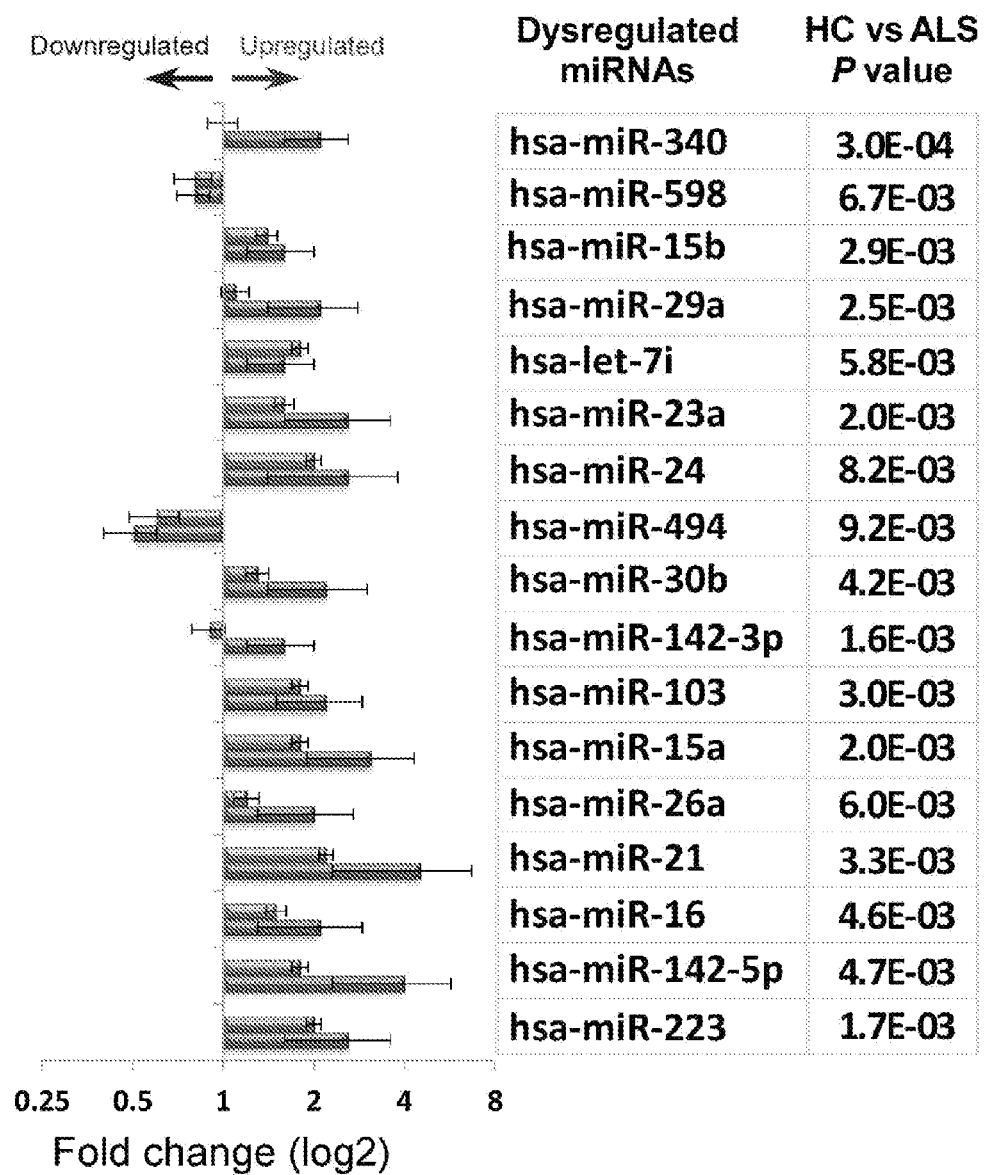
FIG. 20C is a summary of the significantly dysregulated microRNAs in CD14$^+$CD16$^+$ monocytes in ALS and MS subjects compared to the expression of the microRNAs in CD14$^+$CD16$^+$ monocytes from healthy controls. The bars show the relative expression of dysregulated microRNAs in CD14$^+$CD16$^+$ monocytes from ALS and MS subjects compared to the expression of the microRNAs in CD14$^+$CD16$^+$ monocytes in healthy controls.
Figure 21A:
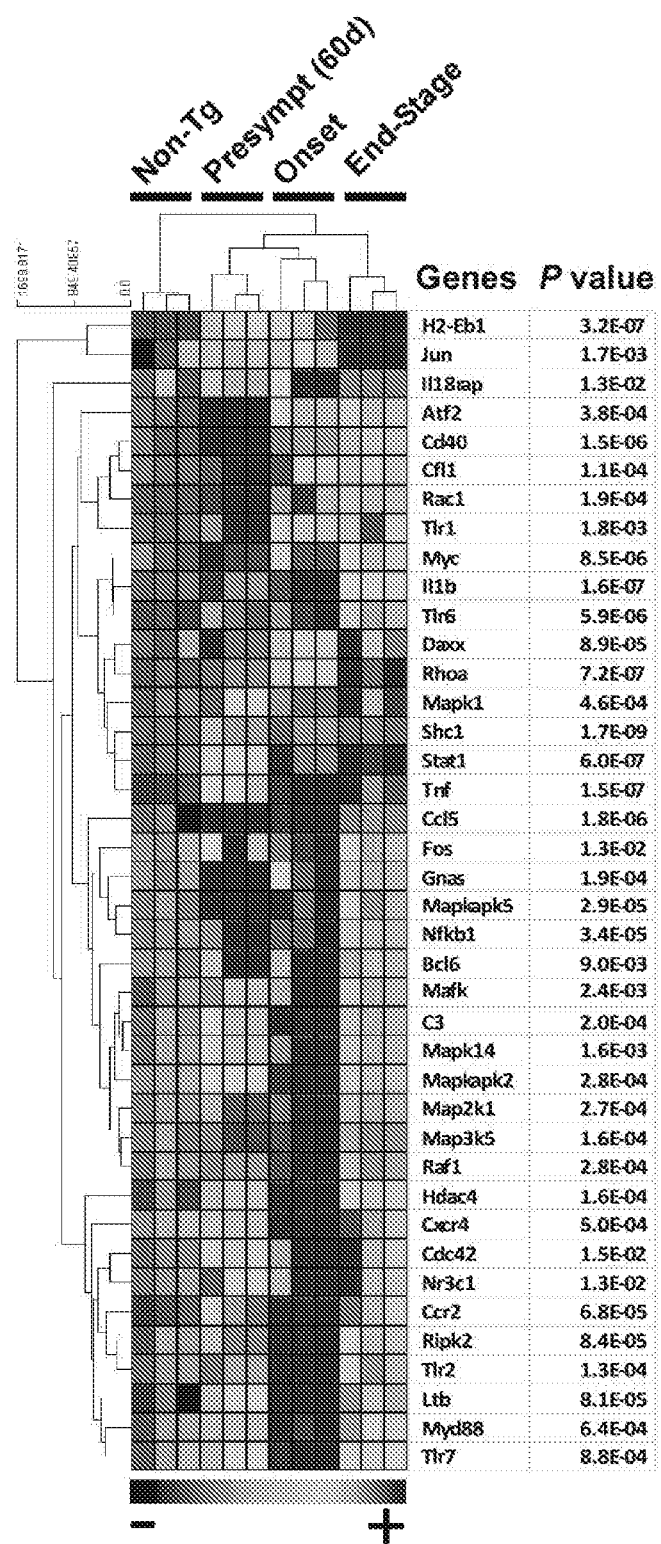
FIG. 21A is nCounter expression profiles of 179 inflammatory marker genes in Ly6C$^{Hi}$ spleen-derived monocyte subsets from SOD1$^{G93A}$ mice compared to the same cells non-transgenic (Tg) litermates at presymptomatic (60 d), onset (defined by body weight loss), and end-stage of disease. A heatmap of the ANOVA with Dunett's post hoc test (P<0.01) results showing genes with at least 2-fold altered transcription levels is shown. Each row of the heatmap represents an individual gene and each column an individual group in biological triplicates (n=3 arrays for each group of pool of 4-5 mice at each time point). Non-transgenic replicates at each disease stage were collapsed and genes hierarchically clustered. Gene expression level was normalized against the geometric mean of six housekeeping genes (CLTC, GAPDH, GUSB, HPRT1, PGK1, and TUBB5).
Figure 21A:
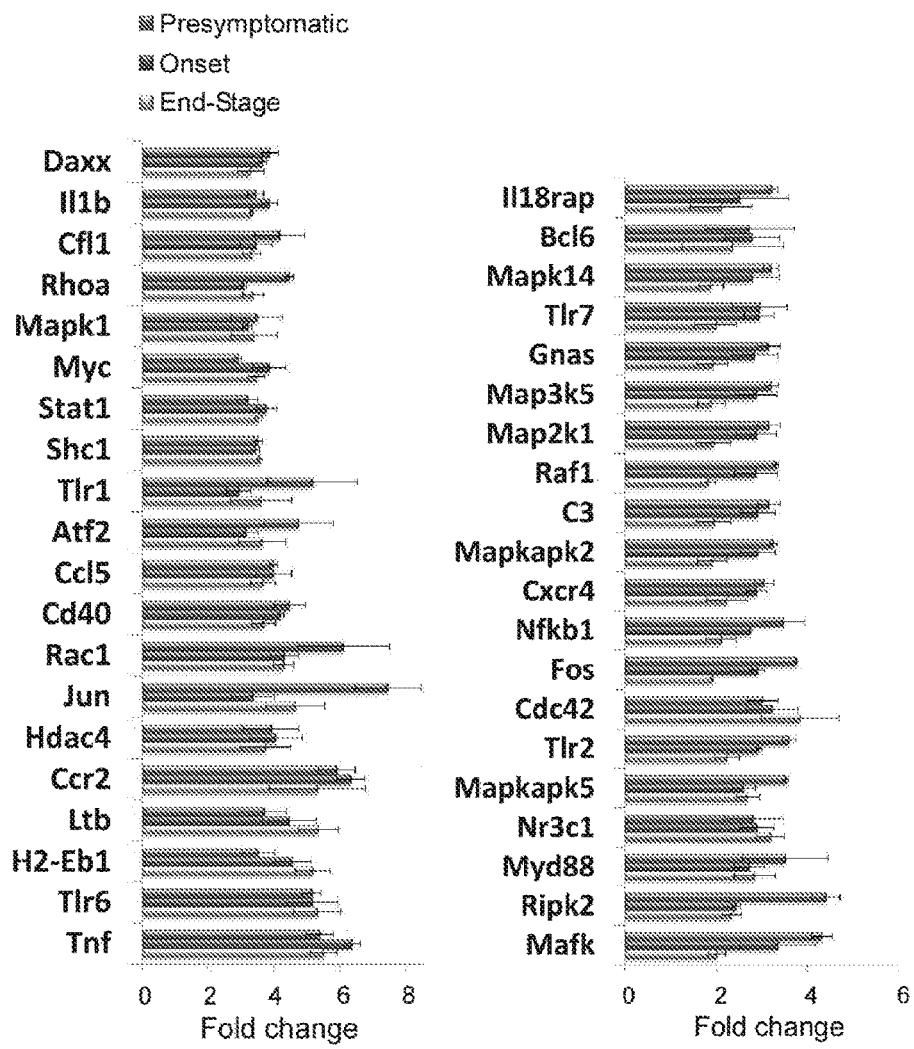

Example 5. MicroRNAs are Also Dysregulated in CD14$^+$CD16$^+$ Monocytes from ALS Subjects MicroRNA expression profiling was also performed using CD14$^+$CD16$^+$ monocytes from both ALS subjects (n=11) and healthy controls (n=8) (FIG. 19). These data show that hsa-miR-708 is increased in CD14$^+$CD16$^+$ monocytes from ALS subjects as compared to the expression of this microRNA in CD14$^+$CD16$^+$ monocytes from healthy subjects.

nCounter expression profiling was performed to identify additional microRNAs dysregulated in CD14$^+$CD16$^-$ monocytes from ALS (n=8) and MS subjects (n=8) compared to the expression of microRNAs in CD14$^+$CD16$^+$ monocytes from healthy subjects (n=8). The data in these experiments were normalized against a geometric mean of five different house-keeping genes (ACTB, B2M, GAPDH, RPL19, and RPL10). In these experiments, the expression of 664 microRNAs were analyzed (FIGS. 20A-C). A heatmap of the relative expression of microRNAs in CD14$^+$CD16$^+$ monocytes from ALS subjects and MS subjects compared to the expression of these microRNAs in CD14$^+$CD16$^+$ monocytes from healthy controls is shown in FIG. 21A and FIG. 20B, respectively. A summary of the microRNAs significantly deregulated in CD14$^+$CD16$^+$ monocytes from ALS and MS subjects compared to the expression of these microRNAs in CD14$^+$CD16$^+$ monocytes from healthy controls is shown in FIG. 20C.

Figure 21B:
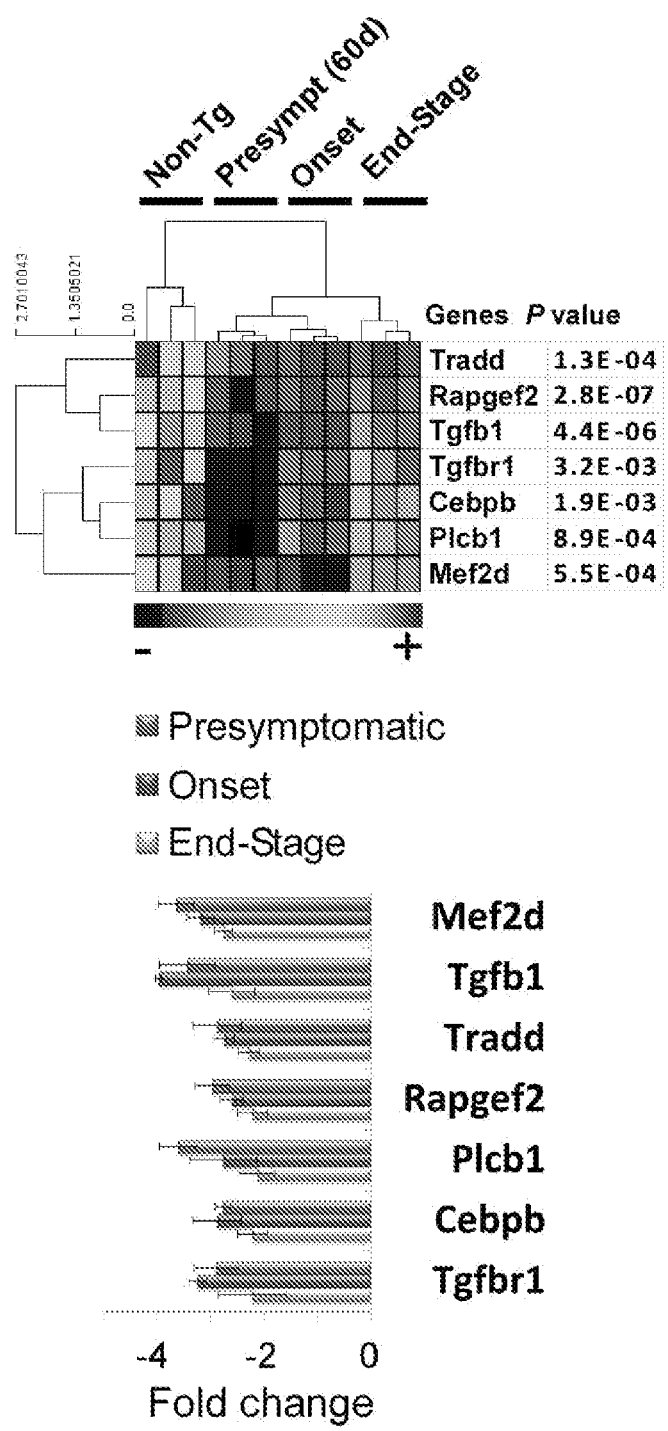
FIG. 21B is nCounter expression profile data showing inflammatory marker genes that are significantly downregulated in Ly6C$^{Hi}$ spleen-derived monocyte subsets from SOD1$^{G93A}$ mice compared to the same cells in non-transgenic (Tg) litermates at presymptomatic (60 d), onset (defined by body weight loss), and end-stage of disease.

Example 6. Proinflammatory Markers Expressed in Ly6C$^{Hi}$ Monocytes and CD39$^+$ Microglia from SOD1$^{G93A}$ Mice The gene expression profile of Ly6C$^{Hi}$ monocytes isolated from the spleen of SOD1 mice one month prior to clinical disease onset and during disease progression. Pro-inflammatory genes were expressed at both time points (FIG. 21A). Out of 179 inflammatory marker genes measured by nCounter, 97 were detected as having altered expression (compared to Ly6C$^{Hi}$ monocytes from non-transgenic litermates): 40 genes were upregulated in Ly6C$^{Hi}$ monocytes from SOD1 mice (as compared to non-transgenic litermates) at least one disease stage. Seven genes were downregulated in Ly6C$^{Hi}$ monocytes in SOD1 mice compared to Ly6C$^{Hi}$ monocytes from non-transgenic litermates, including TGFβ1 and the TGFβ1 receptor (FIG. 21B). Biological network analysis demonstrates that the most significantly affected pathways in the present analysis relative to inflammatory responses, including CREB1, NF-kB, PU.1, and PPARγ (FIG. 21C). These pathways have been shown to play an important role in both monocyte activation and differentiation. The gene expression profiling demonstrates an activated pro-inflammatory Ly6C$^{Hi}$ monocyte population in the peripheral immune compartment of SOD1 mice.

Figure 21D:
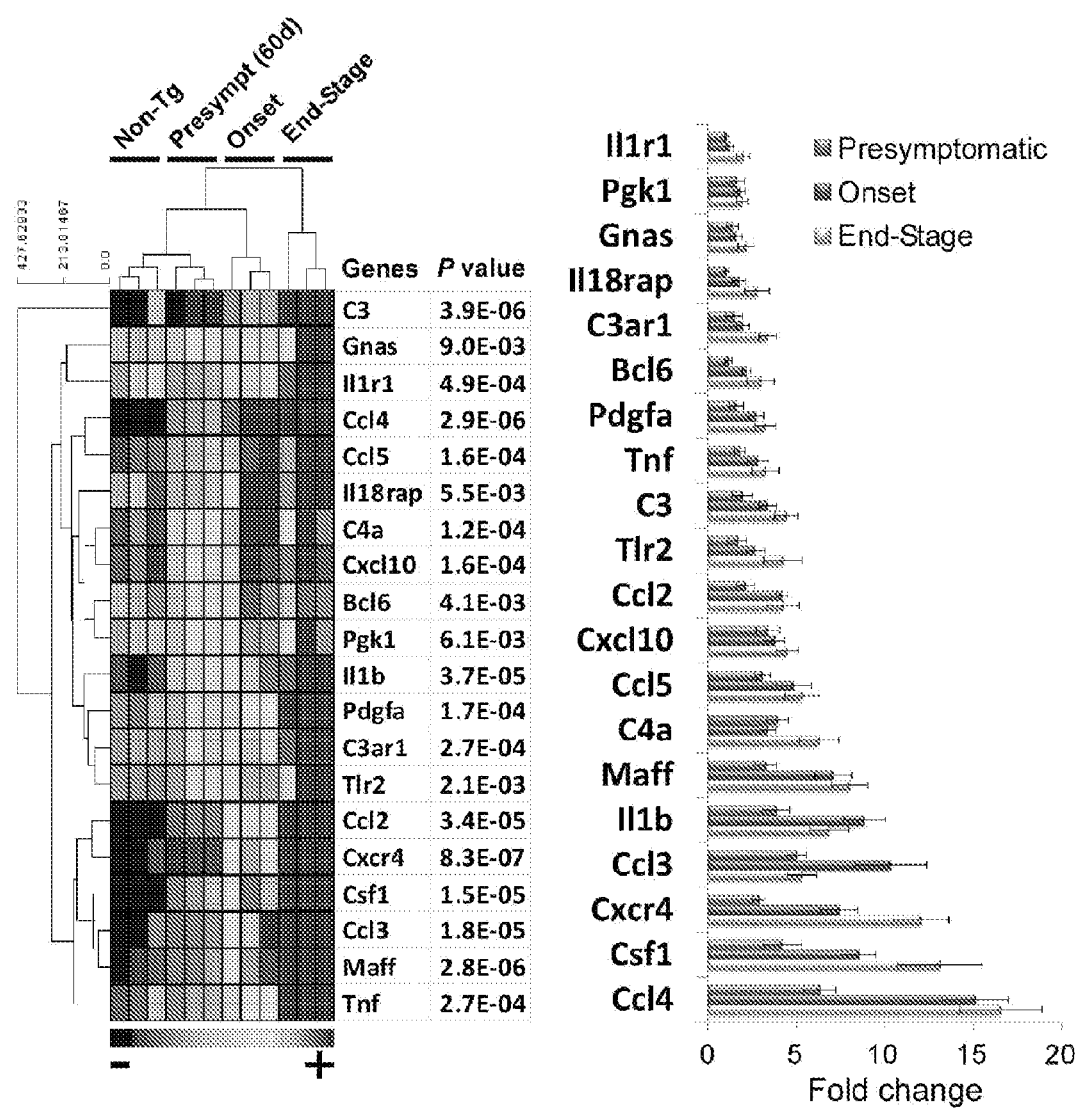
FIG. 21D shows the nCounter expression profile data of genes upregulated in spinal cord-derived CD39$^+$ microglia from SOD1$^{G93A}$ mice compared to the same cells from non-transgenic litermates.
Figure 21E:
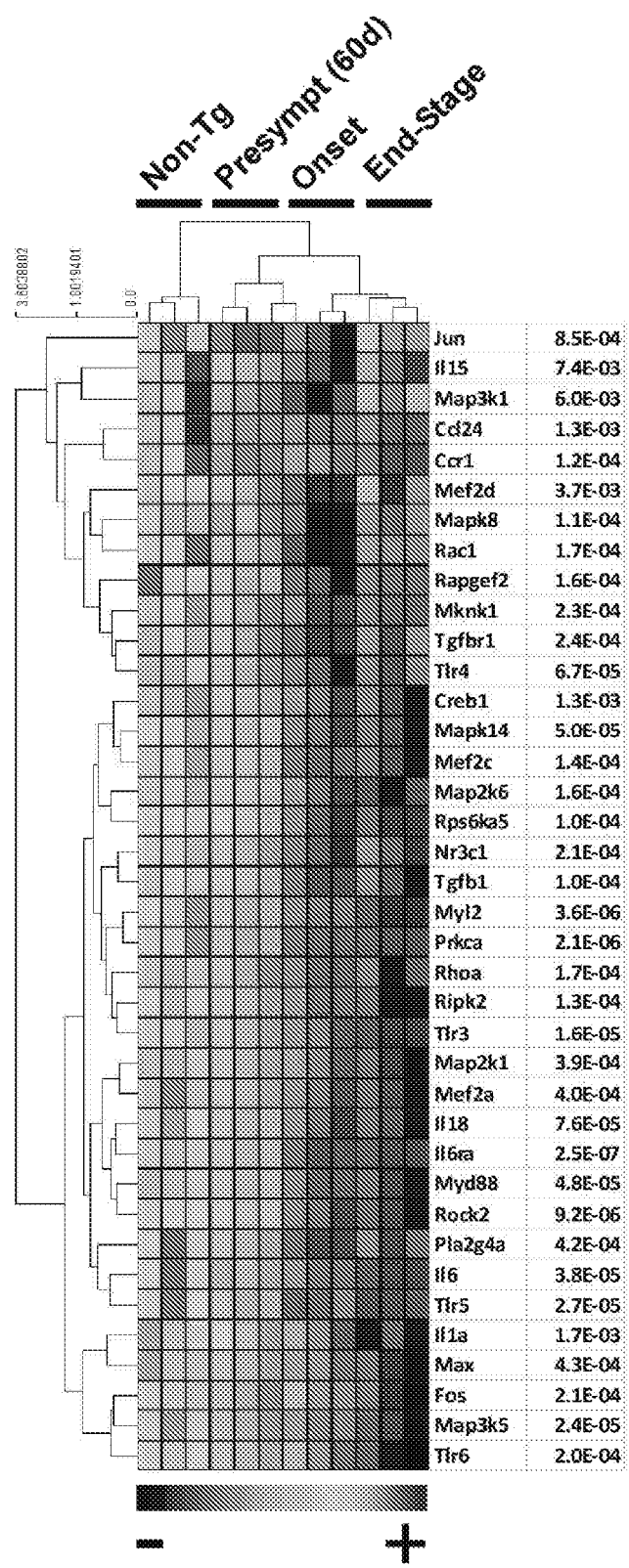
FIG. 21E shows the nCounter expression profile data of genes downregulated in spinal cord-derived CD39$^+$ microglia from SOD1$^{G93A}$ mice compared to the same cells from non-transgenic litermates.
Figure 21E:
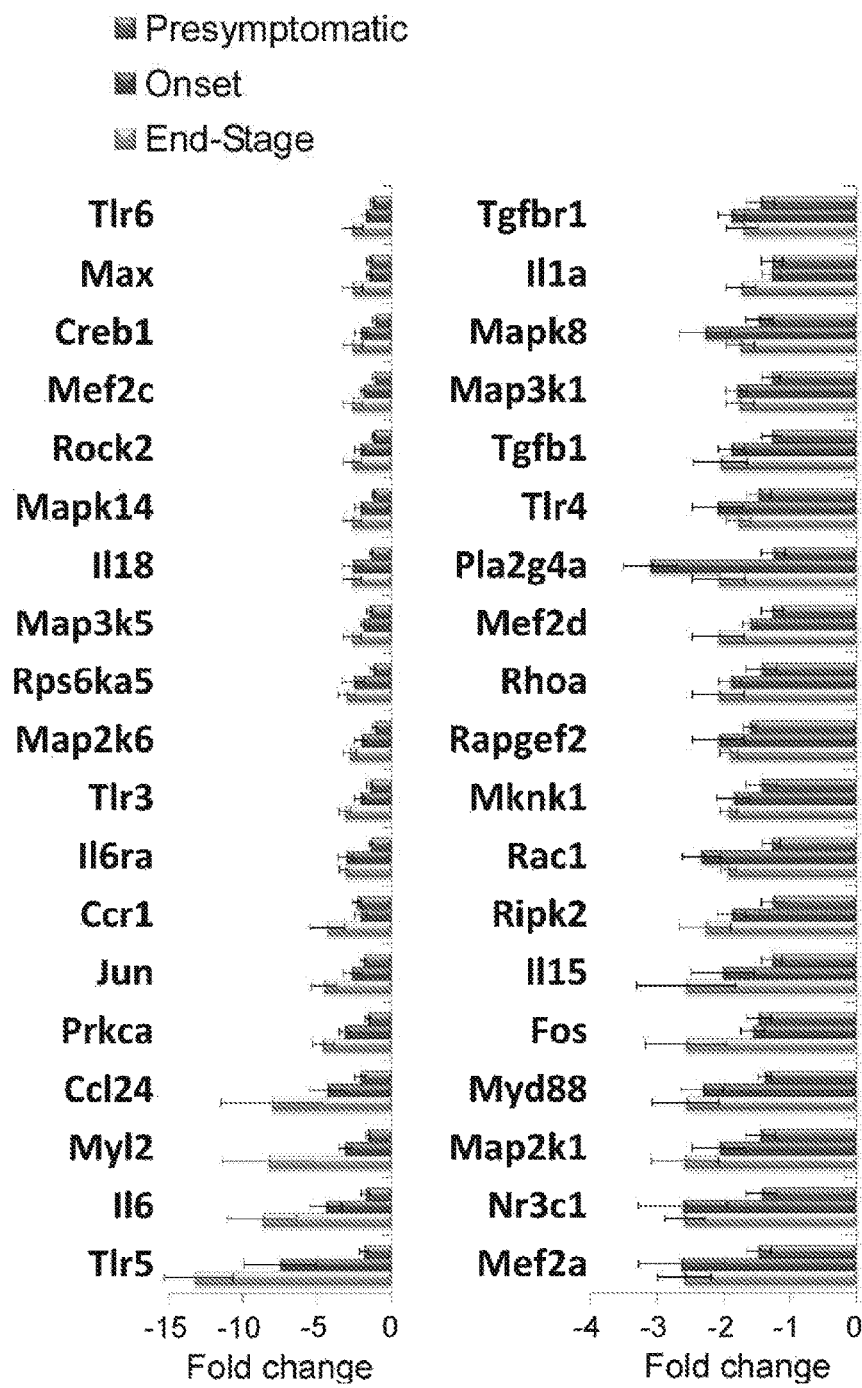
Figure 21G:
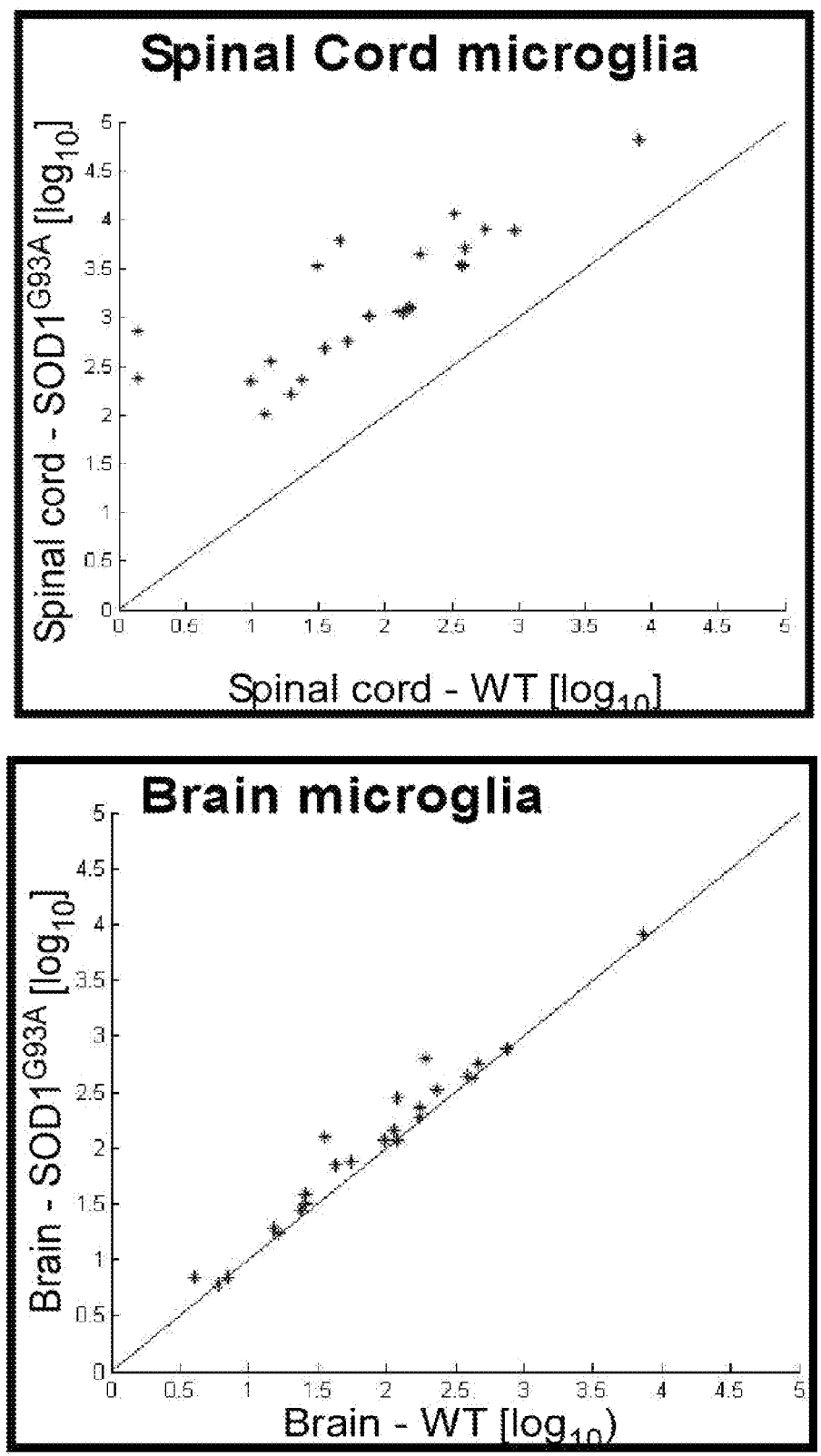
FIG. 21G is a comparative analysis of the significantly upregulated genes in CD39$^+$ microglia from spinal cords of SOD1 mice at the onset versus CD39$^+$ microglia isolated from the brain of the same SOD1 mice.

Expression profiling of CD11b$^+$/CD39$^+$ microglia isolated from the spinal cord and brains of SOD1 mice was performed at different stages of disease. Out of 179 inflammatory marker genes, 120 were detected: 20 genes were upregulated in CD11b$^+$/CD39$^+$ microglia from SOD1 mice (compared to CD11b$^+$/CD39$^+$ microglia from non-transgenic litermates) (FIG. 21D) and 38 genes were downregulated in CD11b$^+$/CD39$^+$ microglia from SOD1 mice (compared to CD11b$^+$/CD39$^+$ microglia from non-transgenic litermates) (FIG. 21E). CD11b$^+$/CD39$^+$ microglia microglia from SOD1 mice as compared to the same cells in non-transgenic litermates had prominent expression of genes related to chemotaxis (e.g., CCL2, CCL3, CCL4, CCL5, CXCR4, and CXCR10). Interestingly, TGFβ1 and the TGFβ1 receptor were among the downregulated genes. Biological network analysis demonstrated activation of inflammatory pathways with the most significant being chemotaxis (FIG. 21F). The expression of these genes preceded symptom onset and was observed in the spinal cord, but not in the brain (FIG. 21G).

Figure 22A:
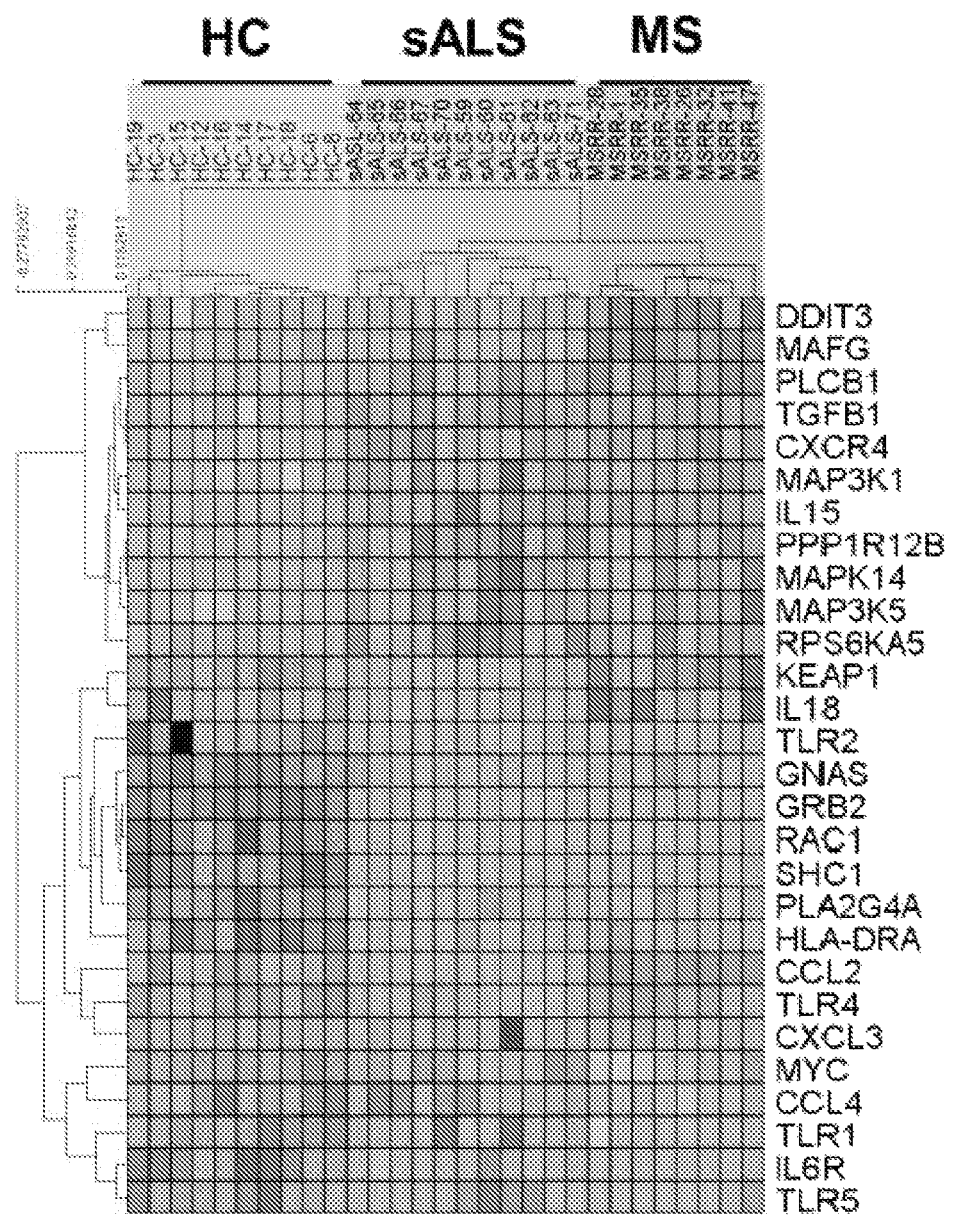
FIG. 22A is an nCounter expression profile of 184 inflammation-related genes in CD14$^+$CD16$^-$ blood monocytes from sporadic ALS (n=11) and MS (n=8) subjects compared to healthy controls (n=10).
Figure 22B:
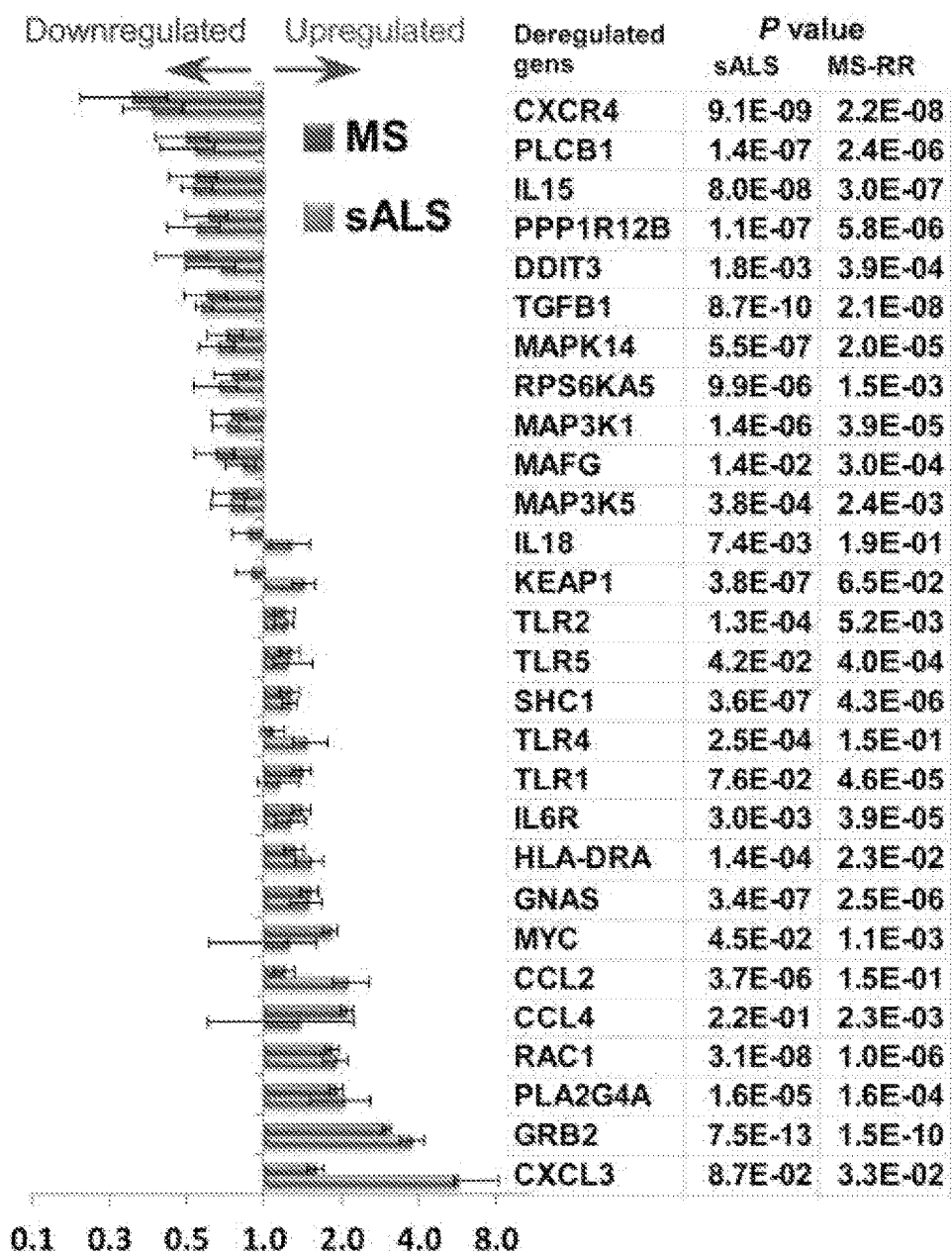
FIG. 22B is a graphic showing the fold differences in expression of significantly dysregulated genes in sporadic ALS and MS subjects as compared to healthy controls. Gene expression level was normalized against the geometric mean of 6 internal reference house-keeping genes (CLTC, GAPDH, GUSB, PGK1, and TUBB5).
Figure 22C:
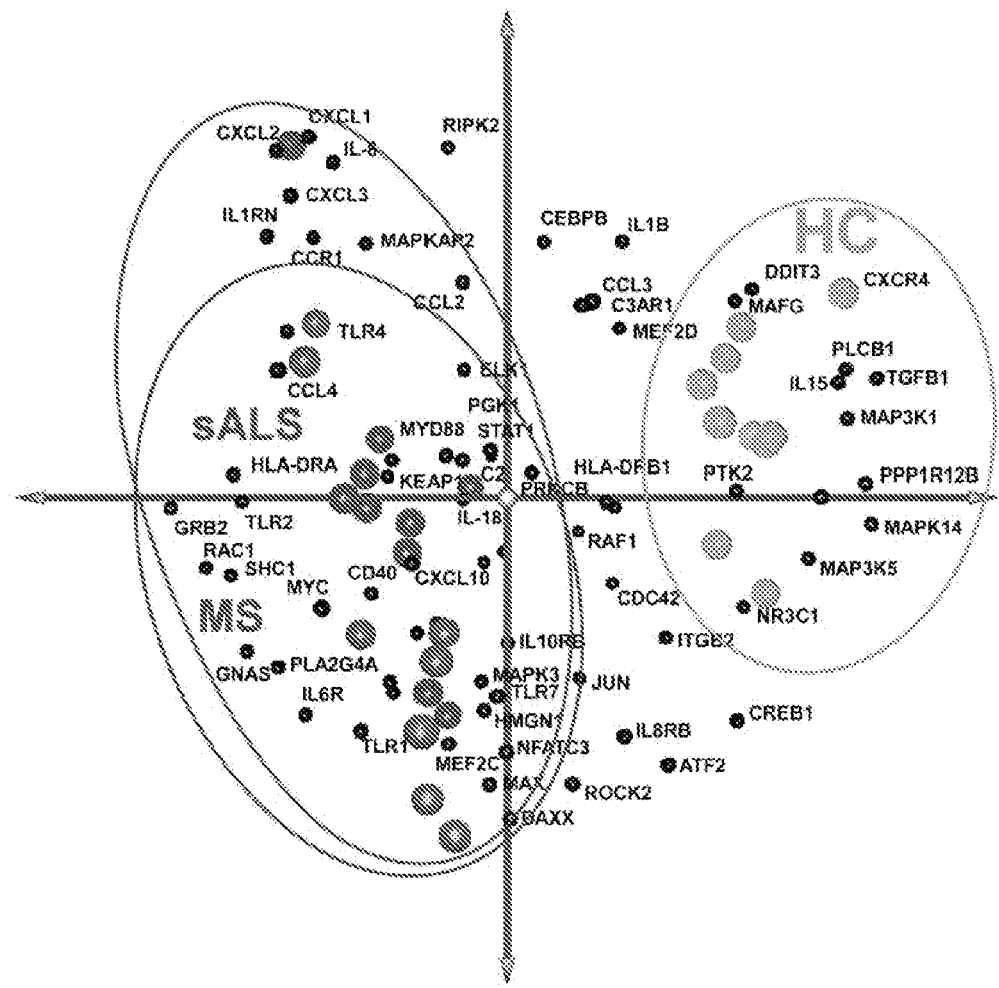
FIG. 22C is a graphic showing the principal components analysis (PCA) analysis of the identified dysregulated genes between sporadic ALS subjects and MS subjects with spatial gene distribution.

Example 7. Proinflammatory Markers Expressed in CD14$^+$CD16$^-$ Monocytes in ALS Subjects Immune-related gene expression in CD14$^+$CD16$^-$ monocytes from ALS subjects was analyzed as described in Example 6. Several inflammatory-related genes were upregulated in CD14$^+$CD16$^-$ monocytes from ALS subjects as compared to healthy controls. Although there were some differences in immune-related gene expression between CD14$^+$CD16$^-$ monocytes from ALS subjects and MS subjects, the immune-related gene expression pattern in CD14$^+$CD16$^-$ monocytes from ALS subjects and MS subjects were similar (FIG. 22A-C).

In a further set of experiments, the expression of 511 immune-related genes was analyzed in CD14$^+$CD16$^-$ monocytes from subjects having ALS (sporadic and familial ALS). These experiments were performed using quantitative NanoString nCounter technology. The data gathered from these experiments and the data described in Example 6 were further analyzed using GeneGo and Ingenuity® pathway analysis.

The differentially upregulated genes in spinal cord CD39$^+$ microglia and splenic Ly6C$^{Hi}$ monocytes in SOD1 mice, and in blood-derived CD14$^+$CD16$^-$ monocytes from sporadic ALS subjects vs. healthy controls were analyzed using GeneGo Metacore pathway analysis (GeneGO, St. Joseph, Mich.). This method identifies transcripts that are overrepresented in defined ontologies. A false discovery rate (FDR) filter was applied to preliminary P values using q-value calculation. After enrichment, the P values were calculated for all the terms within the given ontology and each term was tested as a separate hypothesis. The resulting q-values represent corrected P values with an account of the total terms in the given ontology and the rank order of the particular term. The identified significantly dysregulated genes were further analyzed to identify biological/disease processes and the involved pathway/networks in SOD1 mice and human ALS. The whole data set of 58 dysregulated genes in CD39+ microglia from the spinal cord and 47 dysregulated genes in Ly6C$^{Hi}$ splenic monocytes from SOD1 mice were imported into MetaCore to build an analysis of functional ontologies using GeneGo process, GeneGo disease process, canonical pathway maps, and networks. The calculation of statistical significance throughout MetaCore for the maps, networks, and processes were based on P values, which were calculated based on a hypergeometric distribution. P values represent the probability of a particular mapping arising by chance, given the numbers of genes in the set of all genes present in the maps/networks/processes, the genes on a particular map/network/process, and the genes in the experiment. A P value of 0.01 was used for the cutoff. The degree of relevance for the different categories of the uploaded data sets is defined by P values, so that the lower P value indicates higher priority. The experimental data were input to build the networks. The three different scoring functions that were used to rank the small subnetworks created by the network building algorithms were zScore, gScore, and p value. The zScore ranks the subnetworks (within the analyzed network) with regard to their saturation with genes from the experiment. A high zScore means the network is highly saturated with identified dysregulated genes from the experiment. In other words, it means that relatively larger number of genes/analytes in a particular network were present in the aqueous sample. Each network is comprised of canonical pathways used to build the network. If a network has a high gScore, it is saturated with expressed genes (from the zScore), and it contains many canonical pathways. The analysis was controlled for multiple testing by estimating the false discovery rate. Out of 664 microRNAs measured, 56 were confidently detected, and twenty were differentially expressed in at least one disease group.

Targetscan 14.1 was used to investigate the statistical significance of miRNA-mRNA interactions. Targetscan 14.1 was used for the prediction of 862044 conserved miRNA binding sites with non-zero context score which is a measure of conservation. In the SOD1 mouse data set: miRNA target filtering analysis using Ingenuity® pathway analysis (IPA) results in 34 miRNA families that are predicted to target 10797 mRNAs. These data were filtered to include only those genes involved in the IPA Canonical Pathway categories representing signaling pathways involved in cellular immune response, humoral immune response, and cytokine signaling. This resulted in filtering of the 34 microRNAs to target 971 mRNAs possibly involved in immune response signaling. The mRNA expression studies were integrated using the Nanostring platform into the analysis. 971 filtered targets contain the 47 immune-related genes that are dysregulated in SOD1 mice taking into account the opposite nature of the miRNA-mRNA regulation. This resulted in a final 87 pairs of miRNA-mRNA interactions representing 27 miRNA families and 33 mRNAs. In the miRNA expression of ALS subjects study, 56 miRNAs were found to be significantly dysregulated in ALS subjects. Filtering the predicted 862044 sites to those containing only targets of these 56 miRNAs lead to a reduction in the number of predicted sites (a reduction to 34118 sites). The number of sites was further reduced by limiting the data to mRNA targets to genes found to be regulated with a fold change of >1.4 in the immunological panel nanostring arrays. The final data indicate 68 unique miRNA-mRNA interaction pairs in which the mRNA and miRNA are oppositely regulated. The statistical significance of these 68 miRNA-mRNA interactions formed by 56 dysregulated miRNAs were further assessed as follows: 1) 1000 random networks in which 56 randomly selected, non-regulated miRNAs from the study were used to find mRNAs which contained a 3'-UTR motif for their binding, and 2) the miRNA-mRNA pairs were further filtered to contain only those 59 mRNAs that were dysregulated in ALS subjects. A mean of 44.88 interactions was observed (SD=9.99). The true interactions determined in the expression studies is 68, and corresponds to a significant P value ($<1.1\times10^{-15}$). A similar analysis for the regulated miRNA-mRNA pairs in the SOD1 mice shows an interaction distribution with a mean of 15.26 (SD=4.03), whereas the true miRNA-mRNA interactions determined experimentally is 41, with a significant P-value of $<5.7\times10^{-9}$.

Figure 23A:
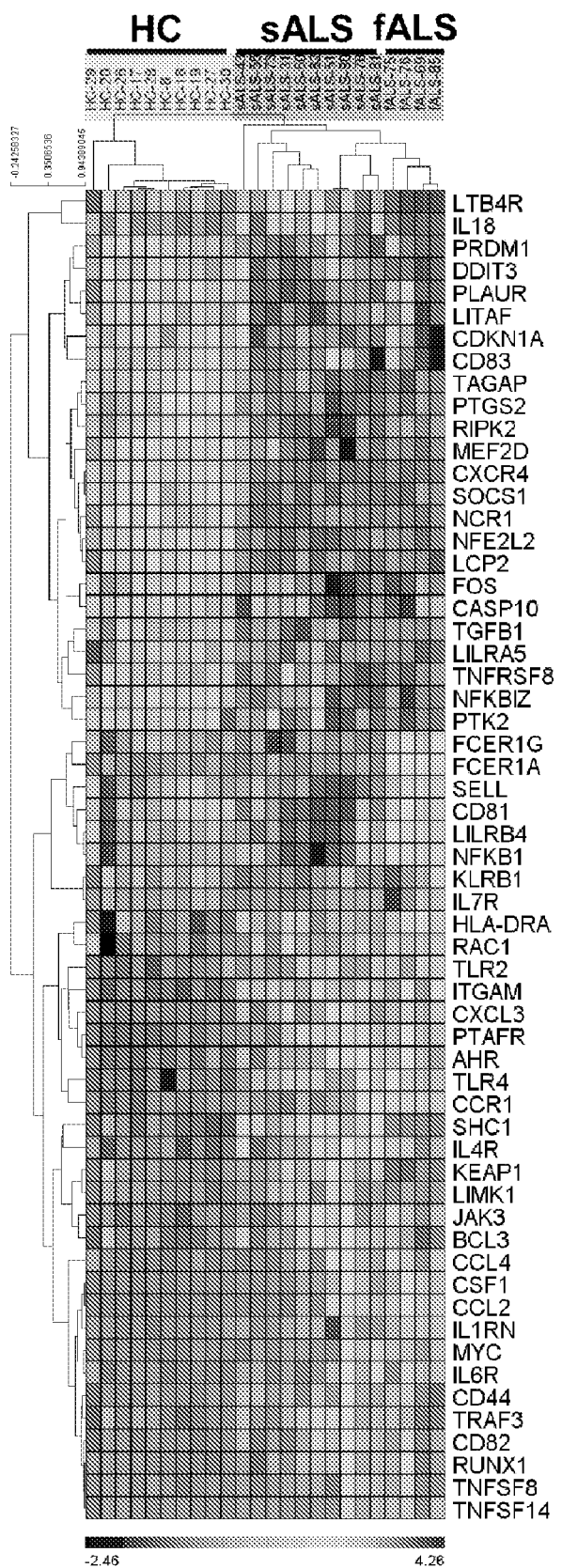
FIG. 23A is an nCounter expression profile of blood-sorted $CD14^+CD16^-$ monocytes for 511 immune- and 184-inflammation-related genes in sporadic ALS (10 subjects), and familial SOD1 ALS (4 subjects) compared to healthy controls (10 subjects). The profile (heatmap) is an unsupervised hierarchial clustering (Pearson correlation) that shows the significantly dysregulated genes (Nonparametric Kruskal-Wallis test; significance based on false discovery rate (FDR) determined by the Benjamini-Hochberg method; selected FDR limit: 0.05; P<0.01). Each row of the heatmap represents an individual gene and each column an individual subject.
Figure 23B:
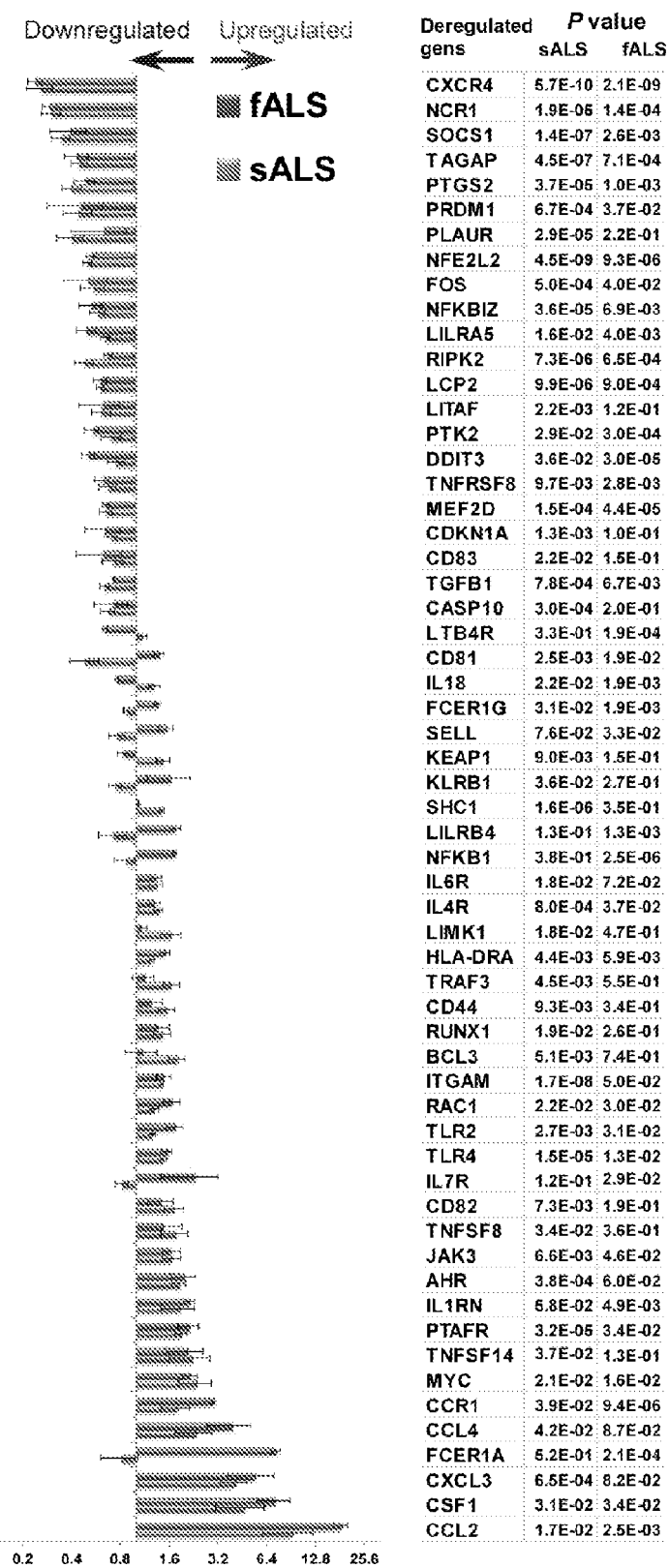
FIG. 23B is a graphic showing the fold differences of significantly dysregulated genes in blood-sorted $CD14^+CD16^-$ monocytes from sporadic ALC and familial ALS subjects versus healthy controls. Gene expression level was normalized against the geometric mean of 15 internal reference house-keeping genes (ABCF1, ALAS1, EEF1G, G6PD, GAPDH, GUSB, HPRT1, OAZ1, POLR1B, POLR2A, PPIA, RPL19, DSHA, TBP, and TUBB).
Figure 23C:
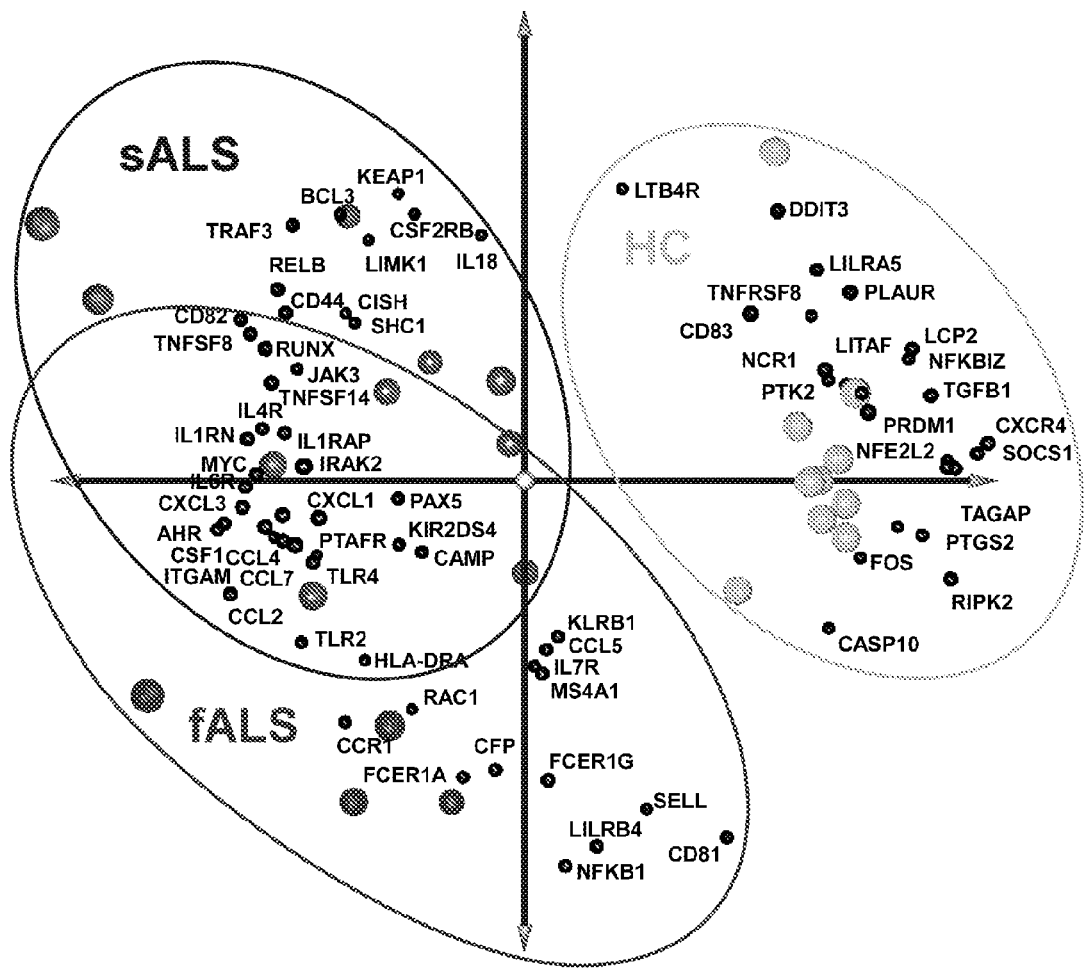
FIG. 23C is a graphic of the PCA analysis of the identified dysregulated genes in blood-sorted $CD14^+CD16^-$ monocytes from sporadic ALS and familial ALS subjects vs. healthy controls with spatial gene distribution.
Figure 24:
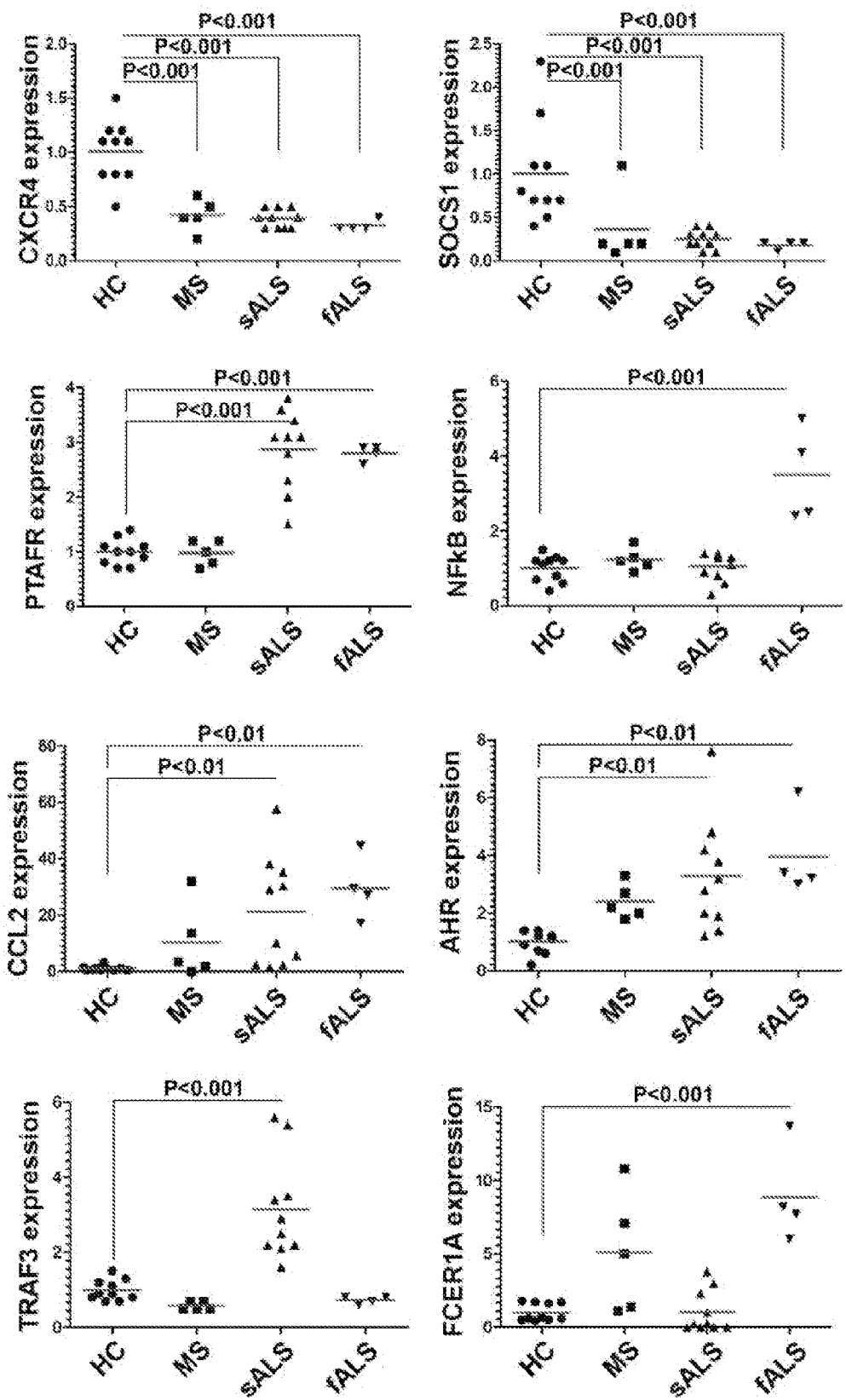
FIG. 24 is a set of eight graphs showing the real-time PCR validation of eight genes that were the most significantly dysregulated in blood-sorted $CD14^+CD16^-$ monocytes from familial and/or sporadic ALS subjects compared to blood-sorted $CD14^+CD16^-$ monocytes from healthy controls. The relative expression in sporadic ALS and familial ALS against healthy controls was calculated using the comparative Ct (2-ΔΔCt) method. Gene expression level was normalized against the geometric mean of three house-keeping genes (GAPDH, TUBB, and GRB2). The polymerase chain reactions were run in duplicate for each subject. The graphs represent one-way analysis of variance (ANOVA) and the Dunett's multiple comparison test of significantly dysregulated genes in ALS subjects.

The data show that CD14+CD16− monocytes from ALS subjects have unique expression of immune-related genes as compared to CD14+CD16− monocytes from healthy controls. In addition, a few immune-related genes are differentially expressed in CD14+CD16− monocytes from sporadic ALS subjects compared to CD14+CD16− monocytes from familial ALS subjects (FIGS. 23A-C). These results were validated using singleplex qPCR in an independent cohort of ALS patients and healthy controls (the changes in the expression of CCL2, AHR, PTAFR, NF-κB, TRAF3, FCER1A, CXCR4, and SOCS1 were validated) (FIG. 24). These data confirm that CCL2, AHR, PTAFR, NF-κB, and TRAF3 are upregulated in CD14+CD16− monocytes from ALS subjects as compared to CD14+CD16− monocytes from healthy controls, and that CXCR4 and SOCS1 are downregulated in CD14+CD16− monocytes from ALS subjects as compared to CD14+CD16− monocytes from healthy controls.

Figure 25:
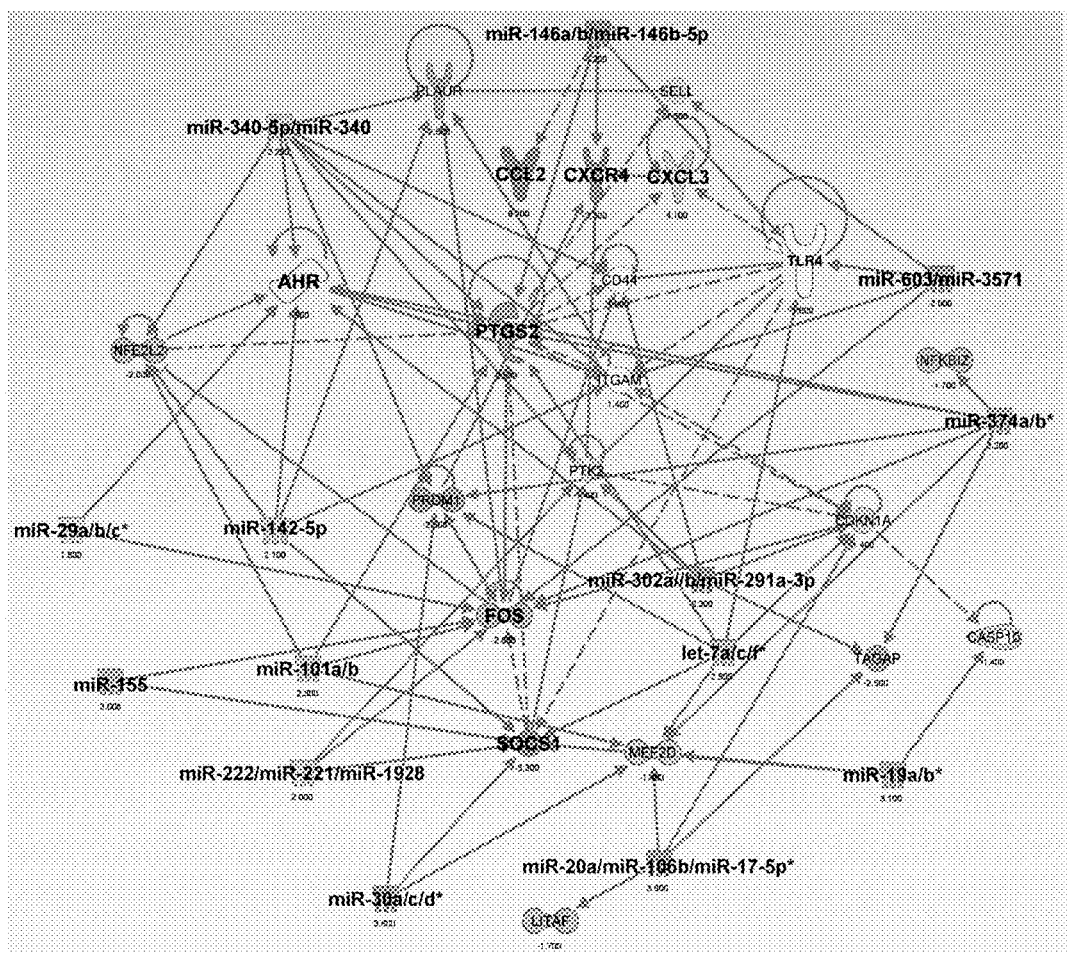
FIG. 25 is a graphic of the Ingenuity target filter analysis showing the top 10 miRNA-mRNA interactions in $CD14^+CD16^-$ blood monocytes from ALS subjects based on the identified significantly dysregulated miRNAs and mRNAs in $CD14^+CD16^-$ blood monocytes from ALS subjects.

Ingenuity microRNA-mRNA target filter analysis further revealed that the top 10 microRNA-miRNA interactions in Ly6C$^{Hi}$ cells from SOD1 mice were linked to the genes found to be the most significantly dysregulated in CD14+CD16− monocytes from ALS subjects (FIG. 25).

Figure 27:
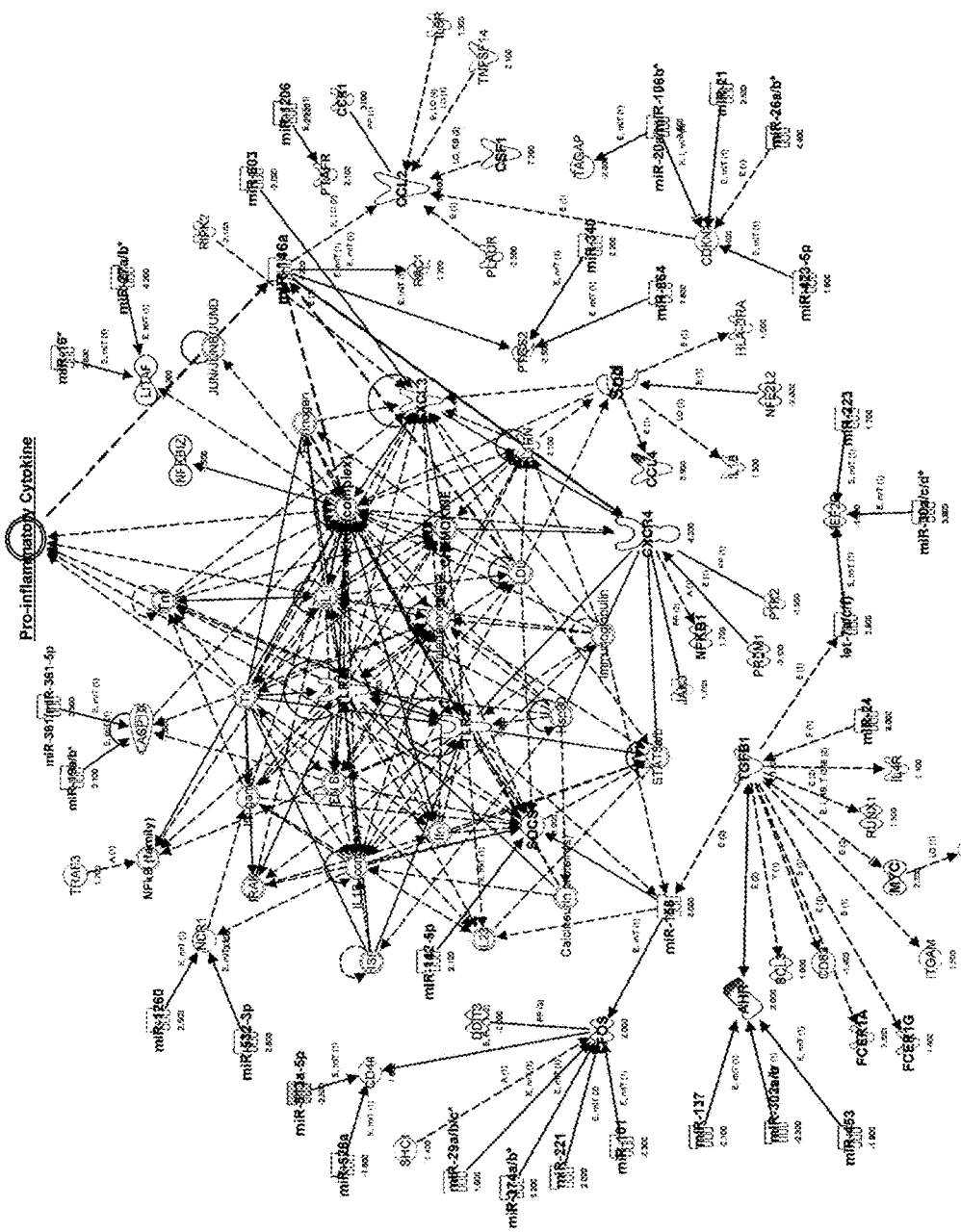
FIG. 27 is a graphic depicting the microRNA-mRNA interactions in blood-sorted $CD14^+CD16^-$ monocytes in ALS. The graphic depicts the results for the significantly dysregulated miRNA and immune-related genes in blood-sorted $CD14^+CD16^-$ monocytes from ALS subjects. A total of 32 miRNAs targeting 27 mRNAs are shown.
Figure 28A:
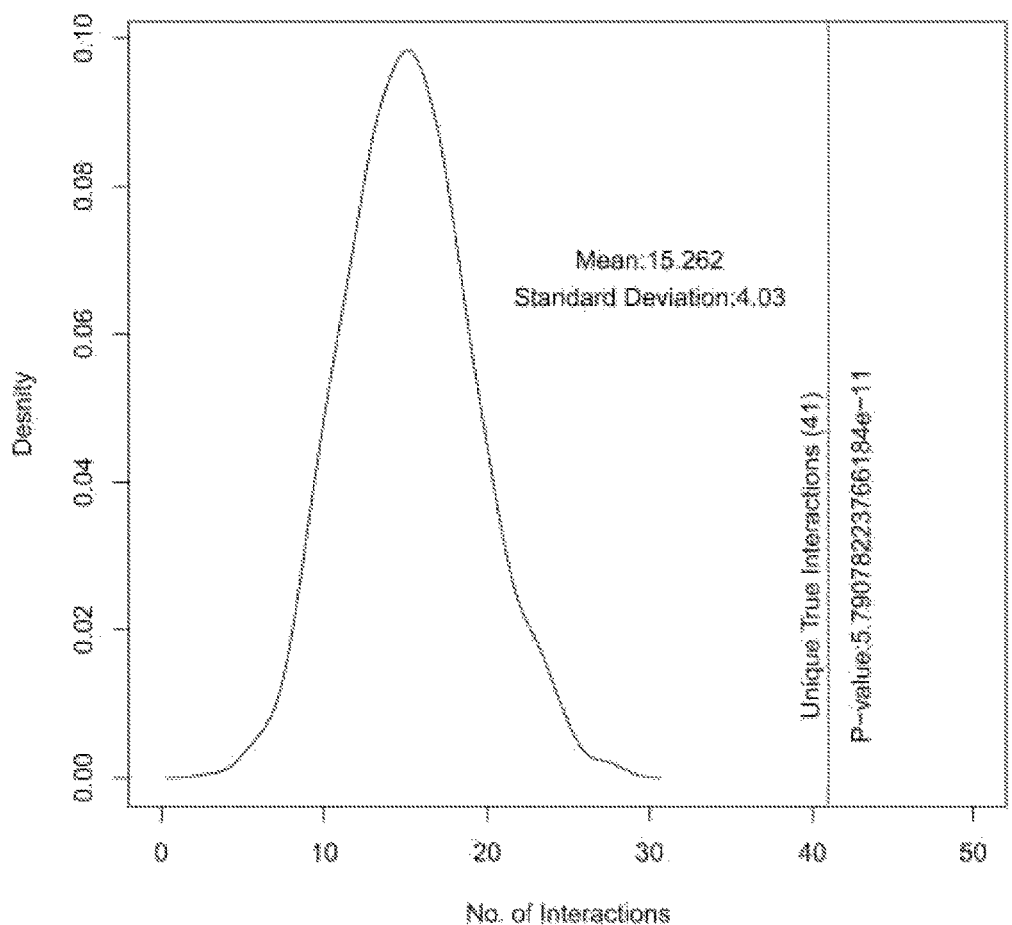
FIG. 28 is two graphs showing the distribution of possible random interactions between 1000 random and non-regulated miRNA-mRNA pairs in comparison to the observed putative miRNA-mRNA pairs in 41 non-regulated highly expressed miRNAs and the 47 dysregulated genes observed in splenic $Lys6C^{Hi}$ monocytes from SOD1 mice (FIG. 28A), and 64 non-regulated highly expressed miRNAs and the 59 dysregulated genes observed in $CD14^+CD16^-$ peripheral blood monocytes from ALS subjects (FIG. 28B) (Targetscan 4.1).
Figure 28B:
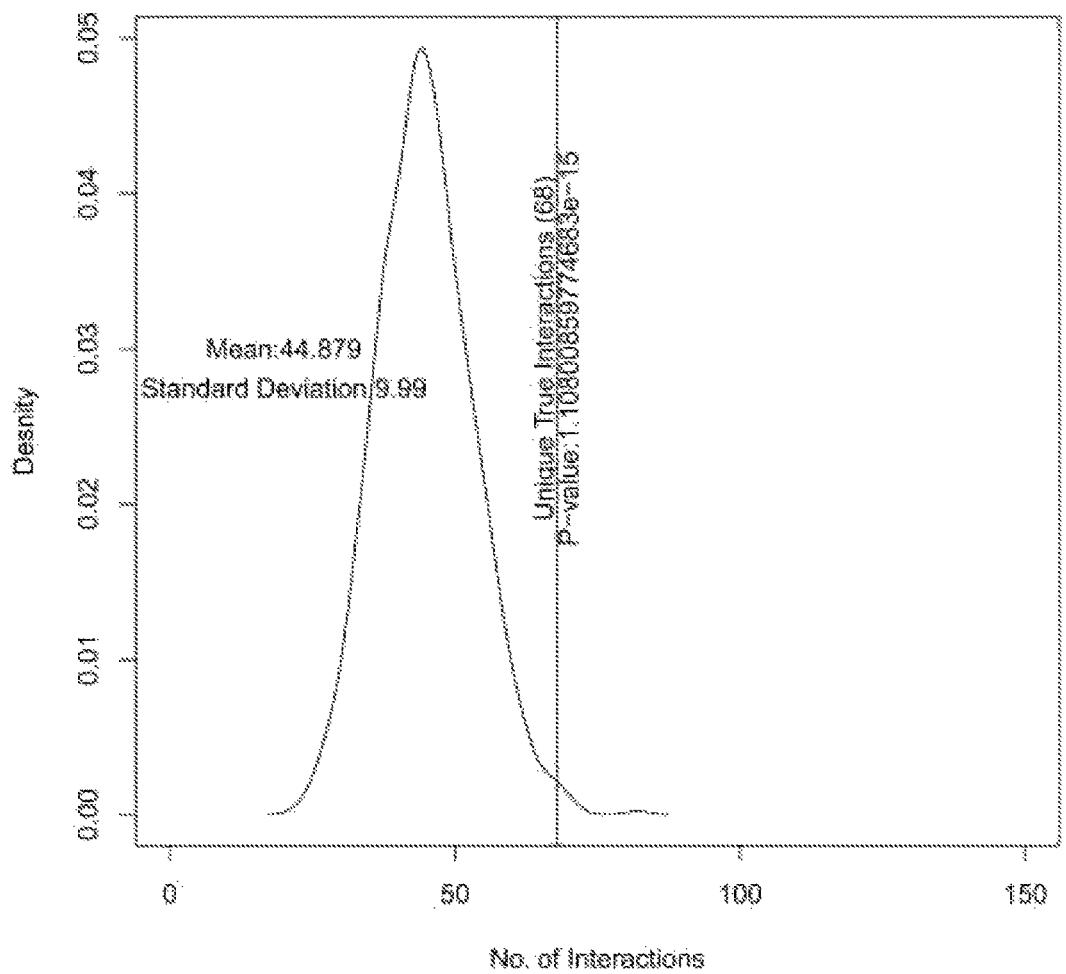
Figure 29:
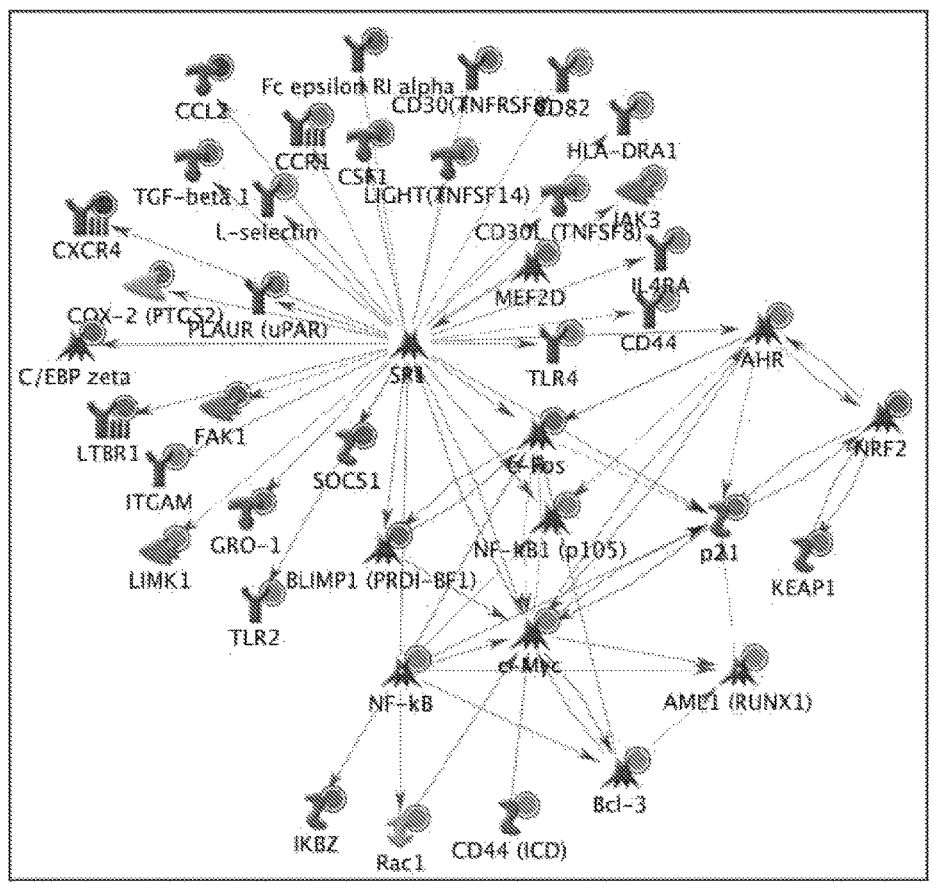
FIG. 29 is a table showing the top 20 transcription factors and target genes dysregulated in blood-sorted CD14+CD16− monocytes from ALS subjects (determined using GeneGo pathway analysis), and a graphic showing the specificity protein-1 (SP1) transcription factor and its targeted genes in blood-sorted CD14+CD16− monocytes in ALS subjects.

A further assessment of both the miRNA and mRNA expression profile in CD14+CD16− monocytes from ALS subjects shows that the abnormalities related to miRNA and gene expression in CD14+CD16− monocytes is linked to inflammatory- and immune-related genes (FIG. 26 and FIG. 27). When these miRNA-mRNA interactions in CD14+CD16− monocytes were analyzed, the interactions were shown to be statistically significant using Targetscan 4.1 prediction analysis both in SOD1 mice and in ALS subjects (FIG. 28). Furthermore, GeneGo pathway analysis identified 9 inflammation-related networks (FIG. 29). These inflammation networks were identical to those that were observed (in the studies described herein) to be dysregulated in Ly6C$^{Hi}$ monocytes in SOD1 mice.

Example 8. Therapeutic Role of miR-155 in the SOD1$^{G93A}$ Model

Significant upregulation of miR-155 occurs in spleen-derived Ly6C$^{Hi}$ monocytes and spinal cord-derived microglia before clinical onset, which increased during all stages of disease progression in SOD1$^{G93A}$ mice (see data above). Additional experiments were performed to determine whether miR-155 plays a role in the development/pathogenesis of ALS. In these experiments, the SOD1 mouse (a model of ALS) was further genetically manipulated to knockdown or knockout expression of miR-155.

Animals and Behavioral Analysis

B6/SJL-SOD1$^{G93A}$ Tg and SOD1-wild type (WT) were provided by Prize4Life or purchased from the Jackson Laboratories. ALS mice were analyzed at day 30 and 60 (presymptomatic), day 90-100 (early symptomatic), and day 120-140 (late symptomatic/end-stage) time points. Onset of symptoms was defined by the peak of the weight curve and visible signs of muscle weakness. End-stage disease was determined by symptomatic progression and animal care guidelines (thus it varied from the 135 time-point by ±5 days). Disease progression was documented according to established methodology provided by Prize4Life and The Jackson Laboratory. Symptomatic analysis was conducted by daily monitoring and weight measurements every 3-4 days starting at day 80. Symptomatic onset was defined as the age at which animals began to decline in weight. Neurological scores for both hind legs were assessed daily for each mouse beginning at 50 days of age. The neurological score used a scale of 0 to 4 developed by ALS Therapy Development Institute (ALSTDI). Criteria used to assign each score level were: 0=full extension of hind legs away from the lateral midline when the mouse is suspended by its tail, and mouse can hold this position for 2 seconds, suspended 2-3 times; 2=collapse or partial collapse of leg extension towards lateral midline (weakness) or trembling of hind legs during tail suspension; 2=curling of the toes and dragging of at least one limb during walking; 3=rigid paralysis or minimal joint movement, foot not being used for forward motion; and 4=mouse cannot right itself within 30 seconds from either side, euthanasia.

Generation of SOD1$^{G93A}$/miR-155$^{-/-}$

Male SOD1$^{G93A}$ [B6.Cg-Tg(SOD1$^{G93A}$)1Gur/J] mice were bred with non-Tg C57Bl/6 miR155$^{-/-}$ females. Non-transgenic miR155$^{-/-}$ were backcross to F1-SOD1$^{G93A}$/miR155$^{-/+}$ to produce F2-SOD1$^{G93A}$/miR155$^{-/-}$ with a deletion of miR155. The mice were assessed clinically by neurobehavioral testing (rotarod performance and neurologic score) and the survival of three experimental groups of SOD1 mice with different expression levels of miR-155 was assessed: 1) SOD1$^{G93A}$/miR155$^{+/+}$; 2) SOD1$^{G93A}$/miR155$^{-/+}$; and 3) SOD1$^{G93A}$/miR155$^{-/-}$.

Targeting of miR-155 in SOD1 Mice

To prove a direct interaction between miRNAs and their targets, a Luciferase reporter bearing 3'UTR with potential miRNA binding sites is utilized. Site-directed mutagenesis of the miRNA binding site abolishes responsiveness of the Luciferase reporter to miRNA modulation, which will provide proof of direct targeting.

Flow Cytometry

Mononuclear cells were directly isolated from the spinal cord of mice as described in Cardona et al. (*Nat. Protoc.* 1:1947-1951, 2006) except that no dispase was used as we found that dispase cleaves several surface molecules and can diminish surface detection of surface molecules. Mice were transcardially perfused with ice cold phosphate-buffer saline (PBS), and the spinal cords and brains were separately dissected. Single cell suspensions were prepared and centrifuged over a 37%/70% discontinuous Percoll gradient (GE Healthcare), mononuclear cells were isolated from the interface, and the total cell count determined. The cells were pre-blocked with anti-CD16/CD32 (Fc Block BD Biosciences), and stained on ice for 30 minutes with combinations of anti-Ly6C-FITC, CD11b-PE-Cy™ 7, and 4D4-APC (unique microglial antibody). 7AAD-PerCP was used to detect or exclude early apoptotic and dead cells (BD Biosciences). The appropriate antibody IgG isotype controls (BD Biosciences) were used for all stains. Fluorescence-activated cell sorting (FACS) analysis was performed on a LSR machine (BD Biosciences), and the data subsequently analyzed with FlowJo Software (TreeStar Software).

Quantitative NanoString nCounter miRNA/Gene Expression Analysis

Nanostring nCounter technology was used to study the expression of up to 800 inflammation-related genes. Multiplexed target profiling of 179 inflammation-related transcripts which consist of genes differentially expressed during inflammation and immune responses was also performed as described above.

Figure 30:
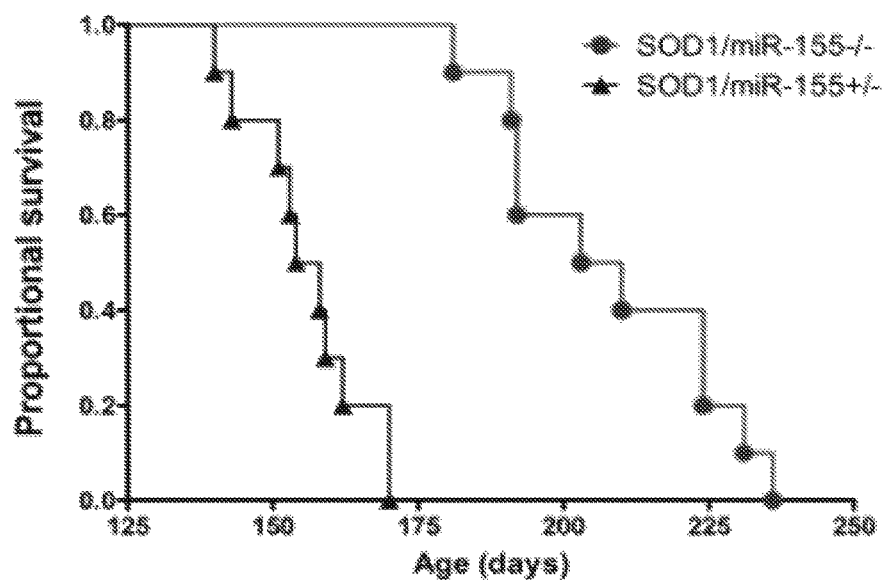
FIG. 30 is a graph of the Kaplan-Meir analysis of the probability of surviving for both the SOD1/miR-155$^{-/-}$ and the SOD1/miR-155$^{+/-}$ mice. Mantel-Cox's F-test comparison between groups SOD1/miR-155$^{-/-}$ vs. SOD1/miR-155$^{+/-}$ mice (P<0.0001).
Figure 31:
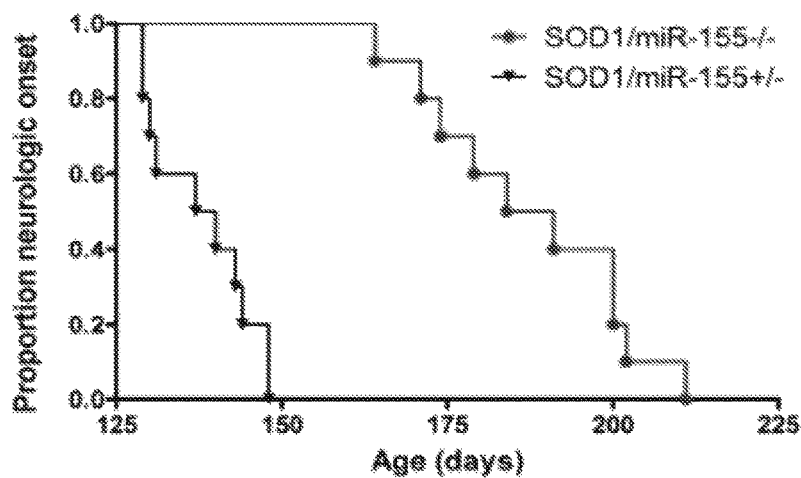
FIG. 31 is graph of the time-to-event analysis for disease neurologic onset (neurological severity score 2). Disease onset was significantly delayed (P<0.0001) in SOD1/miR-155$^{-/-}$ mice compared to the SOD1/miR-155$^{+/-}$ mice.
Figure 32:
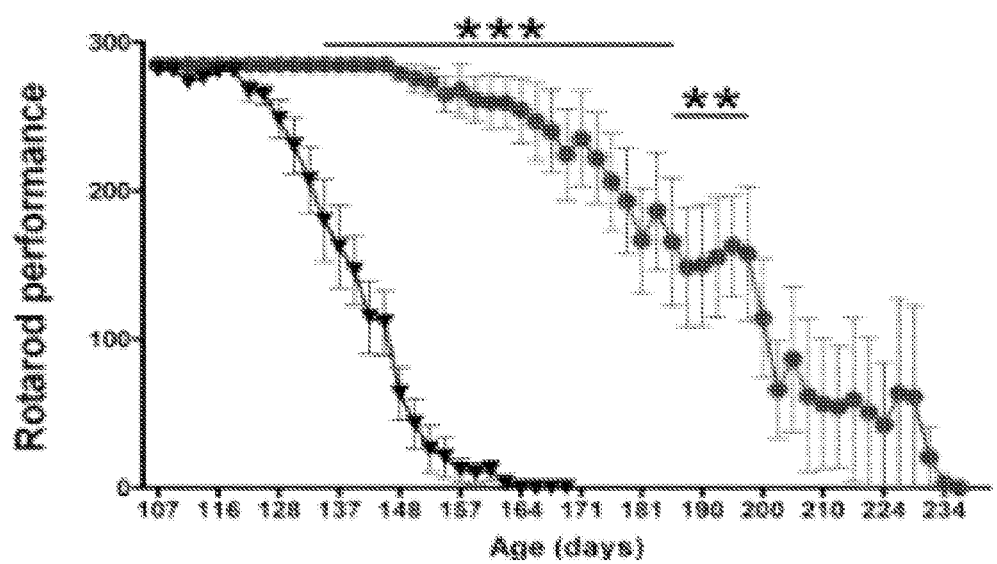
FIG. 32 is a graph of the rotarod performance of the SOD1/miR-155$^{-/-}$ (circles) and SOD1/miR-155$^{+/-}$ (triangles) mice as a function of age. P<0.01; *P<0.001; by factorial ANOVA and Fisher's LSD post-hoc test.
Figure 34:
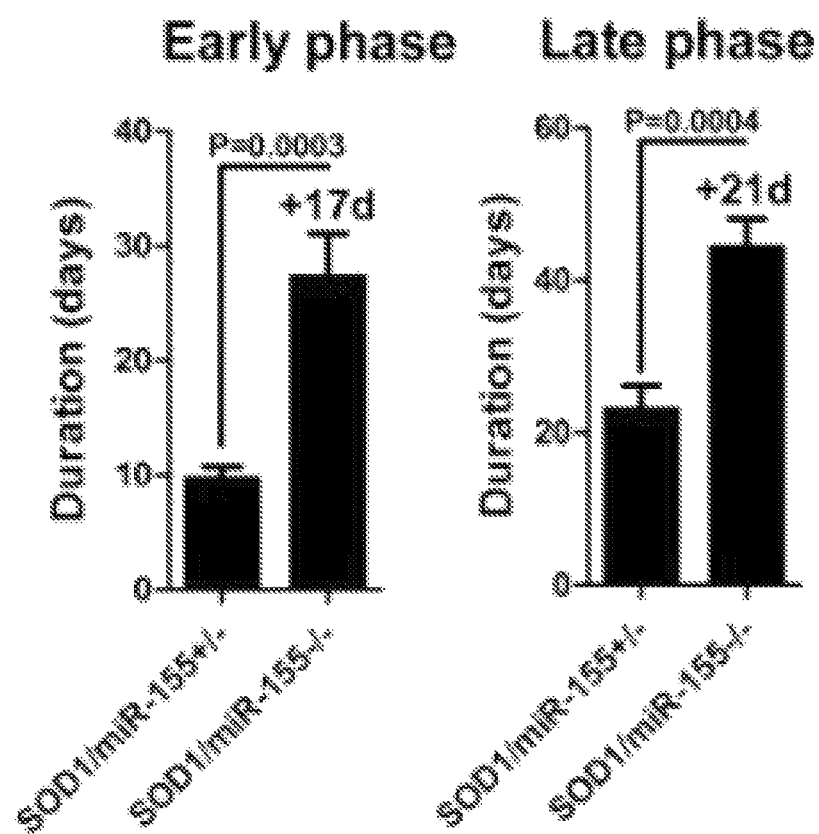
FIG. 34 is a set of two graphs showing the duration of an early disease phase (from onset to 5% weight loss) (left graph) and duration of an later disease phase (from 5% weight loss to end stage) for the SOD1/miR-155$^{-/-}$ and SOD1/miR-155$^{+/-}$ mice.

The resulting data show that SOD1$^{G93A}$/miR155$^{-/-}$ animals have a significant delay in disease onset and survival compared to SOD1$^{G93A}$ animals. (Tables 22 and 23, and FIGS. 30-34). The body weight of the mice was assessed every 3-4 days starting at day 80, the clinical neurologic score of the mice was assessed daily, and rotarod performance was assessed 3 times a week. The data show that genetic ablation of miR-155 prolonged survival by 51 days (P<0.0001; FIG. 30), extended time to reach a neurologic score of two by 49 days (P<0.0001; FIG. 31), enhanced rotarod performance (FIG. 32), reduced body weight loss (FIG. 33), and delayed early (P=0.0003) and late (P=0.0004) disease onset (FIG. 34).

TABLE 22

Delayed onset and increased survival in SOD1/miR155$^{-/-}$ (Summary of Preliminary Results)

| SOD1.miR155+/+ | SOD1/miR155−/− |
|---|---|
| End-stage 145 days | At 162 days, still breading |

TABLE 23

Cumulative Results of Statistical Analysis of SOD1/miR155$^{+/-}$ and SOD1/miR155$^{-/-}$ Mice

| | Kaplan-Meier Survival Fit | | | | |
| | Median time (days) | | | P value | |
| Females | SOD1/ miR-155+/− | SOD1/ miR-155−/− | Change | Log-rank | Wilcoxon |
|---|---|---|---|---|---|
| Neurologic onset (Score 2) | 138 | 187 | 49 | <0.0001 | <0.0001 |
| Peak body weight to death | 32 | 80 | 48 | <0.0001 | <0.0001 |
| 50% survival | 156 | 207 | 51 | <0.0001 | <0.0001 |

| | Median time (days) | | | P value | |
| Males | SOD1/ miR-155+/− | SOD1/ miR-155−/− | Change | Log-rank | Wilcoxon |
|---|---|---|---|---|---|
| Neurologic onset (score 2) | 144 | 168 | 24 | <0.0001 | 0.0003 |
| Peak body weight to death | 56 | 64 | 8 | 0.1397 | 0.0647 |

TABLE 23-continued

Cumulative Results of Statistical Analysis of
SOD1/miR155$^{+/-}$ and SOD1/miR155$^{-/-}$ Mice

| | | | | | |
|---|---|---|---|---|---|
| 50% survival (age at death) | 157 | 184 | 27 | <0.0001 | <0.0001 |

Figure 35A:
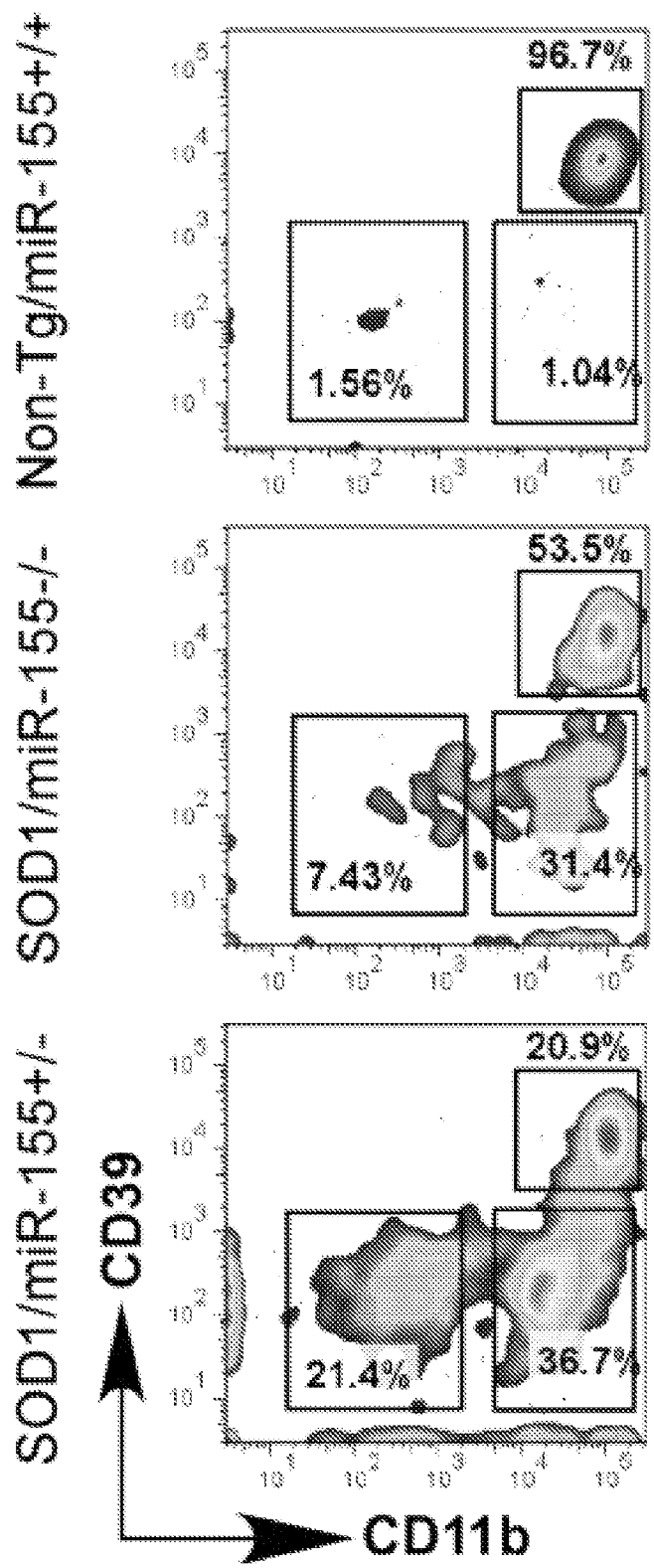
FIG. 35A shows the fluorescence-activated cell sorting (FACS) analysis data of spinal cord-derived mononuclear cells stained with 4D4 (resident microglia) and CD11b (myeloid cells) in wildtype, SOD1/miR155$^{+/+}$, SOD1/miR155$^{-/+}$, and SOD1/miR155$^{-/-}$ mice.
Figure 35B:
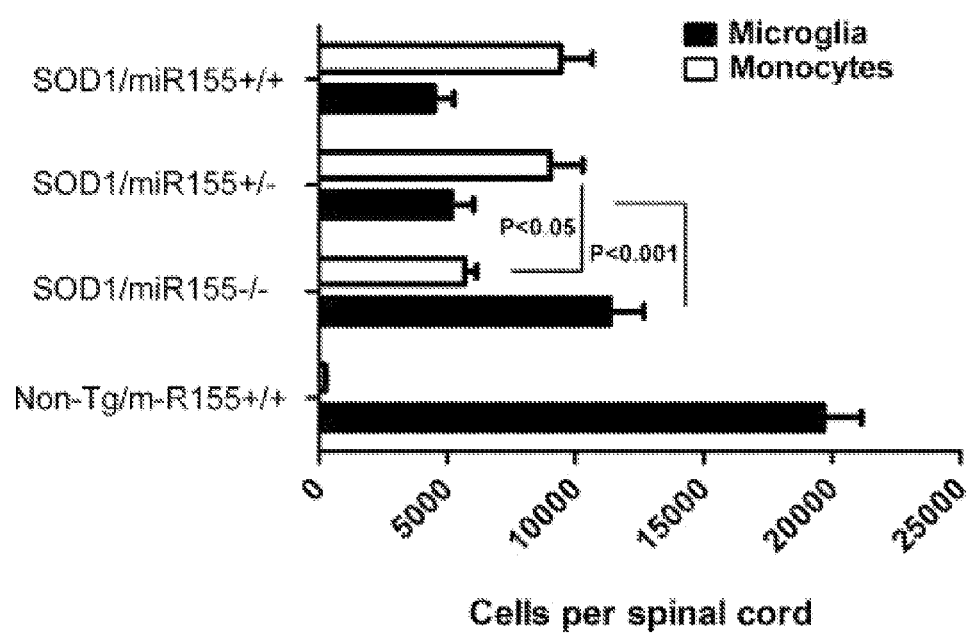
FIG. 35B shows the absolute number of microglia (4D4 positive) and monocyte cells (CD11b positive) cells per spinal cord in wildtype, SOD1/miR155+/+, SOD1/miR155−/+, and SOD1/miR155−/− mice.
Figure 36:
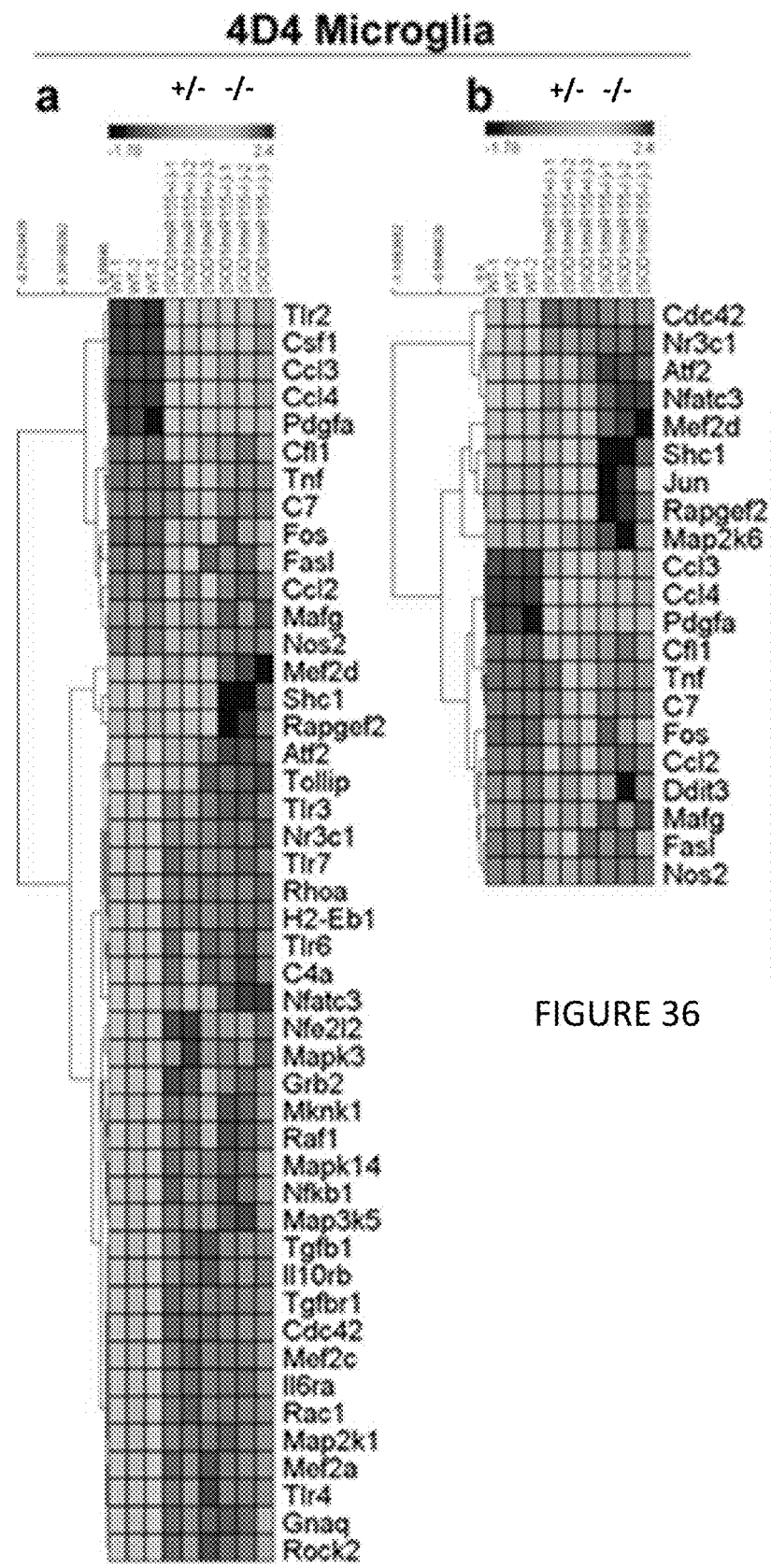
FIG. 36 is a set of four heat maps of showing the expression of inflammation-related genes in spinal cord microglia and $Ly6C^{Hi}$ splenic monocytes in WT, SOD1/miR155$^{-/+}$, and SOD1/miR155$^{-/-}$ mice. The heat maps labeled (a) are from animals at end-stage. (Note that SOD1/miR155$^{-/-}$ mice are still viable and breeding at the end of the study, while SOD1/miR$^{-/+}$ mice experience an onset of symptoms (end stage)). All mice are males C57/Bl6-SOD1 background. The heat maps labeled (b) indicate the genes significantly affected by miR155 in SOD1 mice.

SOD1$^{G93A}$/miR155$^{-/-}$ animals also have a significantly reduction in the recruitment of peripheral monocytes associated with microglia protection in the spinal cord, as compared to SOD1$^{G93A}$ mice (FIG. 35), and significant reduction in inflammation-related gene expression in spinal cord microglia and Ly6C$^{Hi}$ monocytes as compared to SOD1$^{G93A}$ mice (FIG. 36). Fewer inflammation-related genes were affected in splenic T cells, however, the expression of anti-inflammatory genes (IL4 and IL10) reverted to the level of non-transgenic mice, suggesting that miR-155 may primarily affect activation of the M1-associated signature in Ly6C$^{Hi}$ monocytes in SOD1$^{G93A}$ mice.

These data indicate that miR-155 plays a significant role in the development (pathogenesis) of ALS, and that treatment of subjects having a neurodegenerative disorder (e.g., ALS, e.g., familial ALS and/or sporadic ALS) may be achieved by administering at least one an inhibitory nucleic acid targeting hsa-miR-155 (e.g., precursor or mature hsa-miR-155) to a subject a neurodegenerative disorder (e.g., ALS, e.g., familial ALS and/or sporadic ALS). Exemplary inhibitory nucleic acids targeting hsa-miR-155 (e.g., precursor or mature hsa-miR-155) that can be administered to a subject having a neurodegenerative disorder are described herein.

Example 9. Efficacy of miR-155 Antagomir for Treating SOD1$^{G93A}$ Mice

A first set of experiments was performed in the SOD1$^{G93A}$ model of familial ALS to determine whether an antagomir targeting miR-155 would alter miRNA expression and/or inflammatory gene expression in spinal cord-derived microglia and splenic Ly6C$^{Hi}$ monocytes. In these experiments the following five experimental groups were studied.

Group I. Control scrambled miR-155 (intraperitoneal injection, 2 mg per injection, every third day) (n=3). Control scrambled miR-155: +TC+AA+C+A+TTA+G+A+CT+T+A (SEQ ID NO: 263) ("+" indicates the presence of an LNA moiety).

Group II. Antagomir miR-155 low dose (intravenous injection, 0.2 mg per injection, every third day) (n=3). Antogomir miR-155: +TC+AC+A+A+TTA+G+C+AT+T+A (SEQ ID NO: 262) (the "+" indicates the presence of an LNA moiety).

Group III. Antagomir miR-155 high dose (intravenous injection, 2 mg per injection, every third day) (n=3).

Group IV. Antagomir miR-155 low dose (intraperitoneal injection, 0.2 mg per injection, every third day) (n=3).

Group V. Antagomir miR-155 high dose (intraperitoneal injection, 2 mg per injection, every third day) (n=3).

Nanostring inflammatory gene and miRNA expression analysis was performed in spinal cord derived microglia and splenic Ly6C$^{Hi}$ monocytes as described above.

A comparison of the data from microglia and splenic Ly6C monocytes from SOD1 mice administered a low (0.2 mg/kg body weight per injection) vs. high dose (2 mg/kg body weight per injection), every third day (by i.p. or i.v.) show that the low dose doesn't affect splenic Ly6C$^{Hi}$ monocyte M1-phenotype (the same miRNA and inflammatory gene expression is observed in the these mice as compared to untreated SOD1 mice). However, the high dose (administered by either i.p. or i.v.) inhibited the expression of pro-inflammatory cytokines as measured by quantitative nCounter technology for inflammation-related genes. The data also show that spinal-cord derived microglia were not affected by systemic antagomir miR-155 treatment.

A second set of experiments is performed to determine the effect of antagomir miR-155 on the behavior and survival of SOD1 mice. In these experiments, SOD1 mice are either administered a scrambled miR-155 (n=10) or an antogomir miR-155 by intraperitoneal injection at 2 mg/kg body weight per injection, every third day (n=10). The treatment is initiated at the time of disease onset (defined by body weight loss and neurologic score). The mice are treated continuously until the end of the experiment or end-stage. The behavior of the mice is determined, for example, by rotarod performance, and the body weight and survival of the mice is monitored.

A third set of experiments is designed to investigate whether miR-155 in the central nervous system of SOD1 mice can be targeted using lentivirus-mediated inhibition of miR-155. In these experiments, the antigomer miR155 is delivered by lentivurus infection. For miR-155 inhibition, a sequence encoding mutant miR-155 or its specific inhibitor is cloned in a lentiviral vector (Genecopoeia). The virus is produced by infecting target cells according to the user's manual. Approximately 2×10$^7$ transformingunits of recombinant lentivirus is delivered to the SOD1 mice by stereotaxic injection to the CSF or the lateral ventricle. The treatment groups are:

Group I. Mice administered a control lentivirus-scrambled miR-155-GFP-tagged high dose (n=10). (See, control scrambled antagomir sequence of SEQ ID NO: 263.)

Group II. Mice administered an antigomer lentivirus miR-155-GFP tagged high dose (n=10). (See, antogomir miR-155 sequence of SEQ ID NO: 262.)

Figure 37:
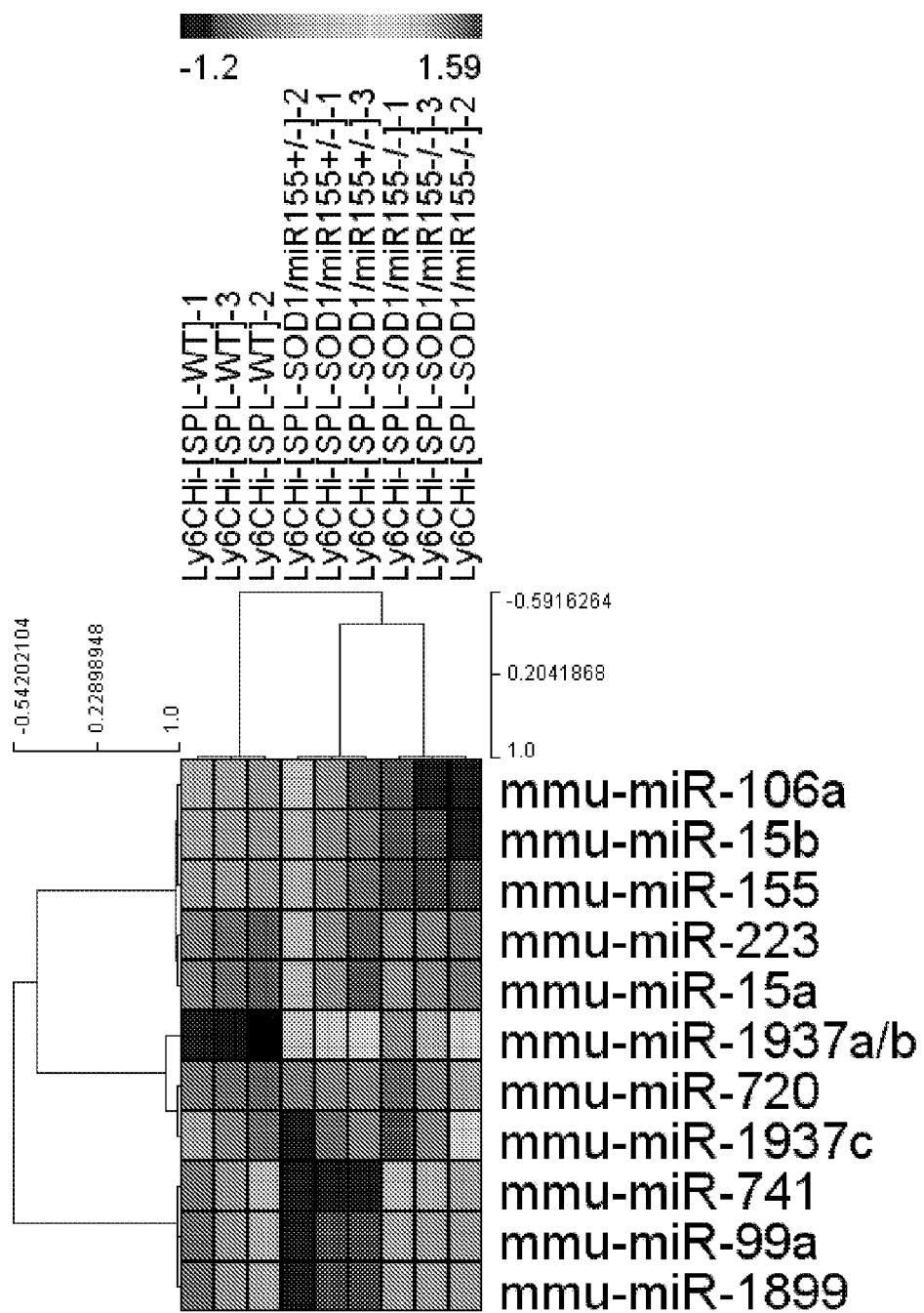
FIG. 37 is nCounter expression profile data showing the expression of several mouse microRNAs in Ly6CHi spleen-derived monocyte subsets from wild type, SOD1/miR155$^{-/+}$, SOD1/miR155$^{-/-}$ mice.
Figure 38:
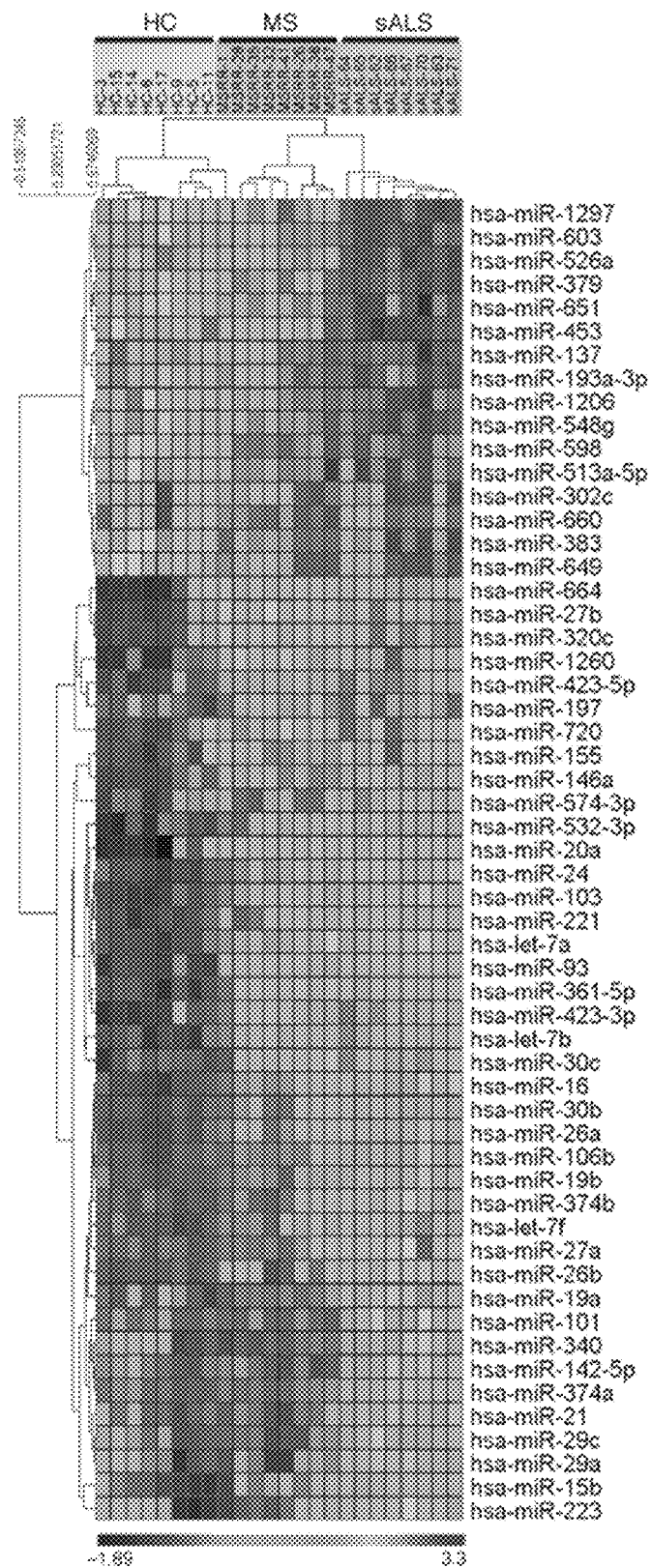
FIG. 38 is a heatmap and bar graphs showing the nCounter expression profiling of blood-derived $CD14^+CD16^-$ monocytes for microRNAs in sporadic ALS (8 subjects) and relapsing-remitting multiple sclerosis (8 subjects) compared to the expression of the microRNAs in $CD14^+CD16^-$ monocytes from healthy controls (8 subjects). The heatmap shows the results of analysis of variance (ANOVA) using Dunnett's post hoc test (P<0.01). The microRNAs upregulated or downregulated in $CD14^+CD16^-$ monocytes from ALS subjects (as compared to expression of these microRNAs in $CD14^+CD16^-$ monocytes from healthy controls) are indicated. Each row of the heatmap represents an individual gene and each column an individual.

The behavior of the mice is followed, e.g., by rotarod performance, and monitoring the body weight and survival of the mice. Nanostring miRNA and immune-related gene profiling of the innate immune system and T-cell inflammatory-related gene profiling is also performed on cells derived from these mice (e.g., peripheral Lys6C$^{Hi}$ cells).

nCounter expression analysis was also performed to determine the expression of several microRNAs in Ly6C$^{Hi}$ spleen-derived monocyte subsets from wild type, SOD1/miR155$^{-/+}$, SOD1/miR155$^{-/-}$ mice. The data show that several microRNAs were differently expressed in wild type mice compared to the SOD1/miR155$^{-/+}$ mice, and between the SOD1/miR155$^{-/+}$ mice and the SOD1/miR155$^{-/-}$ mice (FIG. 37).

nCounter expression profiling of blood-derived CD14$^+$ CD16$^-$ monocytes for microRNAs from sporadic ALS (8 human subjects) and relapsing-remitting multiple sclerosis (8 human subjects) compared to the expression of the microRNAs in CD14+CD16− monocytes from healthy controls (8 subjects) was also performed. The resulting heatmap in FIG. 38 shows the results of analysis of variance (ANOVA) using Dunnett's post hoc test (P<0.01). The microRNAs upregulated or downregulated in CD14$^+$CD16$^-$ monocytes from ALS subjects (as compared to expression of these microRNAs in CD14$^+$CD16$^-$ monocytes from healthy controls) are indicated.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of increasing the longevity of a subject having amyotrophic lateral sclerosis (ALS), the method comprising identifying a subject who has ALS, and administering to the subject having ALS at least one inhibitory nucleic acid comprising a sequence that is complementary to a contiguous sequence of at least 12 nucleotides present in mature microRNA hsa-miR-155 having the sequence of SEQ ID NO:58, wherein at least five of said at least 12 nucleotides are within the seed sequence of mature microRNA hsa-miR-155, wherein the inhibitory nucleic acid comprises at least one locked nucleotide, wherein the inhibitory nucleic acid reduces level or activity of hsa-miR-155 in monocytes of the subject, and wherein the inhibitory nucleic acid is administered intravenously or intrathecally.

2. The method of claim 1, wherein the at least one inhibitory nucleic acid is an antisense oligonucleotide.

3. The method of claim 1, wherein the inhibitory nucleic acid is administered via intrathecal injection.

4. The method of claim 1, wherein the at least one inhibitory nucleic acid is complexed with one or more cationic polymers and/or cationic lipids.

5. The method of claim 1, wherein the at least one inhibitory nucleic acid is complementary to a contiguous sequence of at least 14 nucleotides present in hsa-miR-155.

6. The method of claim 1, wherein the at least one inhibitory nucleic acid is complementary to a contiguous sequence of at least 15 nucleotides present in hsa-miR-155.

7. The method of claim 1, wherein the at least one inhibitory nucleic acid comprises at least one locked nucleic acid (LNA).

8. The method of claim 5, wherein the at least one inhibitory nucleic acid comprises at least one locked nucleic acid (LNA).

9. The method of claim 6, wherein the at least one inhibitory nucleic acid comprises at least one locked nucleic acid (LNA).

10. The method of claim 1, wherein the subject has increased levels of hsa-miR-155 in the subject's monocytes.

11. The method of claim 1, wherein the subject is human.

* * * * *